United States Patent
Natarajan et al.

(10) Patent No.: US 11,964,984 B2
(45) Date of Patent: Apr. 23, 2024

(54) TXNIP-TRX COMPLEX INHIBITORS AND METHODS OF USING THE SAME

(71) Applicant: CITY OF HOPE, Duarte, CA (US)

(72) Inventors: Rama Natarajan, Hacienda Heights, CA (US); Feng Miao, Alhambra, CA (US); Nagarajan Vaidehi, Arcadia, CA (US); Supriyo Bhattacharya, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 32 days.

(21) Appl. No.: 17/231,743

(22) Filed: Apr. 15, 2021

(65) Prior Publication Data
US 2022/0064174 A1  Mar. 3, 2022

Related U.S. Application Data

(60) Provisional application No. 63/011,067, filed on Apr. 16, 2020.

(51) Int. Cl.
C07D 491/048  (2006.01)
A61P 3/10  (2006.01)
A61P 37/06  (2006.01)

(52) U.S. Cl.
CPC ............ *C07D 491/048* (2013.01); *A61P 3/10* (2018.01); *A61P 37/06* (2018.01)

(58) Field of Classification Search
CPC ................................................. C07D 491/04
See application file for complete search history.

(56) References Cited

PUBLICATIONS

STN/Cas Registry # 1529788-65-2 (Jan. 2014).*
STN/Cas Registry # 1528956-92-4 (Jan. 2014).*
STN Registry #1442532-96-8 (Jun. 30, 2013).*
Alhawiti, N.M. et al. (2017). "TXNIP in Metabolic Regulation: Physiological Role and Therapeutic Outlook," *Current Drug Targets* 18(9):1095-1103.
Anders, S. et al. ((2010). "Differential expression analysis for sequence count data," *Genome Biol* 11(10):R106.
Bell, J.A. et al. (2012). "PrimeX and the Schrödinger computational chemistry suite of programs," vol. F, Chapter 18.10 in *International Tables for Crystallography*, pp. 534-538.
Bhattacharya, S. et al. (Jul. 15, 2014). "Differences in Allosteric Communication Pipelines in the Inactive and Active States of a GPCR," *Biophys J* 107(2):422-434.
Bhattacharya, S. et al. (Nov. 8, 2016). "Conserved Mechanism of Conformational Stability and Dynamics in G-Protein-Coupled Receptors," *J Chem Theory Comput* 12(11):5575-5584.
Bolger, A.M. et al. (Aug. 1, 2014). "Trimmomatic: a flexible trimmer for Illumina sequence data," *Bioinformatics* 30(15):2114-2120.
Chen, Z. et al. (May 24, 2016). "Epigenomic profiling reveals an association between persistence of DNA methylation and metabolic memory in the DCCT/EDIC type 1 diabetes cohort," *PNAS USA* 113(21):E3002-3011.
Chen, S. et al. (Sep. 1, 2018). "fastp: an ultra-fast all-in-one FASTQ preprocessor," *Bioinformatics* 34(17):i884-i890.
Chen Z. et al. (Aug. 2020). "DNA methylation mediates development of HbA1c-associated complications in type 1 diabetes," *Nature Metabolism* 2(8):744-762.
Chong, C.R. et al. (Aug. 2014). "Thioredoxin-interacting protein: pathophysiology and emerging pharmacotherapeutics in cardiovascular disease and diabetes," *Cardiovascular Drugs and Therapy* 28(4):347-360.
Dobin, A. et al. (Jan. 2013, e-published Oct. 25, 2012). "STAR: ultrafast universal RNA-seq aligner," *Bioinformatics* 29(1):15-21.
Duan, J. et al. (Sep. 2010). "Analysis and comparison of 2D fingerprints: insights into database screening performance using eight fingerprint methods," *J Mol Graph Model* 29(2):157-170.
Friesner, R.A. et al. (Mar. 25, 2004). "Glide: a new approach for rapid, accurate docking and scoring. 1. Method and assessment of docking accuracy," *J Med Chem* 47(7):1739-1749.
Halgren, T.A. et al. (Mar. 25, 2004). "Glide: a new approach for rapid, accurate docking and scoring. 2. Enrichment factors in database screening," *J Med Chem* 47(7):1750-1759.
Hwang, J. et al. (2014). The structural basis for the negative regulation of thioredoxin by thioredoxin-interacting protein. *Nat Commun* 5:2958.
Li, H. et al. (May 27, 2014). "Computational method to identify druggable binding sites that target protein-protein interactions," *J Chem Inf Model* 54(5):1391-1400.
Li, T. et al. (Jul. 2017). "W2476 ameliorates β-cell dysfunction and exerts therapeutic effects in mouse models of diabetes via modulation of the thioredoxin-interacting protein signaling pathway," *Acta Pharmacol Sin* 38(7):1024-1037.
Lomenick, B. et al. (Dec. 22, 2009). "Target identification using drug affinity responsive target stability (DARTS)," *PNAS USA* 106(51):21984-21989.
Nivedha, A.K. et al. (Apr. 2018). "Identifying Functional Hotspot Residues for Biased Ligand Design in G-Protein-Coupled Receptors," *Mol Pharmacol* 93(4):288-296.
Ovalle, F. et al. (Aug. 2018). "Verapamil and beta cell function in adults with recent-onset type 1 diabetes," *Nat Med* 24(8):1108-1112.
Pai, M.Y. et al. (2015). "Drug affinity responsive target stability (DARTS) for small-molecule target identification," Chapter 22 in *Methods in Molecular Biology* 1263, 287-298.
Robinson, M.D. et al. (Jan. 1, 2010). "edgeR: a Bioconductor package for differential expression analysis of digital gene expression data," *Bioinformatics* 26(1):139-140.
Sastry, M. et al. (May 24, 2010). "Large-scale systematic analysis of 2D fingerprint methods and parameters to improve virtual screening enrichments," *J Chem Inf Model* 50(5):771-784.
Shalev, A. (Aug. 2014). "Minireview: Thioredoxin-interacting protein: regulation and function in the pancreatic β-cell," *Mol Endocrinol* 28(8):1211-1220.

(Continued)

*Primary Examiner* — Paul V Ward

(74) *Attorney, Agent, or Firm* — Mintz, Levin, Cohn, Ferris, Glovsky and Popeo, P.C.

(57) ABSTRACT

Disclosed herein, inter alia, are compounds and methods for inhibiting the thioredoxin-thioredoxin-interacting-protein (TXNIP-TRX) complex.

22 Claims, 24 Drawing Sheets

Specification includes a Sequence Listing.

(56) References Cited

PUBLICATIONS

Tautermann, C.S. et al. (Jan. 10, 2019). "Allosteric Activation of Striatal-Enriched Protein Tyrosine Phosphatase (STEP, PTPN5) by a Fragment-like Molecule," *J Med Chem* 62(1): 306-316.
Thielen L. et al. (Apr. 2018). "Diabetes pathogenic mechanisms and potential new therapies based upon a novel target called TXNIP," *Curr Opin Endocrinol Diabetes Obes.* 25(2):75-80.
Thielen, L.A. et al. (Sep. 1, 2020). "Identification of an Antidiabetic, Orally Available Small Molecule that Regulates TXNIP Expression and Glucagon Action," *Cell Metab* 32(3):353-365.
Vaidehi, N. et al. (Oct. 2016). "Allosteric communication pipelines in G-protein-coupled receptors," *Curr Opin Pharmacol* 30:76-83.
Waldhart, A.N. et al. (Jun. 6, 2017). "Phosphorylation of TXNIP by AKT Mediates Acute Influx of Glucose in Response to Insulin," *Cell Reports* 19(10):2005-2013.
Wu, N. et al. (Mar. 28, 2013). "AMPK-dependent degradation of TXNIP upon energy stress leads to enhanced glucose uptake via GLUT1," *Mol Cell* 49(6):1167-1175.
Berk, B.C. (2007). "Novel approaches to treat oxidative stress and cardiovascular diseases," *Transactions of the American Clinical and Climatological Association* 118:209-214.
Ngo, D.T. et al. (Feb. 2011). "Ramipril retards development of aortic valve stenosis in a rabbit model: mechanistic considerations," *British Journal of Pharmacology* 162(3):722-732.
Ngo, D.T. et al. (Mar. 26, 2018). Abstract 14461: How Does Perhexiline Modulate Myocardial Energetics and Ameliorate Redox Stress? *Circulation* 2011; 124: A14461, 1 page.

* cited by examiner

HG vs NG
Glucose induced genes

C30 treated vs Untreated
C30 inhibited genes

HG vs NG
Glucose induced genes

C38 treated vs Untreated
C38 inhibited genes

TXNIP-TRX COMPLEX INHIBITORS AND METHODS OF USING THE SAME

CROSS-REFERENCES TO RELATED APPLICATIONS

This application claims the benefit of U.S. Provisional Application No. 63/011,067, filed Apr. 16, 2020, which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-742001US_Sequence_Listing_ST25, created Mar. 23, 2021, 4,809 bytes, machine format IBM-PC, MS Windows operating system, is hereby incorporated by reference.

STATEMENT AS TO RIGHTS TO INVENTIONS MADE UNDER FEDERALLY SPONSORED RESEARCH AND DEVELOPMENT

This invention was made with government support under grant number DK106917, awarded by the National Institutes of Health. The government has certain rights in the invention.

BACKGROUND

The thioredoxin system, which includes the thioredoxin (TRX) protein, nicotinamide adenine dinucleotide phosphate (NADPH), and thioredoxin reductase (TXNRD1), is a major anti-oxidant system involved in the maintenance of cellular physiology and survival Dysregulation in this system has been associated with metabolic, cardiovascular, and malignant disorders. Thioredoxin-interacting protein (TXNIP) is an inhibitor of the redox regulator thioredoxin (TRX), an antioxidant. Thioredoxin-interacting protein (TXNIP) was first identified as an inhibitor of the redox regulator thioredoxin (TRX), an antioxidant. TXNIP functions as an inhibitor of TRX, and pathological suppression of TRX by TXNIP (which leads to oxidant stress) has been demonstrated in diabetes and cardiovascular diseases. Disclosed herein, inter alia, are solutions to these and other problems in the art.

BRIEF SUMMARY

In an aspect is provided a compound, or a pharmaceutically acceptable salt thereof, having the formula:

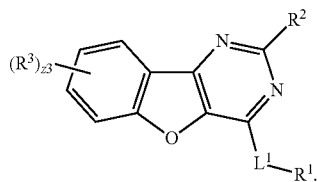

(I)

$L^1$ is a covalent linker.
$R^1$ is independently hydrogen, halogen, $-CX^1_3$, $-CHX^1_2$, $-CH_2X^1$, $-OCX^1_3$, $-OCHX^1_2$, $-OCH_2X^1$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)OR^{1C}$, $-C(O)NR^{1A}R^{1B}$, $-OR^{1D}$, $-SR^{1D}$, $-SeR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, halogen, $-CX^2_3$, $-CHX^2_2$, $-CH_2X^2$, $-OCX^2_3$, $-OCHX^2_2$, $-OCH_2X^2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)OR^{2C}$, $-C(O)NR^{2A}R^{2B}$, $-OR^{2D}$, $-SR^{2D}$, $-SeR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, $R^{1D}$, $R^{2A}$, $R^{2B}$, $R^{2C}$, and $R^{2D}$ are each independently hydrogen, oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl, or substituted or unsubstituted heteroaryl; $R^{2A}$ and $R^{2B}$ substituents bonded to the same nitrogen atom may optionally be joined to form a substituted or unsubstituted heterocycloalkyl, or substituted or unsubstituted heteroaryl.

$X^1$ and $X^2$ are each independently $-F$, $-Cl$, $-Br$, or $-I$.

The symbols n1 and n2 are each independently an integer from 0 to 4.

The symbols m1, m2, v1, and v2 are each independently 1 or 2.

$R^3$ is independently halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl.

The symbol z3 is an integer from 0 to 4.

In an aspect is provided a compound, or a pharmaceutically acceptable salt thereof, having the formula:

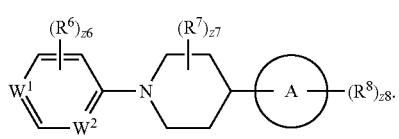

Ring A is cycloalkyl, heterocycloalkyl, aryl, or heteroaryl.
$W^1$ is N or C($R^4$).
$W^2$ is N or C($R^5$).
$R^4$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.
$R^5$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.
$R^6$ is independently halogen, —$CX^6_3$, —$CHX^6_2$, —$CH_2X^6$, —$OCX^6_3$, —$OCHX^6_2$, —$OCH_2X^6$, —CN, —$SO_{n6}R^{6D}$, —$SO_{v6}NR^{6A}R^{6B}$, —$NR^{6C}NR^{6A}R^{6B}$, —$ONR^{6A}R^{6B}$, —NHC(O)$NR^{6C}NR^{6A}R^{6B}$, —NHC(O)$NR^{6A}R^{6B}$, —N(O)$_{m6}$, —$NR^{6A}R^{6B}$, —C(O)$R^{6C}$, —C(O)O$R^{6C}$, —C(O)$NR^{6A}R^{6B}$, —O$R^{6D}$, —S$R^{6D}$, —Se$R^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^6$ substituents may optionally be joined to form a substituted or unsubstituted cycloalkyl, substituted or unsubstituted heterocycloalkyl, substituted or unsubstituted aryl, or substituted or unsubstituted heteroaryl.
$R^7$ is independently halogen, oxo, —$CX^7_3$, —$CHX^7_2$, —$CH_2X^7$, —$OCX^7_3$, —$OCHX^7_2$, —$OCH_2X^7$, —CN, —$SO_{n7}R^{7D}$, —$SO_{v7}NR^{7A}R^{7B}$, —$NR^{7C}NR^{7A}R^{7B}$, —$ONR^{7A}R^{7B}$, —NHC(O)$NR^{7C}NR^{7A}R^{7B}$, —NHC(O)$NR^{7A}R^{7B}$, —N(O)$_{m7}$, —$NR^{7A}R^{7B}$, —C(O)$R^{7C}$, —C(O)O$R^{7C}$, —C(O)$NR^{7A}R^{7B}$, —O$R^{7D}$, —S$R^{7D}$, —Se$R^{7D}$, —$NR^{7A}SO_2R^{7D}$, —$NR^{7A}C(O)R^{7C}$, —$NR^{7A}C(O)OR^{7C}$, —$NR^{7A}OR^{7C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^7$ substituents may optionally be joined to form a substituted or unsubstituted cycloalkyl, substituted or unsubstituted heterocycloalkyl, substituted or unsubstituted aryl, or substituted or unsubstituted heteroaryl; two $R^7$ substituents bonded to the same carbon atom may optionally be joined to form a substituted or unsubstituted cycloalkyl, or substituted or unsubstituted heterocycloalkyl.
$R^8$ is independently halogen, oxo, —$CX^8_3$, —$CHX^8_2$, —$CH_2X^8$, —$OCX^8_3$, —$OCHX^8_2$, —$OCH_2X^8$, —CN, —$SO_{n8}R^{8D}$, —$SO_{v8}NR^{8A}R^{8B}$, —$NR^{8C}NR^{8A}R^{8B}$, —$ONR^{8A}R^{8B}$, —NHC(O)$NR^{8C}NR^{8A}R^{8B}$, —NHC(O)$NR^{8A}R^{8B}$, —N(O)$_{m8}$, —$NR^{8A}R^{8B}$, —C(O)$R^{8C}$, —C(O)O$R^{8C}$, —C(O)$NR^{8A}R^{8B}$, —O$R^{8D}$, —S$R^{8D}$, —Se$R^{8D}$, —$NR^{8A}SO_2R^{8D}$, —$NR^{8A}C(O)R^{8C}$, —$NR^{8A}C(O)OR^{8C}$, —$NR^{8A}OR^{8C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^8$ substituents may optionally be joined to form a substituted or unsubstituted cycloalkyl, substituted or unsubstituted heterocycloalkyl, substituted or unsubstituted aryl, or substituted or unsubstituted heteroaryl.
$R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, and $R^{8D}$ are each independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{8A}$ and $R^{8B}$ substituents bonded to the same nitrogen atom may optionally be joined to form a substituted or unsubstituted heterocycloalkyl or substituted or unsubstituted heteroaryl.
$X^6$, $X^7$, and $X^8$ are each independently —F, —Cl, —Br, or —I.
The symbols n6, n7, and n8 are each independently an integer from 0 to 4.
The symbols m6, m7, m8, v6, v7, and v8 are each independently 1 or 2.
The symbol z6 is an integer from 0 to 3.
The symbol z7 is an integer from 0 to 9.
The symbol z8 is an integer from 0 to 7.
In an aspect is provided a pharmaceutical composition including a compound described herein, or pharmaceutically acceptable salt thereof, and a pharmaceutically acceptable excipient.
In an aspect is provided a method of treating a TXNIP-TRX complex-associated disease, the method including administering to a subject in need thereof an effective amount of a TXNIP-TRX complex inhibitor.
In an aspect is provided a method of treating a metabolic disorder, cardiovascular disease, or inflammatory disease, the method including administering to a subject in need thereof an effective amount of a compound, or pharmaceutically acceptable salt thereof, as described herein, including in embodiments.

In an aspect is provided a method of treating a kidney disease or an eye disease, the method including administering to a subject in need thereof an effective amount of a compound, or pharmaceutically acceptable salt thereof, as described herein, including in embodiments.

In an aspect is provided a method of reducing the level of expression of TXNIP in a cell, the method including contacting the cell with a compound, or pharmaceutically acceptable salt thereof, as described herein, including in embodiments.

In an aspect is provided a method of reducing the level of expression of TNF-α in a cell, the method including contacting the cell with a compound, or pharmaceutically acceptable salt thereof, as described herein, including in embodiments.

In an aspect is provided a method of reducing the level of expression of TXNIP, the method including contacting TXNIP with a compound, or a pharmaceutically acceptable salt thereof, as described herein, including in embodiments.

BRIEF DESCRIPTION OF THE DRAWINGS

FIG. 1A: TXNIP-TRX complex showing the predicted allosteric sites for small molecules. FIG. 1B: Computational small molecule screening strategy. The binding sites were predicted using Allosteer.

FIG. 2A: C30 and C38 inhibited TXNIP mRNA expression in THP1 cells. THP1 cells were cultured under 25 mM glucose with the indicated concentrations of compounds for 72 hours. Cells were then collected for total RNA preparation. RT-PCR was performed, and data shown are the mean±SEM from triplicates. Statistical analysis was performed using one-way ANOVA, $*p<0.0001$. FIG. 2B: C30 and C38 inhibited TNF-α mRNA expression in THP1 cells. THP1 cells were cultured under 25 mM glucose with various concentrations of compounds as indicated for 72 hours and collected for total RNA preparation. RT-PCR was performed, and data shown are the mean±SEM from triplicates. Statistical analysis was performed using one-way ANOVA: $*<0.02$; $**<0.0001$.

FIG. 3A: C30 and C38 inhibited TXNIP mRNA expression in murine RAW macrophages. RAW cells were cultured under 25 mM glucose with various concentration of C30 and C38 as indicated for 72 hours. Total RNA was prepared. RT-PCR was performed and data shown are the mean±SEM from triplicates. Statistical analysis was performed for each column vs. high glucose (HG) DMSO using one-way ANOVA: $*p<0.0001$. FIG. 3B: Treatment with C30 and C38 decreased TNF-α mRNA expression in murine RAW macrophages. RAW cells were cultured under 25 mM glucose with various concentration of C30 and C38 as indicated for 72 hours. Total RNA was prepared. RT-PCR was performed and data shown are the mean±SEM from triplicates. Statistical analysis was performed for each column vs. HG DMSO using one-way ANOVA: $*p<0.0001$.

FIG. 4A: Treatment of murine MIN6 cells with C30 and C38 decreased TXNIP mRNA levels. MIN6 cells were cultured under 25 mM glucose with C30 and C38 at the indicated concentrations for 72 hours. Total RNA was prepared. RT-PCR was performed and data shown are the mean±SEM from triplicates. Statistical analysis was performed for each column vs. HG DMSO using one-way ANOVA: $*p<0.0001$. FIG. 4B: Treatment of murine MIN6 cells with C30 and C38 tended to increase TNF-α mRNA expression. MIN6 cells were cultured under 25 mM glucose and treated with C30 and C38 at the indicated concentrations for 72 hours. Total RNA was prepared. RT-PCR was performed and data shown are the mean±SEM from triplicates. Statistical analysis was performed for each column vs. HG DMSO using one-way ANOVA: $*p<0.0001$.

FIG. 5A: C30 and C38 effects on TXNIP mRNA expression in human pancreas 1.1B4 β cells. Human 1.1B4 β cells were cultured under 25 mM glucose with C30 and C38 at the indicated concentrations for 72 hours. Total RNA was prepared. RT-PCR was performed and data shown are the mean±SEM from triplicates. Statistical analysis was performed for each column vs. HG DMSO using one-way ANOVA: $*p<0.0001$. FIG. 5B: C30 and C38 effects on TNF-α mRNA expression in human pancreas 1.1B4 β cells. Human 1.1B4 β cells were cultured under 25 mM glucose with C30 and C38 at the indicated concentrations for 72 hours. Total RNA was prepared. RT-PCR was performed and data shown are the mean±SEM from triplicates. Statistical analysis was performed for each column vs. HG DMSO using one-way ANOVA: $*p<0.0001$.

FIG. 10A: Overlap between HG-induce genes and C30-inhibited genes in THP1 cells. FIG. 10B: Overlap between HG-induce genes and C38-inhibited genes in THP1 cells. FIG. 10C: Overlap between common genes from FIG. 10A (60 genes) and common genes from FIG. 10B (64 genes). The overlap genes are listed in Table 2 in Example 2.

FIG. 11A: Heatmap of 60 high glucose-responsive and C30/C38-inhibited genes. Differential expression was calculated using these counts with edgeR (5, 6) version 3.0. After correcting for differences in library sizes, a fold change of >1.5 and a p-value of <0.05 were applied to select expressed genes. Overlapped genes were used for generating heatmap using Java TreeView. NG: THP1 under 5 mM glucose; HG: THP1, 25 mM glucose; C30: THP1, 25 mM glucose, 5 uM C30; C38: THP1, 25 mM glucose, 5 uM C38. All are replicates. From top to bottom: HSD11B1, EGR1, NFE2, CCL2, TIFAB, SH2D2A, UHRF1, CD52, TIMP3, TNF, S100P, PAQR4, LY6E, VPS9D-AS, RNASE3, MIR4258, GAS6, LIMD2, MBOAT7, CFD, PKMYT1, CHAC1, MFNG, DEFB1, ICAM2, NT5DC2, GPR35, HINT2, SEPT5-GP1BB, NRSN2, CDH24, SLC37A2, ADAT3, LST1, SPNS3, LTB, H2AFX, FUOM, FAM163A, BATF3, TMEM160, CITED4, MIR3661, TNFSF14, SLC6A9, TONSL, AVEN, SUSD3, TSPO, DDIT4, CKB, SLC22A31, HAAO, MF5SD3, SLC38A5, SIGMAR1, RGMA, DNPH1, ADGRE5, C20orf24, GATA2, RAB37, GDPD5, GAREM2, PIGQ, IMPA2, CRYBB2P1, UCP2, RELB, FOXL2, STC2, HOXA11-AS, MIR1282, RTN2, ZNF511, STARD10, NRM, NF2, ITGB7, POMGNT, KLF10, KLF2, NECAB2, C6orf223, IGFBP4, ACP2, TMEM161A, RHBDD2, YDJC, G0S2, FAM20C, TKTL1, PDIA3P1, HCST, FBXL15, LINC00116, FLNA, TXNIP, MIR3687-1, ARRDC4. FIG. 11B: Ingenuity Pathway Analysis of 60 overlapping genes (shown in Table 2).

FIG. 12A: C30 and C38 target TXNIP mRNA in human pancreatic islets. Human pancreatic islets (500 IEQ) were cultured with PIM(R) (Prodo Labs) medium under 25 mM glucose with 2.5 uM of the indicated compounds for 48 h. Total RNA was collected. RT-PCR was performed in triplicate and data shown are the mean±SEM. Statistical analysis was performed using one-way ANOVA: *p<0.0001. FIG. 12B: Treatment with C30 and C38 does not alter SOD1 mRNA levels. Human pancreatic islets (500 IEQ) were cultured with PIM(R) (Prodo Labs) under 25 mM glucose with 2.5 uM of the indicated compounds for 48 h. Total RNA was collected. RT-PCR was performed in triplicate and data shown are the mean+SEM. Statistical analysis was performed using one-way ANOVA: *p<0.0001.

FIG. 18A: BCL2/BAX ratios are the mean±SEM from triplicates. Statistical analysis was performed for each column vs. HG, 3 cytokines using one-way ANOVA: *p<0.002. FIG. 18B: TXNIP relative mRNA levels. Data shown are the mean±SEM from triplicates. Statistical analysis was performed for each column vs. HG, 3 cytokines using one-way ANOVA: **p<0.0001.

DETAILED DESCRIPTION

I. Definitions

Figure 1A:
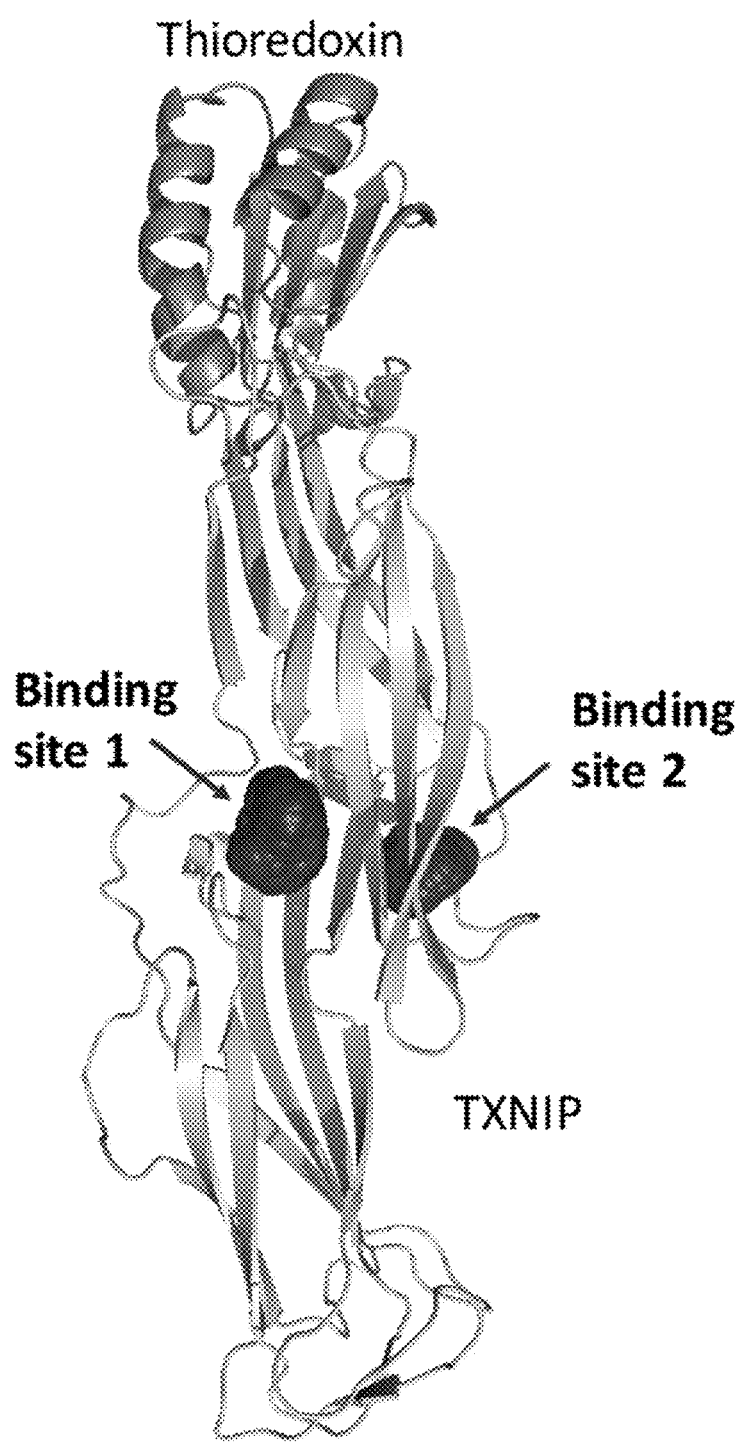
FIGS. 1A-1B.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. In embodiments, the alkyl is fully saturated. In embodiments, the alkyl is monounsaturated. In embodiments, the alkyl is polyunsaturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. In embodiments, an alkenylene includes one or more double bonds. In embodiments, an alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R'', —OR', —SR', and/or —SO$_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. In embodiments, a heteroalkenylene includes one or more double bonds. In embodiments, a heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo [2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, the term "heterocycloalkyl" means a monocyclic, bicyclic, or a multicyclic heterocycloalkyl ring system. In embodiments, heterocycloalkyl groups are fully saturated. In embodiments, a bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings. In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~~~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

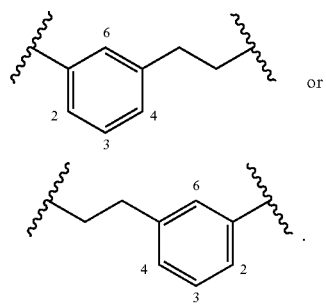

or

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), selenium (Se), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the application (e.g., Examples section, figures, or tables below).

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^5$ 1, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$ $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ ... $R^{100.1}$; $R^{1A.1}$, $R^{2A.1}$, $R^{3A.1}$, $R^{4A.1}$, $R^{5A.1}$ ... $R^{100A.1}$; $R^{L1.1}$, $R^{L2.1}$, $R^{L3.1}$, $R^{L4.1}$, $R^{L5.1}$ ... $R^{L100.1}$) may be further substituted with one or more second substituent groups (e.g., $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$) may be further substituted with one or more third substituent groups (e.g., $R^{1.3}$, $R^{2.3}$, $R^{3.3}$, $R^{4.3}$, $R^{5.3}$ ... $R^{100.3}$; $R^{1A.3}$, $R^{2A.3}$, $R^{3A.3}$, $R^{4A.3}$, $R^{5A.3}$ ... $R^{100A.3}$; $R^{L1.3}$, $R^{L2.3}$, $R^{L3.3}$, $R^{L4.3}$, $R^{L5.3}$ ... $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

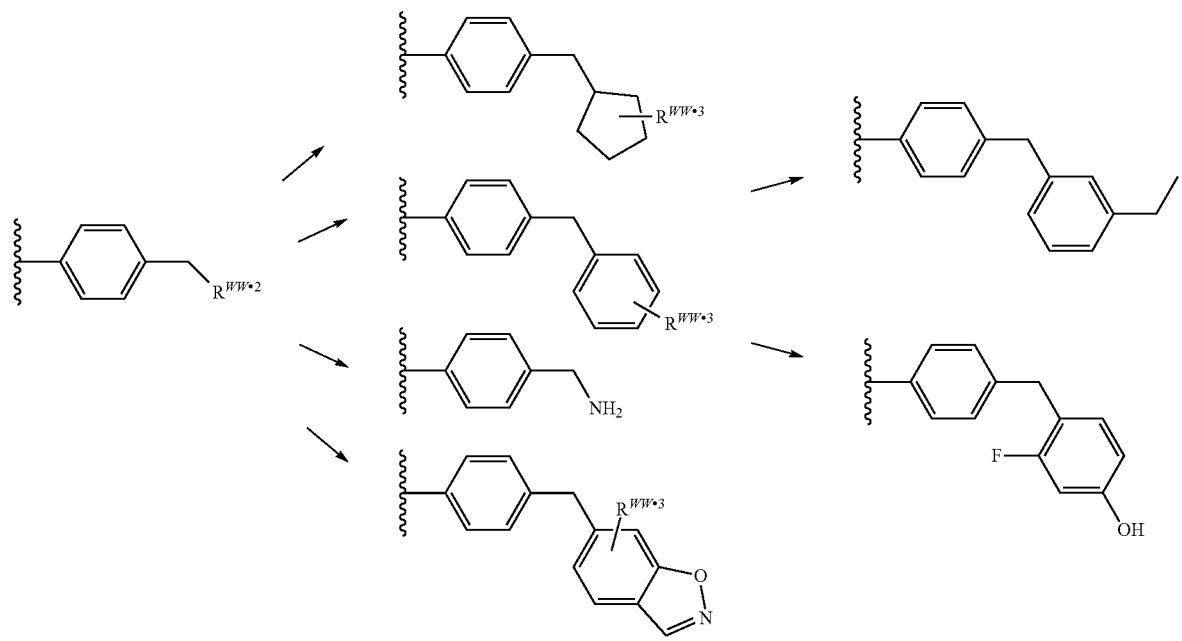

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is $R^{WW.1}$ is independently oxo, halogen, —$CX^{WW.1}{}_3$, —$CHX^{WW.1}{}_2$, —$CH_2X^{WW.1}$, —$OCX^{WW.1}{}_3$, —$OCH_2X^{WW.1}$, —$OCHX^{WW.1}{}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, —$CX^{WW.1}{}_3$, —$CHX^{WW.1}{}_2$, —$CH_2X^{WW.1}$, —$OCX^{WW.1}{}_3$, —$OCH_2X^{WW.1}$, —$OCHX^{WW.1}{}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, —$CX^{WW.3}_3$, —$CHX^{WW.3}_2$, —$CH_2X^{WW.3}$, —$OCX^{WW.3}_3$, —$OCH_2X^{WW.3}$, —$OCHX^{WW.3}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, —$CX^{LWW.2}_3$, —$CHX^{LWW.2}_2$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, —$CX^{LWW.2}_3$, —$CHX^{LWW.2}_2$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, —$CX^{LWW.3}_3$, —$CHX^{LWW.3}_2$, —$CH_2X^{LWW.3}$, —$OCX^{LWW.3}_3$, —$OCH_2X^{LWW.3}$, —$OCHX^{LWW.3}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, —$CX^{WW}_3$, —$CHX^{WW}_2$, —$CH_2X^{WW}$, —$OCX^{WW}_3$, —$OCH_2X^{WW}$, —$OCHX^{WW}_2$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —C(O)O—, —OC(O)—, —S—, —$SO_2$—, —$SO_2NH$—, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; and (o) biotin conjugate can react with avidin or streptavidin to form an avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an", as used in herein means one or more. In addition, the phrase "substituted with a[n]", as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl", the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a substance, element, compound, or composition; or moiety thereof, detectable by appropriate means such as spectroscopic, photochemical, biochemical, immunochemical, chemical, magnetic resonance imaging, or other physical means. For example, useful detectable agents include $^{18}$F, $^{32}$P $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, 169Er, $^{175}$Lu, $^{177}$Lu, $^{186}$Re $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g., fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{62}$Cu, $^{64}$Cu, $^{67}$Cu, $^{67}$Ga $^{68}$Ga, $^{77}$As, $^{86}$Y $^{90}$Y, $^{89}$Sr, $^{89}$Zr, $^{94}$Tc, $^{94}$Tc, $^{99m}$Tc, 99Mo, $^{105}$Pd, $^{105}$Rh $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$I $^{198}$Au, $^{199}$Au, $^{211}$At, $^{211}$Pb, $^{212}$Bi, $^{212}$Pb, $^{213}$Bi, $^{223}$Ra, and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb, and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "TXNIP inhibitor" refers to a compound (e.g., compounds described herein) that reduces the level of activity of TXNIP when compared to a control, such as absence of the compound or a compound with known inactivity. In embodiments, a TXNIP inhibitor reduces the activity or function (e.g., thioredoxin binding) of the TXNIP protein. In embodiments, a TXNIP inhibitor reduces the level of expression of TXNIP (e.g., in a cell).

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments, contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g., increasing) the activity or function of the protein relative to the activity or function of the protein in the absence of the activator. In embodiments activation means positively affecting (e.g., increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In embodiments inhibition means negatively affecting (e.g., decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation). A "TXNIP-TRX complex inhibitor" is a compound that negatively affects (e.g., decreases) the activity or function of the TXNIP-TRX complex relative to the activity or function of TXNIP-TRX complex in the absence of the inhibitor. In embodiments, a TXNIP-TRX complex inhibitor prevents the formation of the TXNIP-TRX complex (e.g., prevents TXNIP from interacting with TRX). A "TXNIP expression inhibitor" is a compound that negatively affects (e.g., decreases) the level of expression of TXNIP relative to the level of expression of TXNIP in the absence of the inhibitor.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "thioredoxin" and "TXN" and "TRX" refer to a protein (including homologs, isoforms, and functional fragments thereof) with thioredoxin activity. The term includes any recombinant or naturally-occurring form of thioredoxin or variants thereof that maintain thioredoxin activity (e.g., within at least 30%, 40%, 50%, 60%, 70%, 80%, 90%, 95%, or 100% activity compared to wildtype thioredoxin). In embodiments, the thioredoxin protein encoded by the thioredoxin gene has the amino acid sequence set forth in or corresponding to Entrez 7295, UniProt P10599, or RefSeq (protein) NP_003320. In embodiments, the thioredoxin gene has the nucleic acid sequence set forth in RefSeq (mRNA) NM_003329. In embodiments, the amino acid sequence or nucleic acid sequence is the sequence known at the time of filing of the present application. In embodiments, the sequence corresponds to NP_003320.2. In embodiments, the sequence corresponds to NM_003329.3. In embodiments, the thioredoxin protein encoded by the thioredoxin gene has the amino acid sequence set forth in or corresponding RefSeq (protein) NP_001231867. In embodiments, the thioredoxin gene has the nucleic acid sequence set forth in RefSeq (mRNA) NM_001244938. In embodiments, the amino acid sequence or nucleic acid sequence is the sequence known at the time of filing of the present application. In embodiments, the sequence corresponds to NP_001231867.1. In embodiments, the sequence corresponds to NM_001244938.1. In embodiments, the thioredoxin is a human thioredoxin. In embodiments, the thioredoxin corresponds to the sequence:

```
                                        (SEQ ID NO: 1)
MVKQIESKTAFQEALDAAGDKLVVVDFSATWCGPCKMIKPFFHSLSEKYS

NVIFLEVDVDDCQDVASECEVKCMPTFQFFKKGQKVGEFSGANKEKLEAT

INELV.
```

The terms "Thioredoxin-interacting protein" and "TXNIP" refer to a protein (including homologs, isoforms, and functional fragments thereof) which interacts with thioredoxin. The term includes any recombinant or naturally-occurring form of TXNIP or variants thereof that maintain TXNIP activity (e.g., within at least 30%, 40%, 50%, 60%, 70%, 80%, 90%, 95%, or 100% activity compared to wildtype TXNIP). In embodiments, the TXNIP protein encoded by the TXNIP gene has the amino acid sequence set forth in or corresponding to Entrez 10628, UniProt Q9H3M7, RefSeq (protein) NP_006463, or RefSeq (protein) NP_001300901. In embodiments, the TXNIP gene has the nucleic acid sequence set forth in RefSeq (mRNA) NM_006472. In embodiments, the TXNIP gene has the nucleic acid sequence set forth in RefSeq (mRNA) NM_001313972. In embodiments, the amino acid sequence or nucleic acid sequence is the sequence known at the time of filing of the present application. In embodiments, the sequence corresponds to NP_001300901. In embodiments, the sequence corresponds to NP_006463. In embodiments, the TXNIP protein encoded by the TXNIP gene has the amino acid sequence set forth in or corresponding RefSeq (protein) NP_00130901. In embodiments, the TXNIP gene has the nucleic acid sequence set forth in RefSeq (mRNA) NM_006472. In embodiments, the amino acid sequence or nucleic acid sequence is the sequence known at the time of filing of the present application. In embodiments, the sequence corresponds to NP_001231867.1. In embodiments, the TXNIP protein corresponds to the sequence:

```
                                        (SEQ ID NO: 2)
MVMFKKIKSFEVVFNDPEKVYGSGEKVAGRVIVEVCEVTRVKAVRILACG

VAKVLWMQGSQQCKQTSEYLRYEDTLLLEDQPTGENEMVIMRPGNKYEYK

FGFELPQGPLGTSFKGKYGCVDYWVKAFLDRPSQPTQETKKNFEVVDLVD

VNTPDLMAPVSAKKEKKVSCMFIPDGRVSVSARIDRKGFCEGDEISIHAD

FENTCSRIVVPKAAIVARHTYLANGQTKVLTQKLSSVRGNHIISGTCASW

RGKSLRVQKIRPSILGCNILRVEYSLLIYVSVPGSKKVILDLPLVIGSRS

GLSSRTSSMASRTSSEMSWVDLNIPDTPEAPPCYMDVIPEDHRLESPTTP

LLDDMDGSQDSPIFMYAPEFKFMPPPTYTEVDPCILNNNVQ.
```

The terms "tumor necrosis factor" and "TNF" and "tumor necrosis factor alpha" and "TNF-α" refer to a protein (including homologs, isoforms, and functional fragments thereof) used by the immune system for cell signaling. The term includes any recombinant or naturally-occurring form of TNF-α or variants thereof that maintain TNF-α activity (e.g., within at least 30%, 40%, 50%, 60%, 70%, 80%, 90%, 95%, or 100% activity compared to wildtype TNF-α). In embodiments, the TNF-α protein encoded by the TNF gene has the amino acid sequence set forth in or corresponding to Entrez 7124, UniProt P01375, or RefSeq (protein) NP_000585. In embodiments, the TNF gene has the nucleic acid sequence set forth in RefSeq (mRNA) NM_000594. In embodiments, the amino acid sequence or nucleic acid sequence is the sequence known at the time of filing of the present application.

The terms "filamin A" and "FLNA" refer to an actin-binding protein (including homologs, isoforms, and functional fragments thereof) involved in remodeling of the cytoskeleton. The term includes any recombinant or naturally-occurring form of FLNA or variants thereof that maintain FLNA activity (e.g., within at least 30%, 40%, 50%, 60%, 70%, 80%, 90%, 95%, or 100% activity compared to wildtype FLNA). In embodiments, the FLNA protein encoded by the FLNA gene has the amino acid sequence set forth in or corresponding to Entrez 2316, UniProt P21333, RefSeq (protein) NP_001104026, or RefSeq (protein) NP_001447. In embodiments, the FLNA gene has the nucleic acid sequence set forth in RefSeq (mRNA) NM_001110556 or RefSeq (mRNA) NM_001456. In embodiments, the amino acid sequence or nucleic acid sequence is the sequence known at the time of filing of the present application.

The terms "macrophage-expressed gene 1" and "MPEG1" refer to a protein (including homologs, isoforms, and functional fragments thereof) involved in immune response. The term includes any recombinant or naturally-occurring form of MPEG1 or variants thereof that maintain MPEG1 activity (e.g., within at least 30%, 40%, 50%, 60%, 70%, 80%, 90%, 95%, or 100% activity compared to wildtype MPEG1). In embodiments, the MPEG1 protein encoded by the MPEG1 gene has the amino acid sequence set forth in or corresponding to UniProt Q2M385 or RefSeq (protein) NP_001034485.1. In embodiments, the MPEG1 gene has the nucleic acid sequence set forth in RefSeq (mRNA) NM 001039396.1. In embodiments, the amino acid sequence or nucleic acid sequence is the sequence known at the time of filing of the present application.

The terms "transketolase-like protein 1" and "TKTL1" refer to a protein (including homologs, isoforms, and functional fragments thereof) that catalyzes the transfer of a ketol group from a ketose donor to an aldose acceptor. The term includes any recombinant or naturally-occurring form of TKTL1 or variants thereof that maintain TKTL1 activity (e.g., within at least 30%, 40%, 50%, 60%, 70%, 80%, 90%, 95%, or 100% activity compared to wildtype TKTL1). In embodiments, the TKTL1 protein encoded by the TKTL1 gene has the amino acid sequence set forth in or corresponding to UniProt P51854, RefSeq (protein) NP_001139406.1, or RefSeq (protein) NP_036385.3. In embodiments, the TKTL1 gene has the nucleic acid sequence set forth in RefSeq (mRNA) NM_001145934.1 or RefSeq (mRNA) NM_012253.3. In embodiments, the amino acid sequence or nucleic acid sequence is the sequence known at the time of filing of the present application.

The terms "N-acetyltransferase domain-containing protein 1" and "NATD1" refer to a protein (including homologs, isoforms, and functional fragments thereof) encoded by the NATD1 gene. The term includes any recombinant or naturally-occurring form of NATD1 or variants thereof that maintain NATD1 activity (e.g., within at least 30%, 40%, 50%, 60%, 70%, 80%, 90%, 95%, or 100% activity compared to wildtype NATD1). In embodiments, the NATD1 protein encoded by the NATD1 gene has the amino acid sequence set forth in or corresponding to UniProt Q8N6N6 or RefSeq (protein) NP_690878.2. In embodiments, the NATD1 gene has the nucleic acid sequence set forth in RefSeq (mRNA) NM_152914.2. In embodiments, the amino acid sequence or nucleic acid sequence is the sequence known at the time of filing of the present application.

The terms "Krueppel-like factor 10" and "KLF10" refer to a protein (including homologs, isoforms, and functional fragments thereof) involved in the regulation of the circadian expression of genes. The term includes any recombinant or naturally-occurring form of KLF10 or variants thereof that maintain KLF10 activity (e.g., within at least 30%, 40%, 50%, 60%, 70%, 80%, 90%, 95%, or 100% activity compared to wildtype KLF10). In embodiments, the KLF10 protein encoded by the KLF10 gene has the amino acid sequence set forth in or corresponding to Entrez 7071, UniProt Q13118, RefSeq (protein) NP_001027453, or RefSeq (protein) NP_005646. In embodiments, the KLF10 gene has the nucleic acid sequence set forth in RefSeq (mRNA) NM_001032282 or RefSeq (mRNA) NM_005655. In embodiments, the amino acid sequence or nucleic acid sequence is the sequence known at the time of filing of the present application.

The terms "Krueppel-like factor 2" and "KLF2" refer to a zinc finger transcription factor (including homologs, isoforms, and functional fragments thereof). The term includes any recombinant or naturally-occurring form of KLF2 or variants thereof that maintain KLF2 activity (e.g., within at least 30%, 40%, 50%, 60%, 70%, 80%, 90%, 95%, or 100% activity compared to wildtype KLF2). In embodiments, the KLF2 protein encoded by the KLF2 gene has the amino acid sequence set forth in or corresponding to Entrez 10365, UniProt Q9Y5W3, or RefSeq (protein) NP_057354. In embodiments, the KLF2 gene has the nucleic acid sequence set forth in RefSeq (mRNA) NM_016270. In embodiments, the amino acid sequence or nucleic acid sequence is the sequence known at the time of filing of the present application.

The terms "CAMPATH-1 antigen" and "cluster of differentiation 52" and "CD52" refer to a glycoprotein (including homologs, isoforms, and functional fragments thereof). The term includes any recombinant or naturally-occurring form of CD52 or variants thereof that maintain CD52 activity (e.g., within at least 30%, 40%, 50%, 60%, 70%, 80%, 90%, 95%, or 100% activity compared to wildtype CD52). In embodiments, the CD52 protein encoded by the CD52 gene has the amino acid sequence set forth in or corresponding to Entrez 1043, UniProt P31358, or RefSeq (protein) NP_001794. In embodiments, the CD52 gene has the nucleic acid sequence set forth in RefSeq (mRNA) NM_001803. In embodiments, the amino acid sequence or nucleic acid sequence is the sequence known at the time of filing of the present application.

The terms "arrestin domain-containing protein 4" and "ARRDC4" refer to a protein (including homologs, isoforms, and functional fragments thereof) involved in recruiting ubiquitin-protein ligases to their specific substrates. The term includes any recombinant or naturally-occurring form of ARRDC4 or variants thereof that maintain ARRDC4 activity (e.g., within at least 30%, 40%, 50%, 60%, 70%, 80%, 90%, 95%, or 100% activity compared to wildtype ARRDC4). In embodiments, the ARRDC4 protein encoded by the ARRDC4 gene has the amino acid sequence set forth in or corresponding to UniProt Q8NCT1 or RefSeq (protein) NP_899232.2. In embodiments, the ARRDC4 gene has the nucleic acid sequence set forth in RefSeq (mRNA) NM_183376.2. In embodiments, the amino acid sequence or nucleic acid sequence is the sequence known at the time of filing of the present application.

The terms "repulsive guidance molecule A" and "RGMA" refer to a protein (including homologs, isoforms, and functional fragments thereof) involved in the nervous system. The term includes any recombinant or naturally-occurring form of RGMA or variants thereof that maintain RGMA activity (e.g., within at least 30%, 40%, 50%, 60%, 70%, 80%, 90%, 95%, or 100% activity compared to wildtype RGMA). In embodiments, the RGMA protein encoded by the RGMA gene has the amino acid sequence set forth in or corresponding to UniProt Q96B86, RefSeq (protein) NP_001159755.1, RefSeq (protein) NP_001159758.1, RefSeq (protein) NP_001159759.1, RefSeq (protein) NP_001159760.1, RefSeq (protein) NP_001159761.1, or RefSeq (protein) NP_064596.2. In embodiments, the RGMA gene has the nucleic acid sequence set forth in RefSeq (mRNA) NM_001166283.1, RefSeq (mRNA) NM_001166286.1, RefSeq (mRNA) NM_001166287.1, RefSeq (mRNA) NM_001166288.1, RefSeq (mRNA) NM_001166289.1, or RefSeq (mRNA) NM_020211.2. In embodiments, the amino acid sequence or nucleic acid sequence is the sequence known at the time of the present application.

The terms "early growth response protein 1" and "EGR1" refer to a protein (including homologs, isoforms, and functional fragments thereof) involved in transcriptional regulation. The term includes any recombinant or naturally-occurring form of EGR1 or variants thereof that maintain EGR1 activity (e.g., within at least 30%, 40%, 50%, 60%, 70%, 80%, 90%, 95%, or 100% activity compared to wildtype EGR1). In embodiments, the EGR1 protein encoded by the EGR1 gene has the amino acid sequence set forth in or corresponding to Entrez 1958, UniProt P18146, or RefSeq (protein) NP_001955. In embodiments, the EGR1 gene has the nucleic acid sequence set forth in RefSeq (mRNA) NM_001964. In embodiments, the amino acid sequence or nucleic acid sequence is the sequence known at the time of filing of the present application.

The terms "nuclear pore complex-interacting protein family member A1" and "NPIPA1" refer to a protein (including homologs, isoforms, and functional fragments thereof) encoded by the NPIPA1 gene. The term includes any recombinant or naturally-occurring form of NPIPA1 or variants thereof that maintain NPIPA1 activity (e.g., within at least 30%, 40%, 50%, 60%, 70%, 80%, 90%, 95%, or 100% activity compared to wildtype NPIPA1). In embodiments, the NPIPA1 protein encoded by the NPIPA1 gene has the amino acid sequence set forth in or corresponding to UniProt Q9UND3, RefSeq (protein) NP_001264253.1, or RefSeq (protein) NP_008916.2. In embodiments, the NPIPA1 gene has the nucleic acid sequence set forth in RefSeq (mRNA) NM_001277324.1 or RefSeq (mRNA) NM_006985.2. In embodiments, the amino acid sequence or nucleic acid sequence is the sequence known at the time of filing of the present application.

The terms "G0/G1 switch protein 2" and "G0S2" refer to a protein (including homologs, isoforms, and functional fragments thereof) involved in apoptosis. The term includes any recombinant or naturally-occurring form of G0S2 or variants thereof that maintain G0S2 activity (e.g., within at least 30%, 40%, 50%, 60%, 70%, 80%, 90%, 95%, or 100% activity compared to wildtype G0S2). In embodiments, the G0S2 protein encoded by the G0S2 gene has the amino acid sequence set forth in or corresponding to Entrez 50486, UniProt P27469, or RefSeq (protein) NP_056529. In embodiments, the G0S2 gene has the nucleic acid sequence set forth in RefSeq (mRNA) NM_015714. In embodiments, the amino acid sequence or nucleic acid sequence is the sequence known at the time of filing of the present application.

The terms "ephrin type-B receptor 1" and "EPHB1" refer to a protein (including homologs, isoforms, and functional fragments thereof) involved in regulation of developmental processes (e.g., in the nervous system). The term includes any recombinant or naturally-occurring form of EPHB1 or variants thereof that maintain EPHB1 activity (e.g., within at least 30%, 40%, 50%, 60%, 70%, 80%, 90%, 95%, or 100% activity compared to wildtype EPHB1). In embodiments, the EPHB1 protein encoded by the EPHB1 gene has the amino acid sequence set forth in or corresponding to Entrez 2047, UniProt P54762, or RefSeq (protein) NP_004432. In embodiments, the EPHB1 gene has the nucleic acid sequence set forth in RefSeq (mRNA) NM_004441. In embodiments, the amino acid sequence or nucleic acid sequence is the sequence known at the time of filing of the present application.

The terms "V-set and immunoglobulin domain containing 4" and "VSIG4" refer to an immune regulatory protein (including homologs, isoforms, and functional fragments thereof). The term includes any recombinant or naturally-occurring form of VSIG4 or variants thereof that maintain VSIG4 activity (e.g., within at least 30%, 40%, 50%, 60%, 70%, 80%, 90%, 95%, or 100% activity compared to wildtype VSIG4). In embodiments, the VSIG4 protein encoded by the VSIG4 gene has the amino acid sequence set forth in or corresponding to Entrez 11326, UniProt Q9Y279, RefSeq (protein) NP_001093901, RefSeq (protein) NP_001171759, RefSeq (protein) NP_001171760, RefSeq (protein) NP_001244332, or RefSeq (protein) NP_009199. In embodiments, the VSIG4 gene has the nucleic acid sequence set forth in RefSeq (mRNA) NM_007268, RefSeq (mRNA) NM_001100431, RefSeq (mRNA) NM_001184830, RefSeq (mRNA) NM_001184831, or RefSeq (mRNA) NM_001257403. In embodiments, the amino acid sequence or nucleic acid sequence is the sequence known at the time of filing of the present application.

The terms "complement factor properdin" and "CFP" refer to a gamma globulin protein (including homologs, isoforms, and functional fragments thereof). The term includes any recombinant or naturally-occurring form of CFP or variants thereof that maintain CFP activity (e.g., within at least 30%, 40%, 50%, 60%, 70%, 80%, 90%, 95%, or 100% activity compared to wildtype CFP). In embodiments, the CFP protein encoded by the CFP gene has the amino acid sequence set forth in or corresponding to Entrez 5199, UniProt P27918, RefSeq (protein) NP_001138724, or RefSeq (protein) NP_002612. In embodiments, the CFP gene has the nucleic acid sequence set forth in RefSeq (mRNA) NM_002624 or RefSeq (mRNA) NM_001145252. In embodiments, the amino acid sequence or nucleic acid sequence is the sequence known at the time of filing of the present application.

The terms "calcyphosin" and "CAPS" refer to a calcium-binding protein (including homologs, isoforms, and functional fragments thereof). The term includes any recombinant or naturally-occurring form of CAPS or variants thereof that maintain CAPS activity (e.g., within at least 30%, 40%, 50%, 60%, 70%, 80%, 90%, 95%, or 100% activity compared to wildtype CAPS). In embodiments, the CAPS protein encoded by the CAPS gene has the amino acid sequence set forth in or corresponding to Entrez 828, UniProt Q13938, RefSeq (protein) NP_004049, or RefSeq (protein) NP_542157. In embodiments, the CAPS gene has the nucleic acid sequence set forth in RefSeq (mRNA) NM_004058 or RefSeq (mRNA) NM_080590. In embodiments, the amino acid sequence or nucleic acid sequence is the sequence known at the time of filing of the present application.

The terms "protocadherin beta-14" and "PCDHB14" refer to a cell adhesion protein (including homologs, isoforms, and functional fragments thereof). The term includes any recombinant or naturally-occurring form of PCDHB14 or variants thereof that maintain PCDHB14 activity (e.g., within at least 30%, 40%, 50%, 60%, 70%, 80%, 90%, 95%, or 100% activity compared to wildtype PCDHB14). In embodiments, the PCDHB14 protein encoded by the PCDHB14 gene has the amino acid sequence set forth in or corresponding to Entrez 56122, UniProt Q9Y5E9, or RefSeq (protein) NP_061757. In embodiments, the PCDHB14 gene has the nucleic acid sequence set forth in RefSeq (mRNA) NM_018934. In embodiments, the amino acid sequence or nucleic acid sequence is the sequence known at the time of filing of the present application.

The terms "coiled-coil domain-containing protein 153" and "CCDC153" refer to a protein (including homologs, isoforms, and functional fragments thereof) encoded by the CCDC153 gene. The term includes any recombinant or naturally-occurring form of CCDC153 or variants thereof that maintain CCDC153 activity (e.g., within at least 30%, 40%, 50%, 60%, 70%, 80%, 90%, 95%, or 100% activity compared to wildtype CCDC153). In embodiments, the CCDC153 protein encoded by the CCDC153 gene has the amino acid sequence set forth in or corresponding to UniProt Q494R4 or RefSeq (protein) NP_001138490.1. In embodiments, the CCDC153 gene has the nucleic acid sequence set forth in RefSeq (mRNA) NM_001145018.1. In embodiments, the amino acid sequence or nucleic acid sequence is the sequence known at the time of filing of the present application.

The terms "family with sequence similarity 229 member A" and "Protein FAM229A" refer to a protein (including homologs, isoforms, and functional fragments thereof) encoded by the FAM229A gene. The term includes any recombinant or naturally-occurring form of FAM229A or variants thereof that maintain FAM229A activity (e.g., within at least 30%, 40%, 50%, 60%, 70%, 80%, 90%, 95%, or 100% activity compared to wildtype FAM229A). In embodiments, the CCDC153 protein encoded by the FAM229A gene has the amino acid sequence set forth in or corresponding to UniProt H3BQW9 or RefSeq (protein) NP_001161148.1. In embodiments, the FAM229A gene has the nucleic acid sequence set forth in RefSeq (mRNA) NM_001167676.1. In embodiments, the amino acid sequence or nucleic acid sequence is the sequence known at the time of filing of the present application.

The terms "E3 ubiquitin-protein ligase SMURF2" and "SMURF2" refer to a protein (including homologs, isoforms, and functional fragments thereof) involved in ubiquitination. The term includes any recombinant or naturally-occurring form of SMURF2 or variants thereof that maintain SMURF2 activity (e.g., within at least 30%, 40%, 50%, 60%, 70%, 80%, 90%, 95%, or 100% activity compared to wildtype SMURF2). In embodiments, the SMURF2 protein encoded by the SMURF2 gene has the amino acid sequence set forth in or corresponding to Entrez 64750, UniProt Q9HAU4, or RefSeq (protein) NP_073576. In embodiments, the SMURF2 gene has the nucleic acid sequence set forth in RefSeq (mRNA) NM_022739. In embodiments, the amino acid sequence or nucleic acid sequence is the sequence known at the time of filing of the present application.

The terms "high addinity cGMP-specific 3',5'-cyclic phosphodiesterase 9A" and "PDE9A" refer to a protein (including homologs, isoforms, and functional fragments thereof) that catalyzes the hydrolysis of cAMP and cGMP to their corresponding monophosphates. The term includes any recombinant or naturally-occurring form of PDE9A or variants thereof that maintain PDE9A activity (e.g., within at least 30%, 40%, 50%, 60%, 70%, 80%, 90%, 95%, or 100% activity compared to wildtype PDE9A). In embodiments, the PDE9A protein encoded by the PDE9A gene has the amino acid sequence set forth in or corresponding to Entrez 5152, UniProt O76083, RefSeq (protein) NP_001001567.1, RefSeq (protein) NP_001001568.1, RefSeq (protein) NP_001001569.1, RefSeq (protein) NP_001001570.1, RefSeq (protein) NP_001001571.1, RefSeq (protein) NP_001001572.1, RefSeq (protein) NP_001001573.1, RefSeq (protein) NP_001001574.1, RefSeq (protein) NP_001001575.1, RefSeq (protein) NP_001001576.1, RefSeq (protein) NP_001001577.1, RefSeq (protein) NP_001001578.1, RefSeq (protein) NP_001001579.1, RefSeq (protein) NP_001001580.1, RefSeq (protein) NP_001001581.1, RefSeq (protein) NP_001001582.1, RefSeq (protein) NP_001001583.1, RefSeq (protein) NP_001001584.1, RefSeq (protein) NP_001001585.1, RefSeq (protein) NP_001302462.1, or RefSeq (protein) NP_002597.1. In embodiments, the PDE9A gene has the nucleic acid sequence set forth in RefSeq (mRNA) NM_001001567.1, RefSeq (mRNA) NM_001001568.1, RefSeq (mRNA) NM_001001569.1, RefSeq (mRNA) NM_001001570.1, RefSeq (mRNA) NM_001001571.1, RefSeq (mRNA) NM_001001572.1, RefSeq (mRNA) NM_001001573.1, RefSeq (mRNA) NM_001001574.1, RefSeq (mRNA) NM_001001575.1, RefSeq (mRNA) NM_001001576.1, RefSeq (mRNA) NM_001001577.1, RefSeq (mRNA) NM_001001578.1, RefSeq (mRNA) NM_001001579.1, RefSeq (mRNA) NM_001001580.1, RefSeq (mRNA) NM_001001581.1, RefSeq (mRNA) NM_001001582.1, RefSeq (mRNA) NM_001001583.1, RefSeq (mRNA) NM_001001584.2, RefSeq (mRNA) NM_001001585.1, RefSeq (mRNA) NM_001315533.1, or RefSeq (mRNA) NM_002606.2. In embodiments, the amino acid sequence or nucleic acid sequence is the sequence known at the time of filing of the present application.

The terms "choline transporter-like protein 2" and "SLC44A2" refer to a protein (including homologs, isoforms, and functional fragments thereof) involved in choline transporter activity. The term includes any recombinant or naturally-occurring form of SLC44A2 or variants thereof that maintain SLC44A2 activity (e.g., within at least 30%, 40%, 50%, 60%, 70%, 80%, 90%, 95%, or 100% activity compared to wildtype SLC44A2). In embodiments, the SLC44A2 protein encoded by the SLC44A2 gene has the amino acid sequence set forth in or corresponding to Entrez 57153, UniProt Q8IWA5, RefSeq (protein) NP_001138528.1, or RefSeq (protein) NP_065161.3. In embodiments, the SLC44A2 gene has the nucleic acid sequence set forth in RefSeq (mRNA) NM_001145056.1 or RefSeq (mRNA) NM)_020428.3. In embodiments, the amino acid sequence or nucleic acid sequence is the sequence known at the time of filing of the present application.

The terms "Rho guanine nucleotide exchange factor 25" and "ARHGEF25" refer to a guanine nucleotide exchange factor protein (including homologs, isoforms, and functional fragments thereof). The term includes any recombinant or naturally-occurring form of ARHGEF25 or variants thereof that maintain ARHGEF25 activity (e.g., within at least 30%, 40%, 50%, 60%, 70%, 80%, 90%, 95%, or 100% activity compared to wildtype ARHGEF25). In embodiments, the ARHGEF25 protein encoded by the ARHGEF25 gene has the amino acid sequence set forth in or corresponding to Entrez 115557, UniProt Q86VW2, RefSeq (protein) NP_001104740.1, or RefSeq (protein) NP_001334862.1. In embodiments, the ARHGEF25 gene has the nucleic acid sequence set forth in RefSeq (mRNA) NM_001111270.2 or RefSeq (mRNA) NM)_001347933.1. In embodiments, the amino acid sequence or nucleic acid sequence is the sequence known at the time of filing of the present application.

The terms "amyloid beta A4 precursor protein-binding family B member 1" and "APBB1" refer to an adaptor protein (including homologs, isoforms, and functional fragments thereof) localized in the nucleus. The term includes any recombinant or naturally-occurring form of APBB1 or variants thereof that maintain APBB1 activity (e.g., within at least 30%, 40%, 50%, 60%, 70%, 80%, 90%, 95%, or 100% activity compared to wildtype APBB1). In embodiments, the APBB1 protein encoded by the APBB1 gene has the amino acid sequence set forth in or corresponding to Entrez 322, UniProt O00213, RefSeq (protein) NP_001155.1, RefSeq (protein) NP_001244248.1, RefSeq (protein) NP_001244249.1, RefSeq (protein) NP_00124450.1, RefSeq (protein) NP_00124452.1, RefSeq (protein) NP_00124454.1, RefSeq (protein) NP_001244255.1, or RefSeq (protein) NP_663722.1. In embodiments, the APBB1 gene has the nucleic acid sequence set forth in RefSeq (mRNA) NM_001164.4, RefSeq (mRNA) NM_001257319.2, RefSeq (mRNA) NM_001257320.2, RefSeq (mRNA) NM_001257321.2, RefSeq (mRNA) NM_001257323.2, RefSeq (mRNA) NM_001257325.2, RefSeq (mRNA) NM_001257326.2, or RefSeq (mRNA) NM)_145689.2. In embodiments, the amino acid sequence or nucleic acid sequence is the sequence known at the time of filing of the present application.

The terms "general transcription factor II-I repeat domain-containing protein 1" and "GTF2IRD1" refer to a transcription regulator protein (including homologs, isoforms, and functional fragments thereof) involved in cell-cycle progression. The term includes any recombinant or naturally-occurring form of GTF2IRD1 or variants thereof that maintain GTF2IRD1 activity (e.g., within at least 30%, 40%, 50%, 60%, 70%, 80%, 90%, 95%, or 100% activity compared to wildtype GTF2IRD1). In embodiments, the GTF2IRD1 protein encoded by the GTF2IRD1 gene has the amino acid sequence set forth in or corresponding to Entrez 9569, UniProt Q9UHL9, RefSeq (protein) NP_001186136.1, RefSeq (protein) NP_005676.3, or RefSeq (protein) NP_057412.1. In embodiments, the GTF2IRD1 gene has the nucleic acid sequence set forth in RefSeq (mRNA) NM_001199207.1, RefSeq (mRNA) NM_005685.3, or RefSeq (mRNA) NM)_016328.2. In embodiments, the amino acid sequence or nucleic acid sequence is the sequence known at the time of filing of the present application.

The terms "protein phosphatase 1K, mitochondrial" and "PPM1K" refer to a protein (including homologs, isoforms, and functional fragments thereof) that regulates the mitochondrial permeability transition pore. The term includes any recombinant or naturally-occurring form of PPM1K variants thereof that maintain PPM1K activity (e.g., within at least 30%, 40%, 50%, 60%, 70%, 80%, 90%, 95%, or 100% activity compared to wildtype PPM1K). In embodiments, the PPM1K protein encoded by the PPM1K gene has the amino acid sequence set forth in or corresponding to UniProt Q8N3J5 or RefSeq (protein) NP_689755.3. In embodiments, the PPM1K gene has the nucleic acid sequence set forth in RefSeq (mRNA) NM_006714111.3. In embodiments, the amino acid sequence or nucleic acid sequence is the sequence known at the time of filing of the present application.

The terms "monocarboxylate transporter 8" and "SLC16A2" refer to a thyroid hormone transporter protein (including homologs, isoforms, and functional fragments thereof). The term includes any recombinant or naturally-occurring form of SLC16A2 variants thereof that maintain SLC16A2 activity (e.g., within at least 30%, 40%, 50%, 60%, 70%, 80%, 90%, 95%, or 100% activity compared to wildtype SLC16A2). In embodiments, the SLC16A2 protein encoded by the SLC16A2 gene has the amino acid sequence set forth in or corresponding to UniProt P36021 or RefSeq (protein) NP_006508.2. In embodiments, the SLC16A2 gene has the nucleic acid sequence set forth in RefSeq (mRNA) NM_006517.4. In embodiments, the amino acid sequence or nucleic acid sequence is the sequence known at the time of filing of the present application.

The terms "polycomb group RING finger protein 2" and "PCGF2" refer to a protein (including homologs, isoforms, and functional fragments thereof) involved in transcription repression of genes involved in embyogenesis, cell cycles, and tumorigenesis. The term includes any recombinant or naturally-occurring form of PCGF2 variants thereof that maintain PCGF2 activity (e.g., within at least 30%, 40%, 50%, 60%, 70%, 80%, 90%, 95%, or 100% activity compared to wildtype PCGF2). In embodiments, the PCGF2 protein encoded by the PCGF2 gene has the amino acid sequence set forth in or corresponding to Entrez 7703, UniProt P35227, RefSeq (protein) NP_009075, RefSeq (protein) NP_001356543, or RefSeq (protein) NP_001356544. In embodiments, the PCGF2 gene has the nucleic acid sequence set forth in RefSeq (mRNA) NM_001163307, RefSeq (mRNA) NM_001163308, or RefSeq (mRNA) NM_009545. In embodiments, the amino acid sequence or nucleic acid sequence is the sequence known at the time of filing of the present application.

The terms "hexokinase 2" and "HK2" refer to a protein (including homologs, isoforms, and functional fragments thereof) that phosphorylates flucose to produce glucose-6-phosphate. The term includes any recombinant or naturally-occurring form of HK2 variants thereof that maintain HK2 activity (e.g., within at least 30%, 40%, 50%, 60%, 70%, 80%, 90%, 95%, or 100% activity compared to wildtype HK2). In embodiments, the HK2 protein encoded by the HK2 gene has the amino acid sequence set forth in or corresponding to Entrez 3099, UniProt P52789, RefSeq (protein) NP_000180, or RefSeq (protein) NP_001358454. In embodiments, the HK2 gene has the nucleic acid sequence set forth in RefSeq (mRNA) NM_000189 or RefSeq (mRNA) NM_001371525. In embodiments, the amino acid sequence or nucleic acid sequence is the sequence known at the time of filing of the present application.

The terms "tetraspanin-2" and "TSPAN2" refer to a cell surface protein (including homologs, isoforms, and functional fragments thereof). The term includes any recombinant or naturally-occurring form of TSPAN2 variants thereof that maintain TSPAN2 activity (e.g., within at least 30%, 40%, 50%, 60%, 70%, 80%, 90%, 95%, or 100% activity compared to wildtype TSPAN2). In embodiments, the TSPAN2 protein encoded by the TSPAN2 gene has the amino acid sequence set forth in or corresponding to Entrez 10100, UniProt 060636, RefSeq (protein) NP_001295244, RefSeq (protein) NP_001295245, or RefSeq (protein) NP_005716. In embodiments, the TSPAN2 gene has the nucleic acid sequence set forth in RefSeq (mRNA) NM_001308315, RefSeq (mRNA) NM_001308316, or RefSeq (mRNA) NM_005725. In embodiments, the amino acid sequence or nucleic acid sequence is the sequence known at the time of filing of the present application.

The terms "sphingosine-1-phosphate receptor 5" and "S1PR5" refer to a G protein-coupled receptor (including homologs, isoforms, and functional fragments thereof). The term includes any recombinant or naturally-occurring form of S1PR5 variants thereof that maintain S1PR5 activity (e.g., within at least 30%, 40%, 50%, 60%, 70%, 80%, 90%, 95%, or 100% activity compared to wildtype S1PR5). In embodiments, the S1PR5 protein encoded by the S1PR5 gene has the amino acid sequence set forth in or corresponding to Entrez 53637, UniProt Q9H228, RefSeq (protein) NP_001159687, or RefSeq (protein) NP_110387. In embodiments, the S1PR5 gene has the nucleic acid sequence set forth in RefSeq (mRNA) NM_030760 or RefSeq (mRNA) NM_001166215. In embodiments, the amino acid sequence or nucleic acid sequence is the sequence known at the time of filing of the present application.

The terms "EF-hand calcium-binding domain-containing protein 7" and "EFCAB7" refer to a protein (including homologs, isoforms, and functional fragments thereof) involved in regulation of ciliary Hedgehog signaling. The term includes any recombinant or naturally-occurring form of EFCAB7 variants thereof that maintain EFCAB7 activity (e.g., within at least 30%, 40%, 50%, 60%, 70%, 80%, 90%, 95%, or 100% activity compared to wildtype EFCAB7). In embodiments, the EFCAB7 protein encoded by the EFCAB7 gene has the amino acid sequence set forth in or corresponding to UniProt A8K855 or RefSeq (protein) NP_115813.2. In embodiments, the EFCAB7 gene has the nucleic acid sequence set forth in RefSeq (mRNA) NM_032437.3. In embodiments, the amino acid sequence or nucleic acid sequence is the sequence known at the time of filing of the present application.

The terms "ADP-ribose glycohydrolase MACROD1" and "MACROD1" refer to a protein (including homologs, isoforms, and functional fragments thereof) that removes ADP-ribose from aspartate and glutamate residues in proteins bearing a single ADP-ribose moiety. The term includes any recombinant or naturally-occurring form of MACROD1 variants thereof that maintain MACROD1 activity (e.g., within at least 30%, 40%, 50%, 60%, 70%, 80%, 90%, 95%, or 100% activity compared to wildtype MACROD1). In embodiments, the MACROD1 protein encoded by the MACROD1 gene has the amino acid sequence set forth in or corresponding to UniProt Q9BQ69 or RefSeq (protein) NP_054756.2. In embodiments, the MACROD1 gene has the nucleic acid sequence set forth in RefSeq (mRNA) NM_014067.3. In embodiments, the amino acid sequence or nucleic acid sequence is the sequence known at the time of filing of the present application.

The terms "guanylate binding protein 5" and "GBP5" refer to a protein (including homologs, isoforms, and functional fragments thereof) involved in innate immunity and inflammation. The term includes any recombinant or naturally-occurring form of GBP5 variants thereof that maintain GBP5 activity (e.g., within at least 30%, 40%, 50%, 60%, 70%, 80%, 90%, 95%, or 100% activity compared to wildtype GBP5). In embodiments, the GBP5 protein encoded by the GBP5 gene has the amino acid sequence set forth in or corresponding to Entrez 115362, UniProt Q96PP8, RefSeq (protein) NP_001127958.1, or RefSeq (protein) NP_443174.1. In embodiments, the GBP5 gene has the nucleic acid sequence set forth in RefSeq (mRNA) NM_001134486.2 or RefSeq (mRNA) NM_052942.3. In embodiments, the amino acid sequence or nucleic acid sequence is the sequence known at the time of filing of the present application.

The terms "DENN domain-containing protein 11" and "LCHN" refer to a probable guanine nucleotide exchange factor protein (including homologs, isoforms, and functional fragments thereof). The term includes any recombinant or naturally-occurring form of LCHN variants thereof that maintain LCHN activity (e.g., within at least 30%, 40%, 50%, 60%, 70%, 80%, 90%, 95%, or 100% activity compared to wildtype LCHN). In embodiments, the LCHN protein encoded by the KIAA1147 gene has the amino acid sequence set forth in or corresponding to Entrez 57189, UniProt A4D1U4, or RefSeq (protein) NP_001073861.1. In embodiments, the KIAA1147 gene has the nucleic acid sequence set forth in RefSeq (mRNA) NM_001080392.1. In embodiments, the amino acid sequence or nucleic acid sequence is the sequence known at the time of filing of the present application.

The terms "Putative adhesion G protein-coupled receptor E4P" and "ADGRE4P" refer to a protein (including homologs, isoforms, and functional fragments thereof) involved in mediation of the cellular interaction between myeloid cells and B-cells. The term includes any recombinant or naturally-occurring form of ADGRE4P variants thereof that maintain ADGRE4P activity (e.g., within at least 30%, 40%, 50%, 60%, 70%, 80%, 90%, 95%, or 100% activity compared to wildtype ADGRE4P). In embodiments, the ADGRE4P protein encoded by the ADGRE4P gene has the amino acid sequence set forth in or corresponding to UniProt Q86SQ3. In embodiments, the ADGRE4P gene has the nucleic acid sequence set forth in RefSeq (RNA) NR_024075.1. In embodiments, the amino acid sequence or nucleic acid sequence is the sequence known at the time of filing of the present application.

The term "cytochrome b-cl complex subunit 6-like, mitochondrial" refers to a protein (including homologs, isoforms, and functional fragments thereof) encoded by the UQCRHL gene. The term includes any recombinant or naturally-occurring form of cytochrome b-cl complex subunit 6-like, mitochondrial variants thereof that maintain cytochrome b-cl complex subunit 6-like, mitochondrial activity (e.g., within at least 30%, 40%, 50%, 60%, 70%, 80%, 90%, 95%, or 100% activity compared to wildtype cytochrome b-cl complex subunit 6-like, mitochondrial). In embodiments, the cytochrome b-cl complex subunit 6-like, mitochondrial protein encoded by the UQCRHL gene has the amino acid sequence set forth in or corresponding to UniProt A0A096LP55 or RefSeq (protein) NP_001083060.1. In embodiments, the UQCRHL gene has the nucleic acid sequence set forth in RefSeq (mRNA) NM_001089591.1. In embodiments, the amino acid sequence or nucleic acid sequence is the sequence known at the time of filing of the present application.

The terms "DICER1 Antisense RNA 1" and "DICER1-AS1" refer to a protein (including homologs, isoforms, and functional fragments thereof) encoded by the DICER1-AS1 gene. The term includes any recombinant or naturally-occurring form of DICER1-AS1 variants thereof that maintain DICER1-AS1 activity (e.g., within at least 30%, 40%, 50%, 60%, 70%, 80%, 90%, 95%, or 100% activity compared to wildtype DICER1-AS1). In embodiments, the DICER1-AS1 protein encoded by the DICER1-AS1 gene has the amino acid sequence set forth in or corresponding to Entrez 400242. In embodiments, the DICER1-AS1 gene has the nucleic acid sequence set forth in RefSeq (mRNA) NM_207443.1. In embodiments, the amino acid sequence or nucleic acid sequence is the sequence known at the time of filing of the present application.

The terms "Protein disulfide isomerase family A member 3 Pseudogene 1" and "PDIA3P1" refer to a protein (including homologs, isoforms, and functional fragments thereof) encoded by the PDIA3P1 gene. The term includes any recombinant or naturally-occurring form of PDIA3P1 variants thereof that maintain PDIA3P1 activity (e.g., within at least 30%, 40%, 50%, 60%, 70%, 80%, 90%, 95%, or 100% activity compared to wildtype PDIA3P1). In embodiments, the PDIA3P1 protein encoded by the PDIA3P1 gene has the amino acid sequence set forth in or corresponding to Entrez 171423. In embodiments, the PDIA3P1 gene has the nucleic acid sequence set forth in RefSeq (DNA) NC_000001.11. In embodiments, the amino acid sequence or nucleic acid sequence is the sequence known at the time of filing of the present application.

The terms "lysosomal acid phosphatase" and "ACP2" refer to a protein (including homologs, isoforms, and functional fragments thereof) encoded by the ACP2 gene. The term includes any recombinant or naturally-occurring form of ACP2 variants thereof that maintain ACP2 activity (e.g., within at least 30%, 40%, 50%, 60%, 70%, 80%, 90%, 95%, or 100% activity compared to wildtype ACP2). In embodiments, the ACP2 protein encoded by the ACP2 gene has the amino acid sequence set forth in or corresponding to Entrez 53, UniProt P11117, RefSeq (protein) NP_001289418, RefSeq (protein) NP_001289419, RefSeq (protein) NP_001289420, RefSeq (protein) NP_001289421, RefSeq (protein) NP_001601, or RefSeq (protein) NP_001343945. In embodiments, the ACP2 gene has the nucleic acid sequence set forth in RefSeq (mRNA) NM_001131064, RefSeq (mRNA) NM_001302489, RefSeq (mRNA) NM_001302490, RefSeq (mRNA) NM_001302491, RefSeq (mRNA) NM_001302492, RefSeq (mRNA) NM_001610, or RefSeq (mRNA) NM_001357016. In embodiments, the amino acid sequence or nucleic acid sequence is the sequence known at the time of filing of the present application.

The terms "Cbp/p300-interacting transactivator 4" and "CITED4" refer to a protein (including homologs, isoforms, and functional fragments thereof) encoded by the CITED4 gene. The term includes any recombinant or naturally-occurring form of CITED4 variants thereof that maintain CITED4 activity (e.g., within at least 30%, 40%, 50%, 60%, 70%, 80%, 90%, 95%, or 100% activity compared to wildtype CITED4). In embodiments, the CITED4 protein encoded by the CITED4 gene has the amino acid sequence set forth in or corresponding to UniProt Q96RK1 or RefSeq (protein) NP_597724.1. In embodiments, the CITED4 gene has the nucleic acid sequence set forth in RefSeq (mRNA) NM_133467.2. In embodiments, the amino acid sequence or nucleic acid sequence is the sequence known at the time of filing of the present application.

The terms "brain-type creatine kinase" and "CKB" refer to a creatine protein (including homologs, isoforms, and functional fragments thereof) encoded by the CKB gene. The term includes any recombinant or naturally-occurring form of CKB variants thereof that maintain CKB activity (e.g., within at least 30%, 40%, 50%, 60%, 70%, 80%, 90%, 95%, or 100% activity compared to wildtype CKB). In embodiments, the CKB protein encoded by the CKB gene has the amino acid sequence set forth in or corresponding to Entrez 1152, UniProt P12277, RefSeq (protein) NP_002925, or RefSeq (protein) NP_001349460. In embodiments, the CKB gene has the nucleic acid sequence set forth in RefSeq (mRNA) NM_001823 or RefSeq (mRNA) NM_001362531. In embodiments, the amino acid sequence or nucleic acid sequence is the sequence known at the time of filing of the present application.

The terms "2'-deoxynucleoside 5'-phosphate N-hydrolase 1" and "DNPH1" refer to a protein (including homologs, isoforms, and functional fragments thereof) encoded by the DNPH1 gene. The term includes any recombinant or naturally-occurring form of DNPH1 variants thereof that maintain DNPH1 activity (e.g., within at least 30%, 40%, 50%, 60%, 70%, 80%, 90%, 95%, or 100% activity compared to wildtype DNPH1). In embodiments, the DNPH1 protein encoded by the DNPH1 gene has the amino acid sequence set forth in or corresponding to UniProt O43598, RefSeq (protein) NP_006434.1, or RefSeq (protein) NP_954653.1. In embodiments, the DNPH1 gene has the nucleic acid sequence set forth in RefSeq (mRNA) NM_006443.2 or RefSeq (mRNA) NM_199184.1. In embodiments, the amino acid sequence or nucleic acid sequence is the sequence known at the time of filing of the present application.

The terms "family with sequence similarity 20, member C" and "FAM20C" refer to a protein (including homologs, isoforms, and functional fragments thereof) encoded by the FAM20C gene. The term includes any recombinant or naturally-occurring form of FAM20C variants thereof that maintain FAM20C activity (e.g., within at least 30%, 40%, 50%, 60%, 70%, 80%, 90%, 95%, or 100% activity compared to wildtype FAM20C). In embodiments, the FAM20C protein encoded by the FAM20C gene has the amino acid sequence set forth in or corresponding to Entrez 56975, UniProt Q8IXL6, or RefSeq (protein) NP_064608. In embodiments, the FAM20C gene has the nucleic acid sequence set forth in RefSeq (mRNA) NM_020223. In embodiments, the amino acid sequence or nucleic acid sequence is the sequence known at the time of filing of the present application.

The terms "H2A histone family member X" and "H2AFX" refer to a protein (including homologs, isoforms, and functional fragments thereof) encoded by the H2AFX gene. The term includes any recombinant or naturally-occurring form of H2AFX variants thereof that maintain H2AFX activity (e.g., within at least 30%, 40%, 50%, 60%, 70%, 80%, 90%, 95%, or 100% activity compared to wildtype H2AFX). In embodiments, the H2AFX protein encoded by the H2AFX gene has the amino acid sequence set forth in or corresponding to Entrez 3014, UniProt P16104, or RefSeq (protein) NP_002096. In embodiments, the H2AFX gene has the nucleic acid sequence set forth in RefSeq (mRNA) NM_002105. In embodiments, the amino acid sequence or nucleic acid sequence is the sequence known at the time of filing of the present application.

The term "HOXA11-AS" refers to an antisense strand in the homeobox A protein (including homologs, isoforms, and functional fragments thereof) encoded by the HOXA gene. The term includes any recombinant or naturally-occurring form of HOXA11-AS variants thereof that maintain HOXA11-AS activity (e.g., within at least 30%, 40%, 50%, 60%, 70%, 80%, 90%, 95%, or 100% activity compared to wildtype HOXA11-AS). In embodiments, the HOXA11-AS protein encoded by the HOXA gene has the amino acid sequence set forth in or corresponding to UniProt P31270, UniProt HOYIA6, or RefSeq (protein) NP_005514.1. In embodiments, the HOXA gene has the nucleic acid sequence set forth in RefSeq (mRNA) NM_005523.5. In embodiments, the amino acid sequence or nucleic acid sequence is the sequence known at the time of filing of the present application.

The terms "inositol monophosphatase 2" and "IMPA2" refer to a protein (including homologs, isoforms, and functional fragments thereof) encoded by the IMPA2 gene. The term includes any recombinant or naturally-occurring form of IMPA2 variants thereof that maintain IPA2 activity (e.g., within at least 30%, 40%, 50%, 60%, 70%, 80%, 90%, 95%, or 100% activity compared to wildtype IMPA2). In embodiments, the IMPA2 protein encoded by the IMPA2 gene has the amino acid sequence set forth in or corresponding to Entrez 3613, UniProt 014732, or RefSeq (protein) NP_055029. In embodiments, the IMPA2 gene has the nucleic acid sequence set forth in RefSeq (mRNA) NM_014214. In embodiments, the amino acid sequence or nucleic acid sequence is the sequence known at the time of filing of the present application.

The terms "LIM domain-containing protein 2" and "LIMD2" refer to a protein (including homologs, isoforms, and functional fragments thereof) encoded by the LIMD2 gene. The term includes any recombinant or naturally-occurring form of LIMD2 variants thereof that maintain LIMD2 activity (e.g., within at least 30%, 40%, 50%, 60%, 70%, 80%, 90%, 95%, or 100% activity compared to wildtype LIMD2). In embodiments, the LIMD2 protein encoded by the LIMD2 gene has the amino acid sequence set forth in or corresponding to UniProt Q9BT23 or RefSeq (protein) NP_085053.1. In embodiments, the LIMD2 gene has the nucleic acid sequence set forth in RefSeq (mRNA) NM_030576.3. In embodiments, the amino acid sequence or nucleic acid sequence is the sequence known at the time of filing of the present application.

The terms "lymphocyte antigen 6E" and "LY6E" refer to a protein (including homologs, isoforms, and functional fragments thereof) encoded by the LY6E gene. The term includes any recombinant or naturally-occurring form of LY6E variants thereof that maintain LY6E activity (e.g., within at least 30%, 40%, 50%, 60%, 70%, 80%, 90%, 95%, or 100% activity compared to wildtype LY6E). In embodiments, the LY6E protein encoded by the LY6E gene has the amino acid sequence set forth in or corresponding to Entrez 4061, UniProt Q16553, RefSeq (protein) NP_001120685, or RefSeq (protein) NP_002337. In embodiments, the LY6E gene has the nucleic acid sequence set forth in RefSeq (mRNA) NM_002346 or RefSeq (mRNA) NM_001127213. In embodiments, the amino acid sequence or nucleic acid sequence is the sequence known at the time of filing of the present application.

The terms "membrane-bound O-acyltransferase domain-containing protein 7" and "MBOAT7" refer to a protein (including homologs, isoforms, and functional fragments thereof) encoded by the MBOAT7 gene. The term includes any recombinant or naturally-occurring form of MBOAT7 variants thereof that maintain MBOAT7 activity (e.g., within at least 30%, 40%, 50%, 60%, 70%, 80%, 90%, 95%, or 100% activity compared to wildtype MBOAT7). In embodiments, the MBOAT7 protein encoded by the MBOAT7 gene has the amino acid sequence set forth in or corresponding to Entrez 79143, UniProt Q96N66, RefSeq (protein) NP_001139529, RefSeq (protein) NP_001139554, RefSeq (protein) NP_001139555, or RefSeq (protein) NP_077274.

In embodiments, the MBOAT7 gene has the nucleic acid sequence set forth in RefSeq (mRNA) NM_001146056, RefSeq (mRNA) NM_001146082, RefSeq (mRNA) NM_001146083, or RefSeq (mRNA) NM_024298. In embodiments, the amino acid sequence or nucleic acid sequence is the sequence known at the time of filing of the present application.

The terms "multiple epidermal growth factor-like domains protein 8" and "MEGF8" refer to a protein (including homologs, isoforms, and functional fragments thereof) encoded by the MEGF8 gene. The term includes any recombinant or naturally-occurring form of MEGF8 variants thereof that maintain MEGF8 activity (e.g., within at least 30%, 40%, 50%, 60%, 70%, 80%, 90%, 95%, or 100% activity compared to wildtype MEGF8). In embodiments, the MEGF8 protein encoded by the MEGF8 gene has the amino acid sequence set forth in or corresponding to UniProt Q7Z7M0, RefSeq (protein) NP_001258867.1, or RefSeq (protein) NP_001401.2. In embodiments, the MEGF8 gene has the nucleic acid sequence set forth in RefSeq (mRNA) NM_001271938.1 or RefSeq (mRNA) NM_001410.2. In embodiments, the amino acid sequence or nucleic acid sequence is the sequence known at the time of filing of the present application.

The terms "progestin and adipoQ receptor family member 4" and "PAQR4" refer to a protein (including homologs, isoforms, and functional fragments thereof) encoded by the PAQR4 gene. The term includes any recombinant or naturally-occurring form of PAQR4 variants thereof that maintain PAQR4 activity (e.g., within at least 30%, 40%, 50%, 60%, 70%, 80%, 90%, 95%, or 100% activity compared to wildtype PAQR4). In embodiments, the PAQR4 protein encoded by the PAQR4 gene has the amino acid sequence set forth in or corresponding to UniProt Q8N4S7, RefSeq (protein) NP_001271440.1, RefSeq (protein) NP_001271441.1, or RefSeq (protein) NP_689554.2. In embodiments, the PAQR4 gene has the nucleic acid sequence set forth in RefSeq (mRNA) NM_001284511.1, RefSeq (mRNA) NM_001284512.1, or RefSeq (mRNA) NM_152341.4. In embodiments, the amino acid sequence or nucleic acid sequence is the sequence known at the time of filing of the present application.

The terms "membrane-associated tyrosine- and threonine-specific cdc2-inhibitory kinase" and "PKMYT1" refer to a protein (including homologs, isoforms, and functional fragments thereof) encoded by the PKMYT1 gene. The term includes any recombinant or naturally-occurring form of PKMYT1 variants thereof that maintain PKMYT1 activity (e.g., within at least 30%, 40%, 50%, 60%, 70%, 80%, 90%, 95%, or 100% activity compared to wildtype PKMYT1). In embodiments, the PKMYT1 protein encoded by the PKMYT1 gene has the amino acid sequence set forth in or corresponding to Entrez 9088, UniProt Q99640, UniProt Q0IJ49, RefSeq (protein) NP_001245379, RefSeq (protein) NP_001245380, RefSeq (protein) NP_004194, RefSeq (protein) NP_872629, or RefSeq (protein) NP_004194.3. In embodiments, the PKMYT1 gene has the nucleic acid sequence set forth in RefSeq (mRNA) NM_001258450, RefSeq (mRNA) NM_001258451, RefSeq (mRNA) NM_004203, or RefSeq (mRNA) NM_182687. In embodiments, the amino acid sequence or nucleic acid sequence is the sequence known at the time of filing of the present application.

The terms "solute carrier family 2, facilitated glucose transporter member 5" and "SLC2A5" refer to a protein (including homologs, isoforms, and functional fragments thereof) encoded by the SLC2A5 gene. The term includes any recombinant or naturally-occurring form of SLC2A5 variants thereof that maintain SLC2A5 activity (e.g., within at least 30%, 40%, 50%, 60%, 70%, 80%, 90%, 95%, or 100% activity compared to wildtype SLC2A5). In embodiments, the SLC2A5 protein encoded by the SLC2A5 gene has the amino acid sequence set forth in or corresponding to UniProt P22732, RefSeq (protein) NP_001129057.1, RefSeq (protein) NP_001315548.1, or RefSeq (protein) NP_003030.1. In embodiments, the SLC2A5 gene has the nucleic acid sequence set forth in RefSeq (mRNA) NM_001135585.1, RefSeq (mRNA) NM_001328619.1, or RefSeq (mRNA) NM_003039.2. In embodiments, the amino acid sequence or nucleic acid sequence is the sequence known at the time of filing of the present application.

The terms "thymidine kinase 1" and "TK1" refer to a protein (including homologs, isoforms, and functional fragments thereof) encoded by the TK1 gene. The term includes any recombinant or naturally-occurring form of TK1 variants thereof that maintain TK1 activity (e.g., within at least 30%, 40%, 50%, 60%, 70%, 80%, 90%, 95%, or 100% activity compared to wildtype TK1). In embodiments, the TK1 protein encoded by the TK1 gene has the amino acid sequence set forth in or corresponding to Entrez 7083, UniProt P04183, RefSeq (protein) NP_001333592, RefSeq (protein) NP_003249, or RefSeq (protein) NP_001350777. In embodiments, the TK1 gene has the nucleic acid sequence set forth in RefSeq (mRNA) NM_003258, RefSeq (mRNA) NM_001346663, or RefSeq (mRNA) NM_001363848. In embodiments, the amino acid sequence or nucleic acid sequence is the sequence known at the time of filing of the present application.

The terms "tubulin alpha-4A chain" and "TUBA4A" refer to a protein (including homologs, isoforms, and functional fragments thereof) encoded by the TUBA4A gene. The term includes any recombinant or naturally-occurring form of TUBA4A variants thereof that maintain TUBA4A activity (e.g., within at least 30%, 40%, 50%, 60%, 70%, 80%, 90%, 95%, or 100% activity compared to wildtype TUBA4A). In embodiments, the TUBA4A protein encoded by the TUBA4A gene has the amino acid sequence set forth in or corresponding to Entrez 7277, UniProt P68366, RefSeq (protein) NP_001265481, or RefSeq (protein) NP_005991. In embodiments, the TUBA4A gene has the nucleic acid sequence set forth in RefSeq (mRNA) NM_001278552, or RefSeq (mRNA) NM_006000. In embodiments, the amino acid sequence or nucleic acid sequence is the sequence known at the time of filing of the present application.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g., a protein associated disease, diabetes associated complication (e.g., nephropathy, retinopathy, neuropathy, cardiovascular disease, and inflammation), metabolic disorder associated disease (e.g., diabetes, inflammatory disease, or infectious disease)) means that the disease is caused by (in whole or in part), or a symptom of the disease is caused by (in whole or in part) the substance or substance activity or function. In embodiments, the TXNIP-associated disease is diabetes, diabetic retinopathy, diabetic nephropathy, diabetic neuropathy, or cardiovascular disease. In embodiments, the TXNIP-TRX-associated disease is diabetic retinopathy, diabetic nephropathy, diabetic neuropathy, or cardiovascular disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propogated to other signaling pathway components. For example, binding of a thioredoxin protein with a compound as described herein may reduce the interactions between the thioredoxin protein and downstream effectors or signaling pathway components, resulting in changes in cell growth, proliferation, or survival.

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "disease" or "condition" refer to a state of being or health status of a patient or subject capable of being treated with the compounds or methods provided herein. The disease may be diabetes. The disease may be a metabolic disorder. The disease may be an inflammatory disease. The disease may be an infectious disease. In embodiments, the disease is diabetes (e.g., type 1 diabetes or type 2 diabetes), insulin resistance, metabolic syndrome, atherosclerosis, obesity, hyperlipidemia, hyperglycemia, high serum triglycerides, and/or high blood pressure.

Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, diabetes mellitus type 2, vascular complications of diabetes, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "inflammatory disease" refers to a disease or condition characterized by aberrant inflammation (e.g., an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, diabetes mellitus type 2, vascular complications of diabetes, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. In embodiments, the inflammatory disease is inflammation.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. In embodiments, treating refers to treating a subject having a disease.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., symptoms of diabetes, for example including increased thirst and urination, fatigue, or blurred vision), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of a disease (e.g., metabolic disorder) or disease symptoms (e.g., diabetes-associated disease symptoms) in a patient. As indicated above, the prevention may be complete (no detectable symptoms) or partial, such that fewer symptoms are observed than would likely occur absent treatment. In embodiments, the diabetes-associated disease symptom is a symptom associated with nephropathy, retinopathy, neuropathy, cardiovascular disease, or inflammation.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g., a first linker or second linker), or indirect, e.g., by non-covalent bond (e.g. electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like).

The term "thioredoxin activity" as used herein refers to the biological activity of the protein. In embodiments, the thioredoxin activity may be antioxidant activity by facilitating the reduction of other proteins, for example by cysteine thiol-disulfide exchange, at a dithiol-disulfide active site. The diseases described herein (e.g., metabolic disorder, cardiovascular disease, or inflammatory disease) may be associated with aberrant (e.g., reduced) thioredoxin activity.

The term "thioredoxin interacting protein-thioredoxin protein (TXNIP-TRX) complex" as used herein refers to a thioredoxin protein bonded (e.g., covalently bonded) to a thioredoxin interacting protein. In embodiments, the TXNIP-TRX complex is detected by co-immunoprecipitation method (e.g., a method in which an antibody to TRX is used to immunoprecipitate it from cells and its association with TXNIP is detected subsequently by Western Blotting with an antibody to TXNIP).

The term "capable of binding" as used herein refers to a moiety (e.g., a compound as described herein) that is able to measurably bind to a target (e.g., aTXNIP protein or a TXNIP-TRX complex). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der Waals bond(s)/interactions, hydrogen bond(s), polar bond(s), or combinations or mixtures thereof).

The term "metabolic disorder" refers to a disorder characterized by one or more abnormal metabolic processes in a subject. In embodiments, a metabolic disorder may be associated with, related to, or may be diabetes (e.g., type 1 diabetes or type 2 diabetes), insulin resistance, metabolic syndrome, obesity, hyperlipidemia, hyperglycemia, high serum triglycerides, and/or high blood pressure. In embodiments, a metabolic disorder may be associated with, related to, or may be a diabetes associated disease selected from nephropathy, retinopathy, neuropathy, cardiovascular disease, or inflammation. In embodiments, a metabolic disorder may be associated with, related to, or may be nephropathy, retinopathy, neuropathy, cardiovascular disease, or inflammation.

A "TXNIP-TRX complex-associated disease" as used herein refers to a disease associated with aberrant TXNIP-TRX complex activity. In embodiments, the TXNIP-TRX complex-associated disease is a metabolic disorder, or cardiovascular disease. The diseases described herein (e.g., metabolic disorder, cardiovascular disease, or inflammatory disease) may be associated with aberrant (e.g., reduced) thioredoxin activity.

II. Compounds

In an aspect is provided a compound (e.g., a TXNIP-TRX complex inhibitor or a TXNIP expression inhibitor), or a pharmaceutically acceptable salt thereof, having the formula:

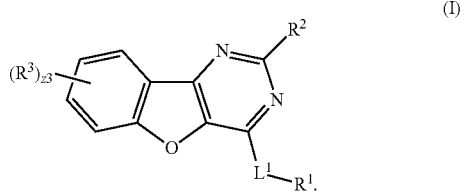

(I)

$L^1$ is a covalent linker.

$R^1$ is independently hydrogen, halogen, —$CX^1_3$, —$CHX^1_2$, —$CH_2X^1$, —$OCX^1_3$, —$OCHX^1_2$, —$OCH_2X^1$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —$NHC(O)NR^{1A}R^{1B}$, —$N(O)_{m1}$, —$NR^{1A}R^{1B}$, —$C(O)R^{1C}$, —$C(O)OR^{1C}$, —$C(O)NR^{1A}R^{1B}$, —$OR^{1D}$, —$SR^{1D}$, —$SeR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^2$ is independently hydrogen, halogen, —$CX^2_3$, —$CHX^2_2$, —$CH_2X^2$, —$OCX^2_3$, —$OCHX^2_2$, —$OCH_2X^2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —$C(O)OR^{2C}$, —$C(O)NR^{2A}R^{2B}$, —$OR^{2D}$, —$SR^{2D}$, —$SeR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^{1A}$, $R^{1B}$, $R^{1C}$, $R^{1D}$, $R^{2A}$, $R^{2B}$, $R^{2C}$, and $R^{2D}$ are each independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); $R^{1A}$ and $R^{1B}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), or substituted (e.g., substituted with at least one substituent group, size-limited substituent group, or lower substituent group) or unsubstituted heteroaryl (e.g., 5 to 10 membered, 5 to 9 membered, or 5 to 6 membered); $R^{2A}$ and $R^{2B}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$X^1$ and $X^2$ are each independently —F, —Cl, —Br, or —I.

The symbols n1 and n2 are each independently an integer from 0 to 4.

The symbols m1, m2, v1, and v2 are each independently 1 or 2.

$R^3$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^3$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

The symbol z3 is an integer from 0 to 4.

In embodiments, $L^1$ is -$L^{101}$-$L^{102}$-$L^{103}$-.

$L^{101}$ is independently a bond, —N($R^{101}$)—, —S—, —O—, —C(O)—, —C(O)O—, —OC(O)—, —N($R^{101}$)C(O)—, —C(O)N($R^{101}$)—, —$NR^{101}$C(O)$NR^{101}$—, —$NR^{101}$C(NH)$NR^{101}$—, —C(S)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

$L^{102}$ is independently a bond, —N($R^{102}$)—, —S—, —O—, —C(O)—, —C(O)O—, —OC(O)—, —N($R^{102}$)C(O)—, —C(O)N($R^{102}$)—, —$NR^{102}$C(O)$NR^{102}$—, —$NR^{102}$C(NH)$NR^{102}$—, —C(S)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

$L^{103}$ is independently a bond, $-N(R^{103})-$, $-S-$, $-O-$, $-C(O)-$, $-C(O)O-$, $-OC(O)-$, $-N(R^{103})C(O)-$, $-C(O)N(R^{103})-$, $-NR^{103}C(O)NR^{103}-$, $-NR^{103}C(NH)NR^{103}-$, $-C(S)-$, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

$R^{101}$, $R^{102}$, and $R^{103}$ are each independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{101}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{101}$ is substituted with a plurality of groups selected from substituent groups, size-limited substituent groups, and lower substituent groups; each substituent group, size-limited substituent group, and/or lower substituent group may optionally be different. In embodiments, when $R^{101}$ is substituted, it is substituted with at least one substituent group. In embodiments, when $R^{101}$ is substituted, it is substituted with at least one size-limited substituent group. In embodiments, when $R^{101}$ is substituted, it is substituted with at least one lower substituent group.

In embodiments, a substituted $R^{102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102}$ is substituted with a plurality of groups selected from substituent groups, size-limited substituent groups, and lower substituent groups; each substituent group, size-limited substituent group, and/or lower substituent group may optionally be different. In embodiments, when $R^{102}$ is substituted, it is substituted with at least one substituent group. In embodiments, when $R^{102}$ is substituted, it is substituted with at least one size-limited substituent group. In embodiments, when $R^{102}$ is substituted, it is substituted with at least one lower substituent group.

In embodiments, a substituted $R^{103}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{103}$ is substituted with a plurality of groups selected from substituent groups, size-limited substituent groups, and lower substituent groups; each substituent group, size-limited substituent group, and/or lower substituent group may optionally be different. In embodiments, when $R^{103}$ is substituted, it is substituted with at least one substituent group. In embodiments, when $R^{103}$ is substituted, it is substituted with at least one size-limited substituent group. In embodiments, when $R^{103}$ is substituted, it is substituted with at least one lower substituent group.

In embodiments, $L^{101}$ is independently a bond, $-NH-$, $-S-$, $-O-$, $-C(O)-$, $-C(O)O-$, $-OC(O)-$, $-NHC(O)-$, $-C(O)NH-$, $-NHC(O)NH-$, $-NHC(NH)NH-$, $-C(S)-$, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{101}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{101}$ is substituted with a plurality of groups selected from substituent groups, size-limited substituent groups, and lower substituent groups; each substituent group, size-limited substituent group, and/or lower substituent group may optionally be different. In embodiments, when $L^{101}$ is substituted, it is substituted with at least one substituent group. In embodiments, when $L^{101}$ is substituted, it is substituted with at least one size-limited substituent group. In embodiments, when $L^{101}$ is substituted, it is substituted with at least one lower substituent group.

In embodiments, $L^{101}$ is independently a substituted or unsubstituted 2 to 6 membered heteroalkylene, or a substituted or unsubstituted 3 to 6 membered heterocycloalkylene. In embodiments, $L^{101}$ is independently a substituted or unsubstituted 2 to 6 membered heteroalkylene. In embodiments, $L^{101}$ is independently a substituted or unsubstituted 3 to 6 membered heterocycloalkylene. In embodiments, $L^{101}$ is independently an unsubstituted 2 to 6 membered heteroalkylene. In embodiments, $L^{101}$ is independently

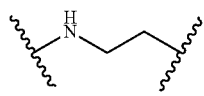

In embodiments, $L^{101}$ is independently

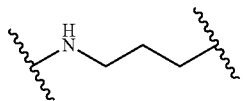

In embodiments, $L^{101}$ is independently

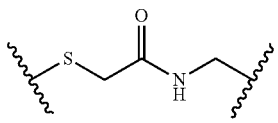

In embodiments, $L^{101}$ is independently

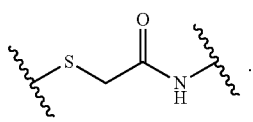 [SMILES: *NC(=O)CS*]

In embodiments, $L^{101}$ is independently

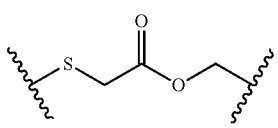

In embodiments, $L^{101}$ is independently

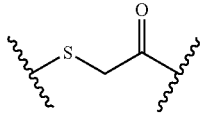

In embodiments, $L^{101}$ is independently

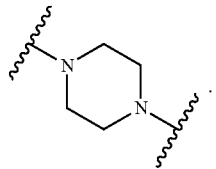 [SMILES: *N1CCN(*)CC1]

In embodiments, $L^{102}$ is independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{102}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{102}$ is substituted with a plurality of groups selected from substituent groups, size-limited substituent groups, and lower substituent groups; each substituent group, size-limited substituent group, and/or lower substituent group may optionally be different. In embodiments, when $L^{102}$ is substituted, it is substituted with at least one substituent group. In embodiments, when $L^{102}$ is substituted, it is substituted with at least one size-limited substituent group. In embodiments, when $L^{102}$ is substituted, it is substituted with at least one lower substituent group.

In embodiments, $L^{102}$ is independently a bond. In embodiments, $L^{102}$ is independently a substituted or unsubstituted $C_1$-$C_4$ alkylene. In embodiments, $L^{102}$ is independently

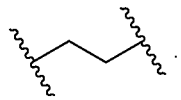 [SMILES: *CC*]

In embodiments, $L^{103}$ is independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{103}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{103}$ is substituted with a plurality of groups selected from substituent groups, size-limited substituent groups, and lower substituent groups; each substituent group, size-limited substituent group, and/or lower substituent group may optionally be different. In embodiments, when $L^{103}$ is substituted, it is substituted with at least one substituent group. In embodiments, when $L^{103}$ is substituted, it is substituted with at least one size-limited substituent group. In embodiments, when $L^{103}$ is substituted, it is substituted with at least one lower substituent group.

In embodiments, $L^{103}$ is independently a bond.

In embodiments, $L^{101}$ is independently a substituted or unsubstituted 2 to 6 membered heteroalkylene, or a substituted or unsubstituted 3 to 6 membered heterocycloalkylene; $L^{102}$ is independently a bond; and $L^{103}$ is independently a bond.

In embodiments, $R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, $R^1$ is independently —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is independently —OH, substituted or unsubstituted $C_1$-$C_4$ alkyl, substituted or unsubstituted 2 to 6 membered heteroalkyl, substituted or unsubstituted 3 to 6 membered heterocycloalkyl, substituted or unsubstituted phenyl, or substituted or unsubstituted 5 to 10 membered heteroaryl.

In embodiments, $R^1$ is independently —OH. In embodiments, $R^1$ is independently a substituted or unsubstituted $C_1$-$C_4$ alkyl. In embodiments, $R^1$ is independently a substituted $C_1$-$C_4$ alkyl. In embodiments, $R^1$ is independently an unsubstituted $C_1$-$C_4$ alkyl. In embodiments, $R^1$ is independently an unsubstituted methyl. In embodiments, $R^1$ is independently an unsubstituted ethyl. In embodiments, $R^1$ is independently an unsubstituted propyl. In embodiments, $R^1$ is independently an unsubstituted n-propyl. In embodiments, $R^1$ is independently an unsubstituted isopropyl. In embodiments, $R^1$ is independently an unsubstituted butyl. In embodiments, $R^1$ is independently an unsubstituted n-butyl. In embodiments, $R^1$ is independently an unsubstituted tert-butyl. In embodiments, $R^1$ is independently

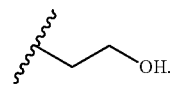

In embodiments, $R^1$ is independently a substituted or unsubstituted 2 to 6 membered heteroalkyl. In embodiments, $R^1$ is independently an unsubstituted 2 to 6 membered heteroalkyl. In embodiments, $R^1$ is independently an unsubstituted alkoxy. In embodiments, $R^1$ is independently an unsubstituted —$O(C_1$-$C_4$ alkyl). In embodiments, $R^1$ is independently an unsubstituted methoxy. In embodiments, $R^1$ is independently an unsubstituted ethoxy. In embodiments, $R^1$ is independently an unsubstituted propoxy. In embodiments, $R^1$ is independently an unsubstituted n-propoxy. In embodiments, $R^1$ is independently an unsubstituted isopropoxy. In embodiments, $R^1$ is independently an unsubstituted butoxy. In embodiments, $R^1$ is independently an unsubstituted n-butoxy. In embodiments, $R^1$ is independently an unsubstituted tert-butoxy. In embodiments, $R^1$ is independently a substituted or unsubstituted 3 to 6 membered heterocycloalkyl. In embodiments, $R^1$ is independently an unsubstituted 3 to 6 membered heterocycloalkyl. In embodiments, $R^1$ is independently a substituted or unsubstituted 3 to 6 membered heterocycloalkyl. In embodiments, $R^1$ is independently

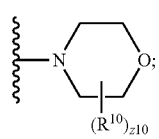

$R^{10}$ and z10 are as described herein, including in embodiments. In embodiments, $R^1$ is independently

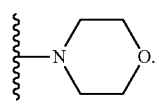

In embodiments, $R^1$ is independently

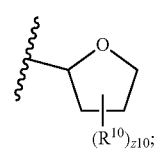

In embodiments, $R^1$ is independently a substituted or unsubstituted $C_6$-$C_{10}$ aryl. In embodiments, $R^1$ is independently a substituted or unsubstituted naphthyl. In embodiments, $R^1$ is independently a substituted or unsubstituted phenyl. In embodiments, $R^1$ is independently an unsubstituted phenyl. In embodiments, $R^1$ is independently a substituted or unsubstituted phenyl. In embodiments, $R^1$ is independently

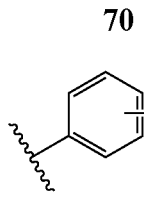

$R^{10}$ and z10 are as described herein, including in embodiments. In embodiments, $R^1$ is independently

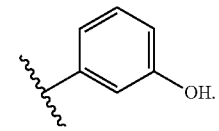 [SMILES: *c1cccc(O)c1]

In embodiments, $R^1$ is independently

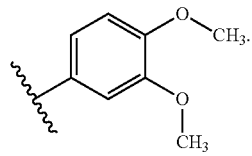 [SMILES: *c1ccc(OC)c(OC)c1]

In embodiments, $R^1$ is independently a substituted or unsubstituted 5 to 10 membered heteroaryl. In embodiments, $R^1$ is independently a substituted 5 to 10 membered heteroaryl. In embodiments, $R^1$ is independently an unsubstituted 5 to 10 membered heteroaryl. In embodiments, $R^1$ is independently a substituted or unsubstituted furyl. In embodiments, $R^1$ is independently an unsubstituted furyl. In embodiments, $R^1$ is independently

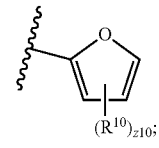

$R^{10}$ and z10 are as described herein, including in embodiments. In embodiments, $R^1$ is independently

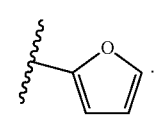

In embodiments, $R^1$ is independently a substituted or unsubstituted thienyl. In embodiments, $R^1$ is independently an unsubstituted thienyl. In embodiments, $R^1$ is independently

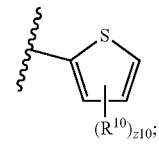

$R^{10}$ and z10 are as described herein, including in embodiments. In embodiments, $R^1$ is independently

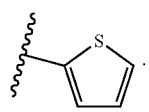

In embodiments, $R^1$ is independently a substituted or unsubstituted indolyl. In embodiments, $R^1$ is independently a substituted indolyl. In embodiments, $R^1$ is independently an unsubstituted indolyl. In embodiments, $R^1$ is independently

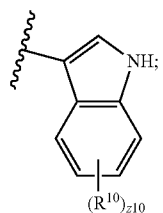

$R^{10}$ and z10 are as described herein, including in embodiments. In embodiments, $R^1$ is independently

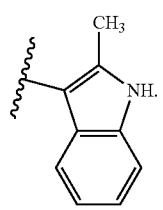 [SMILES: *c1c(C)[nH]c2ccccc12]

In embodiments, $R^1$ is independently

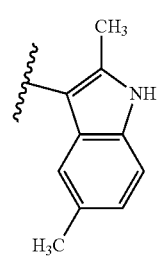 [SMILES: *c1c(C)[nH]c2ccc(C)cc12]

In embodiments, $R^1$ is independently

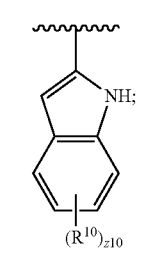

$R^{10}$ and z10 are as described herein, including in embodiments. In embodiments, $R^1$ is independently

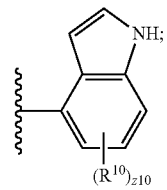

$R^{10}$ and z10 are as described herein, including in embodiments. In embodiments, $R^1$ is independently

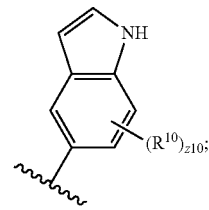

$R^{10}$ and z10 are as described herein, including in embodiments. In embodiments, $R^1$ is independently

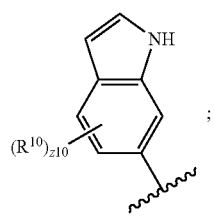

$R^{10}$ and z10 are as described herein, including in embodiments. In embodiments, $R^1$ is independently

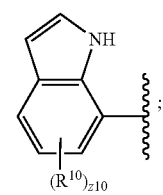

$R^{10}$ and z10 are as described herein, including in embodiments. In embodiments, $R^1$ is independently a substituted or unsubstituted indazolyl. In embodiments, $R^1$ is independently

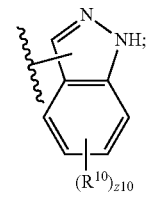

$R^{10}$ and z10 are as described herein, including in embodiments. In embodiments, $R^1$ is independently

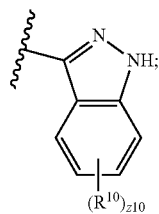

$R^{10}$ and z10 are as described herein, including in embodiments. In embodiments, $R^1$ is independently a substituted or unsubstituted benzimidazolyl. In embodiments, $R^1$ is independently

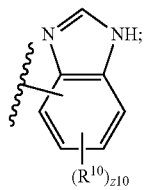

$R^{10}$ and z10 are as described herein, including in embodiments.

$R^{10}$ is independently halogen, oxo, —$CX^{10}_3$, —$CHX^{10}_2$, —$CH_2X^{10}$, —$OCX^{10}_3$, —$OCHX^{10}_2$, —$OCH_2X^{10}$, —CN, —$SO_{n10}R^{10D}$, —$SO_{v10}NR^{10A}R^{10B}$, —$NR^{10C}NR^{10A}R^{10B}$, —$ONR^{10A}R^{10B}$, —$NHC(O)NR^{10C}NR^{10A}R^{10B}$, —$NHC(O)NR^{10A}R^{10B}$, —$N(O)_{m10}$, —$NR^{10A}R^{10B}$, —$C(O)R^{10C}$, —$C(O)OR^{10C}$, —$C(O)NR^{10A}R^{10B}$, —$OR^{10D}$, —$SR^{10D}$, —$SeR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^{10}$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^{10A}$, $R^{10B}$, $R^{10C}$, and $R^{10D}$ are each independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); $R^{10A}$ and $R^{10B}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

$X^{10}$ is independently —F, —Cl, —Br, or —I.

The symbol n10 is independently an integer from 0 to 4.

The symbols m10 and v10 are each independently 1 or 2.

The symbol z10 is an integer from 0 to 7.

In embodiments, $R^{10}$ is independently halogen, oxo, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^{10}$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, a substituted ring formed when two adjacent $R^{10}$ substituents are joined (e.g., substituted heterocycloalkyl and/or substituted heteroaryl) is substituted with at least one substituent group, size-limited substituent group, or lower substituent group; wherein if the substituted ring formed when two adjacent $R^{10}$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two adjacent $R^{10}$ substituents are joined is substituted, it is substituted with at least one substituent group. In embodiments, when the substituted ring formed when two adjacent $R^{10}$ substituents are joined is substituted, it is substituted with at least one size-limited substituent group. In embodiments, when the substituted ring formed when two adjacent $R^{10}$ substituents are joined is substituted, it is substituted with at least one lower substituent group.

In embodiments, $R^{10}$ is independently —F. In embodiments, $R^{10}$ is independently —Cl. In embodiments, $R^{10}$ is independently —Br. In embodiments, $R^{10}$ is independently —I. In embodiments, $R^{10}$ is independently oxo. In embodiments, $R^{10}$ is independently —$CCl_3$. In embodiments, $R^{10}$ is independently —$CBr_3$. In embodiments, $R^{10}$ is independently —$CF_3$. In embodiments, $R^{10}$ is independently —$CI_3$. In embodiments, $R^{10}$ is independently —$CHCl_2$. In embodiments, $R^{10}$ is independently —$CHBr_2$. In embodiments, $R^{10}$ is independently —$CHF_2$. In embodiments, $R^{10}$ is independently —$CHI_2$. In embodiments, $R^{10}$ is independently —$CH_2Cl$. In embodiments, $R^{10}$ is independently —$CH_2Br$. In embodiments, $R^{10}$ is independently —$CH_2F$. In embodiments, $R^{10}$ is independently —$CH_2I$. In embodiments, $R^{10}$ is independently —$OCCl_3$. In embodiments, $R^{10}$ is independently —$OCF_3$. In embodiments, $R^{10}$ is independently —$OCBr_3$. In embodiments, $R^{10}$ is independently —$OCI_3$. In embodiments, $R^{10}$ is independently —$OCHCl_2$. In embodiments, $R^{10}$ is independently —$OCHBr_2$. In embodiments, $R^{10}$ is independently —$OCHI_2$. In embodiments, $R^{10}$ is independently —$OCHF_2$. In embodiments, $R^{10}$ is independently —$OCH_2Cl$. In embodiments, $R^{10}$ is independently —$OCH_2Br$. In embodiments, $R^{10}$ is independently —$OCH_2I$. In embodiments, $R^{10}$ is independently —$OCH_2F$. In embodiments, $R^{10}$ is independently —CN. In embodiments, $R^{10}$ is independently —OH. In embodiments, $R^{10}$ is independently —$NH_2$. In embodiments, $R^{10}$ is independently —COOH. In embodiments, $R^{10}$ is independently —$CONH_2$. In embodiments, $R^{10}$ is independently —$NO_2$. In embodiments, $R^{10}$ is independently —SH. In embodiments, $R^{10}$ is independently —SeH. In embodiments, $R^{10}$ is independently —$SO_3H$. In embodiments, $R^{10}$ is independently —$OSO_3H$. In embodiments, $R^{10}$ is independently —$SO_2NH_2$. In embodiments, $R^{10}$ is independently —$NHNH_2$. In embodiments, $R^{10}$ is independently —$ONH_2$. In embodiments, $R^{10}$ is independently —$NHC(O)NHNH_2$. In embodiments, $R^{10}$ is independently —$NHC(O)NH_2$. In embodiments, $R^{10}$ is independently —$NHSO_2H$. In embodiments, $R^{10}$ is independently —NHC(O)H. In embodiments, $R^{10}$ is independently —NHC(O)OH. In embodiments, $R^{10}$ is independently —NHOH. In embodiments, $R^{10}$ is independently —$N_3$. In embodiments, $R^{10}$ is independently —$SF_5$. In embodiments, $R^{10}$ is independently substituted or unsubstituted alkyl. In embodiments, $R^{10}$ is independently an unsubstituted $C_1$-$C_4$ alkyl. In embodiments, $R^{10}$ is independently an unsubstituted methyl. In embodiments, $R^{10}$ is independently an unsubstituted ethyl. In embodiments, $R^{10}$ is independently an unsubstituted propyl. In embodiments, $R^{10}$ is independently an unsubstituted n-propyl. In embodiments, $R^{10}$ is independently an unsubstituted isopropyl. In embodiments, $R^{10}$ is independently an unsubstituted butyl. In embodiments, $R^{10}$ is independently an unsubstituted n-butyl. In embodiments, $R^{10}$ is independently an unsubstituted tert-butyl. In embodiments, $R^{10}$ is independently substituted or unsubstituted heteroalkyl. In embodiments, $R^{10}$ is independently an unsubstituted —O($C_1$-$C_4$ alkyl). In embodiments, $R^{10}$ is independently an unsubstituted methoxy. In embodiments, $R^{10}$ is independently an unsubstituted ethoxy. In embodiments, $R^{10}$ is independently an unsubstituted propoxy. In embodiments, $R^{10}$ is independently an unsubstituted n-propoxy. In embodiments, $R^{10}$ is independently an unsubstituted isopropoxy. In embodiments, $R^{10}$ is independently an unsubstituted n-butoxy. In embodiments, $R^{10}$ is independently an unsubstituted tert-butoxy. In embodiments, $R^{10}$ is independently substituted or unsubstituted cycloalkyl. In embodiments, $R^{10}$ is independently substituted or unsubstituted heterocycloalkyl. In embodiments, $R^{10}$ is independently substituted or unsubstituted aryl. In embodiments, $R^{10}$ is independently a substituted or unsubstituted phenyl. In embodiments, $R^{10}$ is independently substituted or unsubstituted heteroaryl.

In embodiments, a substituted $R^{10A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10A}$ is substituted with a plurality of groups selected from substituent groups, size-limited substituent groups, and lower substituent groups; each substituent group, size-limited substituent group, and/or lower substituent group may optionally be different. In embodiments, when $R^{10A}$ is substituted, it is substituted with at least one substituent group. In embodiments, when $R^{10A}$ is substituted, it is substituted with at least one size-limited substituent group. In embodiments, when $R^{10A}$ is substituted, it is substituted with at least one lower substituent group.

In embodiments, a substituted $R^{10B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10B}$ is substituted with a plurality of groups selected from substituent groups, size-limited substituent groups, and lower substituent groups; each substituent group, size-limited substituent group, and/or lower substituent group may optionally be different. In embodiments, when $R^{10B}$ is substituted, it is substituted with at least one substituent group. In embodiments, when $R^{10B}$ is substituted, it is substituted with at least one size-limited substituent group. In embodiments, when $R^{10B}$ is substituted, it is substituted with at least one lower substituent group.

In embodiments, a substituted ring formed when $R^{10A}$ and $R^{10B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{10A}$ and $R^{10B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10A}$ and $R^{10B}$ substituents bonded to the same nitrogen atom are joined is substituted, it is substituted with at least one substituent group. In embodiments, when the substituted ring formed when $R^{10A}$ and $R^{10B}$ substituents bonded to the same nitrogen atom are joined is substituted, it is substituted with at least one size-limited substituent group. In embodiments, when the substituted ring formed when $R^{10A}$ and $R^{10B}$ substituents bonded to the same nitrogen atom are joined is substituted, it is substituted with at least one lower substituent group.

In embodiments, a substituted $R^{10C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10C}$ is substituted with a plurality of groups selected from substituent groups, size-limited substituent groups, and lower substituent groups; each substituent group, size-limited substituent group, and/or lower substituent group may optionally be different. In embodiments, when $R^{10C}$ is substituted, it is substituted with at least one substituent group. In embodiments, when $R^{10C}$ is substituted, it is substituted with at least one size-limited substituent group. In embodiments, when $R^{10C}$ is substituted, it is substituted with at least one lower substituent group.

In embodiments, a substituted $R^{10D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10D}$ is substituted with a plurality of groups selected from substituent groups, size-limited substituent groups, and lower substituent groups; each substituent group, size-limited substituent group, and/or lower substituent group may optionally be different. In embodiments, when $R^{10D}$ is substituted, it is substituted with at least one substituent group. In embodiments, when $R^{10D}$ is substituted, it is substituted with at least one size-limited substituent group. In embodiments, when $R^{10D}$ is substituted, it is substituted with at least one lower substituent group.

In embodiments, a substituted $R^{1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, a substituted $R^{1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when $R^{1B}$ is substituted, it is substituted with at least one lower substituent group.

In embodiments, a substituted ring formed when $R^{1A}$ and $R^{1B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{1A}$ and $R^{1B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{1A}$ and $R^{1B}$ substituents bonded to the same nitrogen atom are joined is substituted, it is substituted with at least one substituent group. In embodiments, when the substituted ring formed when $R^{1A}$ and $R^{1B}$ substituents bonded to the same nitrogen atom are joined is substituted, it is substituted with at least one size-limited substituent group. In embodiments, when the substituted ring formed when $R^{1A}$ and $R^{1B}$ substituents bonded to the same nitrogen atom are joined is substituted, it is substituted with at least one lower substituent group.

In embodiments, a substituted $R^{1C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1C}$ is substituted with a plurality of groups selected from substituent groups, size-limited substituent groups, and lower substituent groups; each substituent group, size-limited substituent group, and/or lower substituent group may optionally be different. In embodiments, when $R^{1C}$ is substituted, it is substituted with at least one substituent group. In embodiments, when $R^{1C}$ is substituted, it is substituted with at least one size-limited substituent group. In embodiments, when $R^{1C}$ is substituted, it is substituted with at least one lower substituent group.

In embodiments, a substituted RD (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted RD is substituted with a plurality of groups selected from substituent groups, size-limited substituent groups, and lower substituent groups; each substituent group, size-limited substituent group, and/or lower substituent group may optionally be different. In embodiments, when RD is substituted, it is substituted with at least one substituent group. In embodiments, when RD is substituted, it is substituted with at least one size-limited substituent group. In embodiments, when RD is substituted, it is substituted with at least one lower substituent group.

In embodiments, $R^2$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted (e.g., substituted with at least one substituent group, size-limited substituent group, or lower substituent group) or unsubstituted alkyl (e.g., C$_1$-C$_8$, C$_1$-C$_6$, C$_1$-C$_4$, or C$_1$-C$_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., C$_3$-C$_8$, C$_3$-C$_6$, C$_4$-C$_6$, or C$_5$-C$_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., C$_6$-C$_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^2$ is independently hydrogen, substituted or unsubstituted alkyl, substituted or unsubstituted alkoxy, or substituted or unsubstituted aryl. In embodiments, $R^2$ is independently hydrogen, substituted or unsubstituted C$_1$-C$_4$ alkyl, substituted or unsubstituted —O(C$_1$-C$_4$ alkyl), or substituted or unsubstituted C$_6$-C$_{10}$ aryl. In embodiments, $R^2$ is independently hydrogen, substituted or unsubstituted alkyl, or substituted or unsubstituted aryl. In embodiments, $R^2$ is independently hydrogen, substituted or unsubstituted C$_1$-C$_4$ alkyl, or substituted or unsubstituted C$_6$-C$_{10}$ aryl. In embodiments, $R^2$ is independently hydrogen. In embodiments, $R^2$ is independently a substituted or unsubstituted C$_1$-C$_4$ alkyl. In embodiments, $R^2$ is independently an unsubstituted C$_1$-C$_4$ alkyl. In embodiments, $R^2$ is independently an unsubstituted methyl. In embodiments, $R^2$ is independently an unsubstituted ethyl. In embodiments, $R^2$ is independently an unsubstituted propyl. In embodiments, $R^2$ is independently an unsubstituted n-propyl. In embodiments, $R^2$ is independently an unsubstituted isopropyl. In embodiments, $R^2$ is independently an unsubstituted n-butyl. In embodiments, $R^2$ is independently an unsubstituted tert-butyl. In embodiments, $R^2$ is independently a substituted or unsubstituted —O(C$_1$-C$_4$ alkyl). In embodiments, $R^2$ is independently an unsubstituted —O(C$_1$-C$_4$ alkyl). In embodiments, $R^2$ is independently an unsubstituted methoxy. In embodiments, $R^2$ is independently an unsubstituted ethoxy. In embodiments, $R^2$ is independently an unsubstituted propoxy. In embodiments, $R^2$ is independently an unsubstituted n-propoxy. In embodiments, $R^2$ is independently an unsubstituted isopropoxy. In embodiments, $R^2$ is independently an unsubstituted n-butoxy. In embodiments, $R^2$ is independently an unsubstituted tert-butoxy. In embodiments, $R^2$ is independently a substituted or unsubstituted C$_6$-C$_{10}$ aryl. In embodiments, $R^2$ is independently an unsubstituted C$_6$-C$_{10}$ aryl. In embodiments, $R^2$ is independently a substituted or unsubstituted phenyl. In embodiments, $R^2$ is independently an unsubstituted phenyl.

In embodiments, $R^2$ is independently hydrogen, unsubstituted methyl, unsubstituted ethyl, or unsubstituted phenyl.

In embodiments, a substituted $R^{2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{2A}$ is substituted, it is substituted with at least one size-limited substituent group. In embodiments, when $R^{2A}$ is substituted, it is substituted with at least one lower substituent group.

In embodiments, a substituted $R^{2B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2B}$ is substituted with a plurality of groups selected from substituent groups, size-limited substituent groups, and lower substituent groups; each substituent group, size-limited substituent group, and/or lower substituent group may optionally be different. In embodiments, when $R^{2B}$ is substituted, it is substituted with at least one substituent group. In embodiments, when $R^{2B}$ is substituted, it is substituted with at least one size-limited substituent group. In embodiments, when $R^{2B}$ is substituted, it is substituted with at least one lower substituent group.

In embodiments, a substituted ring formed when $R^{2A}$ and $R^{2B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{2A}$ and $R^{2B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{2A}$ and $R^{2B}$ substituents bonded to the same nitrogen atom are joined is substituted, it is substituted with at least one substituent group. In embodiments, when the substituted ring formed when $R^{2A}$ and $R^{2B}$ substituents bonded to the same nitrogen atom are joined is substituted, it is substituted with at least one size-limited substituent group. In embodiments, when the substituted ring formed when $R^{2A}$ and $R^{2B}$ substituents bonded to the same nitrogen atom are joined is substituted, it is substituted with at least one lower substituent group.

In embodiments, a substituted $R^{2C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, a substituted $R^{2D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2D}$ is substituted with a plurality of groups selected from substituent groups, size-limited substituent groups, and lower substituent groups; each substituent group, size-limited substituent group, and/or lower substituent group may optionally be different. In embodiments, when $R^{2D}$ is substituted, it is substituted with at least one substituent group. In embodiments, when $R^{2D}$ is substituted, it is substituted with at least one size-limited substituent group. In embodiments, when $R^{2D}$ is substituted, it is substituted with at least one lower substituent group.

In embodiments, $R^3$ is independently hydrogen, substituted or unsubstituted alkyl, substituted or unsubstituted alkoxy, or substituted or unsubstituted aryl. In embodiments, $R^3$ is independently hydrogen, substituted or unsubstituted $C_1$-$C_4$ alkyl, substituted or unsubstituted —O($C_1$-$C_4$ alkyl), or substituted or unsubstituted $C_6$-$C_{10}$ aryl. In embodiments, $R^3$ is independently hydrogen. In embodiments, $R^3$ is independently a substituted or unsubstituted $C_1$-$C_4$ alkyl. In embodiments, $R^3$ is independently an unsubstituted $C_1$-$C_4$ alkyl. In embodiments, $R^3$ is independently an unsubstituted methyl. In embodiments, $R^3$ is independently an unsubstituted ethyl. In embodiments, $R^3$ is independently an unsubstituted propyl. In embodiments, $R^3$ is independently an unsubstituted n-propyl. In embodiments, $R^3$ is independently an unsubstituted isopropyl. In embodiments, $R^3$ is independently an unsubstituted n-butyl. In embodiments, $R^3$ is independently an unsubstituted tert-butyl. In embodiments, $R^3$ is independently a substituted or unsubstituted —O($C_1$-$C_4$ alkyl). In embodiments, $R^3$ is independently an unsubstituted —O($C_1$-$C_4$ alkyl). In embodiments, $R^3$ is independently an unsubstituted methoxy. In embodiments, $R^3$ is independently an unsubstituted ethoxy. In embodiments, $R^3$ is independently an unsubstituted propoxy. In embodiments, $R^3$ is independently an unsubstituted n-propoxy. In embodiments, $R^3$ is independently an unsubstituted isopropoxy. In embodiments, $R^3$ is independently an unsubstituted n-butoxy. In embodiments, $R^3$ is independently an unsubstituted tert-butoxy. In embodiments, $R^3$ is independently a substituted or unsubstituted $C_6$-$C_{10}$ aryl. In embodiments, $R^3$ is independently an unsubstituted $C_6$-$C_{10}$ aryl. In embodiments, $R^3$ is independently a substituted or unsubstituted phenyl. In embodiments, $R^3$ is independently an unsubstituted phenyl.

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, a substituted ring formed when two adjacent $R^3$ substituents are joined (e.g., substituted heterocycloalkyl and/or substituted heteroaryl) is substituted with at least one substituent group, size-limited substituent group, or lower substituent group; wherein if the substituted ring formed when two adjacent $R^3$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two adjacent $R^3$ substituents are joined is substituted, it is substituted with at least one substituent group. In embodiments, when the substituted ring formed when two adjacent $R^3$ substituents are joined is substituted, it is substituted with at least one size-limited substituent group. In embodiments, when the substituted ring formed when two adjacent R³ substituents are joined is substituted, it is substituted with at least one lower substituent group.
In embodiments, z3 is 0. In embodiments, z3 is 1. In embodiments, z3 is 2. In embodiments, z3 is 3. In embodiments, z3 is 4.
In embodiments, -L¹-R¹ is
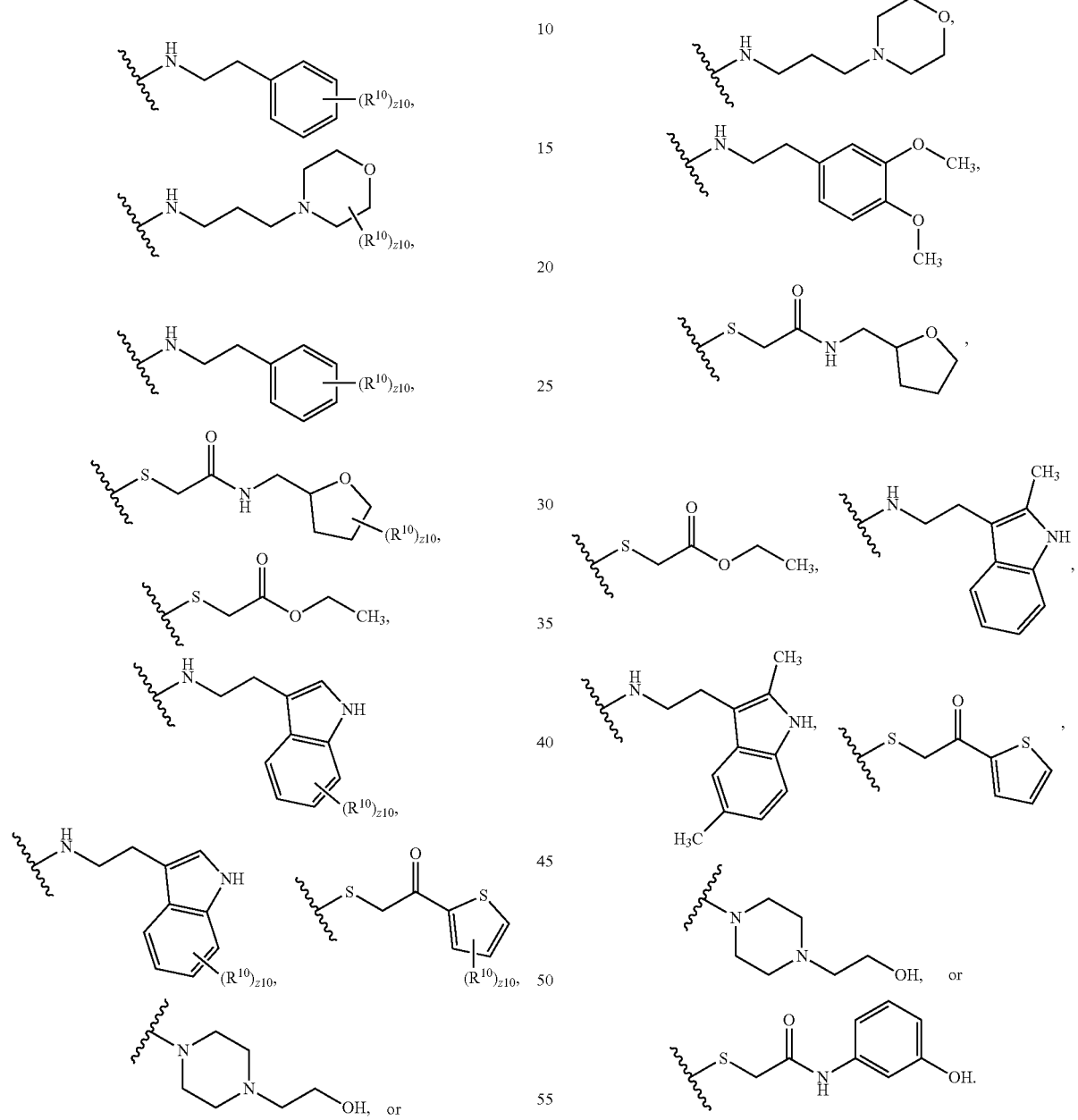
$R^{10}$ and z10 are as described herein, including in embodiments.
In embodiments, -L¹-R¹ is
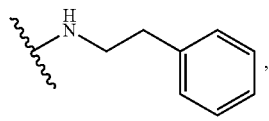
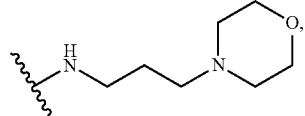
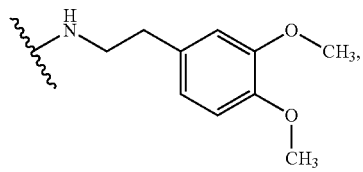
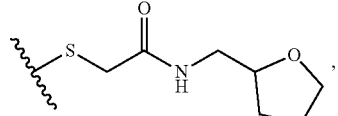
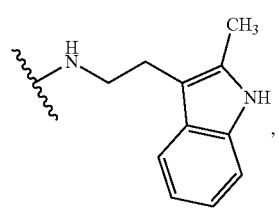
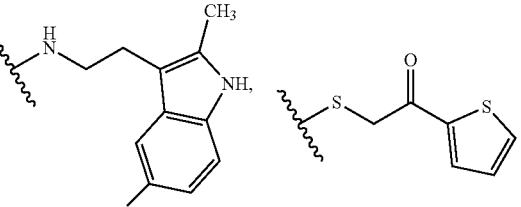
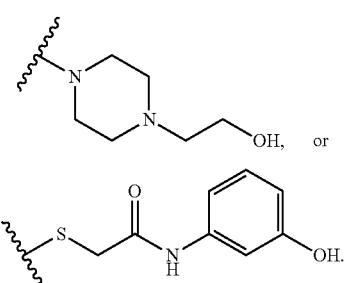
In embodiments, -L¹-R¹ is
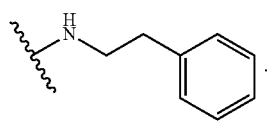 [SMILES: *NCCc1ccccc1]

In embodiments, -L$^1$-R$^1$ is
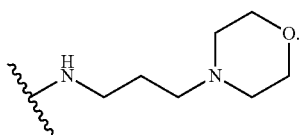 [SMILES: *NCCCN1CCOCC1]
In embodiments, -L$^1$-R$^1$ is
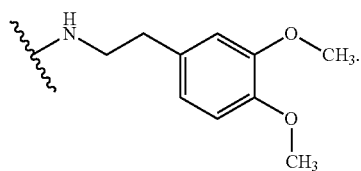
In embodiments, -L$^1$-R$^1$ is
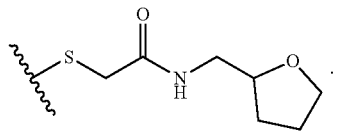 [SMILES: *SCC(=O)NCC1CCCO1]
In embodiments, -L$^1$-R$^1$ is
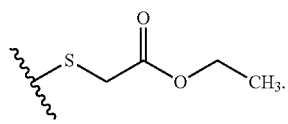 [SMILES: *SCC(=O)OCC]
In embodiments, -L$^1$-R$^1$ is
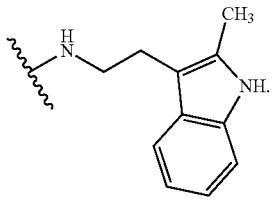 [SMILES: *NCCc1c(C)[nH]c2ccccc12]
In embodiments, -L$^1$-R$^1$ is
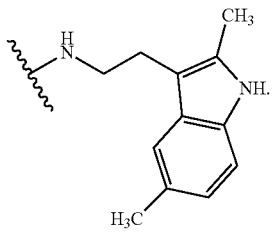 [SMILES: *NCCc1c(C)[nH]c2ccc(C)cc12]
In embodiments, -L$^1$-R$^1$ is
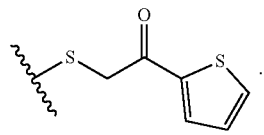 [SMILES: *SCC(=O)c1cccs1]
In embodiments, -L$^1$-R$^1$ is
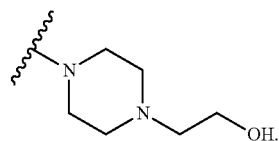 [SMILES: *N1CCN(CCO)CC1]
In embodiments, -L$^1$-R$^1$ is
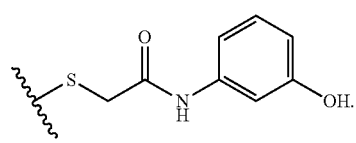 [SMILES: *SCC(=O)Nc1cccc(O)c1]
In embodiments, -L$^1$-R$^1$ is not
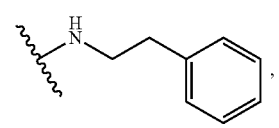
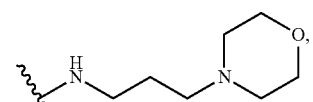
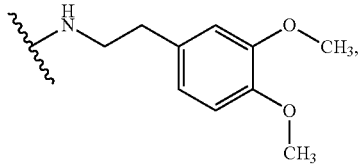
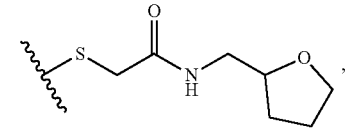
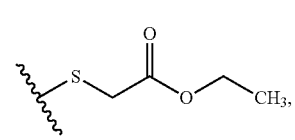 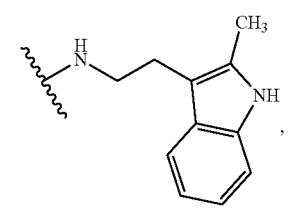

-continued

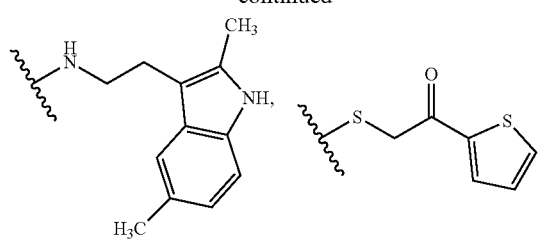
,

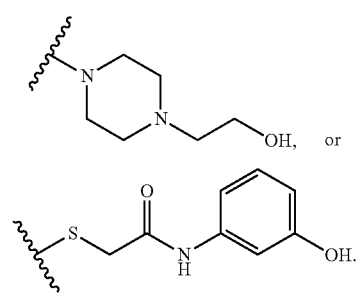

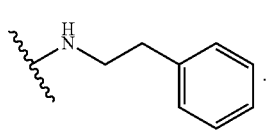 [SMILES: *NCCc1ccccc1]

In embodiments, -L¹-R¹ is not

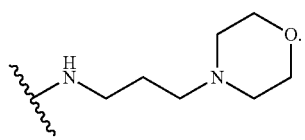 [SMILES: *NCCCN1CCOCC1]

In embodiments, -L¹-R¹ is not

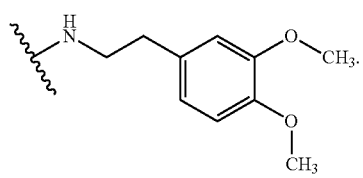 [SMILES: *NCCc1ccc(OC)c(OC)c1]

In embodiments, -L¹-R¹ is not

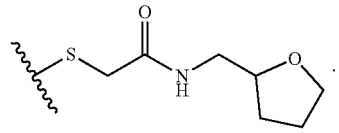 [SMILES: *SCC(=O)NCC1CCCO1]

In embodiments, -L¹-R¹ is not

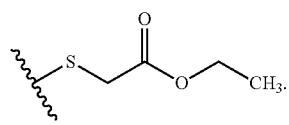

In embodiments, -L¹-R¹ is not

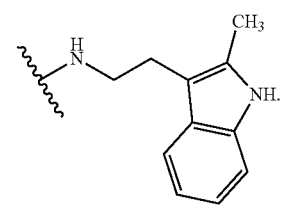 [SMILES: *NCCc1c(C)[nH]c2ccccc12]

In embodiments, -L¹-R¹ is not

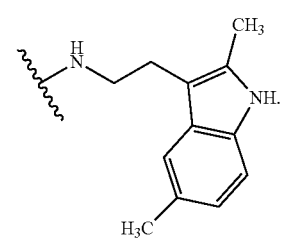 [SMILES: *NCCc1c(C)[nH]c2ccc(C)cc12]

In embodiments, -L¹-R¹ is not

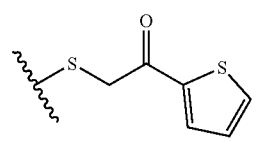 [SMILES: *SCC(=O)c1cccs1]

In embodiments, -L¹-R¹ is not

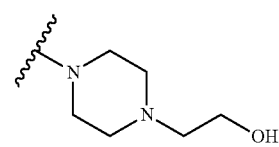

In embodiments, -L¹-R¹ is not

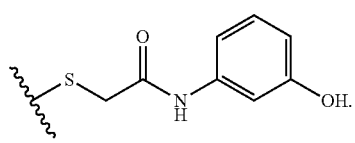 [SMILES: *SCC(=O)Nc1cccc(O)c1]

In an aspect is provided a compound (e.g., a TXNIP-TRX complex inhibitor or a TXNIP expression inhibitor), or a pharmaceutically acceptable salt thereof, having the formula:

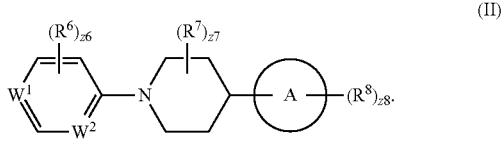

(II)

Ring A is cycloalkyl (e.g., $C_3$-$C_8$, $C_3$-$C_6$, $C_4$-$C_6$, or $C_5$-$C_6$), heterocycloalkyl (e.g., 3 to 8 membered, 3 to 6 membered, 4 to 6 membered, 4 to 5 membered, or 5 to 6 membered), aryl (e.g., $C_6$-$C_{10}$ or phenyl), or heteroaryl (e.g., 5 to 10 membered, 5 to 9 membered, or 5 to 6 membered).

$W^1$ is N or $C(R^4)$.

$W^2$ is N or $C(R^5)$.

$R^4$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^5$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^6$ is independently halogen, —$CX^6_3$, —$CHX^6_2$, —$CH_2X^6$, —$OCX^6_3$, —$OCHX^6_2$, —$OCH_2X^6$, —CN, —$SO_{n6}R^{6D}$, —$SO_{v6}NR^{6A}R^{6B}$, —$NR^{6C}NR^{6A}R^{6B}$, —$ONR^{6A}R^{6B}$, —NHC(O)$NR^{6C}NR^{6A}R^{6B}$, —NHC(O)$NR^{6A}R^{6B}$, —$N(O)_{m6}$, —$NR^{6A}R^{6B}$, —$C(O)R^{6C}$, —$C(O)OR^{6C}$, —$C(O)NR^{6A}R^{6B}$, —$OR^{6D}$, —$SR^{6D}$, —$SeR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^6$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^7$ is independently halogen, oxo, —$CX^7_3$, —$CHX^7_2$, —$CH_2X^7$, —$OCX^7_3$, —$OCHX^7_2$, —$OCH_2X^7$, —CN, —$SO_{n7}R^{7D}$, —$SO_{v7}NR^{7A}R^{7B}$, —$NR^{7C}NR^{7A}R^{7B}$, —$ONR^{7A}R^{7B}$, —NHC(O)$NR^{7C}NR^{7A}R^{7B}$, —NHC(O)$NR^{7A}R^{7B}$, —$N(O)_{m7}$, —$NR^{7A}R^{7B}$, —$C(O)R^{7C}$, —$C(O)OR^{7C}$, —$C(O)NR^{7A}R^{7B}$, —$OR^{7D}$, —$SR^{7D}$, —$SeR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^7$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two $R^7$ substituents bonded to the same carbon atom may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), or substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered).

$R^8$ is independently halogen, oxo, —$CX^8_3$, —$CHX^8_2$, —$CH_2X^8$, —$OCX^8_3$, —$OCHX^8_2$, —$OCH_2X^8$, —CN, —$SO_{n8}R^{8D}$, —$SO_{v8}NR^{8A}R^{8B}$, —$NR^{8C}NR^{8A}R^{8B}$, —$ONR^{8A}R^{8B}$, —$NHC(O)NR^{8C}NR^{8A}R^{8B}$, —$NHC(O)NR^{8A}R^{8B}$, —$N(O)_{m8}$, —$NR^{8A}R^{8B}$, —$C(O)R^{8C}$, —$C(O)OR^{8C}$, —$C(O)NR^{8A}R^{8B}$, —$OR^{8D}$, —$SR^{8D}$, —$SeR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, —$SF_5$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^8$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^{6A}$, $R^{6B}$, $R^{6C}$, $R^{6D}$, $R^{7A}$, $R^{7B}$, $R^{7C}$, $R^{7D}$, $R^{7A}$, $R^{7B}$, $R^{7C}$, and $R^{7D}$ are each independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); $R^{6A}$ and $R^{6B}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered); $R^{7A}$ and $R^{7B}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered); $R^{8A}$ and $R^{8B}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

$X^6$, $X^7$, and $X^8$ are each independently —F, —Cl, —Br, or —I.

The symbols n6, n7, and n8 are each independently an integer from 0 to 4.

The symbols m6, m7, m8, v6, v7, and v8 are each independently 1 or 2.

The symbol z6 is an integer from 0 to 3.
The symbol z7 is an integer from 0 to 9.
The symbol z8 is an integer from 0 to 7.

In embodiments, the compound has the formula:

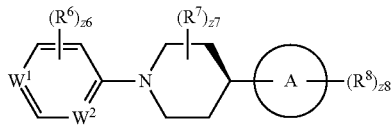

(II-1). Ring A, $W^1$, $W^2$, $R^6$, $R^7$, $R^8$, z6, z7, and z8 are as described herein, including in embodiments.

In embodiments, the compound has the formula:

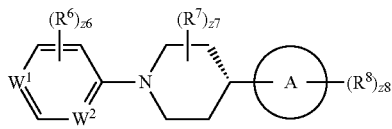

(II-2). Ring A, $W^1$, $W^2$, $R^6$, $R^7$, $R^8$, z6, z7, and z8 are as described herein, including in embodiments.

In embodiments, the compound has the formula:

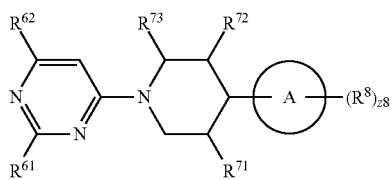

(IIA). Ring A, $R^8$, and z8 are as described herein, including in embodiments.

$R^{61}$ and $R^{62}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

$R^{71}$, $R^{72}$, and $R^{73}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, the compound has the formula:

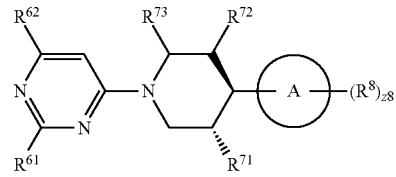

(IIA-1). Ring A, $R^8$, z8, $R^{61}$, $R^{62}$, $R^{71}$, $R^{72}$, and $R^{73}$ are as described herein, including in embodiments.

In embodiments, the compound has the formula:

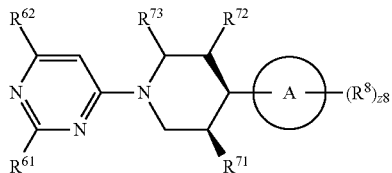

(IIA-2). Ring A, $R^8$, z8, $R^{61}$, $R^{62}$, $R^{71}$, $R^{72}$, and $R^{73}$ are as described herein, including in embodiments.

In embodiments, the compound has the formula:

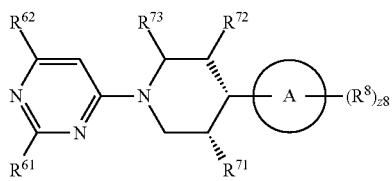

(IIA-3). Ring A, $R^8$, z8, $R^{61}$, $R^{62}$, $R^{71}$, $R^{72}$, and $R^{73}$ are as described herein, including in embodiments.

In embodiments, the compound has the formula:

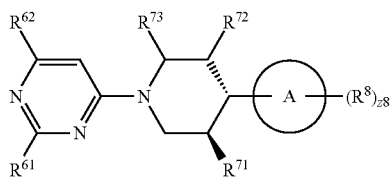

(IIA-4). Ring A, $R^8$, z8, $R^{61}$, $R^{62}$, $R^{71}$, $R^{72}$, and $R^{73}$ are as described herein, including in embodiments.

In embodiments, the compound has the formula:

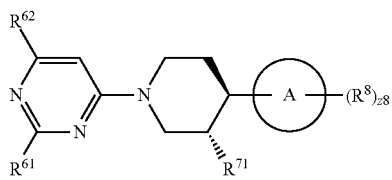

(IIA-5). Ring A, $R^8$, z8, $R^{61}$, $R^{62}$, and $R^{71}$ are as described herein, including in embodiments.

In embodiments, the compound has the formula:

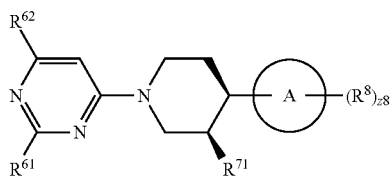

(IIA-6). Ring A, $R^8$, z8, $R^{61}$, $R^{62}$, and $R^{71}$ are as described herein, including in embodiments.

In embodiments, the compound has the formula:

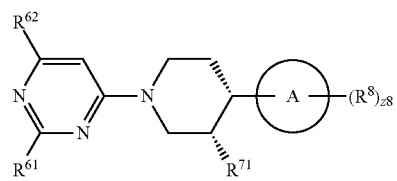

(IIA-7). Ring A, $R^8$, z8, $R^{61}$, $R^{62}$, and $R^{71}$ are as described herein, including in embodiments.

In embodiments, the compound has the formula:

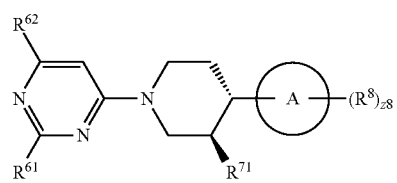

(IIA-8). Ring A, $R^8$, z8, $R^{61}$, $R^{62}$, and $R^{71}$ are as described herein, including in embodiments.

In embodiments, $W^1$ is N. In embodiments, $W^1$ is $C(R^4)$; $R^4$ is as described herein, including in embodiments. In embodiments, $W^1$ is CH.

In embodiments, $R^4$ is independently hydrogen. In embodiments, $R^4$ is independently substituted or unsubstituted alkyl. In embodiments, $R^4$ is independently an unsubstituted $C_1$-$C_4$ alkyl. In embodiments, $R^4$ is independently an unsubstituted methyl. In embodiments, $R^4$ is independently an unsubstituted ethyl. In embodiments, $R^4$ is independently an unsubstituted propyl. In embodiments, $R^4$ is independently an unsubstituted n-propyl. In embodiments, $R^4$ is independently an unsubstituted isopropyl. In embodiments, $R^4$ is independently an unsubstituted butyl. In embodiments, $R^4$ is independently an unsubstituted n-butyl. In embodiments, $R^4$ is independently an unsubstituted tert-butyl. In embodiments, $R^4$ is independently substituted or unsubstituted heteroalkyl. In embodiments, $R^4$ is independently an unsubstituted —O($C_1$-$C_4$ alkyl). In embodiments, $R^4$ is independently an unsubstituted methoxy. In embodiments, $R^4$ is independently an unsubstituted ethoxy. In embodiments, $R^4$ is independently an unsubstituted propoxy. In embodiments, $R^4$ is independently an unsubstituted n-propoxy. In embodiments, $R^4$ is independently an unsubstituted isopropoxy. In embodiments, $R^4$ is independently an unsubstituted n-butoxy. In embodiments, $R^4$ is independently an unsubstituted tert-butoxy.

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $W^2$ is N. In embodiments, $W^2$ is $C(R^5)$; $R^5$ is as described herein, including in embodiments. In embodiments, $W^2$ is CH.

In embodiments, $R^5$ is independently hydrogen. In embodiments, $R^5$ is independently substituted or unsubstituted alkyl. In embodiments, $R^5$ is independently an unsubstituted $C_1$-$C_4$ alkyl. In embodiments, $R^5$ is independently an unsubstituted methyl. In embodiments, $R^5$ is independently an unsubstituted ethyl. In embodiments, $R^5$ is independently an unsubstituted propyl. In embodiments, $R^5$ is independently an unsubstituted n-propyl. In embodiments, $R^5$ is independently an unsubstituted isopropyl. In embodiments, $R^5$ is independently an unsubstituted butyl. In embodiments, $R^5$ is independently an unsubstituted n-butyl. In embodiments, $R^5$ is independently an unsubstituted tert-butyl. In embodiments, $R^5$ is independently substituted or unsubstituted heteroalkyl. In embodiments, $R^5$ is independently an unsubstituted —O($C_1$-$C_4$ alkyl). In embodiments, $R^5$ is independently an unsubstituted methoxy. In embodiments, $R^5$ is independently an unsubstituted ethoxy. In embodiments, $R^5$ is independently an unsubstituted propoxy. In embodiments, $R^5$ is independently an unsubstituted n-propoxy. In embodiments, $R^5$ is independently an unsubstituted isopropoxy. In embodiments, $R^5$ is independently an unsubstituted n-butoxy. In embodiments, $R^5$ is independently an unsubstituted tert-butoxy.

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, Ring A is cycloalkyl. In embodiments, Ring A is heterocycloalkyl. In embodiments, Ring A is aryl. In embodiments, Ring A is heteroaryl. In embodiments, Ring A is $C_6$-$C_{10}$ aryl. In embodiments, Ring A is phenyl. In embodiments, Ring A is naphthyl. In embodiments, Ring A is 1-naphthyl. In embodiments, Ring A is 2-naphthyl. In embodiments, Ring A is quinolinyl. In embodiments, Ring A is isoquinolinyl.

In embodiments, $R^6$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^6$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, a substituted ring formed when two adjacent $R^6$ substituents are joined (e.g., substituted heterocycloalkyl and/or substituted heteroaryl) is substituted with at least one substituent group, size-limited substituent group, or lower substituent group; wherein if the substituted ring formed when two adjacent $R^6$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two adjacent $R^6$ substituents are joined is substituted, it is substituted with at least one substituent group. In embodiments, when the substituted ring formed when two adjacent $R^6$ substituents are joined is substituted, it is substituted with at least one size-limited substituent group. In embodiments, when the substituted ring formed when two adjacent $R^6$ substituents are joined is substituted, it is substituted with at least one lower substituent group.

In embodiments, $R^6$ is independently —F. In embodiments, $R^6$ is independently —Cl. In embodiments, $R^6$ is independently —Br. In embodiments, $R^6$ is independently —I. In embodiments, $R^6$ is independently —$CCl_3$. In embodiments, $R^6$ is independently —$CBr_3$. In embodiments, $R^6$ is independently —$CF_3$. In embodiments, $R^6$ is independently —$CI_3$. In embodiments, $R^6$ is independently —$CHCl_2$. In embodiments, $R^6$ is independently —$CHBr_2$. In embodiments, $R^6$ is independently —$CHF_2$. In embodiments, $R^6$ is independently —$CHI_2$. In embodiments, $R^6$ is independently —$CH_2Cl$. In embodiments, $R^6$ is independently —$CH_2Br$. In embodiments, $R^6$ is independently —$CH_2F$. In embodiments, $R^6$ is independently —$CH_2I$. In embodiments, $R^6$ is independently —$OCCl_3$. In embodiments, $R^6$ is independently —$OCF_3$. In embodiments, $R^6$ is independently —$OCBr_3$. In embodiments, $R^6$ is independently —$OCI_3$. In embodiments, $R^6$ is independently —$OCHCl_2$. In embodiments, $R^6$ is independently —$OCHBr_2$. In embodiments, $R^6$ is independently —$OCHI_2$. In embodiments, $R^6$ is independently —$OCHF_2$. In embodiments, $R^6$ is independently —$OCH_2Cl$. In embodiments, $R^6$ is independently —$OCH_2Br$. In embodiments, $R^6$ is independently —$OCH_2I$. In embodiments, $R^6$ is independently —$OCH_2F$. In embodiments, $R^6$ is independently —CN. In embodiments, $R^6$ is independently —OH. In embodiments, $R^6$ is independently —$NH_2$. In embodiments, $R^6$ is independently —COOH. In embodiments, $R^6$ is independently —$CONH_2$. In embodiments, $R^6$ is independently —$NO_2$. In embodiments, $R^6$ is independently —SH. In embodiments, $R^6$ is independently —SeH. In embodiments, $R^6$ is independently —$SO_3H$. In embodiments, $R^6$ is independently —$OSO_3H$. In embodiments, $R^6$ is independently —$SO_2NH_2$. In embodiments, $R^6$ is independently —$NHNH_2$. In embodiments, $R^6$ is independently —$ONH_2$. In embodiments, $R^6$ is independently —$NHC(O)NHNH_2$. In embodiments, $R^6$ is independently —$NHC(O)NH_2$. In embodiments, $R^6$ is independently —$NHSO_2H$. In embodiments, $R^6$ is independently —$NHC(O)H$. In embodiments, $R^6$ is independently —$NHC(O)OH$. In embodiments, $R^6$ is independently —NHOH. In embodiments, $R^6$ is independently —$N_3$. In embodiments, $R^6$ is independently —$SF_5$. In embodiments, $R^6$ is independently substituted or unsubstituted alkyl. In embodiments, $R^6$ is independently an unsubstituted $C_1$-$C_4$ alkyl. In embodiments, $R^6$ is independently an unsubstituted methyl. In embodiments, $R^6$ is independently an unsubstituted ethyl. In embodiments, $R^6$ is independently an unsubstituted propyl. In embodiments, $R^6$ is independently an unsubstituted n-propyl. In embodiments, $R^6$ is independently an unsubstituted isopropyl. In embodiments, $R^6$ is independently an unsubstituted butyl. In embodiments, $R^6$ is independently an unsubstituted n-butyl. In embodiments, $R^6$ is independently an unsubstituted tert-butyl. In embodiments, $R^6$ is independently substituted or unsubstituted heteroalkyl. In embodiments, $R^6$ is independently an unsubstituted —$O(C_1$-$C_4$ alkyl). In embodiments, $R^6$ is independently an unsubstituted methoxy. In embodiments, $R^6$ is independently an unsubstituted ethoxy. In embodiments, $R^6$ is independently an unsubstituted propoxy. In embodiments, $R^6$ is independently an unsubstituted n-propoxy. In embodiments, $R^6$ is independently an unsubstituted isopropoxy. In embodiments, $R^6$ is independently an unsubstituted n-butoxy. In embodiments, $R^6$ is independently an unsubstituted tert-butoxy. In embodiments, $R^6$ is independently substituted or unsubstituted cycloalkyl. In embodiments, $R^6$ is independently substituted or unsubstituted heterocycloalkyl. In embodiments, $R^6$ is independently substituted or unsubstituted aryl. In embodiments, $R^6$ is independently a substituted or unsubstituted phenyl. In embodiments, $R^6$ is independently substituted or unsubstituted heteroaryl.

In embodiments, a substituted $R^{6A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6A}$ is substituted with a plurality of groups selected from substituent groups, size-limited substituent groups, and lower substituent groups; each substituent group, size-limited substituent group, and/or lower substituent group may optionally be different. In embodiments, when $R^{6A}$ is substituted, it is substituted with at least one substituent group. In embodiments, when $R^{6A}$ is substituted, it is substituted with at least one size-limited substituent group. In embodiments, when $R^{6A}$ is substituted, it is substituted with at least one lower substituent group.

In embodiments, a substituted $R^{6B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6B}$ is substituted with a plurality of groups selected from substituent groups, size-limited substituent groups, and lower substituent groups; each substituent group, size-limited substituent group, and/or lower substituent group may optionally be different. In embodiments, when $R^{6B}$ is substituted, it is substituted with at least one substituent group. In embodiments, when $R^{6B}$ is substituted, it is substituted with at least one size-limited substituent group. In embodiments, when $R^{6B}$ is substituted, it is substituted with at least one lower substituent group.

In embodiments, a substituted ring formed when $R^{6A}$ and $R^{6B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{6A}$ and $R^{6B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{6A}$ and $R^{6B}$ substituents bonded to the same nitrogen atom are joined is substituted, it is substituted with at least one substituent group. In embodiments, when the substituted ring formed when $R^{6A}$ and $R^{6B}$ substituents bonded to the same nitrogen atom are joined is substituted, it is substituted with at least one size-limited substituent group. In embodiments, when the substituted ring formed when $R^{6A}$ and $R^{6B}$ substituents bonded to the same nitrogen atom are joined is substituted, it is substituted with at least one lower substituent group.

In embodiments, a substituted $R^{6C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6C}$ is substituted with a plurality of groups selected from substituent groups, size-limited substituent groups, and lower substituent groups; each substituent group, size-limited substituent group, and/or lower substituent group may optionally be different. In embodiments, when $R^{6C}$ is substituted, it is substituted with at least one substituent group. In embodiments, when $R^{6C}$ is substituted, it is substituted with at least one size-limited substituent group. In embodiments, when $R^{6C}$ is substituted, it is substituted with at least one lower substituent group.

In embodiments, a substituted $R^{6D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6D}$ is substituted with a plurality of groups selected from substituent groups, size-limited substituent groups, and lower substituent groups; each substituent group, size-limited substituent group, and/or lower substituent group may optionally be different. In embodiments, when $R^{6D}$ is substituted, it is substituted with at least one substituent group. In embodiments, when $R^{6D}$ is substituted, it is substituted with at least one size-limited substituent group. In embodiments, when $R^{6D}$ is substituted, it is substituted with at least one lower substituent group.

In embodiments, $R^7$ is independently halogen, oxo, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two $R^7$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two $R^7$ substituents bonded to the same carbon atom may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), or substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered).

In embodiments, a substituted $R^7$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, a substituted ring formed when two adjacent $R^7$ substituents are joined (e.g., substituted heterocycloalkyl and/or substituted heteroaryl) is substituted with at least one substituent group, size-limited substituent group, or lower substituent group; wherein if the substituted ring formed when two adjacent $R^7$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two adjacent $R^7$ substituents are joined is substituted, it is substituted with at least one substituent group. In embodiments, when the substituted ring formed when two adjacent $R^7$ substituents are joined is substituted, it is substituted with at least one size-limited substituent group. In embodiments, when the substituted ring formed when two adjacent $R^7$ substituents are joined is substituted, it is substituted with at least one lower substituent group.

In embodiments, a substituted ring formed when two $R^7$ substituents bonded to the same carbon atom are joined (e.g., substituted heterocycloalkyl and/or substituted heteroaryl) is substituted with at least one substituent group, size-limited substituent group, or lower substituent group; wherein if the substituted ring formed when two $R^7$ substituents bonded to the same carbon atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two $R^7$ substituents bonded to the same carbon atom are joined is substituted, it is substituted with at least one substituent group. In embodiments, when the substituted ring formed when two $R^7$ substituents bonded to the same carbon atom are joined is substituted, it is substituted with at least one size-limited substituent group. In embodiments, when the substituted ring formed when two $R^7$ substituents bonded to the same carbon atom are joined is substituted, it is substituted with at least one lower substituent group.

In embodiments, $R^7$ is independently —F. In embodiments, $R^7$ is independently —Cl. In embodiments, $R^7$ is independently —Br. In embodiments, $R^7$ is independently —I. In embodiments, $R^7$ is independently oxo. In embodiments, $R^7$ is independently —CCl$_3$. In embodiments, $R^7$ is independently —CBr$_3$. In embodiments, $R^7$ is independently —CF$_3$. In embodiments, $R^7$ is independently —CI$_3$. In embodiments, $R^7$ is independently —CHCl$_2$. In embodiments, $R^7$ is independently —CHBr$_2$. In embodiments, $R^7$ is independently —CHF$_2$. In embodiments, R$^7$ is independently —CHI$_2$. In embodiments, R$^7$ is independently —CH$_2$Cl. In embodiments, R$^7$ is independently —CH$_2$Br. In embodiments, R$^7$ is independently —CH$_2$F. In embodiments, R$^7$ is independently —CH$_2$I. In embodiments, R$^7$ is independently —OCCl$_3$. In embodiments, R$^7$ is independently —OCF$_3$. In embodiments, R$^7$ is independently —OCBr$_3$. In embodiments, R$^7$ is independently —OCI$_3$. In embodiments, R$^7$ is independently —OCHCl$_2$. In embodiments, R$^7$ is independently —OCHBr$_2$. In embodiments, R$^7$ is independently —OCHI$_2$. In embodiments, R$^7$ is independently —OCHF$_2$. In embodiments, R$^7$ is independently —OCH$_2$Cl. In embodiments, R$^7$ is independently —OCH$_2$Br. In embodiments, R$^7$ is independently —OCH$_2$I. In embodiments, R$^7$ is independently —OCH$_2$F. In embodiments, R$^7$ is independently —CN. In embodiments, R$^7$ is independently —OH. In embodiments, R$^7$ is independently —NH$_2$. In embodiments, R$^7$ is independently —COOH. In embodiments, R$^7$ is independently —CONH$_2$. In embodiments, R$^7$ is independently —NO$_2$. In embodiments, R$^7$ is independently —SH. In embodiments, R$^7$ is independently —SeH. In embodiments, R$^7$ is independently —SO$_3$H. In embodiments, R$^7$ is independently —OSO$_3$H. In embodiments, R$^7$ is independently —SO$_2$NH$_2$. In embodiments, R$^7$ is independently —NHNH$_2$. In embodiments, R$^7$ is independently —ONH$_2$. In embodiments, R$^7$ is independently —NHC(O)NHNH$_2$. In embodiments, R$^7$ is independently —NHC(O)NH$_2$. In embodiments, R$^7$ is independently —NHSO$_2$H. In embodiments, R$^7$ is independently —NHC(O)H. In embodiments, R$^7$ is independently —NHC(O)OH. In embodiments, R$^7$ is independently —NHOH. In embodiments, R$^7$ is independently —N$_3$. In embodiments, R$^7$ is independently —SF$_5$. In embodiments, R$^7$ is independently substituted or unsubstituted alkyl. In embodiments, R$^7$ is independently an unsubstituted C$_1$-C$_4$ alkyl. In embodiments, R$^7$ is independently an unsubstituted methyl. In embodiments, R$^7$ is independently an unsubstituted ethyl. In embodiments, R$^7$ is independently an unsubstituted propyl. In embodiments, R$^7$ is independently an unsubstituted n-propyl. In embodiments, R$^7$ is independently an unsubstituted isopropyl. In embodiments, R$^7$ is independently an unsubstituted butyl. In embodiments, R$^7$ is independently an unsubstituted n-butyl. In embodiments, R$^7$ is independently an unsubstituted tert-butyl. In embodiments, R$^7$ is independently substituted or unsubstituted heteroalkyl. In embodiments, R$^7$ is independently an unsubstituted —O(C$_1$-C$_4$ alkyl). In embodiments, R$^7$ is independently an unsubstituted methoxy. In embodiments, R$^7$ is independently an unsubstituted ethoxy. In embodiments, R$^7$ is independently an unsubstituted propoxy. In embodiments, R$^7$ is independently an unsubstituted n-propoxy. In embodiments, R$^7$ is independently an unsubstituted isopropoxy. In embodiments, R$^7$ is independently an unsubstituted n-butoxy. In embodiments, R$^7$ is independently an unsubstituted tert-butoxy. In embodiments, R$^7$ is independently substituted or unsubstituted cycloalkyl. In embodiments, R$^7$ is independently substituted or unsubstituted heterocycloalkyl. In embodiments, R$^7$ is independently substituted or unsubstituted aryl. In embodiments, R$^7$ is independently a substituted or unsubstituted phenyl. In embodiments, R$^7$ is independently substituted or unsubstituted heteroaryl.

In embodiments, a substituted R$^{7A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{7A}$ is substituted with a plurality of groups selected from substituent groups, size-limited substituent groups, and lower substituent groups; each substituent group, size-limited substituent group, and/or lower substituent group may optionally be different. In embodiments, when R$^{7A}$ is substituted, it is substituted with at least one substituent group. In embodiments, when R$^{7A}$ is substituted, it is substituted with at least one size-limited substituent group. In embodiments, when R$^{7A}$ is substituted, it is substituted with at least one lower substituent group.

In embodiments, a substituted R$^{7B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{7B}$ is substituted with a plurality of groups selected from substituent groups, size-limited substituent groups, and lower substituent groups; each substituent group, size-limited substituent group, and/or lower substituent group may optionally be different. In embodiments, when R$^{7B}$ is substituted, it is substituted with at least one substituent group. In embodiments, when R$^{7B}$ is substituted, it is substituted with at least one size-limited substituent group. In embodiments, when R$^{7B}$ is substituted, it is substituted with at least one lower substituent group.

In embodiments, a substituted ring formed when R$^{7A}$ and R$^{7B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when R$^{7A}$ and R$^{7B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when R$^{7A}$ and R$^{7B}$ substituents bonded to the same nitrogen atom are joined is substituted, it is substituted with at least one substituent group. In embodiments, when the substituted ring formed when R$^{7A}$ and R$^{7B}$ substituents bonded to the same nitrogen atom are joined is substituted, it is substituted with at least one size-limited substituent group. In embodiments, when the substituted ring formed when R$^{7A}$ and R$^{7B}$ substituents bonded to the same nitrogen atom are joined is substituted, it is substituted with at least one lower substituent group.

In embodiments, a substituted R$^{7C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{7C}$ is substituted with a plurality of groups selected from substituent groups, size-limited substituent groups, and lower substituent groups; each substituent group, size-limited substituent group, and/or lower substituent group may optionally be different. In embodiments, when R$^{7C}$ is substituted, it is substituted with at least one substituent group. In embodiments, when R$^{7C}$ is substituted, it is substituted with at least one size-limited substituent group. In embodiments, when R$^{7C}$ is substituted, it is substituted with at least one lower substituent group.

In embodiments, a substituted R$^{7D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{7D}$ is substituted with a plurality of groups selected from substituent groups, size-limited substituent groups, and lower substituent groups; each substituent group, size-limited substituent group, and/or lower substituent group may optionally be different. In embodiments, when $R^{7D}$ is substituted, it is substituted with at least one substituent group. In embodiments, when $R^{7D}$ is substituted, it is substituted with at least one size-limited substituent group. In embodiments, when $R^{7D}$ is substituted, it is substituted with at least one lower substituent group.

In embodiments, $R^8$ is independently halogen, oxo, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered); two adjacent $R^8$ substituents may optionally be joined to form a substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^8$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^8$ is substituted with a plurality of groups selected from substituent groups, size-limited substituent groups, and lower substituent groups; each substituent group, size-limited substituent group, and/or lower substituent group may optionally be different. In embodiments, when $R^8$ is substituted, it is substituted with at least one substituent group. In embodiments, when $R^8$ is substituted, it is substituted with at least one size-limited substituent group. In embodiments, when $R^8$ is substituted, it is substituted with at least one lower substituent group.

In embodiments, a substituted ring formed when two adjacent $R^8$ substituents are joined (e.g., substituted heterocycloalkyl and/or substituted heteroaryl) is substituted with at least one substituent group, size-limited substituent group, or lower substituent group; wherein if the substituted ring formed when two adjacent $R^8$ substituents are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when two adjacent $R^8$ substituents are joined is substituted, it is substituted with at least one substituent group. In embodiments, when the substituted ring formed when two adjacent $R^8$ substituents are joined is substituted, it is substituted with at least one size-limited substituent group. In embodiments, when the substituted ring formed when two adjacent $R^8$ substituents are joined is substituted, it is substituted with at least one lower substituent group.

In embodiments, $R^8$ is independently —F. In embodiments, $R^8$ is independently —Cl. In embodiments, $R^8$ is independently —Br. In embodiments, $R^8$ is independently —I. In embodiments, $R^8$ is independently oxo. In embodiments, $R^8$ is independently —CCl$_3$. In embodiments, $R^8$ is independently —CBr$_3$. In embodiments, $R^8$ is independently —CF$_3$. In embodiments, $R^8$ is independently —CI$_3$. In embodiments, $R^8$ is independently —CHCl$_2$. In embodiments, $R^8$ is independently —CHBr$_2$. In embodiments, $R^8$ is independently —CHF$_2$. In embodiments, $R^8$ is independently —CHI$_2$. In embodiments, $R^8$ is independently —CH$_2$Cl. In embodiments, $R^8$ is independently —CH$_2$Br. In embodiments, $R^8$ is independently —CH$_2$F. In embodiments, $R^8$ is independently —CH$_2$I. In embodiments, $R^8$ is independently —OCCl$_3$. In embodiments, $R^8$ is independently —OCF$_3$. In embodiments, $R^8$ is independently —OCBr$_3$. In embodiments, $R^8$ is independently —OCI$_3$. In embodiments, $R^8$ is independently —OCHCl$_2$. In embodiments, $R^8$ is independently —OCHBr$_2$. In embodiments, $R^8$ is independently —OCHI$_2$. In embodiments, $R^8$ is independently —OCHF$_2$. In embodiments, $R^8$ is independently —OCH$_2$Cl. In embodiments, $R^8$ is independently —OCH$_2$Br. In embodiments, $R^8$ is independently —OCH$_2$I. In embodiments, $R^8$ is independently —OCH$_2$F. In embodiments, $R^8$ is independently —CN. In embodiments, $R^8$ is independently —OH. In embodiments, $R^8$ is independently —NH$_2$. In embodiments, $R^8$ is independently —COOH. In embodiments, $R^8$ is independently —CONH$_2$. In embodiments, $R^8$ is independently —NO$_2$. In embodiments, $R^8$ is independently —SH. In embodiments, $R^8$ is independently —SeH. In embodiments, $R^8$ is independently —SO$_3$H. In embodiments, $R^8$ is independently —OSO$_3$H. In embodiments, $R^8$ is independently —SO$_2$NH$_2$. In embodiments, $R^8$ is independently —NHNH$_2$. In embodiments, $R^8$ is independently —ONH$_2$. In embodiments, $R^8$ is independently —NHC(O)NHNH$_2$. In embodiments, $R^8$ is independently —NHC(O)NH$_2$. In embodiments, $R^8$ is independently —NHSO$_2$H. In embodiments, $R^8$ is independently —NHC(O)H. In embodiments, $R^8$ is independently —NHC(O)OH. In embodiments, $R^8$ is independently —NHOH. In embodiments, $R^8$ is independently —N$_3$. In embodiments, $R^8$ is independently —SF$_5$. In embodiments, $R^8$ is independently substituted or unsubstituted alkyl. In embodiments, $R^8$ is independently an unsubstituted $C_1$-$C_4$ alkyl. In embodiments, $R^8$ is independently an unsubstituted methyl. In embodiments, $R^8$ is independently an unsubstituted ethyl. In embodiments, $R^8$ is independently an unsubstituted propyl. In embodiments, $R^8$ is independently an unsubstituted n-propyl. In embodiments, $R^8$ is independently an unsubstituted isopropyl. In embodiments, $R^8$ is independently an unsubstituted butyl. In embodiments, $R^8$ is independently an unsubstituted n-butyl. In embodiments, $R^8$ is independently an unsubstituted tert-butyl. In embodiments, $R^8$ is independently substituted or unsubstituted heteroalkyl. In embodiments, $R^8$ is independently an unsubstituted —O($C_1$-$C_4$ alkyl). In embodiments, $R^8$ is independently an unsubstituted methoxy. In embodiments, $R^8$ is independently an unsubstituted ethoxy. In embodiments, $R^8$ is independently an unsubstituted propoxy. In embodiments, $R^8$ is independently an unsubstituted n-propoxy. In embodiments, $R^8$ is independently an unsubstituted isopropoxy. In embodiments, $R^8$ is independently an unsubstituted n-butoxy. In embodiments, $R^8$ is independently an unsubstituted tert-butoxy. In embodiments, $R^8$ is independently substituted or unsubstituted cycloalkyl. In embodiments, $R^8$ is independently substituted or unsubstituted heterocycloalkyl. In embodiments, $R^8$ is independently substituted or unsubstituted aryl. In embodiments, $R^8$ is independently a substituted or unsubstituted phenyl. In embodiments, $R^8$ is independently substituted or unsubstituted heteroaryl.

In embodiments, a substituted $R^{8A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8A}$ is substituted with a plurality of groups selected from substituent groups, size-limited substituent groups, and lower substituent groups; each substituent group, size-limited substituent group, and/or lower substituent group may optionally be different. In embodiments, when $R^{8A}$ is substituted, it is substituted with at least one substituent group. In embodiments, when $R^{8A}$ is substituted, it is substituted with at least one size-limited substituent group. In embodiments, when $R^{8A}$ is substituted, it is substituted with at least one lower substituent group.

In embodiments, a substituted $R^{8B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8B}$ is substituted with a plurality of groups selected from substituent groups, size-limited substituent groups, and lower substituent groups; each substituent group, size-limited substituent group, and/or lower substituent group may optionally be different. In embodiments, when $R^{8B}$ is substituted, it is substituted with at least one substituent group. In embodiments, when $R^{8B}$ is substituted, it is substituted with at least one size-limited substituent group. In embodiments, when $R^{8B}$ is substituted, it is substituted with at least one lower substituent group.

In embodiments, a substituted ring formed when $R^{8A}$ and $R^{8B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{8A}$ and $R^{8B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{8A}$ and $R^{8B}$ substituents bonded to the same nitrogen atom are joined is substituted, it is substituted with at least one substituent group. In embodiments, when the substituted ring formed when $R^{8A}$ and $R^{8B}$ substituents bonded to the same nitrogen atom are joined is substituted, it is substituted with at least one size-limited substituent group. In embodiments, when the substituted ring formed when $R^{8A}$ and $R^{8B}$ substituents bonded to the same nitrogen atom are joined is substituted, it is substituted with at least one lower substituent group.

In embodiments, a substituted $R^{8C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8C}$ is substituted with a plurality of groups selected from substituent groups, size-limited substituent groups, and lower substituent groups; each substituent group, size-limited substituent group, and/or lower substituent group may optionally be different. In embodiments, when $R^{8C}$ is substituted, it is substituted with at least one substituent group. In embodiments, when $R^{8C}$ is substituted, it is substituted with at least one size-limited substituent group. In embodiments, when $R^{8C}$ is substituted, it is substituted with at least one lower substituent group.

In embodiments, a substituted $R^{8D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{8D}$ is substituted with a plurality of groups selected from substituent groups, size-limited substituent groups, and lower substituent groups; each substituent group, size-limited substituent group, and/or lower substituent group may optionally be different. In embodiments, when $R^{8D}$ is substituted, it is substituted with at least one substituent group. In embodiments, when $R^{8D}$ is substituted, it is substituted with at least one size-limited substituent group. In embodiments, when $R^{8D}$ is substituted, it is substituted with at least one lower substituent group.

In embodiments, z6 is 0. In embodiments, z6 is 1. In embodiments, z6 is 2. In embodiments, z6 is 3.

In embodiments, z7 is 0. In embodiments, z7 is 1. In embodiments, z7 is 2. In embodiments, z7 is 3. In embodiments, z7 is 4. In embodiments, z7 is 5. In embodiments, z7 is 6. In embodiments, z7 is 7. In embodiments, z7 is 8. In embodiments, z7 is 9.

In embodiments, z8 is 0. In embodiments, z8 is 1. In embodiments, z8 is 2. In embodiments, z8 is 3. In embodiments, z8 is 4. In embodiments, z8 is 5. In embodiments, z8 is 6. In embodiments, z8 is 7.

In embodiments, $R^{61}$ is independently hydrogen. In embodiments, $R^{61}$ is independently —F. In embodiments, $R^{61}$ is independently —Cl. In embodiments, $R^{61}$ is independently —Br. In embodiments, $R^{61}$ is independently —I. In embodiments, $R^{61}$ is independently —$CCl_3$. In embodiments, $R^{61}$ is independently —$CBr_3$. In embodiments, $R^{61}$ is independently —$CF_3$. In embodiments, $R^{61}$ is independently —$CI_3$. In embodiments, $R^{61}$ is independently —$CHCl_2$. In embodiments, $R^{61}$ is independently —$CHBr_2$. In embodiments, $R^{61}$ is independently —$CHF_2$. In embodiments, $R^{61}$ is independently —$CHI_2$. In embodiments, $R^{61}$ is independently —$CH_2Cl$. In embodiments, $R^{61}$ is independently —$CH_2Br$. In embodiments, $R^{61}$ is independently —$CH_2F$. In embodiments, $R^{61}$ is independently —$CH_2I$. In embodiments, $R^{61}$ is independently —OCCl$_3$. In embodiments, $R^{61}$ is independently —OCF$_3$. In embodiments, $R^{61}$ is independently —OCBr$_3$. In embodiments, $R^{61}$ is independently —OCI$_3$. In embodiments, $R^{61}$ is independently —OCHCl$_2$. In embodiments, $R^{61}$ is independently —OCHBr$_2$. In embodiments, $R^{61}$ is independently —OCHI$_2$. In embodiments, $R^{61}$ is independently —OCHF$_2$. In embodiments, $R^{61}$ is independently —OCH$_2$Cl. In embodiments, $R^{61}$ is independently —OCH$_2$Br. In embodiments, $R^{61}$ is independently —OCH$_2$I. In embodiments, $R^{61}$ is independently —OCH$_2$F. In embodiments, $R^{61}$ is independently —CN. In embodiments, $R^{61}$ is independently —OH. In embodiments, $R^{61}$ is independently —NH$_2$. In embodiments, $R^{61}$ is independently —COOH. In embodiments, $R^{61}$ is independently —CONH$_2$. In embodiments, $R^{61}$ is independently —NO$_2$. In embodiments, $R^{61}$ is independently —SH. In embodiments, $R^{61}$ is independently —SeH. In embodiments, $R^{61}$ is independently —SO$_3$H. In embodiments, $R^{61}$ is independently —OSO$_3$H. In embodiments, $R^{61}$ is independently —SO$_2$NH$_2$. In embodiments, $R^{61}$ is independently —NHNH$_2$. In embodiments, $R^{61}$ is independently —ONH$_2$. In embodiments, $R^{61}$ is independently —NHC(O)NHNH$_2$. In embodiments, $R^{61}$ is independently —NHC(O)NH$_2$. In embodiments, $R^{61}$ is independently —NHSO$_2$H. In embodiments, $R^{61}$ is independently —NHC(O)H. In embodiments, $R^{61}$ is independently —NHC(O)OH. In embodiments, $R^{61}$ is independently —NHOH. In embodiments, $R^{61}$ is independently —N$_3$. In embodiments, $R^{61}$ is independently —SF$_5$. In embodiments, $R^{61}$ is independently substituted or unsubstituted heteroalkyl. In embodiments, $R^{61}$ is independently an unsubstituted —O(C$_1$-C$_4$ alkyl). In embodiments, $R^{61}$ is independently an unsubstituted methoxy. In embodiments, $R^{61}$ is independently an unsubstituted ethoxy. In embodiments, $R^{61}$ is independently an unsubstituted propoxy. In embodiments, $R^{61}$ is independently an unsubstituted n-propoxy. In embodiments, $R^{61}$ is independently an unsubstituted isopropoxy. In embodiments, $R^{61}$ is independently an unsubstituted n-butoxy. In embodiments, $R^{61}$ is independently an unsubstituted tert-butoxy.

In embodiments, a substituted $R^{61}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{61}$ is substituted with a plurality of groups selected from substituent groups, size-limited substituent groups, and lower substituent groups; each substituent group, size-limited substituent group, and/or lower substituent group may optionally be different. In embodiments, when $R^{61}$ is substituted, it is substituted with at least one substituent group. In embodiments, when $R^{61}$ is substituted, it is substituted with at least one size-limited substituent group. In embodiments, when $R^{61}$ is substituted, it is substituted with at least one lower substituent group.

In embodiments, $R^{61}$ is independently hydrogen, halogen, —OH, —NH$_2$, or unsubstituted 2 to 6 membered heteroalkyl.

In embodiments, $R^{62}$ is independently hydrogen. In embodiments, $R^{62}$ is independently —F. In embodiments, $R^{62}$ is independently —Cl. In embodiments, $R^{62}$ is independently —Br. In embodiments, $R^{62}$ is independently —I. In embodiments, $R^{62}$ is independently —CCl$_3$. In embodiments, $R^{62}$ is independently —CBr$_3$. In embodiments, $R^{62}$ is independently —CF$_3$. In embodiments, $R^{62}$ is independently —CI$_3$. In embodiments, $R^{62}$ is independently —CHCl$_2$. In embodiments, $R^{62}$ is independently —CHBr$_2$. In embodiments, $R^{62}$ is independently —CHF$_2$. In embodiments, $R^{62}$ is independently —CHI$_2$. In embodiments, $R^{62}$ is independently —CH$_2$Cl. In embodiments, $R^{62}$ is independently —CH$_2$Br. In embodiments, $R^{62}$ is independently —CH$_2$F. In embodiments, $R^{62}$ is independently —CH$_2$I. In embodiments, $R^{62}$ is independently —OCCl$_3$. In embodiments, $R^{62}$ is independently —OCF$_3$. In embodiments, $R^{62}$ is independently —OCBr$_3$. In embodiments, $R^{62}$ is independently —OCI$_3$. In embodiments, $R^{62}$ is independently —OCHCl$_2$. In embodiments, $R^{62}$ is independently —OCHBr$_2$. In embodiments, $R^{62}$ is independently —OCHI$_2$. In embodiments, $R^{62}$ is independently —OCHF$_2$. In embodiments, $R^{62}$ is independently —OCH$_2$Cl. In embodiments, $R^{62}$ is independently —OCH$_2$Br. In embodiments, $R^{62}$ is independently —OCH$_2$I. In embodiments, $R^{62}$ is independently —OCH$_2$F. In embodiments, $R^{62}$ is independently —CN. In embodiments, $R^{62}$ is independently —OH. In embodiments, $R^{62}$ is independently —NH$_2$. In embodiments, $R^{62}$ is independently —COOH. In embodiments, $R^{62}$ is independently —CONH$_2$. In embodiments, $R^{62}$ is independently —NO$_2$. In embodiments, $R^{62}$ is independently —SH. In embodiments, $R^{62}$ is independently —SeH. In embodiments, $R^{62}$ is independently —SO$_3$H. In embodiments, $R^{62}$ is independently —OSO$_3$H. In embodiments, $R^{62}$ is independently —SO$_2$NH$_2$. In embodiments, $R^{62}$ is independently —NHNH$_2$. In embodiments, $R^{62}$ is independently —ONH$_2$. In embodiments, $R^{62}$ is independently —NHC(O)NHNH$_2$. In embodiments, $R^{62}$ is independently —NHC(O)NH$_2$. In embodiments, $R^{62}$ is independently —NHSO$_2$H. In embodiments, $R^{62}$ is independently —NHC(O)H. In embodiments, $R^{62}$ is independently —NHC(O)OH. In embodiments, $R^{62}$ is independently —NHOH. In embodiments, $R^{62}$ is independently —N$_3$. In embodiments, $R^{62}$ is independently —SF$_5$. In embodiments, $R^{62}$ is independently substituted or unsubstituted alkyl. In embodiments, $R^{62}$ is independently an unsubstituted C$_1$-C$_4$ alkyl. In embodiments, $R^{62}$ is independently an unsubstituted methyl. In embodiments, $R^{62}$ is independently an unsubstituted ethyl. In embodiments, $R^{62}$ is independently an unsubstituted propyl. In embodiments, $R^{62}$ is independently an unsubstituted n-propyl. In embodiments, $R^{62}$ is independently an unsubstituted isopropyl. In embodiments, $R^{62}$ is independently an unsubstituted butyl. In embodiments, $R^{62}$ is independently an unsubstituted n-butyl. In embodiments, $R^{62}$ is independently an unsubstituted tert-butyl. In embodiments, $R^{62}$ is independently substituted or unsubstituted heteroalkyl. In embodiments, $R^{62}$ is independently an unsubstituted —O(C$_1$-C$_4$ alkyl). In embodiments, $R^{62}$ is independently an unsubstituted methoxy. In embodiments, $R^{62}$ is independently an unsubstituted ethoxy. In embodiments, $R^{62}$ is independently an unsubstituted propoxy. In embodiments, $R^{62}$ is independently an unsubstituted n-propoxy. In embodiments, $R^{62}$ is independently an unsubstituted isopropoxy. In embodiments, $R^{62}$ is independently an unsubstituted n-butoxy. In embodiments, $R^{62}$ is independently an unsubstituted tert-butoxy.

In embodiments, a substituted $R^{62}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{62}$ is substituted with a plurality of groups selected from substituent groups, size-limited substituent groups, and lower substituent groups; each substituent group, size-limited substituent group, and/or lower substituent group may optionally be different. In embodiments, when $R^{62}$ is substituted, it is substituted with at least one substituent group. In embodiments, when $R^{62}$ is substituted, it is substituted with at least one size-limited substituent group. In embodiments, when $R^{62}$ is substituted, it is substituted with at least one lower substituent group.

In embodiments, $R^{62}$ is independently hydrogen, halogen, —OH, —NH$_2$, or unsubstituted 2 to 6 membered heteroalkyl. In embodiments, $R^{62}$ is independently —OCH$_3$.

In embodiments, $R^{71}$ is independently hydrogen. In embodiments, $R^{71}$ is independently —F. In embodiments, $R^{71}$ is independently —Cl. In embodiments, $R^{71}$ is independently —Br. In embodiments, $R^{71}$ is independently —I. In embodiments, $R^{71}$ is independently —CCl$_3$. In embodiments, $R^{71}$ is independently —CBr$_3$. In embodiments, $R^{71}$ is independently —CF$_3$. In embodiments, $R^{71}$ is independently —CI$_3$. In embodiments, $R^{71}$ is independently —CHCl$_2$. In embodiments, $R^{71}$ is independently —CHBr$_2$. In embodiments, $R^{71}$ is independently —CHF$_2$. In embodiments, $R^{71}$ is independently —CHI$_2$. In embodiments, $R^{71}$ is independently —CH$_2$Cl. In embodiments, $R^{71}$ is independently —CH$_2$Br. In embodiments, $R^{71}$ is independently —CH$_2$F. In embodiments, $R^{71}$ is independently —CH$_2$I. In embodiments, $R^{71}$ is independently —OCCl$_3$. In embodiments, $R^{71}$ is independently —OCF$_3$. In embodiments, $R^{71}$ is independently —OCBr$_3$. In embodiments, $R^{71}$ is independently —OCI$_3$. In embodiments, $R^{71}$ is independently —OCHCl$_2$. In embodiments, $R^{71}$ is independently —OCHBr$_2$. In embodiments, $R^{71}$ is independently —OCHI$_2$. In embodiments, $R^{71}$ is independently —OCHF$_2$. In embodiments, $R^{71}$ is independently —OCH$_2$Cl. In embodiments, $R^{71}$ is independently —OCH$_2$Br. In embodiments, $R^{71}$ is independently —OCH$_2$I. In embodiments, $R^{71}$ is independently —OCH$_2$F. In embodiments, $R^{71}$ is independently —CN. In embodiments, $R^{71}$ is independently —OH. In embodiments, $R^{71}$ is independently —NH$_2$. In embodiments, $R^{71}$ is independently —COOH. In embodiments, $R^{71}$ is independently —CONH$_2$. In embodiments, $R^{71}$ is independently —NO$_2$. In embodiments, $R^{71}$ is independently —SH. In embodiments, $R^{71}$ is independently —SeH. In embodiments, $R^{71}$ is independently —SO$_3$H. In embodiments, $R^{71}$ is independently —OSO$_3$H. In embodiments, $R^{71}$ is independently —SO$_2$NH$_2$. In embodiments, $R^{71}$ is independently —NHNH$_2$. In embodiments, $R^{71}$ is independently —ONH$_2$. In embodiments, $R^{71}$ is independently —NHC(O)NHNH$_2$. In embodiments, $R^{71}$ is independently —NHC(O)NH$_2$. In embodiments, $R^{71}$ is independently —NHSO$_2$H. In embodiments, $R^{71}$ is independently —NHC(O)H. In embodiments, $R^{71}$ is independently —NHC(O)OH. In embodiments, $R^{71}$ is independently —NHOH. In embodiments, $R^{71}$ is independently —N$_3$. In embodiments, $R^{71}$ is independently —SF$_5$. In embodiments, $R^{71}$ is independently substituted or unsubstituted alkyl. In embodiments, $R^{71}$ is independently an unsubstituted $C_1$-$C_4$ alkyl. In embodiments, $R^{71}$ is independently an unsubstituted methyl. In embodiments, $R^{71}$ is independently an unsubstituted ethyl. In embodiments, $R^{71}$ is independently an unsubstituted propyl. In embodiments, $R^{71}$ is independently an unsubstituted n-propyl. In embodiments, $R^{71}$ is independently an unsubstituted isopropyl. In embodiments, $R^{71}$ is independently an unsubstituted butyl. In embodiments, $R^{71}$ is independently an unsubstituted n-butyl. In embodiments, $R^{71}$ is independently an unsubstituted tert-butyl. In embodiments, $R^{71}$ is independently substituted or unsubstituted heteroalkyl. In embodiments, $R^{71}$ is independently an unsubstituted —O($C_1$-$C_4$ alkyl). In embodiments, $R^{71}$ is independently an unsubstituted methoxy. In embodiments, $R^{71}$ is independently an unsubstituted ethoxy. In embodiments, $R^{71}$ is independently an unsubstituted propoxy. In embodiments, $R^{71}$ is independently an unsubstituted n-propoxy. In embodiments, $R^{71}$ is independently an unsubstituted isopropoxy. In embodiments, $R^{71}$ is independently an unsubstituted n-butoxy. In embodiments, $R^{71}$ is independently an unsubstituted tert-butoxy. In embodiments, $R^{71}$ is independently substituted or unsubstituted cycloalkyl. In embodiments, $R^{71}$ is independently substituted or unsubstituted heterocycloalkyl. In embodiments, $R^{71}$ is independently substituted or unsubstituted aryl. In embodiments, $R^{71}$ is independently a substituted or unsubstituted $C_6$-$C_{10}$ aryl. In embodiments, $R^{71}$ is independently an unsubstituted $C_6$-$C_{10}$ aryl. In embodiments, $R^{71}$ is independently a substituted or unsubstituted phenyl. In embodiments, $R^{71}$ is independently an unsubstituted phenyl. In embodiments, $R^{71}$ is independently substituted or unsubstituted heteroaryl.

In embodiments, a substituted $R^{71}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{71}$ is substituted with a plurality of groups selected from substituent groups, size-limited substituent groups, and lower substituent groups; each substituent group, size-limited substituent group, and/or lower substituent group may optionally be different. In embodiments, when $R^{71}$ is substituted, it is substituted with at least one substituent group. In embodiments, when $R^{71}$ is substituted, it is substituted with at least one size-limited substituent group. In embodiments, when $R^{71}$ is substituted, it is substituted with at least one lower substituent group.

In embodiments, $R^{71}$ is independently —OH, —NH$_2$, unsubstituted $C_1$-$C_4$ alkyl, unsubstituted 2 to 6 membered heteroalkyl, unsubstituted $C_3$-$C_5$ cycloalkyl, unsubstituted 3 to 8 membered heterocycloalkyl, unsubstituted $C_6$-$C_{10}$ aryl, or unsubstituted 5 to 10 membered heteroaryl.

In embodiments, $R^{72}$ is independently hydrogen or unsubstituted $C_1$-$C_4$ alkyl. In embodiments, $R^{72}$ is independently hydrogen. In embodiments, $R^{72}$ is independently an unsubstituted $C_1$-$C_4$ alkyl. In embodiments, $R^{72}$ is independently an unsubstituted methyl. In embodiments, $R^{72}$ is independently an unsubstituted ethyl. In embodiments, $R^{72}$ is independently an unsubstituted propyl. In embodiments, $R^{72}$ is independently an unsubstituted n-propyl. In embodiments, $R^{72}$ is independently an unsubstituted isopropyl. In embodiments, $R^{72}$ is independently an unsubstituted butyl. In embodiments, $R^{72}$ is independently an unsubstituted n-butyl. In embodiments, $R^{72}$ is independently an unsubstituted tert-butyl.

In embodiments, a substituted $R^{72}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{72}$ is substituted with a plurality of groups selected from substituent groups, size-limited substituent groups, and lower substituent groups; each substituent group, size-limited substituent group, and/or lower substituent group may optionally be different. In embodiments, when $R^{72}$ is substituted, it is substituted with at least one substituent group. In embodiments, when $R^{72}$ is substituted, it is substituted with at least one size-limited substituent group. In embodiments, when $R^{72}$ is substituted, it is substituted with at least one lower substituent group.

In embodiments, $R^{73}$ is independently hydrogen or unsubstituted $C_1$-$C_4$ alkyl. In embodiments, $R^{73}$ is independently hydrogen. In embodiments, $R^{73}$ is independently an unsubstituted $C_1$-$C_4$ alkyl. In embodiments, $R^{73}$ is independently an unsubstituted methyl. In embodiments, $R^{73}$ is independently an unsubstituted ethyl. In embodiments, $R^{73}$ is independently an unsubstituted propyl. In embodiments, $R^{73}$ is independently an unsubstituted n-propyl. In embodiments, $R^{73}$ is independently an unsubstituted isopropyl. In embodiments, $R^{73}$ is independently an unsubstituted butyl. In embodiments, $R^{73}$ is independently an unsubstituted n-butyl. In embodiments, $R^{73}$ is independently an unsubstituted tert-butyl.

In embodiments, a substituted $R^{73}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{73}$ is substituted with a plurality of groups selected from substituent groups, size-limited substituent groups, and lower substituent groups; each substituent group, size-limited substituent group, and/or lower substituent group may optionally be different. In embodiments, when $R^{73}$ is substituted, it is substituted with at least one substituent group. In embodiments, when $R^{73}$ is substituted, it is substituted with at least one size-limited substituent group. In embodiments, when $R^{73}$ is substituted, it is substituted with at least one lower substituent group.

In embodiments, when $R^1$ is substituted, $R^1$ is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^{1A}$ is substituted, $R^{1A}$ is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A}$, $R^{1A.1}$, $R^{1A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, and $R^{1A.3}$, respectively.

In embodiments, when $R^{1B}$ is substituted, $R^{1B}$ is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B}$, $R^{1B.1}$, $R^{1B.2}$, and $R^{1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$, respectively.

In embodiments, when $R^{1A}$ and $R^{1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A.1}$, $R^{1A.2}$, and $R^{1A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{1A.1}$, $R^{1A.2}$, and $R^{1A.3}$ respectively.

In embodiments, when $R^{1A}$ and $R^{1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B.1}$, $R^{1B.2}$, and $R^{1B.3}$ have values corresponding to the values of $R^{WW.1}$, $R^{WW.2}$ and $R^{WW.3}$, respectively, as explained in the definitions section above in the description of "first substituent group(s)", wherein $R^{WW.1}$, $R^{WW.2}$, and $R^{WW.3}$ correspond to $R^{1B.1}$, $R^{1B.2}$, and $R^{1B.3}$, respectively.

In embodiments, when $R^{1C}$ is substituted, $R^{1C}$ is substituted with one or more first substituent groups denoted by $R^{1C.1}$ as explained in the definitions section above in the description of "first substituent group(s)". In embodiments, when an $R^{1C.1}$ substituent group is substituted, the $R^{1C.1}$ substituent group is substituted with one or more second substituent groups denoted by $R^{1C.2}$ as explained in the definitions section above in the description of "first substituent group(s)". In embodiments, when an $R^{1C.2}$ substituent group is substituted, the $R^{1C.2}$ substituent group is substituted with one or more third substituent groups denoted by $R^{1C.3}$ as explained in the definitions section above in the description of "first substituent group(s)". In the above embodiments, $R^{1C}$, $R^{1C.1}$, $R^{1C.2}$, and $R^{1C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1C}$, $R^{1C.1}$, $R^{1C.2}$, and $R^{1C.3}$, respectively.

In embodiments, when RD is substituted, RD is substituted with one or more first substituent groups denoted by $R^{1D}$ as explained in the definitions section above in the description of "first substituent group(s)". In embodiments, when an $R^{1D.1}$ substituent group is substituted, the $R^{1D.1}$ substituent group is substituted with one or more second substituent groups denoted by $R^{1D.2}$ as explained in the definitions section above in the description of "first substituent group(s)". In embodiments, when an $R^{1D.2}$ substituent group is substituted, the $R^{1D.2}$ substituent group is substituted with one or more third substituent groups denoted by $R^{1D.3}$ as explained in the definitions section above in the description of "first substituent group(s)". In the above embodiments, $R^{1D}$, $R^{1D.1}$, $R^{1D.2}$, and $R^{1D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1D}$, $R^{1D.1}$, $R^{1D.2}$, and $R^{1D.3}$, respectively.

In embodiments, when $R^2$ is substituted, $R^2$ is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^{2A}$ is substituted, $R^{2A}$ is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^{2B}$ is substituted, $R^{2B}$ is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}$, $R^{2B.1}$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A.1}$, $R^{2A.2}$, and $R^{2A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{2A.1}$, $R^{2A.2}$, and $R^{2A.3}$ respectively.

In embodiments, when $R^{2A}$ and $R^{2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B.1}$, $R^{2B.2}$, and $R^{2B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{2B.1}$, $R^{2B.2}$, and $R^{2B.3}$, respectively.

In embodiments, when $R^{2C}$ is substituted, $R^{2C}$ is substituted with one or more first substituent groups denoted by $R^{2C.1}$ as explained in the definitions section above in the description of "first substituent group(s)". In embodiments, when an $R^{2C.1}$ substituent group is substituted, the $R^{2C.1}$ substituent group is substituted with one or more second substituent groups denoted by $R^{2C.2}$ as explained in the definitions section above in the description of "first substituent group(s)". In embodiments, when an $R^{2C.2}$ substituent group is substituted, the $R^{2C.2}$ substituent group is substituted with one or more third substituent groups denoted by $R^{2C.3}$ as explained in the definitions section above in the description of "first substituent group(s)". In the above embodiments, $R^{2C}$, $R^{2C.1}$, $R^{2C.2}$, and $R^{2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2C}$, $R^{2C.1}$, $R^{2C.2}$, and $R^{2C.3}$, respectively.

In embodiments, when $R^{2D}$ is substituted, $R^{2D}$ is substituted with one or more first substituent groups denoted by $R^{2D.1}$ as explained in the definitions section above in the description of "first substituent group(s)". In embodiments, when an $R^{2D.1}$ substituent group is substituted, the $R^{2D.1}$ substituent group is substituted with one or more second substituent groups denoted by $R^{2D.2}$ as explained in the definitions section above in the description of "first substituent group(s)". In embodiments, when an $R^{2D.2}$ substituent group is substituted, the $R^{2D.2}$ substituent group is substituted with one or more third substituent groups denoted by $R^{2D.3}$ as explained in the definitions section above in the description of "first substituent group(s)". In the above embodiments, $R^{2D}$, $R^{2D.1}$, $R^{2D.2}$, and $R^{2D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2D}$, $R^{2D.1}$, $R^{2D.2}$, and $R^{2D.3}$, respectively.

In embodiments, when $R^3$ is substituted, $R^3$ is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.2}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$, and $R^{3.3}$, respectively.

In embodiments, when two adjacent $R^3$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.2}$ substituent group is substituted with one or more third substituent groups denoted by $R^{3.3}$ as explained in the definitions section above in the description of "first substituent group(s)". In the above embodiments, $R^{3.1}$, $R^{3.2}$, and $R^{3.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{3.1}$, $R^{3.2}$, and $R^{3.3}$, respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$, and $R^{4.3}$, respectively.

In embodiments, when $R^5$ is substituted, $R^5$ is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group(s)". In embodiments, when an $R^{5.2}$ substituent group is substituted, the $R^{5.2}$ substituent group is substituted with one or more third substituent groups denoted by $R^{53}$ as explained in the definitions section above in the description of "first substituent group(s)". In the above embodiments, $R^5$, $R^{5.1}$, $R^{5.2}$, and $R^{5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$, and $R^{5.3}$, respectively.

In embodiments, when $R^6$ is substituted, $R^6$ is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^{6.2}$ as explained in the definitions section above in the description of "first substituent group(s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^6$, $R^{6.1}$, $R^{6.2}$, and $R^{6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^6$, $R^{6.1}$, $R^{6.2}$, and $R^{6.3}$, respectively.

In embodiments, when two adjacent $R^6$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^{6.2}$ as explained in the definitions section above in the description of "first substituent group(s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^6$, $R^{6.1}$, $R^{6.2}$, and $R^{6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^6$, $R^{6.1}$, $R^{6.2}$, and $R^{6.3}$, respectively.

In embodiments, when $R^{6A}$ is substituted, $R^{6A}$ is substituted with one or more first substituent groups denoted by $R^{6A.1}$ as explained in the definitions section above in the description of "first substituent group(s)". In embodiments, when an $R^{6A.1}$ substituent group is substituted, the $R^{6A.1}$ substituent group is substituted with one or more second substituent groups denoted by $R^{6A.2}$ as explained in the definitions section above in the description of "first substituent group(s)". In embodiments, when an $R^{6A.2}$ substituent group is substituted, the $R^{6A.2}$ substituent group is substituted with one or more third substituent groups denoted by $R^{6A.3}$ as explained in the definitions section above in the description of "first substituent group(s)". In the above embodiments, $R^{6A}$, $R^{6A.1}$, $R^{6A.2}$, and $R^{6A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6A}$, $R^{6A.1}$, $R^{6A.2}$, and $R^{6A.3}$, respectively.

In embodiments, when $R^{6B}$ is substituted, $R^{6B}$ is substituted with one or more first substituent groups denoted by $R^{6B.1}$ as explained in the definitions section above in the description of "first substituent group(s)". In embodiments, when an $R^{6B.1}$ substituent group is substituted, the $R^{6B.1}$ substituent group is substituted with one or more second substituent groups denoted by $R^{6B.2}$ as explained in the definitions section above in the description of "first substituent group(s)". In embodiments, when an $R^{6B.2}$ substituent group is substituted, the $R^{6B.2}$ substituent group is substituted with one or more third substituent groups denoted by $R^{6B.3}$ as explained in the definitions section above in the description of "first substituent group(s)". In the above embodiments, $R^{6B}$, $R^{6B.1}$, $R^{6B.2}$, and $R^{6B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6B}$, $R^{6B.1}$, $R^{6B.2}$, and $R^{6B.3}$, respectively.

In embodiments, when $R^{6A}$ and $R^{6B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{6A.1}$ as explained in the definitions section above in the description of "first substituent group(s)". In embodiments, when an $R^{6A.1}$ substituent group is substituted, the $R^{6A.1}$ substituent group is substituted with one or more second substituent groups denoted by $R^{6A.2}$ as explained in the definitions section above in the description of "first substituent group(s)". In embodiments, when an $R^{6A.2}$ substituent group is substituted, the $R^{6A.2}$ substituent group is substituted with one or more third substituent groups denoted by $R^{6A.3}$ as explained in the definitions section above in the description of "first substituent group(s)". In the above embodiments, $R^{6A.1}$, $R^{6A.2}$, and $R^{6A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{6A.1}$, $R^{6A.2}$, and $R^{6A.3}$ respectively.

In embodiments, when $R^{6A}$ and $R^{6B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{6B.1}$ as explained in the definitions section above in the description of "first substituent group(s)". In embodiments, when an $R^{6B.1}$ substituent group is substituted, the $R^{6B.1}$ substituent group is substituted with one or more second substituent groups denoted by $R^{6B.2}$ as explained in the definitions section above in the description of "first substituent group(s)". In embodiments, when an $R^{6B.2}$ substituent group is substituted, the $R^{6B.2}$ substituent group is substituted with one or more third substituent groups denoted by $R^{6B.3}$ as explained in the definitions section above in the description of "first substituent group(s)". In the above embodiments, $R^{6B.1}$, $R^{6B.2}$, and $R^{6B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{6B.1}$, $R^{6B.2}$, and $R^{6B.3}$, respectively.

In embodiments, when $R^{6C}$ is substituted, $R^{6C}$ is substituted with one or more first substituent groups denoted by $R^{6C.1}$ as explained in the definitions section above in the description of "first substituent group(s)". In embodiments, when an $R^{6C.1}$ substituent group is substituted, the $R^{6C.1}$ substituent group is substituted with one or more second substituent groups denoted by $R^{6C.2}$ as explained in the definitions section above in the description of "first substituent group(s)". In embodiments, when an $R^{6C.2}$ substituent group is substituted, the $R^{6C.2}$ substituent group is substituted with one or more third substituent groups denoted by $R^{6C.3}$ as explained in the definitions section above in the description of "first substituent group(s)". In the above embodiments, $R^{6C}$, $R^{6C.1}$, $R^{6C.2}$, and $R^{6C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6C}$, $R^{6C.1}$, $R^{6C.2}$, and $R^{6C.3}$, respectively.

In embodiments, when $R^{6D}$ is substituted, $R^{6D}$ is substituted with one or more first substituent groups denoted by $R^{6D.1}$ as explained in the definitions section above in the description of "first substituent group(s)". In embodiments, when an $R^{6D.1}$ substituent group is substituted, the $R^{6D.1}$ substituent group is substituted with one or more second substituent groups denoted by $R^{6D.2}$ as explained in the definitions section above in the description of "first substituent group(s)". In embodiments, when an $R^{6D.2}$ substituent group is substituted, the $R^{6D.2}$ substituent group is substituted with one or more third substituent groups denoted by $R^{6D.3}$ as explained in the definitions section above in the description of "first substituent group(s)". In the above embodiments, $R^{6D}$, $R^{6D.1}$, $R^{6D.2}$, and $R^{6D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{6D}$, $R^{6D.1}$, $R^{6D.2}$, and $R^{6D.3}$, respectively.

In embodiments, when $R^7$ is substituted, $R^7$ is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^7$, $R^{7.1}$, $R^{7.2}$, and $R^{7.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^7$, $R^{7.1}$, $R^{7.2}$, and $R^{7.3}$, respectively.

In embodiments, when two adjacent $R^7$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^7$, $R^{7.1}$, $R^{7.2}$, and $R^{7.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^7$, $R^{7.1}$, $R^{7.2}$, and $R^{7.3}$, respectively.

In embodiments, when two $R^7$ substituents bonded to the same carbon atom are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^7$, $R^{7.1}$, $R^{7.2}$, and $R^{7.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^7$, $R^{7.1}$, $R^{7.2}$, and $R^{7.3}$, respectively.

In embodiments, when $R^{7A}$ is substituted, $R^{7A}$ is substituted with one or more first substituent groups denoted by $R^{7A.1}$ as explained in the definitions section above in the description of "first substituent group(s)". In embodiments, when an $R^{7A.1}$ substituent group is substituted, the $R^{7A.1}$ substituent group is substituted with one or more second substituent groups denoted by $R^{7A.2}$ as explained in the definitions section above in the description of "first substituent group(s)". In embodiments, when an $R^{7A.2}$ substituent group is substituted, the $R^{7A.2}$ substituent group is substituted with one or more third substituent groups denoted by $R^{7A.3}$ as explained in the definitions section above in the description of "first substituent group(s)". In the above embodiments, $R^{7A}$, $R^{7A.1}$, $R^{7A.2}$, and $R^{7A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7A}$, $R^{7A.1}$, $R^{7A.2}$, and $R^{7A.3}$, respectively.

In embodiments, when $R^{7B}$ is substituted, $R^{7B}$ is substituted with one or more first substituent groups denoted by $R^{7B.1}$ as explained in the definitions section above in the description of "first substituent group(s)". In embodiments, when an $R^{7B.1}$ substituent group is substituted, the $R^{7B.1}$ substituent group is substituted with one or more second substituent groups denoted by $R^{7B.2}$ as explained in the definitions section above in the description of "first substituent group(s)". In embodiments, when an $R^{7B.2}$ substituent group is substituted, the $R^{7B.2}$ substituent group is substituted with one or more third substituent groups denoted by $R^{7B.3}$ as explained in the definitions section above in the description of "first substituent group(s)". In the above embodiments, $R^{7B}$, $R^{7B.1}$, $R^{7B.2}$, and $R^{7B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7B}$, $R^{7B.1}$, $R^{7B.2}$, and $R^{7B.3}$, respectively.

In embodiments, when $R^{7A}$ and $R^{7B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{7A.1}$ as explained in the definitions section above in the description of "first substituent group(s)". In embodiments, when an $R^{7A.1}$ substituent group is substituted, the $R^{7A.1}$ substituent group is substituted with one or more second substituent groups denoted by $R^{7A.2}$ as explained in the definitions section above in the description of "first substituent group(s)". In embodiments, when an $R^{7A.2}$ substituent group is substituted, the $R^{7A.2}$ substituent group is substituted with one or more third substituent groups denoted by $R^{7A.3}$ as explained in the definitions section above in the description of "first substituent group(s)". In the above embodiments, $R^{7A.1}$, $R^{7A.2}$, and $R^{7A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{7A.1}$, $R^{7A.2}$, and $R^{7A.3}$, respectively.

In embodiments, when $R^{7A}$ and $R^{7B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{7B.1}$ as explained in the definitions section above in the description of "first substituent group(s)". In embodiments, when an $R^{7B.1}$ substituent group is substituted, the $R^{7B.1}$ substituent group is substituted with one or more second substituent groups denoted by $R^{7B.2}$ as explained in the definitions section above in the description of "first substituent group(s)". In embodiments, when an $R^{7B.2}$ substituent group is substituted, the $R^{7B.2}$ substituent group is substituted with one or more third substituent groups denoted by $R^{7B.3}$ as explained in the definitions section above in the description of "first substituent group(s)". In the above embodiments, $R^{7B.1}$, $R^{7B.2}$, and $R^{7B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{7B.1}$, $R^{7B.2}$, and $R^{7B.3}$, respectively.

In embodiments, when $R^{7C}$ is substituted, $R^{7C}$ is substituted with one or more first substituent groups denoted by $R^{7C.1}$ as explained in the definitions section above in the description of "first substituent group(s)". In embodiments, when an $R^{7C.1}$ substituent group is substituted, the $R^{7C.1}$ substituent group is substituted with one or more second substituent groups denoted by $R^{7C.2}$ as explained in the definitions section above in the description of "first substituent group(s)". In embodiments, when an $R^{7C.2}$ substituent group is substituted, the $R^{7C.2}$ substituent group is substituted with one or more third substituent groups denoted by $R^{7C.3}$ as explained in the definitions section above in the description of "first substituent group(s)". In the above embodiments, $R^{7C}$, $R^{7C.1}$, $R^{7C.2}$, and $R^{7C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7C}$, $R^{7C.1}$, $R^{7C.2}$, and $R^{7C.3}$, respectively.

In embodiments, when $R^{7D}$ is substituted, $R^{7D}$ is substituted with one or more first substituent groups denoted by $R^{7D.1}$ as explained in the definitions section above in the description of "first substituent group(s)". In embodiments, when an $R^{7D.1}$ substituent group is substituted, the $R^{7D.1}$ substituent group is substituted with one or more second substituent groups denoted by $R^{7D.2}$ as explained in the definitions section above in the description of "first substituent group(s)". In embodiments, when an $R^{7D.2}$ substituent group is substituted, the $R^{7D.2}$ substituent group is substituted with one or more third substituent groups denoted by $R^{7D.3}$ as explained in the definitions section above in the description of "first substituent group(s)". In the above embodiments, $R^{7D}$, $R^{7D.1}$, $R^{7D.2}$, and $R^{7D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7D}$, $R^{7D.1}$, $R^{7D.2}$, and $R^{7D.3}$, respectively.

In embodiments, when $R^8$ is substituted, $R^8$ is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^{8.2}$ as explained in the definitions section above in the description of "first substituent group(s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^8$, $R^{8.1}$, $R^{8.2}$, and $R^{8.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^8$, $R^{8.1}$, $R^{8.2}$, and $R^{8.3}$, respectively.

In embodiments, when two adjacent $R^8$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^{8.2}$ as explained in the definitions section above in the description of "first substituent group(s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^8$, $R^{8.1}$, $R^{8.2}$, and $R^{8.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^8$, $R^{8.1}$, $R^{8.2}$, and $R^{8.3}$, respectively.

In embodiments, when $R^{8A}$ is substituted, $R^{8A}$ is substituted with one or more first substituent groups denoted by $R^{8A.1}$ as explained in the definitions section above in the description of "first substituent group(s)". In embodiments, when an $R^{8A.1}$ substituent group is substituted, the $R^{8A.1}$ substituent group is substituted with one or more second substituent groups denoted by $R^{8A.2}$ as explained in the definitions section above in the description of "first substituent group(s)". In embodiments, when an $R^{8A.2}$ substituent group is substituted, the $R^{8A.2}$ substituent group is substituted with one or more third substituent groups denoted by $R^{8A.3}$ as explained in the definitions section above in the description of "first substituent group(s)". In the above embodiments, $R^{8A}$, $R^{8A.1}$, $R^{8A.2}$, and $R^{8A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8A}$, $R^{8A.1}$, $R^{8A.2}$, and $R^{8A.3}$, respectively.

In embodiments, when $R^{8B}$ is substituted, $R^{8B}$ is substituted with one or more first substituent groups denoted by $R^{8B.1}$ as explained in the definitions section above in the description of "first substituent group(s)". In embodiments, when an $R^{8B.1}$ substituent group is substituted, the $R^{8B.1}$ substituent group is substituted with one or more second substituent groups denoted by $R^{8B.2}$ as explained in the definitions section above in the description of "first substituent group(s)". In embodiments, when an $R^{8B.2}$ substituent group is substituted, the $R^{8B.2}$ substituent group is substituted with one or more third substituent groups denoted by $R^{8B.3}$ as explained in the definitions section above in the description of "first substituent group(s)". In the above embodiments, $R^{8B}$, $R^{8B.1}$, $R^{8B.2}$, and $R^{8B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8B}$, $R^{8B.1}$, $R^{8B.2}$, and $R^{8B.3}$, respectively.

In embodiments, when $R^{8A}$ and $R^{8B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{8A.1}$ as explained in the definitions section above in the description of "first substituent group(s)". In embodiments, when an $R^{8A.1}$ substituent group is substituted, the $R^{8A.1}$ substituent group is substituted with one or more second substituent groups denoted by $R^{8A.2}$ as explained in the definitions section above in the description of "first substituent group(s)". In embodiments, when an $R^{8A.2}$ substituent group is substituted, the $R^{8A.2}$ substituent group is substituted with one or more third substituent groups denoted by $R^{8A.3}$ as explained in the definitions section above in the description of "first substituent group(s)". In the above embodiments, $R^{8A.1}$, $R^{8A.2}$, and $R^{8A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{8A.1}$, $R^{8A.2}$, and $R^{8A.3}$ respectively.

In embodiments, when $R^{8A}$ and $R^{8B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{8B.1}$ as explained in the definitions section above in the description of "first substituent group(s)". In embodiments, when an $R^{8B.1}$ substituent group is substituted, the $R^{8B.1}$ substituent group is substituted with one or more second substituent groups denoted by $R^{8B.2}$ as explained in the definitions section above in the description of "first substituent group(s)". In embodiments, when an $R^{8B.2}$ substituent group is substituted, the $R^{8B.2}$ substituent group is substituted with one or more third substituent groups denoted by $R^{8B.3}$ as explained in the definitions section above in the description of "first substituent group(s)". In the above embodiments, $R^{8B.1}$, $R^{8B.2}$, and $R^{8B.3}$ have values corresponding to the values of $R^{WW.1}$, $R^{WW.2}$ and $R^{WW.3}$, respectively, as explained in the definitions section above in the description of "first substituent group(s)", wherein $R^{WW.1}$, $R^{WW.2}$, and $R^{WW.3}$ correspond to $R^{8B.1}$, $R^{8B.2}$, and $R^{8B.3}$ respectively.

In embodiments, when $R^{8C}$ is substituted, $R^{8C}$ is substituted with one or more first substituent groups denoted by $R^{8C.1}$ as explained in the definitions section above in the description of "first substituent group(s)". In embodiments, when an $R^{8C.1}$ substituent group is substituted, the $R^{8C.1}$ substituent group is substituted with one or more second substituent groups denoted by $R^{8C.2}$ as explained in the definitions section above in the description of "first substituent group(s)". In embodiments, when an $R^{8C.2}$ substituent group is substituted, the $R^{8C.2}$ substituent group is substituted with one or more third substituent groups denoted by $R^{8C.3}$ as explained in the definitions section above in the description of "first substituent group(s)". In the above embodiments, $R^{8C}$, $R^{8C.1}$, $R^{8C.2}$, and $R^{8C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8C}$, $R^{8C.1}$, $R^{8C.2}$, and $R^{8C.3}$, respectively.

In embodiments, when $R^{8D}$ is substituted, $R^{8D}$ is substituted with one or more first substituent groups denoted by $R^{8D.1}$ as explained in the definitions section above in the description of "first substituent group(s)". In embodiments, when an $R^{8D.1}$ substituent group is substituted, the $R^{8D.1}$ substituent group is substituted with one or more second substituent groups denoted by $R^{8D.2}$ as explained in the definitions section above in the description of "first substituent group(s)". In embodiments, when an $R^{8D.2}$ substituent group is substituted, the $R^{8D.2}$ substituent group is substituted with one or more third substituent groups denoted by $R^{8D.3}$ as explained in the definitions section above in the description of "first substituent group(s)". In the above embodiments, $R^{8D}$, $R^{8D.1}$, $R^{8D.2}$, and $R^{8D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8D}$, $R^{8D.1}$, $R^{8D.2}$, and $R^{8D.3}$, respectively.

In embodiments, when $R^{10}$ is substituted, $R^{10}$ is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10}$, $R^{10.1}$, $R^{10.2}$, and $R^{10.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, when two adjacent $R^{10}$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10}$, $R^{10.1}$, $R^{10.2}$, and $R^{10.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, when $R^{10A}$ is substituted, $R^{10A}$ is substituted with one or more first substituent groups denoted by $R^{10A.1}$ as explained in the definitions section above in the description of "first substituent group(s)". In embodiments, when an $R^{10A.1}$ substituent group is substituted, the $R^{10A.1}$ substituent group is substituted with one or more second substituent groups denoted by $R^{10A.2}$ as explained in the definitions section above in the description of "first substituent group(s)". In embodiments, when an $R^{10A.2}$ substituent group is substituted, the $R^{10A.2}$ substituent group is substituted with one or more third substituent groups denoted by $R^{10A.3}$ as explained in the definitions section above in the description of "first substituent group(s)". In the above embodiments, $R^{10A}$, $R^{10A.1}$, $R^{10A.2}$, and $R^{10A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10A}$, $R^{10A.1}$, $R^{10A.2}$, and $R^{10A.3}$, respectively.

In embodiments, when $R^{10B}$ is substituted, $R^{10B}$ is substituted with one or more first substituent groups denoted by $R^{10B.1}$ as explained in the definitions section above in the description of "first substituent group(s)". In embodiments, when an $R^{10B.1}$ substituent group is substituted, the $R^{10B.1}$ substituent group is substituted with one or more second substituent groups denoted by $R^{10B.2}$ as explained in the definitions section above in the description of "first substituent group(s)". In embodiments, when an $R^{10B.2}$ substituent group is substituted, the $R^{10B.2}$ substituent group is substituted with one or more third substituent groups denoted by $R^{10B.3}$ as explained in the definitions section above in the description of "first substituent group(s)". In the above embodiments, $R^{10B}$, $R^{10B.1}$, $R^{10B.2}$, and $R^{10B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10B}$, $R^{10B.1}$, $R^{10B.2}$, and $R^{10B.3}$ respectively.

In embodiments, when $R^{10A}$ and $R^{10B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10A.1}$ as explained in the definitions section above in the description of "first substituent group(s)". In embodiments, when an $R^{10A.1}$ substituent group is substituted, the $R^{10A.1}$ substituent group is substituted with one or more second substituent groups denoted by $R^{10A.2}$ as explained in the definitions section above in the description of "first substituent group(s)". In embodiments, when an $R^{10A.2}$ substituent group is substituted, the $R^{10A.2}$ substituent group is substituted with one or more third substituent groups denoted by $R^{10A.3}$ as explained in the definitions section above in the description of "first substituent group(s)". In the above embodiments, $R^{10A.1}$, $R^{10A.2}$, and $R^{10A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10A.1}$, $R^{10A.2}$, and $R^{10A.3}$, respectively.

In embodiments, when $R^{10A}$ and $R^{10B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10B}$ as explained in the definitions section above in the description of "first substituent group(s)". In embodiments, when an $R^{10B.1}$ substituent group is substituted, the $R^{10B.1}$ substituent group is substituted with one or more second substituent groups denoted by $R^{1B.2}$ as explained in the definitions section above in the description of "first substituent group(s)". In embodiments, when an $R^{10B.2}$ substituent group is substituted, the $R^{10B.2}$ substituent group is substituted with one or more third substituent groups denoted by $R^{10B.3}$ as explained in the definitions section above in the description of "first substituent group(s)". In the above embodiments, $R^{10B.1}$, $R^{10B.2}$, and $R^{10B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10B.1}$, $R^{10B.2}$, and $R^{10B.3}$, respectively.

In embodiments, when $R^{10C}$ is substituted, $R^{10C}$ is substituted with one or more first substituent groups denoted by $R^{10C.1}$ as explained in the definitions section above in the description of "first substituent group(s)". In embodiments, when an $R^{10C.1}$ substituent group is substituted, the $R^{10C.1}$ substituent group is substituted with one or more second substituent groups denoted by $R^{10C.2}$ as explained in the definitions section above in the description of "first substituent group(s)". In embodiments, when an $R^{10C.2}$ substituent group is substituted, the $R^{10C.2}$ substituent group is substituted with one or more third substituent groups denoted by $R^{10C.3}$ as explained in the definitions section above in the description of "first substituent group(s)". In the above embodiments, $R^{10C}$, $R^{10C.1}$, $R^{10C.2}$, and $R^{10C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10C}$, $R^{10C.1}$, $R^{10C.2}$, and $R^{10C.3}$ respectively.

In embodiments, when $R^{10D}$ is substituted, $R^{10D}$ is substituted with one or more first substituent groups denoted by $R^{10D.1}$ as explained in the definitions section above in the description of "first substituent group(s)". In embodiments, when an $R^{10D.1}$ substituent group is substituted, the $R^{10D.1}$ substituent group is substituted with one or more second substituent groups denoted by $R^{10D.2}$ as explained in the definitions section above in the description of "first substituent group(s)". In embodiments, when an $R^{10D.2}$ substituent group is substituted, the $R^{10D.2}$ substituent group is substituted with one or more third substituent groups denoted by $R^{10D.3}$ as explained in the definitions section above in the description of "first substituent group(s)". In the above embodiments, $R^{10D}$, $R^{10D.1}$, $R^{10D.2}$, and $R^{10D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10D}$, $R^{10D.1}$, $R^{10D.2}$, and $R^{10D.3}$, respectively.

In embodiments, when $R^{61}$ is substituted, $R^{61}$ is substituted with one or more first substituent groups denoted by $R^{61.1}$ as explained in the definitions section above in the description of "first substituent group(s)". In embodiments, when an $R^{61.1}$ substituent group is substituted, the $R^{61.1}$ substituent group is substituted with one or more second substituent groups denoted by $R^{61.2}$ as explained in the definitions section above in the description of "first substituent group(s)". In embodiments, when an $R^{61.2}$ substituent group is substituted, the $R^{61.2}$ substituent group is substituted with one or more third substituent groups denoted by $R^{61.3}$ as explained in the definitions section above in the description of "first substituent group(s)". In the above embodiments, $R^{61}$, $R^{61.1}$, $R^{61.2}$, and $R^{61.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{61}$, $R^{61.1}$, $R^{61.2}$, and $R^{61.3}$, respectively.

In embodiments, when $R^{62}$ is substituted, $R^{62}$ is substituted with one or more first substituent groups denoted by $R^{62.1}$ as explained in the definitions section above in the description of "first substituent group(s)". In embodiments, when an $R^{62.1}$ substituent group is substituted, the $R^{62.1}$ substituent group is substituted with one or more second substituent groups denoted by $R^{62.2}$ as explained in the definitions section above in the description of "first substituent group(s)". In embodiments, when an $R^{62.2}$ substituent group is substituted, the $R^{62.2}$ substituent group is substituted with one or more third substituent groups denoted by $R^{62.3}$ as explained in the definitions section above in the description of "first substituent group(s)". In the above embodiments, $R^{62}$, $R^{62.1}$, $R^{62.2}$, and $R^{62.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{62}$, $R^{62.1}$, $R^{62.2}$, and $R^{62.3}$, respectively.

In embodiments, when $R^{71}$ is substituted, $R^{71}$ is substituted with one or more first substituent groups denoted by $R^{71.1}$ as explained in the definitions section above in the description of "first substituent group(s)". In embodiments, when an $R^{71.1}$ substituent group is substituted, the $R^{71.1}$ substituent group is substituted with one or more second substituent groups denoted by $R^{71.2}$ as explained in the definitions section above in the description of "first substituent group(s)". In embodiments, when an $R^{71.2}$ substituent group is substituted, the $R^{71.2}$ substituent group is substituted with one or more third substituent groups denoted by $R^{71.3}$ as explained in the definitions section above in the description of "first substituent group(s)". In the above embodiments, $R^{71}$, $R^{71.1}$, $R^{71.2}$, and $R^{71.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{71}$, $R^{71.1}$, $R^{71.2}$, and $R^{71.3}$, respectively.

In embodiments, when $R^{72}$ is substituted, $R^{72}$ is substituted with one or more first substituent groups denoted by $R^{72.1}$ as explained in the definitions section above in the description of "first substituent group(s)". In embodiments, when an $R^{72.1}$ substituent group is substituted, the $R^{72.1}$ substituent group is substituted with one or more second substituent groups denoted by $R^{72.2}$ as explained in the definitions section above in the description of "first substituent group(s)". In embodiments, when an $R^{72.2}$ substituent group is substituted, the $R^{72.2}$ substituent group is substituted with one or more third substituent groups denoted by $R^{72.3}$ as explained in the definitions section above in the description of "first substituent group(s)". In the above embodiments, $R^{72}$, $R^{72.1}$, $R^{72.2}$, and $R^{72.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{72}$, $R^{72.1}$, $R^{72.2}$, and $R^{72.3}$, respectively.

In embodiments, when $R^{73}$ is substituted, $R^{73}$ is substituted with one or more first substituent groups denoted by $R^{73.1}$ as explained in the definitions section above in the description of "first substituent group(s)". In embodiments, when an $R^{73.1}$ substituent group is substituted, the $R^{73.1}$ substituent group is substituted with one or more second substituent groups denoted by $R^{73.2}$ as explained in the definitions section above in the description of "first substituent group(s)". In embodiments, when an $R^{73.2}$ substituent group is substituted, the $R^{73.2}$ substituent group is substituted with one or more third substituent groups denoted by $R^{73.3}$ as explained in the definitions section above in the description of "first substituent group(s)". In the above embodiments, $R^{73}$, $R^{73.1}$, $R^{73.2}$, and $R^{73.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{73}$, $R^{73.1}$, $R^{73.2}$, and $R^{73.3}$, respectively.

In embodiments, when $R^{101}$ is substituted, $R^{101}$ is substituted with one or more first substituent groups denoted by $R^{101.1}$ as explained in the definitions section above in the description of "first substituent group(s)". In embodiments, when an $R^{101.1}$ substituent group is substituted, the $R^{101.1}$ substituent group is substituted with one or more second substituent groups denoted by $R^{101.2}$ as explained in the definitions section above in the description of "first substituent group(s)". In embodiments, when an $R^{101.2}$ substituent group is substituted, the $R^{101.2}$ substituent group is substituted with one or more third substituent groups denoted by $R^{101.3}$ as explained in the definitions section above in the description of "first substituent group(s)". In the above embodiments, $R^{101}$, $R^{101.1}$, $R^{101.2}$, and $R^{101.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{101}$, $R^{101.1}$, $R^{101.2}$, and $R^{101.3}$, respectively.

In embodiments, when $R^{102}$ is substituted, $R^{102}$ is substituted with one or more first substituent groups denoted by $R^{102.1}$ as explained in the definitions section above in the description of "first substituent group(s)". In embodiments, when an $R^{102.1}$ substituent group is substituted, the $R^{102.1}$ substituent group is substituted with one or more second substituent groups denoted by $R^{102.2}$ as explained in the definitions section above in the description of "first substituent group(s)". In embodiments, when an $R^{102.2}$ substituent group is substituted, the $R^{102.2}$ substituent group is substituted with one or more third substituent groups denoted by $R^{102.3}$ as explained in the definitions section above in the description of "first substituent group(s)". In the above embodiments, $R^{102}$, $R^{102.1}$, $R^{102.2}$, and $R^{102.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{102}$, $R^{102.1}$, $R^{102.2}$, and $R^{102.3}$, respectively.

In embodiments, when $R^{103}$ is substituted, $R^{103}$ is substituted with one or more first substituent groups denoted by $R^{103.1}$ as explained in the definitions section above in the description of "first substituent group(s)". In embodiments, when an $R^{103.1}$ substituent group is substituted, the $R^{103.1}$ substituent group is substituted with one or more second substituent groups denoted by $R^{103.2}$ as explained in the definitions section above in the description of "first substituent group(s)". In embodiments, when an $R^{103.2}$ substituent group is substituted, the $R^{103.2}$ substituent group is substituted with one or more third substituent groups denoted by $R^{103.3}$ as explained in the definitions section above in the description of "first substituent group(s)". In the above embodiments, $R^{103}$, $R^{103.1}$, $R^{103.2}$, and $R^{103.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{103}$, $R^{103.1}$, $R^{103.2}$, and $R^{103.3}$, respectively.

In embodiments, when $L^1$ is substituted, $L^1$ is substituted with one or more first substituent groups denoted by $R^{L1.1}$ as explained in the definitions section above in the description of "first substituent group(s)". In embodiments, when an $R^{L1.1}$ substituent group is substituted, the $R^{L1.1}$ substituent group is substituted with one or more second substituent groups denoted by $R^{L1.2}$ as explained in the definitions section above in the description of "first substituent group(s)". In embodiments, when an $R^{L1.2}$ substituent group is substituted, the $R^{L1.2}$ substituent group is substituted with one or more third substituent groups denoted by $R^{L1.3}$ as explained in the definitions section above in the description of "first substituent group(s)". In the above embodiments, $L^1$, $R^{L1.1}$, $R^{L1.2}$, and $R^{L1.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are L, $R^{L1.1}$, $R^{L1.2}$, and $R^{L1.3}$, respectively.

In embodiments, when $L^{101}$ is substituted, $L^{101}$ is substituted with one or more first substituent groups denoted by $R^{L101.1}$ as explained in the definitions section above in the description of "first substituent group(s)". In embodiments, when an $R^{L101.1}$ substituent group is substituted, the $R^{L101.1}$ substituent group is substituted with one or more second substituent groups denoted by $R^{L101.2}$ as explained in the definitions section above in the description of "first substituent group(s)". In embodiments, when an $R^{L101.2}$ substituent group is substituted, the $R^{L101.2}$ substituent group is substituted with one or more third substituent groups denoted by $R^{L101.3}$ as explained in the definitions section above in the description of "first substituent group(s)". In the above embodiments, $L^{101}$, $R^{L101.1}$, $R^{L101.2}$, and $R^{L101.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{101}$, $R^{L101.1}$, $R^{L101.2}$, and $R^{L101.3}$, respectively.

In embodiments, when $L^{102}$ is substituted, $L^{102}$ is substituted with one or more first substituent groups denoted by $R^{L102.1}$ as explained in the definitions section above in the description of "first substituent group(s)". In embodiments, when an $R^{L102.1}$ substituent group is substituted, the $R^{L102.1}$ substituent group is substituted with one or more second substituent groups denoted by $R^{L102.2}$ as explained in the definitions section above in the description of "first substituent group(s)". In embodiments, when an $R^{L102.2}$ substituent group is substituted, the $R^{L102.2}$ substituent group is substituted with one or more third substituent groups denoted by $R^{L102.3}$ as explained in the definitions section above in the description of "first substituent group(s)". In the above embodiments, $L^{102}$, $R^{L102.1}$, $R^{L102.2}$, and $R^{L102.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{102}$, $R^{L102.1}$, $R^{L102.2}$, and $R^{L102.3}$, respectively.

In embodiments, when $L^{103}$ is substituted, $L^{103}$ is substituted with one or more first substituent groups denoted by $R^{L103.1}$ as explained in the definitions section above in the description of "first substituent group(s)". In embodiments, when an $R^{L103.1}$ substituent group is substituted, the $R^{L103.1}$ substituent group is substituted with one or more second substituent groups denoted by $R^{L103.2}$ as explained in the definitions section above in the description of "first substituent group(s)". In embodiments, when an $R^{L103.2}$ substituent group is substituted, the $R^{L103.2}$ substituent group is substituted with one or more third substituent groups denoted by $R^{L103.3}$ as explained in the definitions section above in the description of "first substituent group(s)". In the above embodiments, $L^{103}$, $R^{L103.1}$, $R^{L103.2}$, and $R^{L103.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{103}$, $R^{L103.1}$, $R^{L103.2}$, and $R^{L103.3}$, respectively.

In embodiments, the compound is:

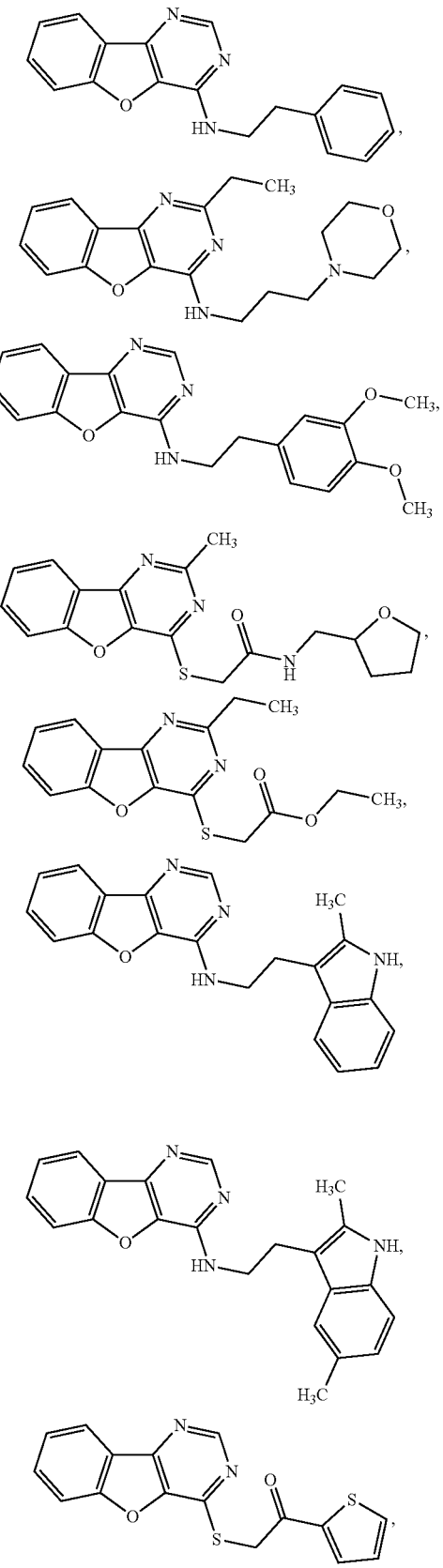

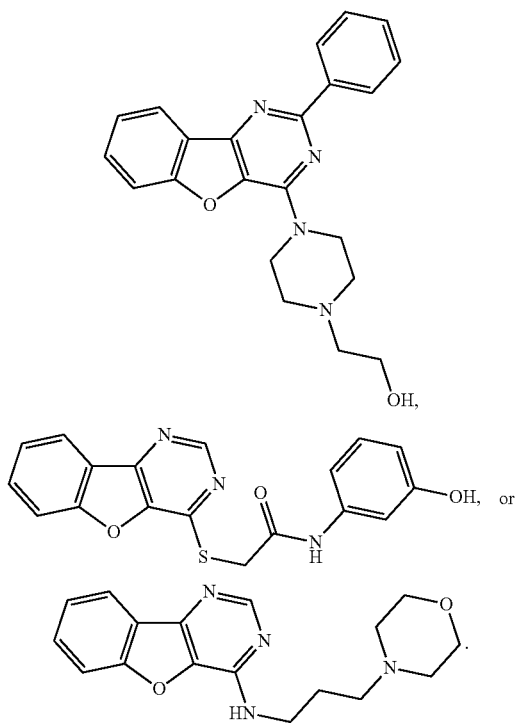
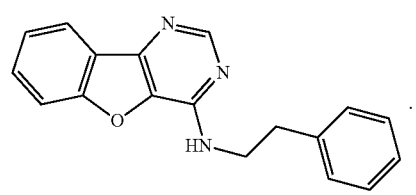 [SMILES: c1ccc(CCNc2ncnc3c2oc2ccccc23)cc1]
In embodiments, the compound is
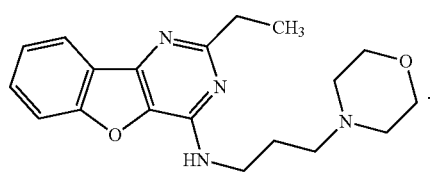 [SMILES: CCc1nc(NCCCN2CCOCC2)c2oc3ccccc3c2n1]
In embodiments, the compound is
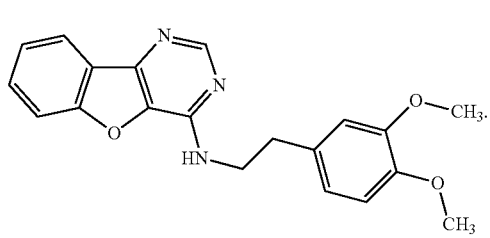 [SMILES: COc1ccc(CCNc2ncnc3c2oc2ccccc23)cc1OC]
In embodiments, the compound is
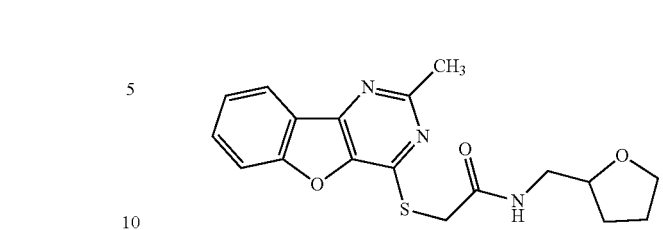
In embodiments, the compound is
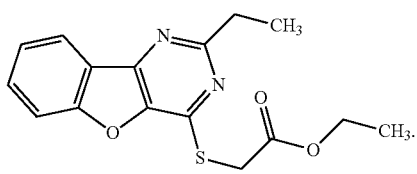 [SMILES: CCOC(=O)CSc1nc(CC)nc2c1oc1ccccc12]
In embodiments, the compound is
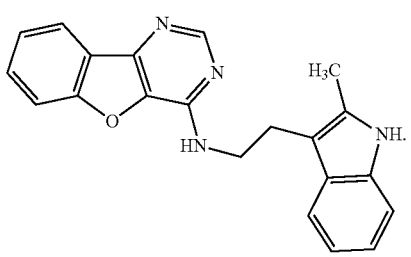 [SMILES: Cc1[nH]c2ccccc2c1CCNc1ncnc2c1oc1ccccc12]
In embodiments, the compound is
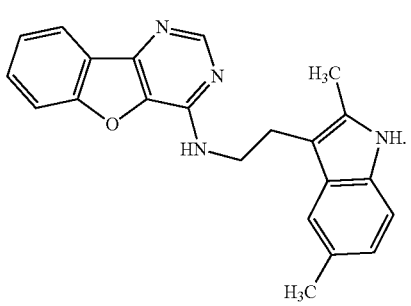 [SMILES: Cc1ccc2[nH]c(C)c(CCNc3ncnc4c3oc3ccccc34)c2c1]
In embodiments, the compound is
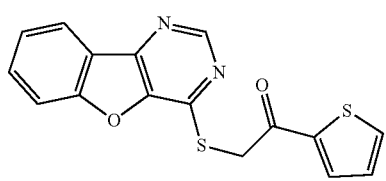

In embodiments, the compound is
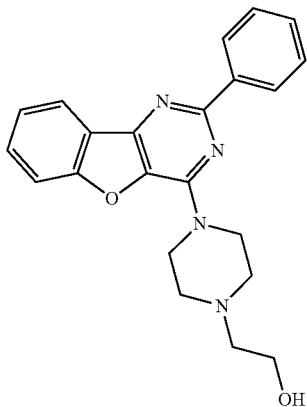
In embodiments, the compound is
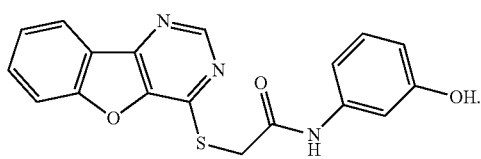 [SMILES: O=C(CSc1ncnc2c1oc1ccccc12)Nc1cccc(O)c1]
In embodiments, the compound is
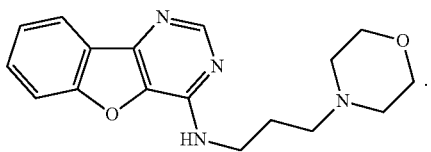 [SMILES: c1ccc2c(c1)oc1c(NCCCN3CCOCC3)ncnc12]
In embodiments, the compound is not
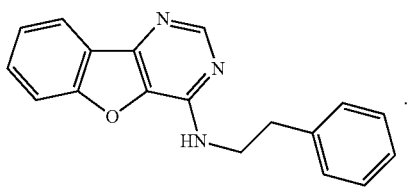 [SMILES: c1ccc(CCNc2ncnc3c2oc2ccccc23)cc1]
In embodiments, the compound is not
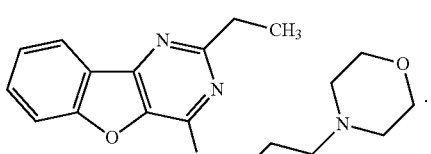
In embodiments, the compound is not
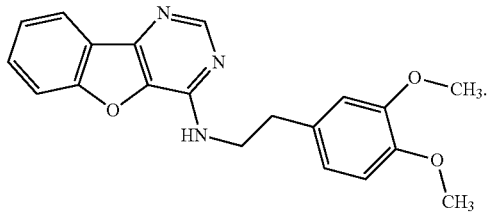 [SMILES: COc1ccc(CCNc2ncnc3c2oc2ccccc23)cc1OC]
In embodiments, the compound is not
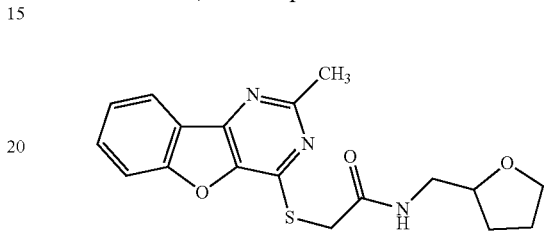
In embodiments, the compound is not
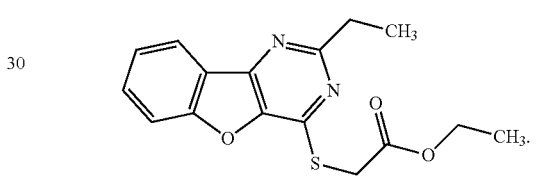
In embodiments, the compound is not
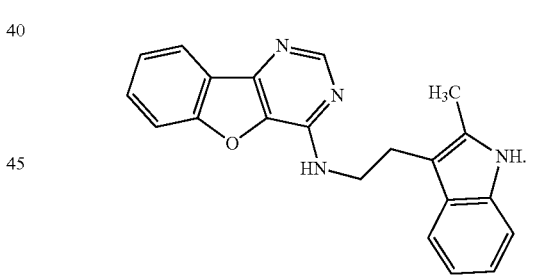
In embodiments, the compound is not
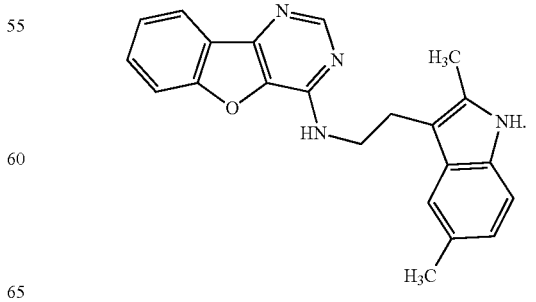

In embodiments, the compound is not

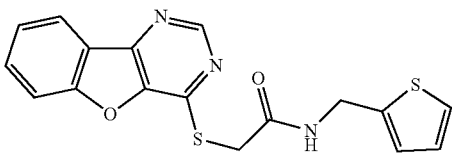 [SMILES: O=C(CSc1ncnc2c1oc1ccccc12)NCc1cccs1]

In embodiments, the compound is not

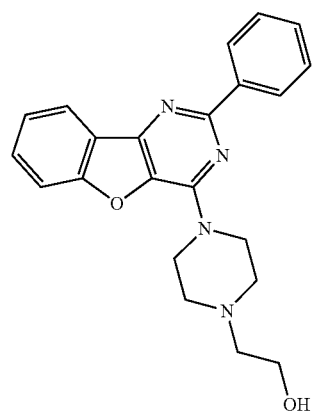

In embodiments, the compound is not

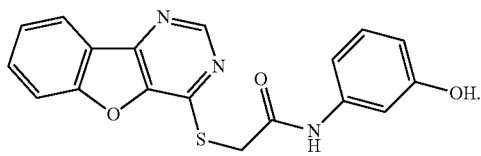 [SMILES: O=C(CSc1ncnc2c1oc1ccccc12)Nc1cccc(O)c1]

In embodiments, the compound is not

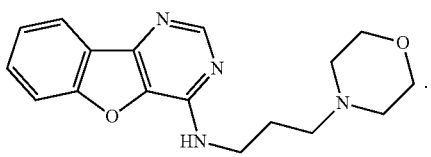 [SMILES: c1ccc2c(c1)oc1c(NCCCN3CCOCC3)ncnc12]

In embodiments, the compound is

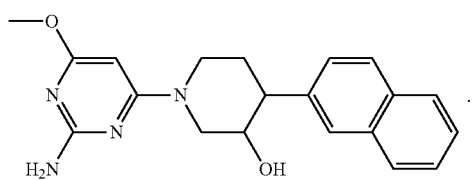 [SMILES: COc1cc(N2CCC(c3ccc4ccccc4c3)C(O)C2)nc(N)n1]

In embodiments, the compound is

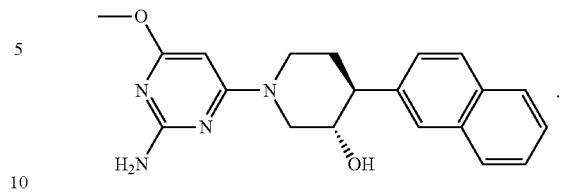

In embodiments, the compound is not

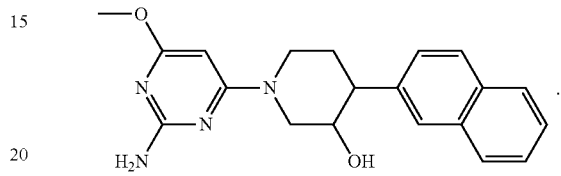

In embodiments, the compound is not

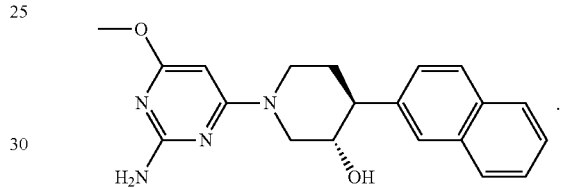

In embodiments, the compound is useful as a comparator compound. In embodiments, the comparator compound can be used to assess the activity of a test compound in an assay (e.g., an assay as described herein, for example in the examples section, figures, or tables).

In embodiments, the compound is a compound described herein (e.g., in an aspect, embodiment, example, table, figure, or claim).

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments, the pharmaceutical composition includes a second agent (e.g., therapeutic agent). In embodiments, the pharmaceutical composition includes a second agent (e.g., therapeutic agent) in a therapeutically effective amount. In embodiments, the second agent is an agent for treating inflammation. In embodiments, the second agent is an agent for treating diabetes. In embodiments, the second agent is insulin, metformin, an angiotensin converting enzyme inhibitor, or a calcium channel blocker. In embodiments, the second agent is acarbose, miglitol, bromocriptine, aloglipton, linagliptin, saxagliptin, sitagliptin, albiglutide, dulaglutide, exenatide, liraglutide, semaglutide, nateglinide, repaglinide, dapagliflozin, canagliflozin, empagliflozin, ertugliflozin, glimepiride, gliclazide, glipizide, glyburide, chlorpropamide, tolazamide, tolbutamide, rosiglitazone, or pioglitazone.

IV. Methods of Use

In an aspect is provided a method of treating a TXNIP-TRX complex-associated disease, the method including administering to a subject in need thereof an effective amount of a TXNIP-TRX complex inhibitor. In an aspect is provided a method of treating a TXNIP-TRX complex-associated disease, the method including administering to a subject in need thereof an effective amount of a TXNIP-TRX complex inhibitor, wherein the TXNIP-TRX complex inhibitor is a compound as described herein, including in embodiments.

In embodiments, the TXNIP-TRX complex-associated disease is a metabolic disorder, cardiovascular disease, or inflammatory disease. In embodiments, the TXNIP-TRX complex-associated disease is a metabolic disorder. In embodiments, the TXNIP-TRX complex-associated disease is cardiovascular disease. In embodiments, the TXNIP-TRX complex-associated disease is inflammation.

In embodiments, the TXNIP-TRX complex-associated disease is a kidney disease or an eye disease. In embodiments, the TXNIP-TRX complex-associated disease is a kidney disease. In embodiments, the TXNIP-TRX complex-associated disease is an eye disease.

In embodiments, the compound binds (e.g., forms a covalent bond) to TXNIP. In embodiments, the compound forms a non-covalent bond to TXNIP.

In an aspect is provided a method of treating a metabolic disorder, cardiovascular disease, or inflammatory disease, the method including administering to a subject in need thereof an effective amount of a compound, or pharmaceutically acceptable salt thereof, as described herein, including in embodiments.

In embodiments, the method includes reducing side effects (e.g., lower incidences of side effects) relative to alternative forms of treatment (e.g., administering verapamil). In embodiments, the method includes reducing side effects (e.g., lower incidences of side effects) relative to an identical method of treatment lacking the compound as described herein. In embodiments, the side effects include constipation, dizziness, headache, increased liver enzymes, indigestion, low blood pressure (hypotension), nausea, rash, shortness of breath, sleep disturbance, swelling (edema), or swollen gums. In embodiments, the side effect is constipation, dizziness, headache, increased liver enzymes, indigestion, low blood pressure (hypotension), nausea, rash, shortness of breath, sleep disturbance, swelling (edema), or swollen gums.

In embodiments, the compound is capable of inhibiting TXNIP protein activity or function. In embodiments, the compound is capable of inhibiting TXNIP protein activity or function, the method including contacting the TXNIP protein with the compound. In embodiments, the compound is capable of inhibiting TXNIP protein activity or function, the method including modulating (e.g., reducing) the level of expression of TXNIP. In embodiments, the compound inhibits TXNIP protein activity or function. In embodiments, the compound inhibits TXNIP protein activity or function, the method including contacting the TXNIP protein with the compound. In embodiments, the compound inhibits TXNIP protein activity or function, the method including modulating (e.g., reducing) the level of expression of TXNIP.

In embodiments, the compound is capable of inhibiting TXNIP protein binding to TRX. In embodiments, the compound is capable of inhibiting TXNIP protein binding to TRX, the method including contacting the TXNIP protein with the compound. In embodiments, the compound is capable of inhibiting TXNIP protein binding to TRX, the method including modulating (e.g., reducing) the level of expression of TXNIP. In embodiments, the compound inhibits TXNIP protein binding to TRX. In embodiments, the compound inhibits TXNIP protein binding to TRX, the method including contacting the TXNIP protein with the compound. In embodiments, the compound inhibits TXNIP protein binding to TRX, the method including modulating (e.g., reducing) the level of expression of TXNIP. In embodiments, the method includes inhibiting TXNIP protein binding to TRX.

In embodiments, the method includes modulating (e.g., reducing) the level of expression of TXNIP. In embodiments, the compound is capable of modulating (e.g., reducing) the level of expression of TXNIP. In embodiments, the compound modulates (e.g., reduces) the level of expression of TXNIP. In embodiments, the level of expression of TXNIP is reduced by greater than 10%, 20%, 30%, 40%, 50%, 60%, 70%, 80%, or greater than 90% in comparison to a control in the absence of the compound. In embodiments, the level of expression of TXNIP is reduced by about 10%, 20%, 30%, 40%, 50%, 60%, 70%, 80%, 90%, or about 100% in comparison to a control in the absence of the compound. In embodiments, the level of expression of TXNIP is reduced by 10%, 20%, 30%, 40%, 50%, 60%, 70%, 80%, 90%, or 100% in comparison to a control in the absence of the compound. In embodiments, the level of expression of TXNIP is reduced by 1.5-fold, 2-fold, 3-fold, 4-fold, 5-fold, 10-fold or lower than the expression or activity in the absence of the compound.

In embodiments, the metabolic disorder is diabetes. In embodiments, the metabolic disorder is type 1 diabetes (T1D). In embodiments, the metabolic disorder is type 2 diabetes (T2D). In embodiments, the diabetes is associated with islet beta cell dysfunction. In embodiments, the cardiovascular disease is atherosclerosis. In embodiments, the cardiovascular disease is coronary artery disease (e.g., angina or myocardial infarction), stroke, heart failure, hypertensive heart disease, rheumatic heart disease, cardiomyopathy, abnormal heart rhythms, congenital heart disease, valvular heart disease, carditis, aortic aneurysms, peripheral artery disease, thromboembolic disease, or venous thrombosis.

In embodiments, the disease (e.g., metabolic disorder) is diabetes (e.g., type 1 diabetes or type 2 diabetes), insulin resistance, metabolic syndrome, atherosclerosis, obesity, hyperlipidemia, hyperglycemia, high serum triglycerides, and/or high blood pressure.

In embodiments, the metabolic disorder is a diabetes associated complication selected from nephropathy, retinopathy, neuropathy, cardiovascular disease, and inflammation. In embodiments, the metabolic disorder is a diabetes associated disease selected from nephropathy, retinopathy, neuropathy, cardiovascular disease, and inflammation.

In embodiments, the method does not increase the risk for an infectious disease.

In embodiments, the method inhibits high glucose-induced TXNIP-TRX co-immunoprecipitation (e.g., in cell extracts or in vivo in cells). In embodiments, the compound can bind to TXNIP and prevent its proteolysis. In embodiments, the method reduces expression of inflammatory cytokine molecules in monocytes (e.g., TNF-α, IL-1β, IL-6, or chemokines).

In an aspect is provided a method of treating a kidney disease or an eye disease, the method including administering to a subject in need thereof an effective amount of a compound, or pharmaceutically acceptable salt thereof, as described herein, including in embodiments.

In an aspect is provided a method of reducing the level of expression of TXNIP in a cell, the method including contacting the cell with a compound, or pharmaceutically acceptable salt thereof, as described herein, including in embodiments. In embodiments, the method includes reducing the level of mRNA expression of TXNIP in a cell. In embodiments, the cell is an inflammatory white cell. In embodiments, the cell is a human inflammatory cell. In embodiments, the cell is a mouse inflammatory cell. In embodiments, the cell is a pancreatic beta cell. In embodiments, the pancreatic beta cell is a mouse pancreatic beta cell. In embodiments, the pancreatic beta cell is a human pancreatic beta cell. In embodiments, the pancreatic beta cell is a primary human islet beta cell. In embodiments, the cell is a THP1 cell. In embodiments, the cell is a human monocyte THP1 cell. In embodiments, the cell is a macrophage cell.

In embodiments, the level of expression of TXNIP is reduced by greater than 10%, 20%, 30%, 40%, 50%, 60%, 70%, 80%, or greater than 90% in comparison to a control in the absence of the compound. In embodiments, the level of expression of TXNIP is reduced by about 10%, 20%, 30%, 40%, 50%, 60%, 70%, 80%, 90%, or about 100% in comparison to a control in the absence of the compound. In embodiments, the level of expression of TXNIP is reduced by 10%, 20%, 30%, 40%, 50%, 60%, 70%, 80%, 90%, or 100% in comparison to a control in the absence of the compound. In embodiments, the level of expression of TXNIP is reduced by 1.5-fold, 2-fold, 3-fold, 4-fold, 5-fold, 10-fold or lower than the expression or activity in the absence of the compound.

In an aspect is provided a method of reducing the level of expression of TNF-α in a cell, the method including contacting the cell with a compound, or pharmaceutically acceptable salt thereof, as described herein, including in embodiments. In embodiments, the method includes reducing the level of mRNA expression of TNF-α in a cell. In embodiments, the cell is an inflammatory white cell. In embodiments, the cell is a human inflammatory cell. In embodiments, the cell is a mouse inflammatory cell. In embodiments, the cell is a pancreatic beta cell. In embodiments, the pancreatic beta cell is a mouse pancreatic beta cell. In embodiments, the pancreatic beta cell is a human pancreatic beta cell. In embodiments, the pancreatic beta cell is a primary human islet beta cell. In embodiments, the cell is a THP1 cell. In embodiments, the cell is a human monocyte THP1 cell. In embodiments, the cell is a macrophage cell.

In embodiments, the level of expression of TNF-α is reduced by greater than 10%, 20%, 30%, 40%, 50%, 60%, 70%, 80%, or greater than 90% in comparison to a control in the absence of the compound. In embodiments, the level of expression of TNF-α is reduced by about 10%, 20%, 30%, 40%, 50%, 60%, 70%, 80%, 90%, or about 100% in comparison to a control in the absence of the compound. In embodiments, the level of expression of TNF-α is reduced by 10%, 20%, 30%, 40%, 50%, 60%, 70%, 80%, 90%, or 100% in comparison to a control in the absence of the compound. In embodiments, the level of expression of TNF-α is reduced by 1.5-fold, 2-fold, 3-fold, 4-fold, 5-fold, 10-fold or lower than the expression or activity in the absence of the compound.

In an aspect is provided a method of reducing the level of expression of TXNIP, the method including contacting TXNIP with a compound, or a pharmaceutically acceptable salt thereof, as described herein, including in embodiments.

In embodiments, the level of expression of TXNIP is reduced by greater than 10%, 20%, 30%, 40%, 50%, 60%, 70%, 80%, or greater than 90% in comparison to a control in the absence of the compound. In embodiments, the level of expression of TXNIP is reduced by about 10%, 20%, 30%, 40%, 50%, 60%, 70%, 80%, 90%, or about 100% in comparison to a control in the absence of the compound. In embodiments, the level of expression of TXNIP is reduced by 10%, 20%, 30%, 40%, 50%, 60%, 70%, 80%, 90%, or 100% in comparison to a control in the absence of the compound. In embodiments, the level of expression of TXNIP is reduced by 1.5-fold, 2-fold, 3-fold, 4-fold, 5-fold, 10-fold or lower than the expression or activity in the absence of the compound.

In embodiments, the compound modulates (e.g., inhibits or reduces) the level of expression of FLNA. In embodiments, the compound modulates (e.g., inhibits or reduces) the level of expression of MPEG1. In embodiments, the compound modulates (e.g., inhibits or reduces) the level of expression of TKTL1. In embodiments, the compound modulates (e.g., inhibits or reduces) the level of expression of NATD1. In embodiments, the compound modulates (e.g., inhibits or reduces) the level of expression of TXNIP. In embodiments, the compound modulates (e.g., inhibits or reduces) the level of expression of KLF10. In embodiments, the compound modulates (e.g., inhibits or reduces) the level of expression of KLF2. In embodiments, the compound modulates (e.g., inhibits or reduces) the level of expression of CD52. In embodiments, the compound modulates (e.g., inhibits or reduces) the level of expression of TNF. In embodiments, the compound modulates (e.g., inhibits or reduces) the level of expression of ARRDC4. In embodiments, the compound modulates (e.g., inhibits or reduces) the level of expression of JMJ1C-AS1. In embodiments, the compound modulates (e.g., inhibits or reduces) the level of expression of RGMA. In embodiments, the compound modulates (e.g., inhibits or reduces) the level of expression of EGR1. In embodiments, the compound modulates (e.g., inhibits or reduces) the level of expression of NPIPA1. In embodiments, the compound modulates (e.g., inhibits or reduces) the level of expression of G0S2. In embodiments, the compound modulates (e.g., inhibits or reduces) the level of expression of EPHB1. In embodiments, the compound modulates (e.g., inhibits or reduces) the level of expression of VSIG4. In embodiments, the compound modulates (e.g., inhibits or reduces) the level of expression of CFP. In embodiments, the compound modulates (e.g., inhibits or reduces) the level of expression of CAPS. In embodiments, the compound modulates (e.g., inhibits or reduces) the level of expression of GLUD1P3. In embodiments, the compound modulates (e.g., inhibits or reduces) the level of expression of PCDHB14. In embodiments, the compound modulates (e.g., inhibits or reduces) the level of expression of CCDC153. In embodiments, the compound modulates (e.g., inhibits or reduces) the level of expression of FAM229A. In embodiments, the compound modulates (e.g., inhibits or reduces) the level of expression of SMURF2. In embodiments, the compound modulates (e.g., activates or increases) the level of expression of PDE9A. In embodiments, the compound modulates (e.g., activates or increases) the level of expression of SLC44A2. In embodiments, the compound modulates (e.g., activates or increases) the level of expression of ARHGEF25. In embodiments, the compound modulates (e.g., activates or increases) the level of expression of APBB1. In embodiments, the compound modulates (e.g., activates or increases) the level of expression of GTF2IRD1. In embodiments, the compound modulates (e.g., activates or increases) the level of expression of LOC100506688. In embodiments, the compound modulates (e.g., activates or increases) the level of expression of PPM1K. In embodiments, the compound modulates (e.g., activates or increases) the level of expression of SLC16A2. In embodiments, the compound modulates (e.g., activates or increases) the level of expression of PCGF2. In embodiments, the compound modulates (e.g., activates or increases) the level of expression of HK2. In embodiments, the compound modulates (e.g., activates or increases) the level of expression of TSPAN2. In embodiments, the compound modulates (e.g., activates or increases) the level of expression of S1PR5. In embodiments, the compound modulates (e.g., activates or increases) the level of expression of EFCAB7. In embodiments, the compound modulates (e.g., activates or increases) the level of expression of MACROD1. In embodiments, the compound modulates (e.g., activates or increases) the level of expression of GBP5. In embodiments, the compound modulates (e.g., activates or increases) the level of expression of KIAA1147. In embodiments, the compound modulates (e.g., activates or increases) the level of expression of ADGRE4P. In embodiments, the compound modulates (e.g., activates or increases) the level of expression of UQCRHL. In embodiments, the compound modulates (e.g., activates or increases) the level of expression of DICER1-AS1. In embodiments, the compound modulates (e.g., activates or increases) the level of expression of PDIA3P1. In embodiments, the compound modulates (e.g., inhibits or reduces) the level of expression of ACP2. In embodiments, the compound modulates (e.g., inhibits or reduces) the level of expression of CITED4. In embodiments, the compound modulates (e.g., inhibits or reduces) the level of expression of CKB. In embodiments, the compound modulates (e.g., inhibits or reduces) the level of expression of DNPH1. In embodiments, the compound modulates (e.g., inhibits or reduces) the level of expression of FAM20C. In embodiments, the compound modulates (e.g., inhibits or reduces) the level of expression of H2AFX. In embodiments, the compound modulates (e.g., inhibits or reduces) the level of expression of HOXA11-AS. In embodiments, the compound modulates (e.g., inhibits or reduces) the level of expression of IMPA2. In embodiments, the compound modulates (e.g., inhibits or reduces) the level of expression of LIMD2. In embodiments, the compound modulates (e.g., inhibits or reduces) the level of expression of LY6E. In embodiments, the compound modulates (e.g., inhibits or reduces) the level of expression of MBOAT7. In embodiments, the compound modulates (e.g., inhibits or reduces) the level of expression of MEGF8. In embodiments, the compound modulates (e.g., inhibits or reduces) the level of expression of PAQR4. In embodiments, the compound modulates (e.g., inhibits or reduces) the level of expression of PKMYT1. In embodiments, the compound modulates (e.g., inhibits or reduces) the level of expression of SLC2A5. In embodiments, the compound modulates (e.g., inhibits or reduces) the level of expression of TK1. In embodiments, the compound modulates (e.g., inhibits or reduces) the level of expression of TUBA4A.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A compound, or a pharmaceutically acceptable salt thereof, having the formula:

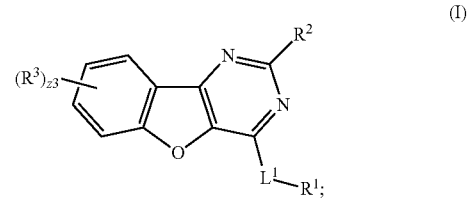

(I)

wherein
$L^1$ is a covalent linker;
$R^1$ is independently hydrogen, halogen, —$CX^1_3$, —$CHX^1_2$, —$CH_2X^1$, —$OCX^1_3$, —$OCHX^1_2$, —$OCH_2X^1$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —NHC(O)$NR^{1C}NR^{1A}R^{1B}$, —NHC(O)$NR^{1A}R^{1B}$, —$N(O)_{m1}$, —$NR^{1A}R^{1B}$, —$C(O)R^{1C}$, —$C(O)OR^{1C}$, —$C(O)NR^{1A}R^{1B}$, —$OR^{1D}$, —$SR^{1D}$, —$SeR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is independently hydrogen, halogen, —$CX^2_3$, —$CHX^2_2$, —$CH_2X^2$, —$OCX^2_3$, —$OCHX^2_2$, —$OCH_2X^2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —$C(O)R^{2C}$, —$C(O)OR^{2C}$, —$C(O)NR^{2A}R^{2B}$, —$OR^{2D}$, —$SR^{2D}$, —$SeR^{2D}$, —$NR^{2A}SO_2R^{2D}$, —$NR^{2A}C(O)R^{2C}$, —$NR^{2A}C(O)OR^{2C}$, —$NR^{2A}OR^2$, —$SF_5$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1A}$, $R^{1B}$, $R^{1C}$, $R^{1D}$, $R^{2A}$, $R^{2B}$, $R^{2C}$, and $R^{2D}$ are each independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —CN, —OH, —$NH_2$, —COOH, —$CONH_2$, —$NO_2$, —SH, —SeH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl;

$X^1$ and $X^2$ are each independently —F, —Cl, —Br, or —I;

n1 and n2 are each independently an integer from 0 to 4;

m1, m2, v1, and v2 are each independently 1 or 2;

$R^3$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; and z3 is an integer from 0 to 4.

Embodiment P2. The compound of embodiment P1, wherein $L^1$ is -$L^{101}$-$L^{102}$-$L^{103}$;

$L^{101}$ is independently a bond, —N(R$^{101}$)—, —S—, —O—, —C(O)—, —C(O)O—, —OC(O)—, —N(R$^{101}$)C(O)—, —C(O)N(R$^{101}$)—, —NR$^{101}$C(O)NR$^{101}$—, —NR$^{101}$C(NH)NR$^{101}$—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{102}$ is independently a bond, —N(R$^{102}$)—, —S—, —O—, —C(O)—, —C(O)O—, —OC(O)—, —N(R$^{102}$)C(O)—, —C(O)N(R$^{102}$)—, —NR$^{102}$C(O)NR$^{102}$—, —NR$^{102}$C(NH)NR$^{102}$—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{103}$ is independently a bond, —N(R$^{103}$)—, —S—, —O—, —C(O)—, —C(O)O—, —OC(O)—, —N(R$^{103}$)C(O)—, —C(O)N(R$^{103}$)—, —NR$^{103}$C(O)NR$^{103}$—, —NR$^{103}$C(NH)NR$^{103}$—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{101}$, $R^{102}$, and $R^{103}$ are each independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P3. The compound of embodiment P2, wherein $L^{101}$ is a substituted or unsubstituted 2 to 6 membered heteroalkylene, or a substituted or unsubstituted 3 to 6 membered heterocycloalkylene;

$L^{102}$ is a bond; and $L^{103}$ is a bond.

Embodiment P4. The compound of one of embodiments P1 to P3, wherein $R^1$ is —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P5. The compound of one of embodiments P1 to P3, wherein $R^1$ is —OH, substituted or unsubstituted $C_1$-$C_4$ alkyl, substituted or unsubstituted 2 to 6 membered heteroalkyl, substituted or unsubstituted 3 to 6 membered heterocycloalkyl, substituted or unsubstituted phenyl, or substituted or unsubstituted 5 to 10 membered heteroaryl.

Embodiment P6. The compound of one of embodiments P1 to P5, wherein $R^2$ is hydrogen, substituted or unsubstituted alkyl, or substituted or unsubstituted aryl.

Embodiment P7. The compound of one of embodiments P1 to P5, wherein $R^2$ is hydrogen, unsubstituted methyl, unsubstituted ethyl, or unsubstituted phenyl.

Embodiment P8. The compound of one of embodiments P1 to P7, wherein z3 is 0.

Embodiment P9. The compound of embodiment P1, having the formula

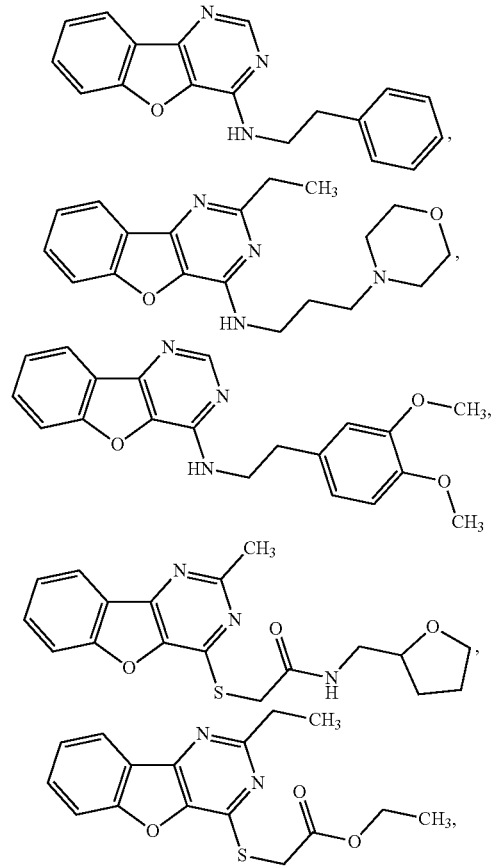

-continued

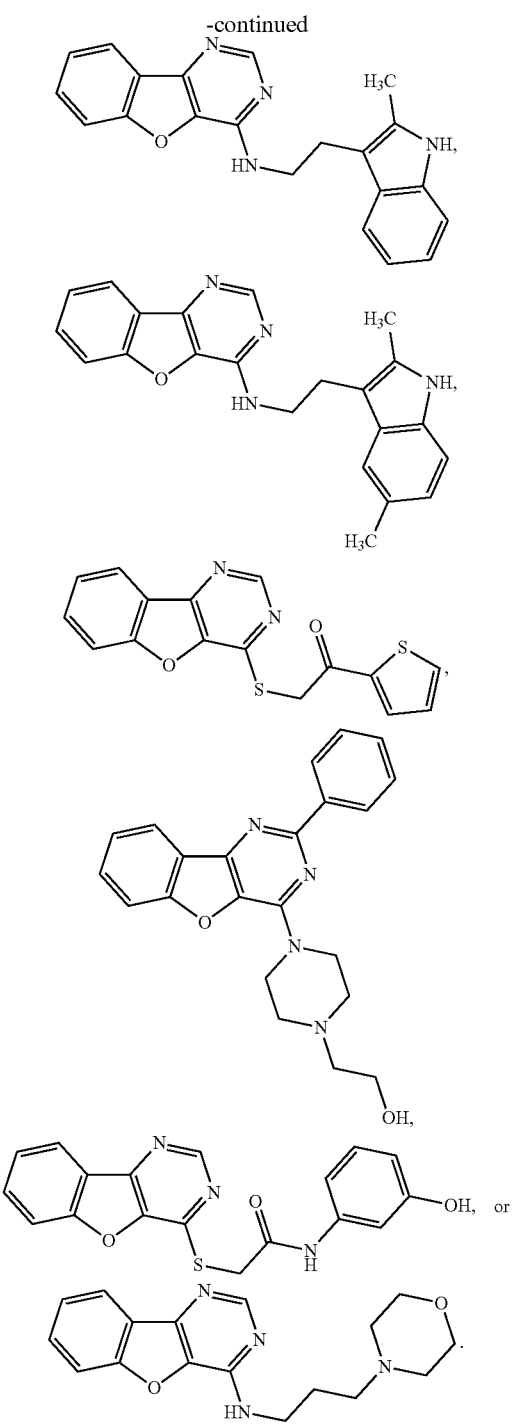

Embodiment P10. The compound of embodiment P1, having the formula

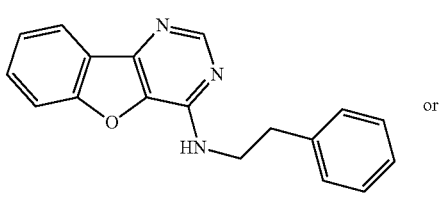

-continued

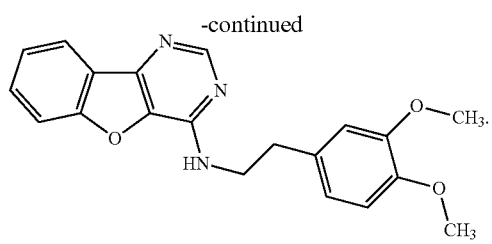

Embodiment P11. A compound, or a pharmaceutically acceptable salt thereof, having the formula:

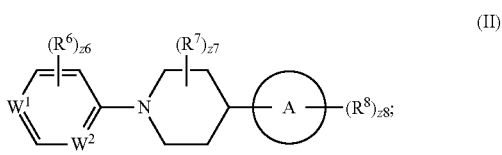

wherein
Ring A is cycloalkyl, heterocycloalkyl, aryl, or heteroaryl;
$W^1$ is N or $C(R^4)$;
$W^2$ is N or $C(R^5)$;
$R^4$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^6$ is independently halogen, —CX$^6_3$, —CHX$^6_2$, —CH$_2$X$^6$, —OCX$^6_3$, —OCHX$^6_2$, —OCH$_2$X$^6$, —CN, —SO$_{n6}$R$^{6D}$, —SO$_{v6}$NR$^{6A}$R$^{6B}$, —NR$^{6C}$NR$^{6A}$R$^{6B}$, —ONR$^{6A}$R$^{6B}$, —NHC(O)NR$^{6C}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)OR$^{6C}$, —C(O)NR$^{6A}$R$^{6B}$, —OR$^{6D}$, —SR$^{6D}$, —SeR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, —SF$_5$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^6$ substituents may optionally be joined to form a substituted or unsubstituted cycloalkyl, substituted or unsubstituted heterocycloalkyl, substituted or unsubstituted aryl, or substituted or unsubstituted heteroaryl;

$R^7$ is independently halogen, oxo, $-CX^7{}_3$, $-CHX^7{}_2$, $-CH_2X^7$, $-OCX^7{}_3$, $-OCHX^7{}_2$, $-OCH_2X^7$, $-CN$, $-SO_{n7}R^{7D}$, $-SO_{v7}NR^{7A}R^{7B}$, $-NR^{7C}NR^{7A}R^{7B}$, $-ONR^{7A}R^{7B}$, $-NHC(O)NR^{7A}R^{7A}R^{7B}$, $-NHC(O)NR^{7A}R^{7B}$, $-N(O)_{m7}$, $-NR^{7A}R^{7B}$, $-C(O)R^{7C}$, $-C(O)OR^{7C}$, $-C(O)NR^{7A}R^{7B}$, $-OR^{7D}$, $-SR^{7D}$, $-SeR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^7$ substituents may optionally be joined to form a substituted or unsubstituted cycloalkyl, substituted or unsubstituted heterocycloalkyl, substituted or unsubstituted aryl, or substituted or unsubstituted heteroaryl; two $R^7$ substituents bonded to the same carbon atom may optionally be joined to form a substituted or unsubstituted cycloalkyl, or substituted or unsubstituted heterocycloalkyl;

$R^8$ is independently halogen, oxo, $-CX^8{}_3$, $-CHX^8{}_2$, $-CH_2X^8$, $-OCX^8{}_3$, $-OCHX^8{}_2$, $-OCH_2X^8$, $-CN$, $-SO_{n8}R^{8D}$, $-SO_{v8}NR^{8A}R^{8B}$, $-NR^{8C}NR^{8A}R^{8B}$, $-ONR^{8A}R^{8B}$, $-NHC(O)NR^{8C}NR^{8A}R^{8B}$, $-NHC(O)NR^{8A}R^{8B}$, $-N(O)_{m8}$, $-NR^{8A}R^{8B}$, $-C(O)R^{8C}$, $-C(O)OR^{8C}$, $-C(O)NR^{8A}R^{8B}$, $-OR^{8D}$, $-SR^{8D}$, $-SeR^{8D}$, $-NR^{8A}SO_2R^{8D}$, $-NR^{8A}C(O)R^{8C}$, $-NR^{8A}C(O)OR^{8C}$, $-NR^{8A}OR^{8C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^8$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, and $R^{8D}$ are each independently hydrogen, oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{8A}$ and $R^{8B}$ substituents bonded to the same nitrogen atom may optionally be joined to form a substituted or unsubstituted heterocycloalkyl or substituted or unsubstituted heteroaryl;

$X^6$, $X^7$, and $X^8$ are each independently $-F$, $-Cl$, $-Br$, or $-I$;

n6, n7, and n8 are each independently an integer from 0 to 4;

m6, m7, m8, v6, v7, and v8 are each independently 1 or 2;

z6 is an integer from 0 to 3;

z7 is an integer from 0 to 9; and z8 is an integer from 0 to 7.

Embodiment P1$_2$. The compound of embodiment P11, having the formula:

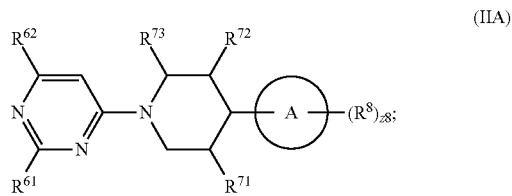

(IIA)

$R^{61}$ and $R^{62}$ are independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{71}$, $R^{72}$, and $R^{73}$ are independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P13. The compound of one of embodiments P11 to P12, wherein Ring A is $C_6$-$C_{10}$ aryl.

Embodiment P14. The compound of one of embodiments P11 to P12, wherein Ring A is naphthyl.

Embodiment P15. The compound of one of embodiments P11 to P14, wherein $R^{61}$ and $R^{62}$ are independently hydrogen, halogen, $-OH$, $-NH_2$, or unsubstituted 2 to 6 membered heteroalkyl.

Embodiment P16. The compound of embodiment P15, wherein $R^{61}$ is $-NH_2$.

Embodiment P17. The compound of one of embodiments P15 to P16, wherein $R^{62}$ is $-OCH_3$.

Embodiment P18. The compound of one of embodiments P11 to P17, wherein $R^{71}$ is —OH, —NH$_2$, unsubstituted $C_1$-$C_4$ alkyl, unsubstituted 2 to 6 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

Embodiment P19. The compound of one of embodiments P11 to P17, wherein $R^{71}$ is —OH.

Embodiment P20. The compound of one of embodiments P11 to P19, wherein $R^{72}$ and $R^{73}$ are independently hydrogen or unsubstituted $C_1$-$C_4$ alkyl.

Embodiment P21. The compound of embodiment P11, having the formula

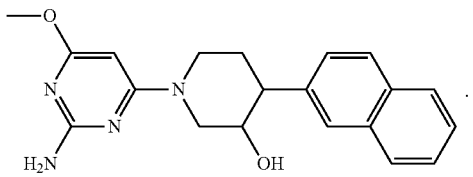

Embodiment P22. The compound of embodiment P11, having the formula

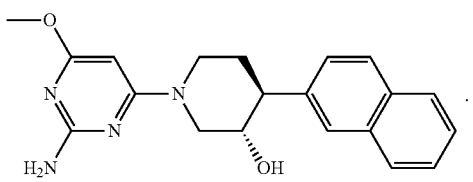

Embodiment P23. A pharmaceutical composition comprising a compound of one of embodiments P1 to P22, or pharmaceutically acceptable salt thereof, and a pharmaceutically acceptable excipient.

Embodiment P24. A method of treating a TXNIP-TRX complex-associated disease, said method comprising administering to a subject in need thereof an effective amount of a compound of one of embodiments P1 to P22, or a pharmaceutically acceptable salt thereof.

Embodiment P25. A method of treating a metabolic disorder, cardiovascular disease, or inflammatory disease, said method comprising administering to a subject in need thereof an effective amount of a compound of one of embodiments P1 to P22, or a pharmaceutically acceptable salt thereof.

Embodiment P26. The method of embodiment P25, wherein the metabolic disorder is diabetes.

Embodiment P27. The method of embodiment P25, wherein the metabolic disorder is a diabetes associated disease selected from nephropathy, retinopathy, neuropathy, cardiovascular disease, and inflammation.

Embodiment P28. The method of one of embodiments P25 to P27, wherein the compound is capable of inhibiting TXNIP protein activity or function, said method comprising contacting the TXNIP protein with the compound.

Embodiment P29. The method of one of embodiments P25 to P27, wherein the compound is capable of inhibiting TXNIP protein activity or function, said method comprising modulating the level of expression of TXNIP.

Embodiment P30. The method of one of embodiments P25 to P27, wherein the compound is capable of inhibiting TXNIP protein binding to TRX, said method comprising contacting the TXNIP protein with the compound.

Embodiment P31. The method of one of embodiments P25 to P27, wherein the compound is capable of inhibiting TXNIP protein binding to TRX, said method comprising modulating the level of expression of TXNIP.

EXAMPLES

Example 1: Inhibitors of TXNIP Action to Target Oxidant Stress, Inflammation, Diabetes, its Complications and Metabolic Memory The thioredoxin system, which consists of thioredoxin (TRX), nicotinamide adenine dinucleotide phosphate (NADPH) and thioredoxin reductase (TXNRD1), is a major anti-oxidant system involved in the maintenance of cellular physiology and survival. Dysregulation in this system has been associated with metabolic, cardiovascular, and malignant disorders. Thioredoxin-interacting protein (TXNIP) was first identified as an inhibitor of the redox regulator thioredoxin (TRX), an antioxidant. TXNIP functions as an inhibitor of TRX, and pathological suppression of TRX by TXNIP (which leads to oxidant stress) has been demonstrated in diabetes and cardiovascular diseases.

In cells, TXNIP expression is modulated by redox stress, glucose levels, hypoxia and inflammatory activators etc. and is highly sensitive to glucose. High glucose [HG] mimicking the diabetic milieu, greatly increases TXNIP expression. TXNIP expression is also significantly increased in pancreatic beta cells in diabetes, and is associated with beta cell dysfunction and diabetes development. Furthermore, increased TXNIP expression is associated with several major diabetic complications, including diabetic retinopathy, diabetic nephropathy, diabetic neuropathy and cardiovascular disease. Evidence shows that clinically used therapeutic agents for diabetes including insulin, metformin, angiotensin converting enzyme inhibitors and calcium channel blockers reduce TXNIP expression. Verapamil, a clinically used compound for hypertension was recently shown (Nature Med. 2018) to inhibit the expression of TXNIP and improve beta cell function in subjects with type 1 diabetes (Nat Med 2018). This provides strong evidence for the proof of concept that inhibition of TXNIP is clinically viable therapeutic strategy in treatment of T1D and T2D, as well as their associated complications.

Recent studies from our laboratory (Chen et al., PNAS 2016) have demonstrated a novel connection between epigenetic modification (DNA methylation) of TXNIP and Metabolic Memory, in which prior episodes of hyperglycemia can lead to the continued/persistent development of diabetic complications in certain diabetic patients despite subsequent glucose control: a major challenge in the clinical management of diabetes. Our data from that study, as well as our recent data from a much bigger cohort, shows TXNIP is highly induced by HG and inflammatory cytokines, and TXNIP molecule depicts the most significant changes in epigenetic DNA methylation in patients with metabolic memory of diabetic complications. Notably, we found that this alteration in TXNIP DNA methylation remained sustained in the same patient at two different time points 17 years apart (i.e., it depicts epigenetic memory). Furthermore, our data suggests that the known connections between HbA1c and diabetic complications can also be explained by epigenetic changes at TXNIP and other genomic loci.

A similar memory effect has also been documented in type 2 diabetes (T2D), referred as "legacy effect". Interestingly, studies from other groups have recently shown that a similar epigenetic modification of TXNIP (as that noted by us) is also seen in patients with type 2 diabetes, insulin resistance (obesity) and dyslipidemia.

Taken together the data from our lab show strong connections between TXNIP and its epigenetic modifications in inflammation, diabetic complications, metabolic memory and hyperglycemia. Data from others have also shown its pathological role in beta cell function, in both T1D and T2D, as well as in major diabetic complications. Thus, our objective is to identify small molecules that can inactivate TXNIP functions by directly binding/interacting with it in a way that will disrupt its interaction with TRX. This approach is different from how some of the known compounds that target the expression of TXNIP. The TXNIP inhibitors available to date, target the expression of TXNIP. Given the importance of epigenetic modification of TXNIP, targeting the interaction of TXNIP with TRX would be an effective therapeutic strategy especially for complications and metabolic memory, and diabetes itself.

Computational screening of small molecule TXNIP inhibitors: To find small molecule inhibitors of TXNIP we collaborated with the Computational Therapeutics Core (CTC). The TXNIP-TRX protein-protein complex is a challenging target because TXNIP interacts with TRX through a covalent disulfide bond that requires more energy to break. Therefore, the direct interacting interface of the TXNIP-TRX complex is difficult to be targeted for small molecules. There is no known small molecule binding site in TXNIP. This posed a challenge to identify and target an allosteric small molecule binding site to screen for candidate molecules. An innovative computational method and software called Allosteer to identify allosteric binding sites that are effective in allosteric inhibition (Bhattacharya 2014, 2016, Vaidehi 2016) was used. Using Allosteer we identified two putative binding sites as shown in FIG. 1A. We subsequently used a virtual ligand screening protocol to screen 263,000 small molecules from four small molecule databases in two putative binding sites predicted using Allosteer. The virtual screening of 263,000 compounds generated a list of 40 compounds, which was then trimmed to 26 for further experimental testing.

Experimental testing of small molecules: We developed several different bench-based assays to perform rigorous and reproducible tests for the predicted hit molecules. These assays include testing direct binding to TXNIP as well as functional assays including under diabetic high glucose conditions. The assays are: (1) drug affinity responsive target stability test that tests the direct binding of the compounds. In this assay, when a compound binds to its target molecule, it can reduce the rate of its proteolytic digestion. (2) This assay looks for compounds that can interfere with the interaction between TXNIP and TRX in THP-1 monocytes treated with high glucose. TXNIP is highly expressed in cells treated with high glucose, and therefore would have high concentration of TXNIP/TRX complexes in the cell extract. Co-immunoprecipitation was done in these extracts through adding TRX antibody, and then the effects of compounds added were tested. If a compound can break the pre-formed TXNIP/TRX complex, there will be a reduced signal (band intensity) in the assay. (3) The third assay is designed to test whether the compounds attenuate high glucose induced adverse effects (TXNIP expression, inflammatory cytokine production, apoptosis, etc.) in cells relevant to diabetes and complications (4) We also used lead compounds to examine if they have anti-apoptotic protective effects in primary human islets under in vitro diabetic conditions (high glucose+cytokines).

Testing of 26 compounds was performed rigorously using the experimental assays described above led to the initial identification of two putative lead small molecule inhibitors of TXNIP, namely Compounds C30 and C38, which can inhibit high glucose-induced TXNIP-TRX co-immunoprecipitation in cell extracts, in vivo in cells, can bind to TXNIP and prevent its proteolysis, and also attenuate high glucose induced expression of inflammatory cytokine molecules and TXNIP in monocytes.

The compounds C30 and C38 (shown in Table 1) work at micromolar concentrations. To find additional hit compounds, we tested analogs of C38 (Table 1). These efforts resulted in identification of the compound E2, which also showed a positive inhibitory effect on TXNIP.

TABLE 1

Structures of lead compounds and analogs.

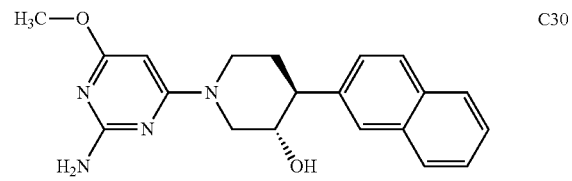

C30

C38

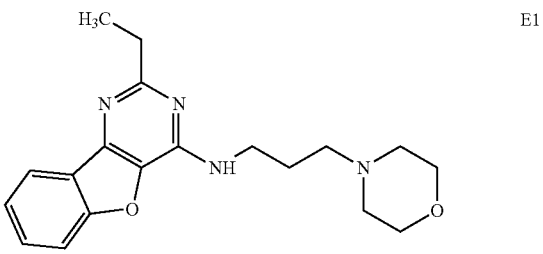

E1

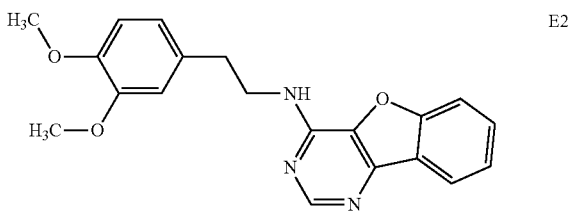

E2

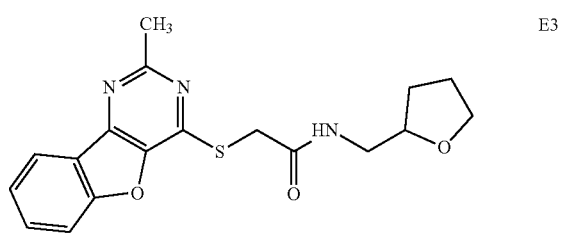

E3

TABLE 1-continued

Structures of lead compounds and analogs.

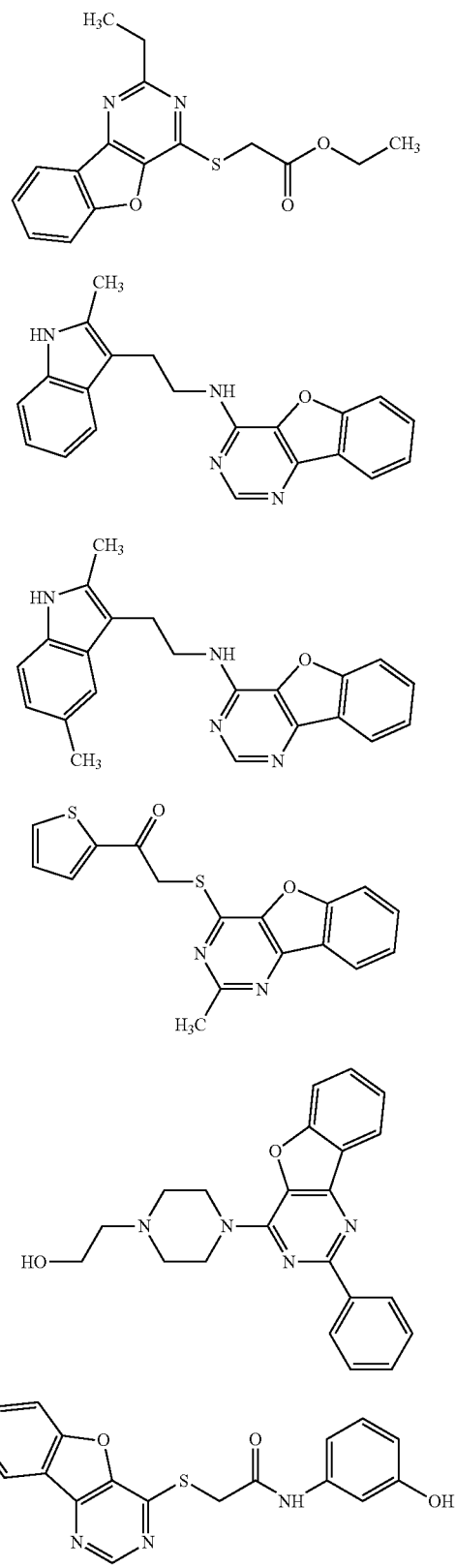

E4

E5

E6

E7

E8

E9

TABLE 1-continued

Structures of lead compounds and analogs.

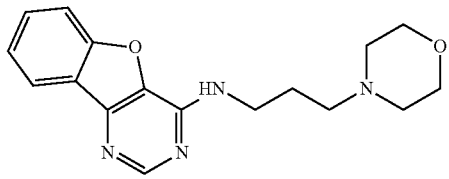

E10

Therefore, compounds C30, C38 and other analogs such as E2, with substitutions at several positions as shown in Table 1 can be developed as effective drug candidates for a) preventing complications of diabetes (e.g., nephropathy, retinopathy, neuropathy, cardiovascular, inflammation); b) diabetes itself (because they could reduce oxidative stress to protect against type 1 and type 2 diabetes caused by oxidant stress, as well as HG mediated inflammation and HG induced pancreatic islet beta cell destruction and dysfunction); and c) for patients depicting metabolic memory (because TXNIP epigenetic modification is involved in metabolic memory, and, by blocking oxidant stress, it may also reduce the epigenetic modification of TXNIP).

Example 2: Screening TXNIP-Targeting Small Molecules in Murine and Human Cells

Thioredoxin interacting protein (TXNIP) is a glucose response protein and a major regulator of cellular redox signaling. It promotes oxidative stress in the pancreas and other organs, and is emerging as a key therapeutic target in diabetes and its complications. Glucose induced overexpression of TXNIP results in increased interaction with its partner thioredoxin, an antioxidant. This reduces the activity of thioredoxin and raises oxidative stress leading to pancreatic beta cell death as well as dysfunction of several target organs (e.g., kidneys, eyes, heart). Therefore, inhibiting TXNIP expression and its interaction with thioredoxin (TRX) is a promising therapeutic route towards protecting islet beta cells against diabetes induced attrition, as well as diabetic complications. We report several novel small molecule inhibitors of TXNIP that reduce TXNIP and TNF-α expression in glucose stimulated THP1 human monocytes and human pancreatic islet cells. Our evidence suggest that these compounds disrupt the interaction between TXNIP and its partner thioredoxin by directly binding to TXNIP. The reported compounds were discovered through combined computational screening of small molecule databases and testing of the predicted hits in experimental assays. The reported hit compounds offer promising therapeutic potential in both type I and type II diabetes.

Initial screening efforts identified several TXNIP-targeting compounds, referred to herein as C30 and C38. Later, screening of analogous compounds of C38 identified another positive hit, E2. Data is presented that demonstrates the effects these three leading compounds upon TXNIP signaling in a range of cell types including THP1 cells (a human monocyte cell line), mouse RAW264.7 macrophage cells, MIN6 mouse pancreas beta cells and 1.1 B4 human pancreas beta cells. Each cell type was treated with the lead compounds and changes in TXNIP, TNF-α (as a marker of cell activation) quantified and other assays performed. Results obtained in cell experiments will be employed to inform in vivo animal studies.

Figure 2A:
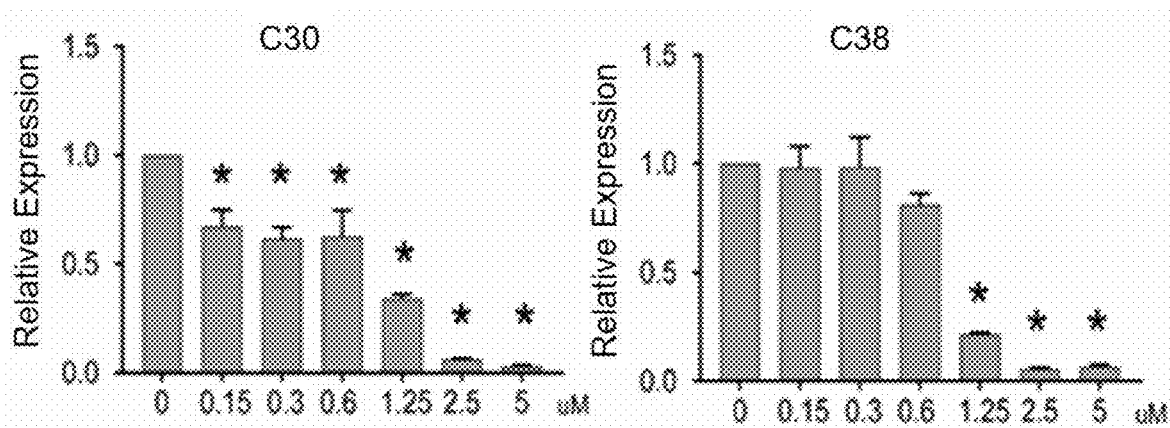
FIGS. 2A-2B.

C30 and C38 inhibited TXNIP mRNA expression in THP1 cells. FIG. 2A shows the effects of concentration ranges of C30 and C38 on TXNIP mRNA expression in THP1 human monocyte cell line. These results confirmed that C30 and C38 inhibit TXNIP expression in a dose-dependent manner. Among the two compounds, C30 seems be the more potent inhibitor of TXNIP mRNA being effective at concentrations as low as 0.15 uM.

Figure 2B:
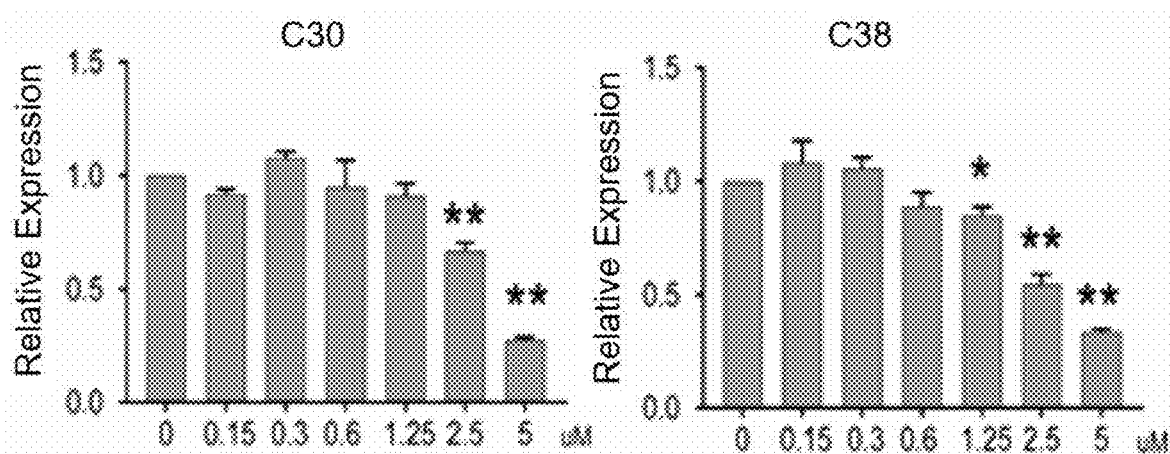

C30 and C38 also reduced TNF-α expression in THP1 cells. FIG. 2B shows the effects of treatment with the compounds on mRNA levels of the proinflammatory cytokine TNF-α. Treatment with both agents lead to lower levels of TNF-α mRNA, although this required relatively higher concentrations compared to those that suppressed TXNIP mRNA (see FIG. 2A).

Figure 3A:
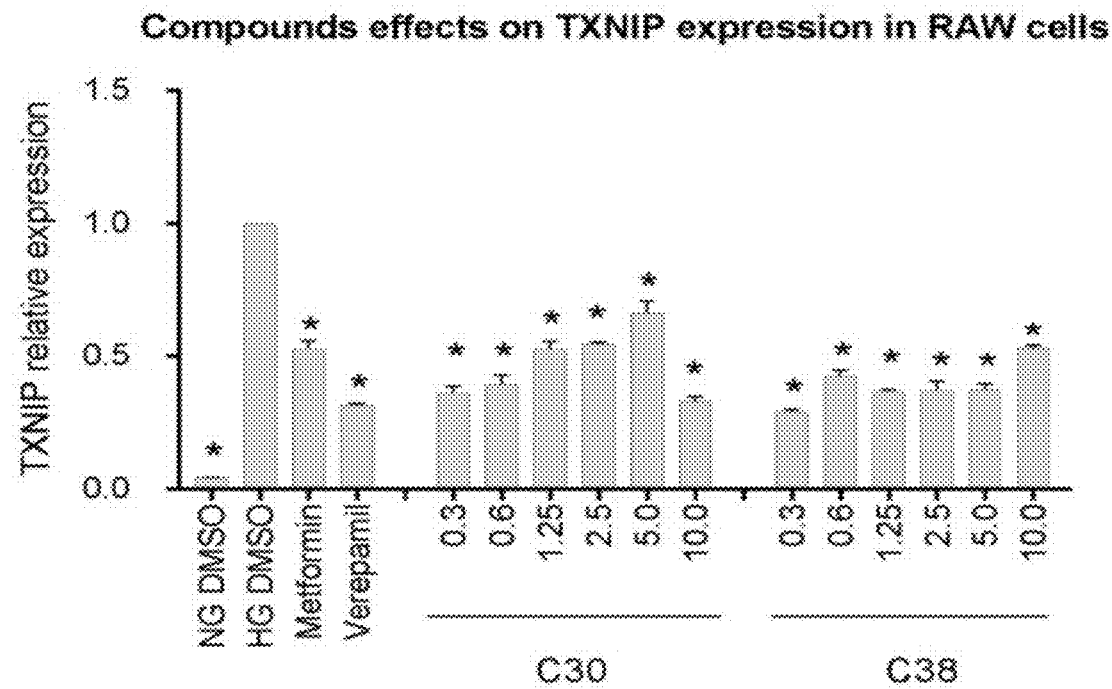
FIGS. 3A-3B.
Figure 3B:
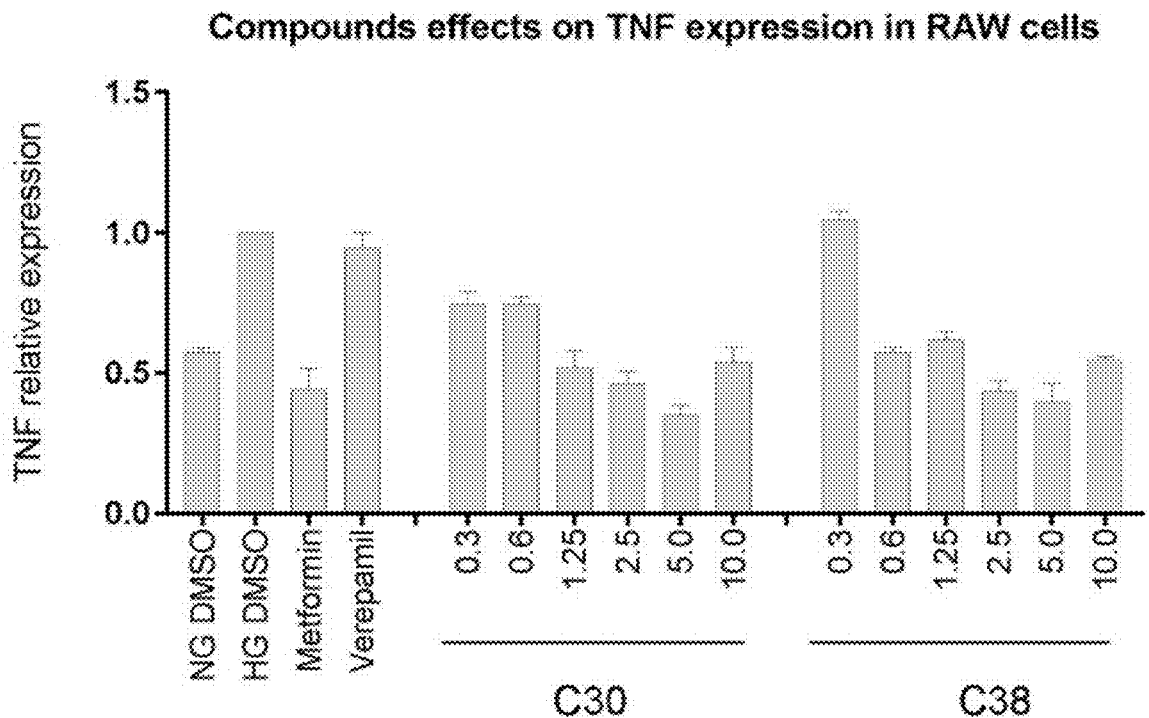

Treatment of murine RAW macrophages with lead compounds C30 and C38 decreased TXNIP and TNF-α. We have also tested the effects of the lead compound in murine RAW264.7 (RAW) macrophages. As in human THP1 cells, C30 and C38 inhibited TXNIP and TNF-α mRNA expression in mouse RAW cells (FIGS. 3A-3B) showing they are also effective in mouse cells. Thus C30 and C38 alter mRNA levels in both human and mouse monocyte/macrophage cells.

Figure 4A:
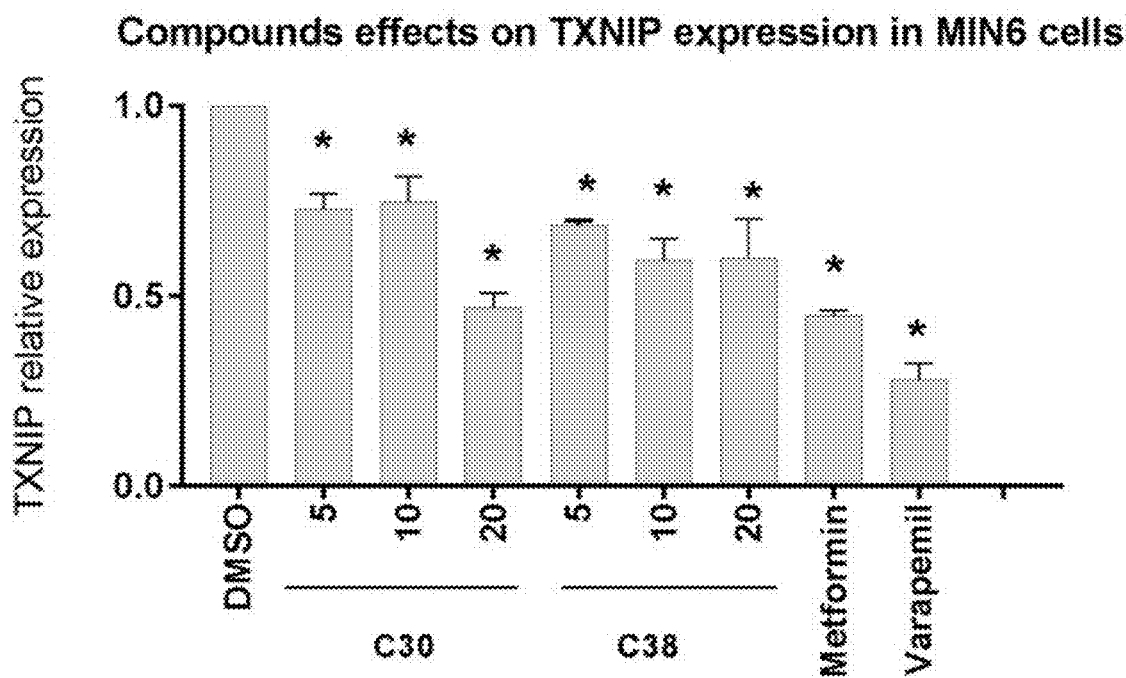
FIGS. 4A-4B.
Figure 4B:
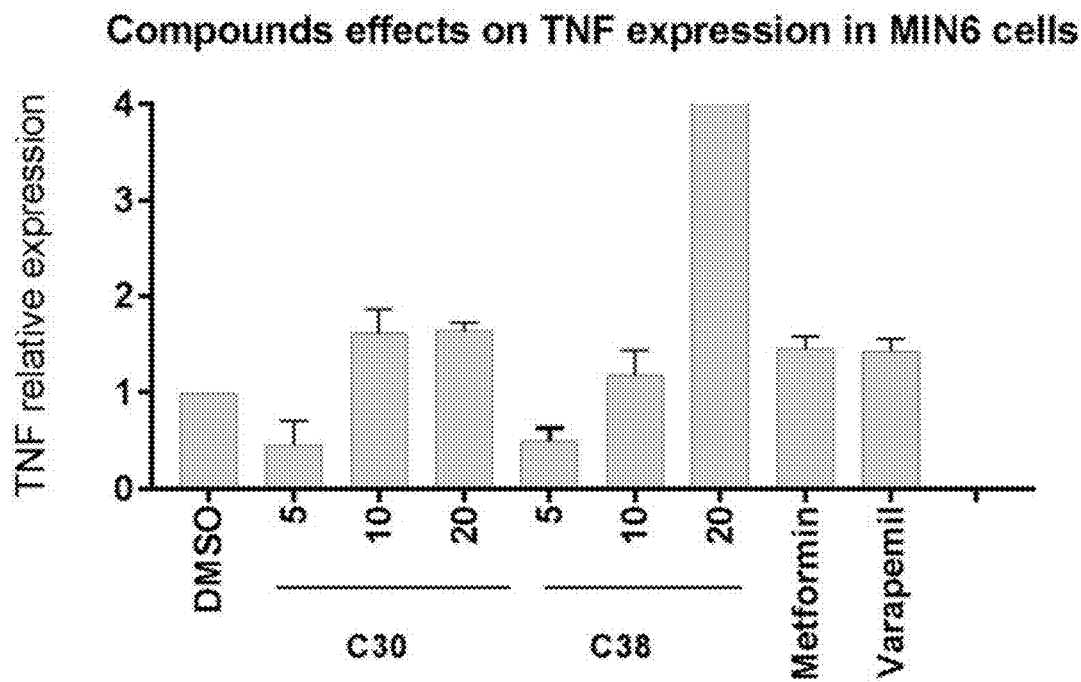

Treating murine MIN6 pancreatic beta cells with lead compounds showed varying effects on key mRNA levels. To ascertain the relevance to pancreatic beta cells, we tested the effects of the lead compounds on key target gene mRNA levels in murine MIN6 pancreatic beta cells. Both compounds reduced TXNIP mRNA expression (FIG. 4A), but MIN6 cells appeared to be less sensitive to the agents. The compounds also did not have much effect on TNF expression (FIG. 4B).

Figure 5A:
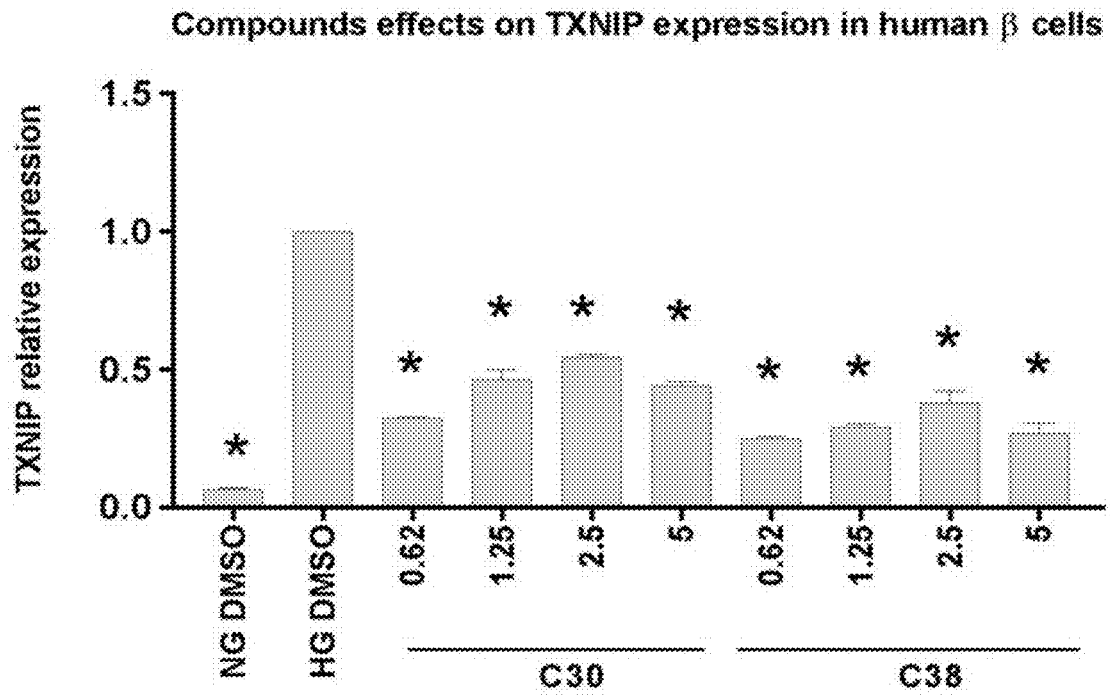
FIGS. 5A-5B.
Figure 5B:
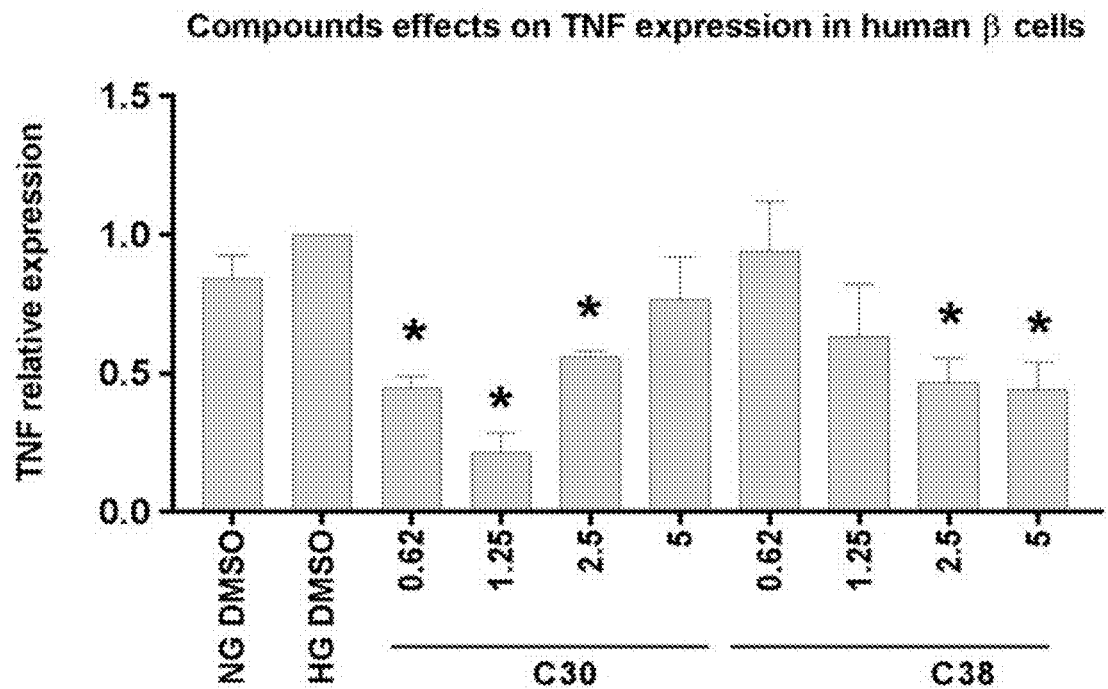

Treating a human pancreatic β-cell line 1.1 B4 with the lead compounds decreased TXNIP and TNF-α mRNA levels. To determine relevance to human clinical development, we next tested the effects of the lead compounds in the human 1.1 B4 cell line. The lead compounds strongly inhibited TXNP mRNA expression (FIG. 5A). Furthermore, the compounds decreased TNF-α expression in these cells (FIG. 5B). Overall, human 1.1B4 beta cells were found to be sensitive to the lead compounds.

Figure 6:
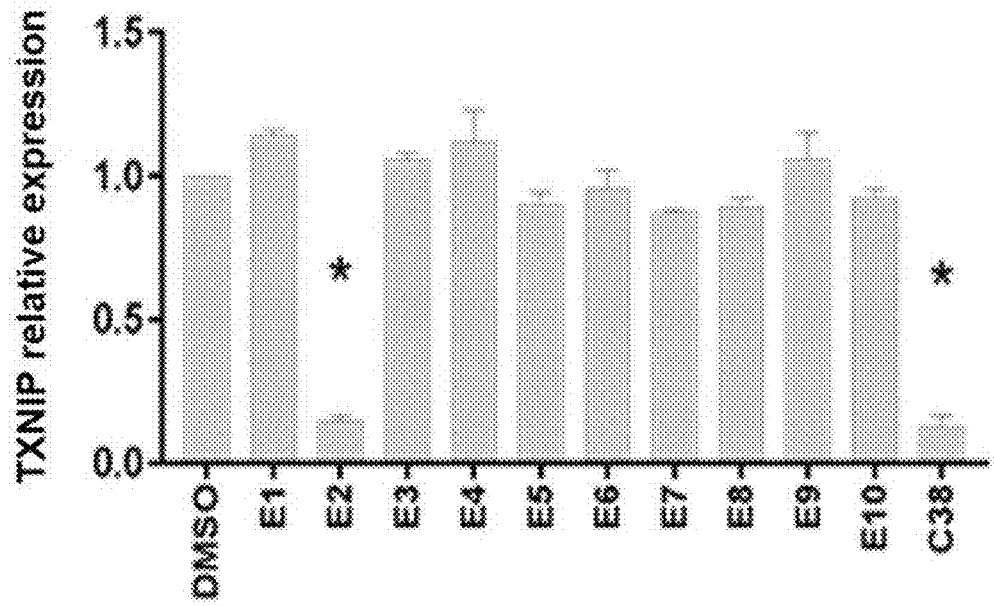
FIG. 6. C38 analogues effects on TXNIP mRNA expression in THP1 cells. THP1 cells were cultured under 25 mM glucose with 2.5 uM of compounds for 72 h. Total RNA was collected. RT-PCR was performed in triplicate and data shown are the mean±SEM. Statistical analysis was performed using one-way ANOVA: $*p<0.0001$.
Figure 7:
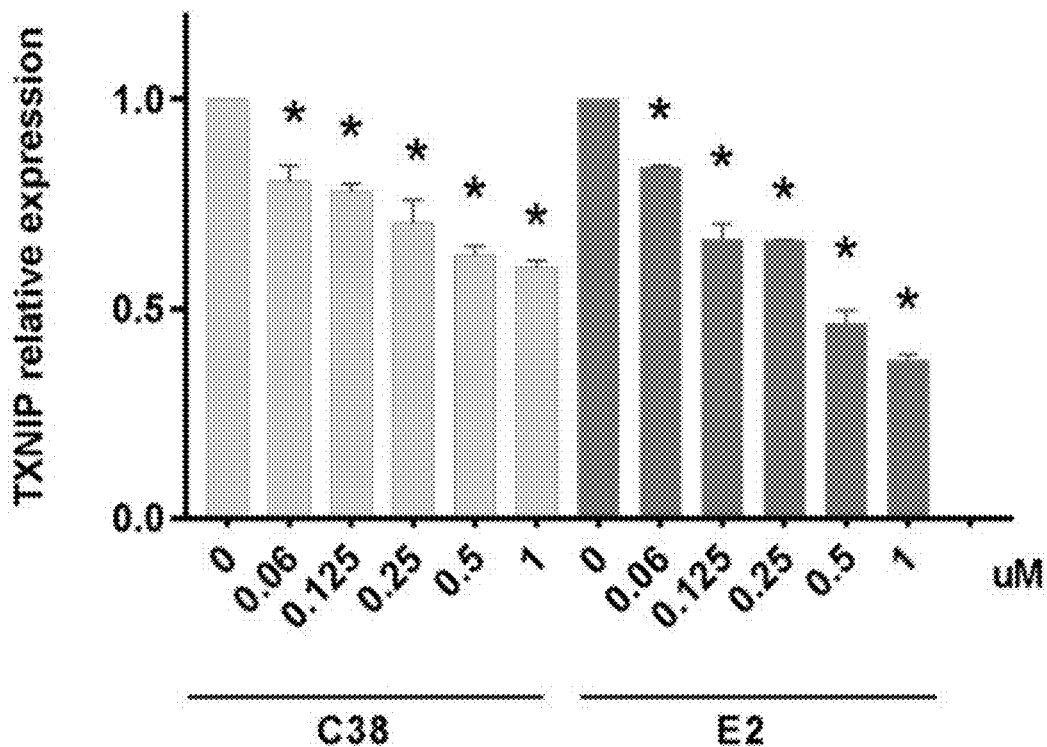
FIG. 7. C38 and analogue E2 effects on TXNIP mRNA levels in THP cells. THP1 cells were cultured under 25 mM glucose with several concentration of C38 and E2 as indicated for 72 hours. Total RNA was prepared. RT-PCR was performed in triplicate and data shown are the mean±SEM. Statistical analysis was performed for each column vs. without compound control using one-way ANOVA: $*p<0.0001$.

Discovery of lead compound analogues. A search of chemical libraries was performed in the interest of identifying possible lead compound analogues. Analogues to C38 were identified. They are named "E" batch compounds (shown in Table 1). To determine the properties of the analogues, we treated THP1 cells with the E batch compounds for three days, prepared RNA and measured TXNIP mRNA levels. Among E batch analogues, E2, similar to C38, strongly inhibited TXNIP mRNA expression (FIG. 6). Further tests showed that E2 was moderately better than C38 (FIG. 7). In summary, the C38 analogue E2 shows similar activity as C38 in THP1 cells.

Figure 8:
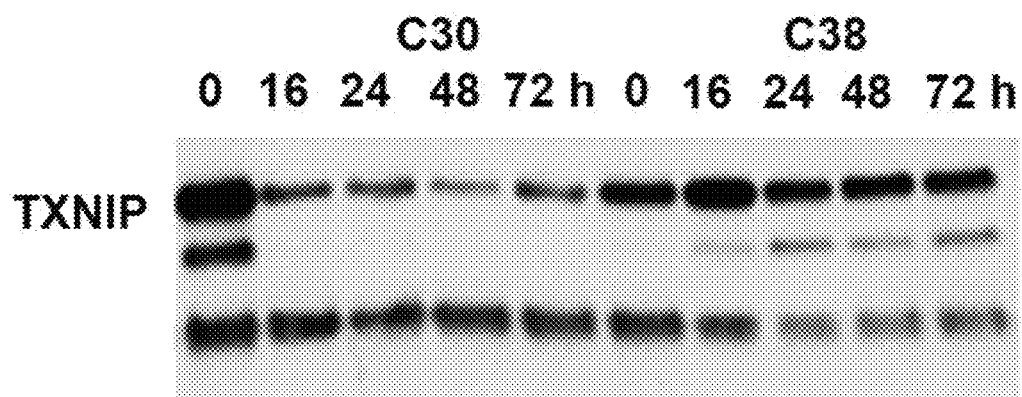
FIG. 8. Effects of C30 and C38 on TXNIP/TRX interaction. THP1 cells were cultured under 25 mM glucose with 5 uM C30 or C38 for 72 hours. Aliquots were taken at different time points as indicated and nuclear cell extracts were prepared. Standard co-IP was performed with mouse anti-TRX Ab overnight. Beads were washed with buffer and blots treated with rabbit anti-TXNIP antibody (Ab) for detection of the complex (upper band).

TXNIP interaction/binding with TRX is inhibited by C30. A primary goal of this research is to identify chemical compounds that block TXNIP interactions with the target thioredoxin (TRX). To confirm such activity in a lead compound, we employed the well-established technique of co-immuno-precipitation (co-IP). Our results indicated that basal TXNIP association/interaction with TRX was significantly reduced by treatment with C30 but this interference was clearly reduced in cells treated with C38 (FIG. 8, upper band).

Figure 9:
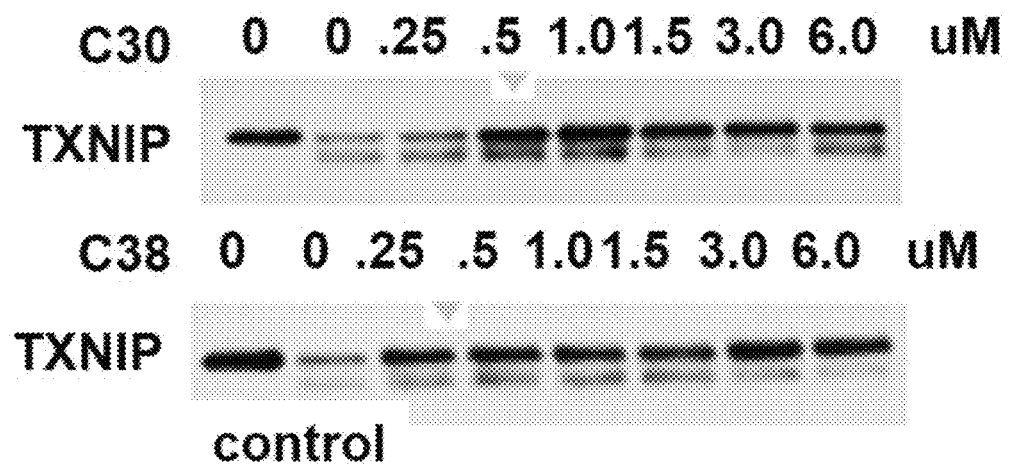
FIG. 9. Treatment with C30 and C38 protects TXNIP from proteolysis in a DARTS assay. THP1 cell were cultured in RPMI 1640 medium under 25 mM glucose for 72 hours. Cell extracts were prepared. C30 and C38 were added at the indicated concentrations and protease was added except control lanes. Aliquots were withdrawn at 7 minutes and loaded on 10% SDS gels. Control: without protease.

Treatment with lead compounds protects TXNIP from proteolysis. The drug affinity response target stability assay (DARTS assay) is a method to identify potential protein targets for small molecules. The advantage of this method is being able to use the native small molecule without having to immobilize or modify the protein (e.g., by incorporation of biotin, fluorescent molecules, radioisotope, or photo-affinity labels). In this case, it relies on the protection against proteolysis conferred on TXNIP by interaction with a small molecule (lead compound). FIG. 9 shows that C30 and C38 have the ability to protect TXNIP from proteolysis from ~0.5 uM in THP-1 cells.

Figure 10A:
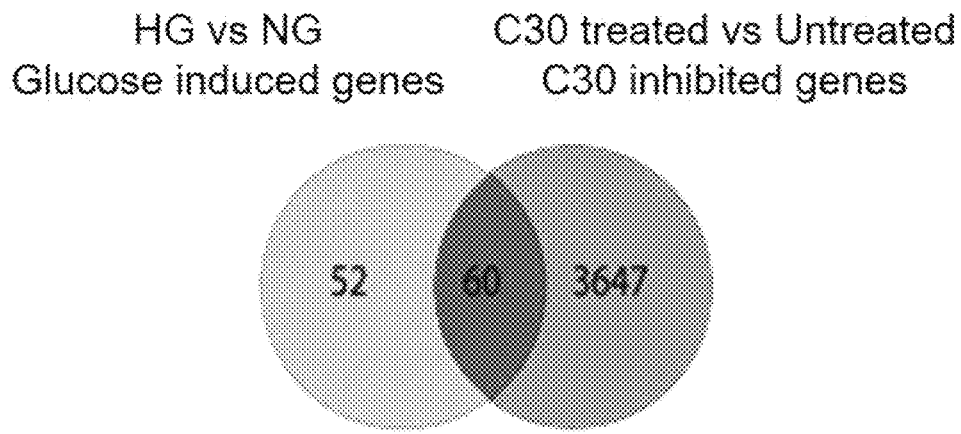
FIGS. 10A-10C. C30 and C38 inhibit the same subset of genes induced by high glucose (HG). THP1 cell were cultured in RPMI 1640 medium under 25 mM glucose for 72 hours with 2.5 um C30 or C38. Total RNA was prepared and sent for RNA-seq. Differential expression analysis was conducted as described in the Methods. Genes with a fold change (FC) greater than 2 or less than 0.5 and an FDR-adjusted p-value less than 0.05 were considered significant up- and down-regulated genes, respectively.
Figure 10B:
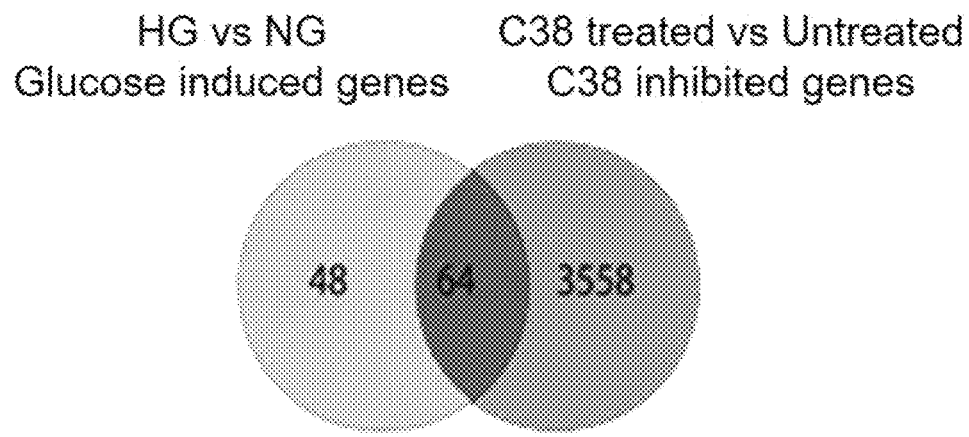
Figure 10C:
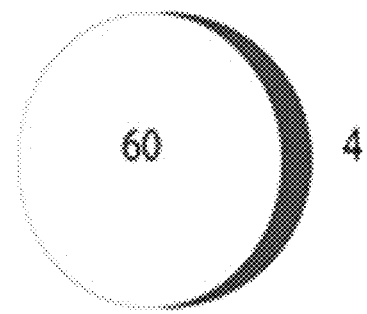
Figure 11A:
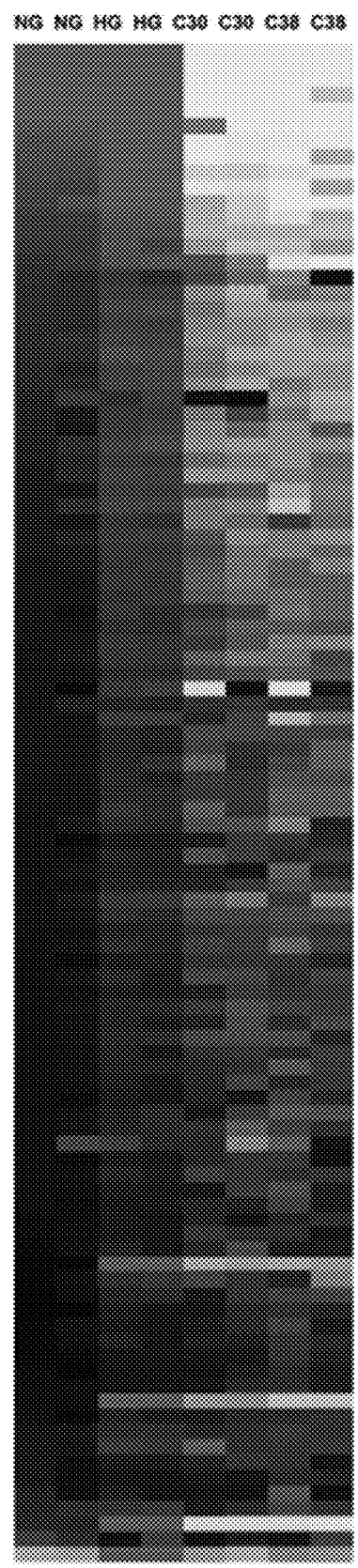
FIGS. 11A-11B.
Figure 11B:
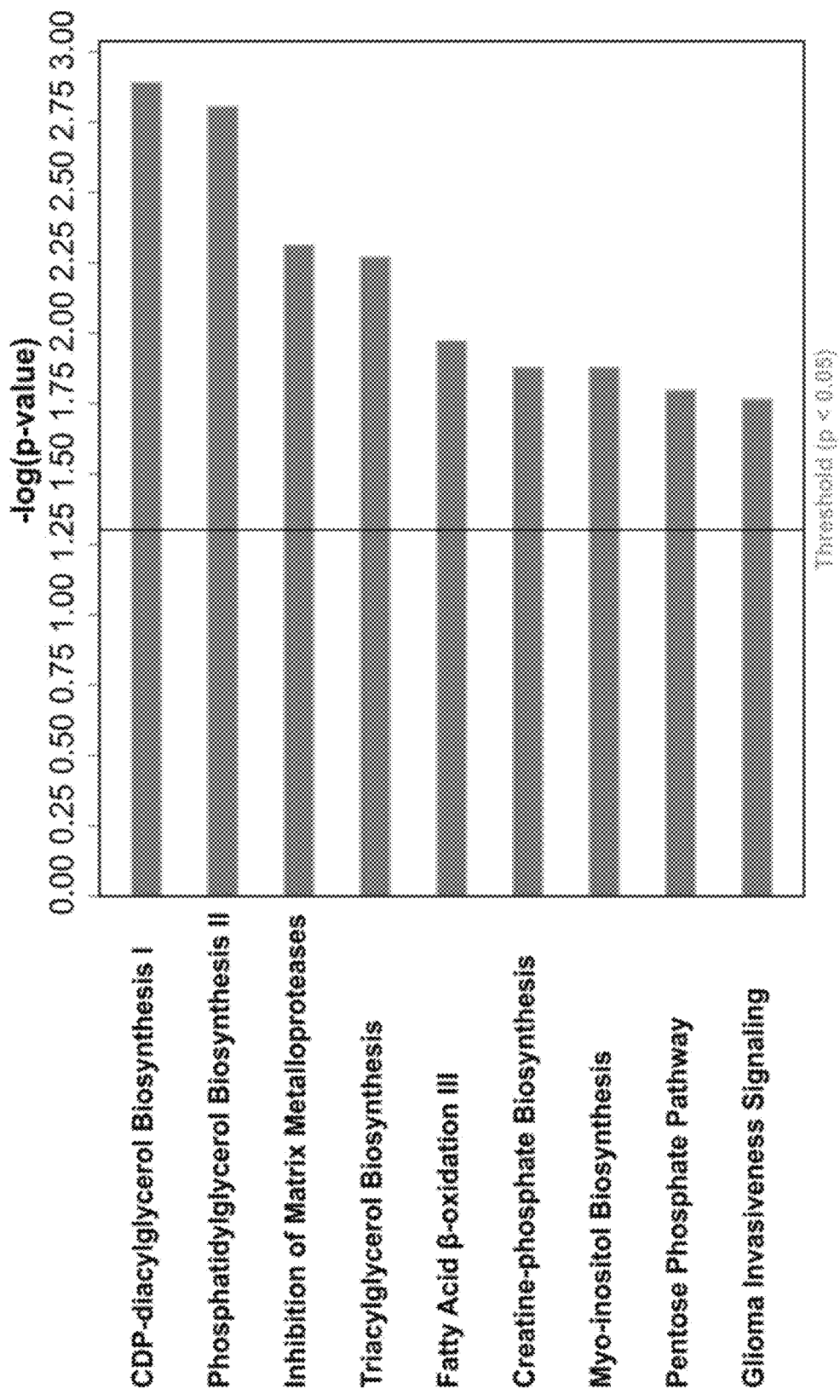

RNA-seq analysis finds that the lead compounds inhibit similar genes. In cells, TXNIP gene transcription is upregulated by glucose via the transcription complexes carbohydrate-responsive element-binding protein (chREBP)/max-likeprotein (Mlx) and Mlx-interacting protein (MondoA)/Mlx. TXNIP expression is modulated by redox stress, glucose levels, hypoxia and inflammatory activators. To determine the kinds of genes affected by the compounds, we treated THP1 cells with 25 mM glucose (HG) plus C30 or C38 for 72 hours and prepared total RNA for RNA seq. Initial analysis of RNA-seq data reveals that there is good overlap in HG-induced genes that are inhibited by C30 or C38 (FIGS. 10A-10C and FIG. 11A). We found that high glucose (HG) induced/C30 inhibited overlapping genes were almost the same as HG-induced/C38-inhibited genes (FIG. 10, FIG. 11A, and Table 2). This suggested that the mechanism of action of both compounds to inhibit TXNIP may be very similar. Interestingly, TXNIP and arrestin-4, both glucose-sensitive genes, are among those found by RNA-seq (Table 2). Others have reported that TXNIP can directly bind to GLUT1, induce GLUT endocytosis and reduce glucose influx (Wu et al, 2013). TXNIP can also function as an adaptor for the basal endocytosis of GLUT4 (Waldhart et al., 2017). Therefore, TXNIP is a key molecule for modulating glucose influx through GLUT1 and GLUT4. It is possible C30 and C38 bind to TXNIP, and possibly enhance its ability to promote GLUT1 and GLUT4 endocytosis or, directly bind to GLUT1, to reduce glucose influx into cells.

TABLE 2

HG-responsive and C30/C38-inhibited genes.

| | | | |
|---|---|---|---|
| ACP2 | FAM20C | MAMDC4 | SEPT5-GP1BB |
| ADGRE5 | FLNA | MBOAT7 | SIGMAR1 |
| AGPAT2 | G0S2 | MFNG | SLC16A2 |
| ARRDC4 | GAREM2 | MMP2 | SP9 |
| BEGAIN | GPR137 | NF2 | SPI1 |
| C3AR1 | GUCD1 | NRSN2 | SPNS3 |
| CITED4 | H2AFX | NTN1 | TIMP3 |
| CKB | HOXA11-AS | PAQR4 | TK1 |
| CSF3R | IMPA2 | PKMYT1 | TKTL1 |
| DNPH1 | KIAA1522 | PLEKHA4 | TMEM54 |
| DOK2 | KLF10 | PLEKHH3 | TNFSF14 |
| ECI1 | KREMEN1 | PTMS | TSPO |
| EGFL7 | LAMB3 | PTPRF | TUBA4A |
| EHD2 | LIMD2 | RAB3D | TXNIP |
| FAM163A | LY6E | SEMA4A | UHRF1 |

Also, results of Ingenuity Pathway Analysis indicate these shared 60 genes are involved in CDP-diacylglycerol Biosynthesis, Phosphatidylglycerol Biosynthesis, Triglycerol Biosynthesis, and Fatty Acid beta-oxidation etc., which are glucose-related metabolism pathways.

Figure 12A:
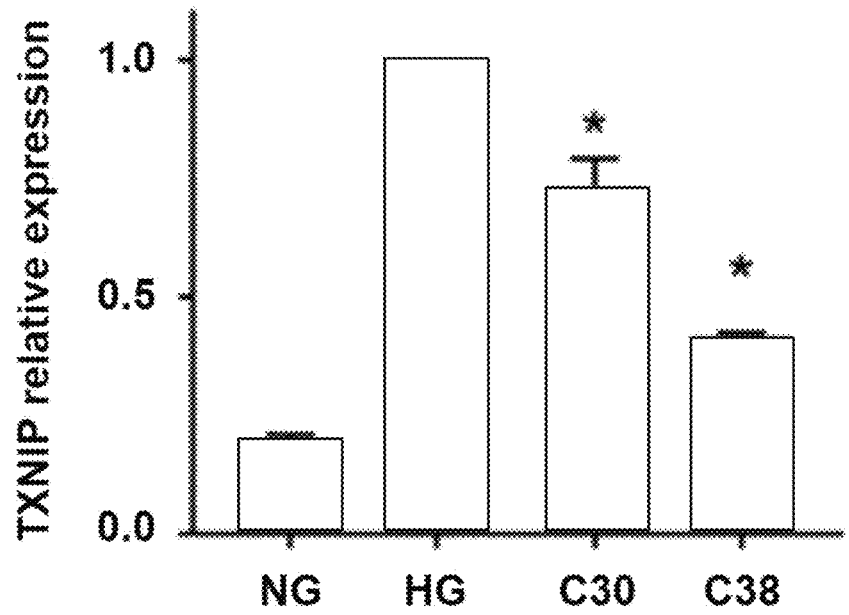
FIGS. 12A-12B.
Figure 12B:
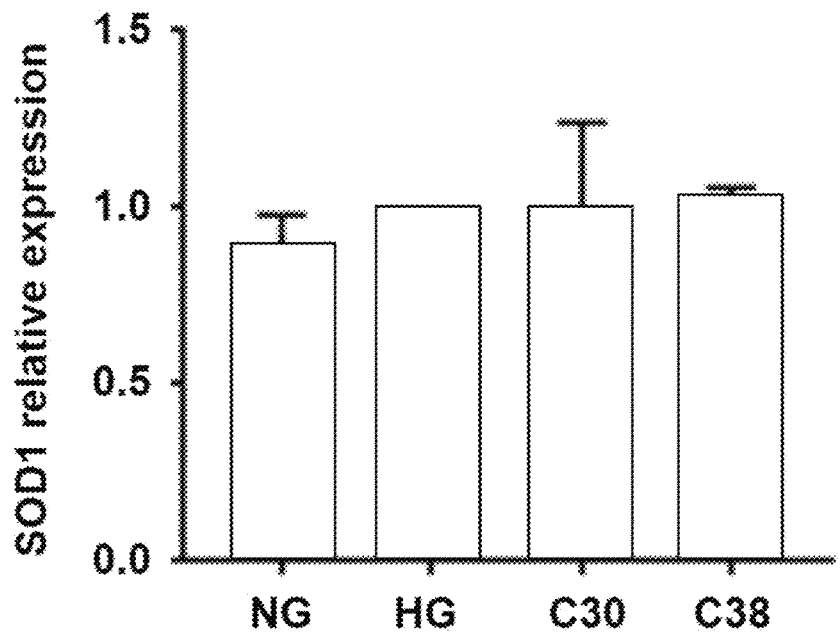

Testing lead compounds in human pancreatic islets. To further explore the effects of the lead compounds as possible therapies in diabetes, we conducted translational studies in primary human pancreatic islets (obtained from the City of Hope islet isolation center). Results indicated these compounds efficiently inhibited TXNIP mRNA even in isolated primary human islets (FIG. 12A), but did not alter expression of the protective antioxidative gene (SOD) in these cells (FIG. 121B), suggesting potential lower toxicity or off-target effects.

Example 3: Materials and Methods

Computational protocol for identifying allosteric binding sites and small molecule inhibitors of TXNIP. Conventional high throughput virtual screening methods have shown some success in identifying small molecule binders for protein targets. However, these methods are inadequate for challenging targets such as TXNIP. TXNIP interacts with its partner TRX using covalent disulfide bonds making it impossible to target the protein-protein interface using small molecules. While it is possible to identify small molecules that disrupt the interaction between TXNIP and TRX by binding to a distant site in TXNIP (allosteric site), such a problem is challenging due to (A) difficulty of discovering novel druggable sites over the entire protein surface, and (B) determining which of these sites will have the desired inhibitory effect on TRX interaction upon drug binding. We have addressed this by developing a combination of in-silico methods and applied them to TXNIP.

Our protocol for identifying small molecule inhibitors of TXNIP may be divided into three steps: (a) Identification of druggable binding sites in TXNIP using the in-house program 'FindBindSite'; (b) selection of suitable binding site(s) from step (a) for inhibitor screening using the in-house program 'Allosteer'; and (c) hierarchical screening of small molecule databases in the selected sites in TXNIP, enhanced by an in-house filtering algorithm based on fragment pharmacophores, and selection of the final hits.

FindBindSite (FBS) is a method and software developed for identifying small molecule binding sites in proteins (Li et al., 2014). FBS has been validated against multiple protein targets (Li et al., 2014). As part of the FBS procedure, we first docked a database of 10,000 chemically diverse drug-like compounds to the entire protein surface of TXNIP. Then we clustered the docked compounds and analyzed the energetic and chemical properties of each cluster. The sites which docked the highest number of small molecules and showed the best overall binding energy scores were selected for further consideration.

Figure 13:
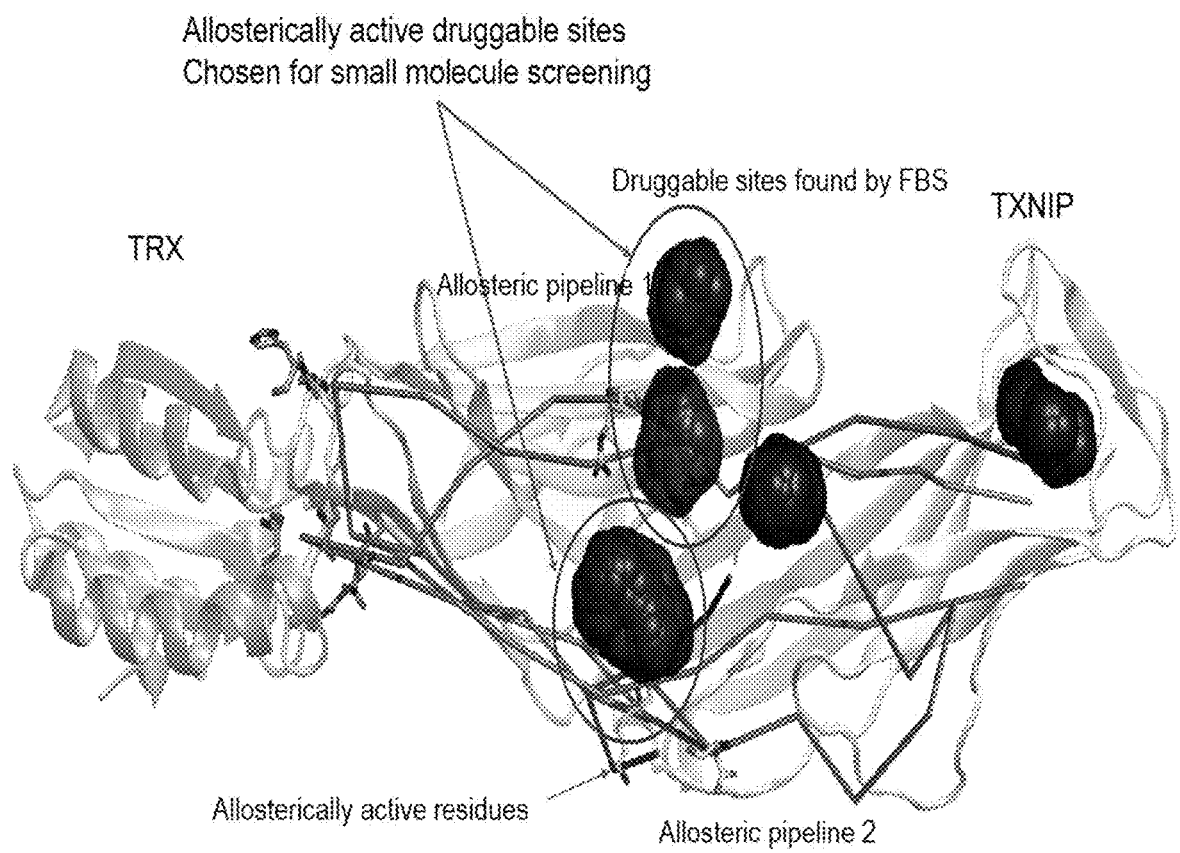
FIG. 13. TXNIP-TRX complex showing the predicted allosteric sites for small molecule design. The communication pipelines connecting the TRX site to the allosteric sites were calculated from multiple MD (molecular dynamics).

To determine which of the binding sites have the desired inhibitory effect on TXNIP-TRX interaction, we calculated the allosteric communication between the druggable sites and the TRX interface using the in-house method Allosteer. The method Allosteer and the associated software has been validated by applying to multiple protein targets including several GPCRs and the phosphotyrosine phosphatase PTPN5 (Bhattacharya et al., 2016; Bhattacharya and Vaidehi, 2014; Nivedha et al., 2018; Tautermann et al., 2019; Vaidehi and Bhattacharya, 2016). Using molecular dynamics simulations starting from the crystal structure of the TXNIP-TRX complex (Hwang et al., 2014), we calculated the allosteric communication pipelines between the druggable sites and the TRX interface. Two of the sites that showed the strongest allosteric communication with the TRX interface were selected for drug design. Using Allosteer, we also identified the allosteric hotspots in each binding site (amino acid residues that play vital role in allosteric modulation of TRX binding), that would be critical in selecting the final hits. FIG. 13 shows the major allosteric pipelines as lines and the hotspot residues as sticks. The binding sites which were selected for drug design are circled.

Figure 1B:
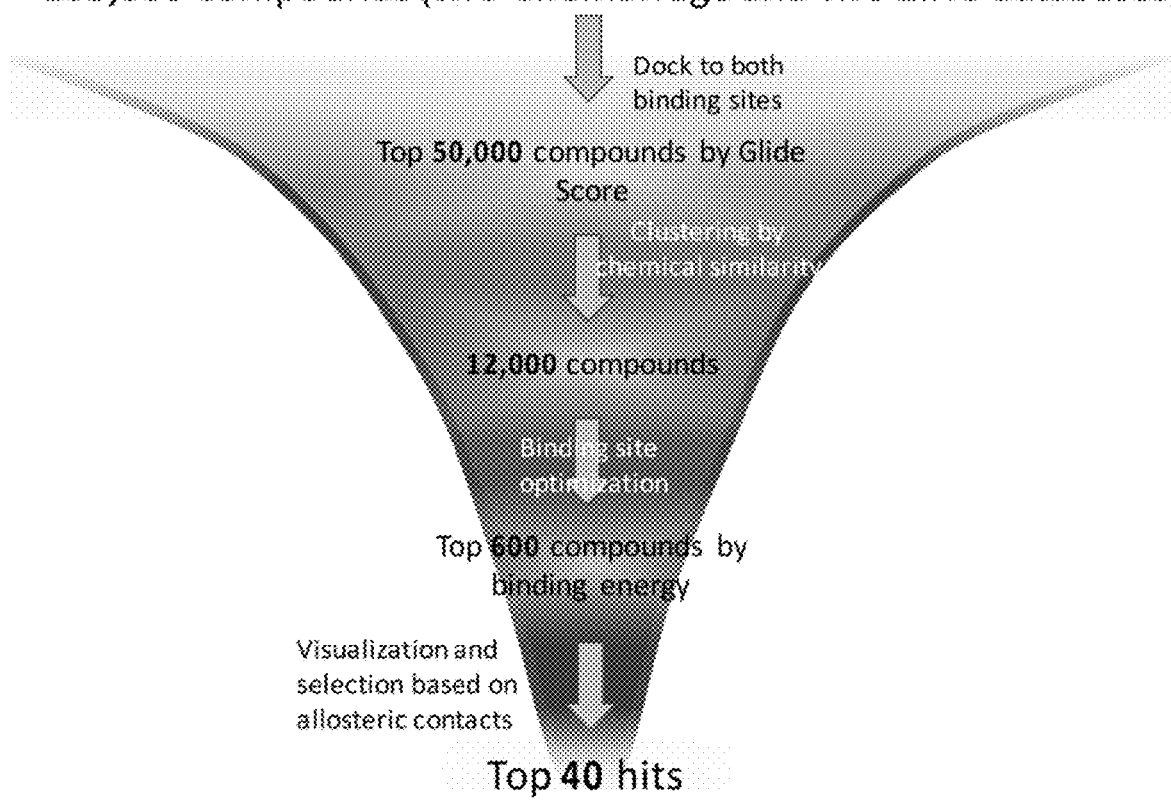

For drug screening, we used >250,000 compounds from two small molecule databases from the vendors ZINC and ChemBridge Inc. The screening of small molecules to TXNIP was performed using the Glide software from Schrodinger (Friesner et al., 2004; Halgren et al., 2004). However, the screening databases were first pre-filtered using a fragment pharmacophore based approach. In this method, multiple (10,000) low molecular weight compounds (fragments) were docked to the two binding sites in TXNIP, followed by identification of the top pharmacophores in each site using Canvas (Schrodinger™) (Duan et al., 2010; Sastry et al., 2010). The small molecule databases from ZINC and ChemBridge were then filtered, retaining only the compounds that resembled the top three pharmacophores. This step enriched the small molecule databases with likely binders, thereby improving the accuracy of the virtual screening. The pre-filtered databases were then docked to the two binding sites in TXNIP using the Glide SP protocol, retaining the top 1000 compounds from each database by Glide score. The bound poses of the top compounds were next optimized using Prime and MacroModel (Schrodinger™) (Bell et al., 2012), followed by rapid binding free energy calculation. The top 50 compounds by binding energy were retained from each database in each binding site, and these poses were subject to thorough optimization and more accurate binding free energy calculation using the Prime/MMGBSA module of Maestro (Bell et al., 2012). The top 10 compounds (per database, per binding site) by binding energy were retained and the final hits were selected based on low binding free energy, interaction with the allosteric hotspot residues, and manual visualization of bound poses. A schematic of the screening process is shown in FIG. 1B. This step generated the two lead compounds, C30 and C38 (shown in Table 1).

In the next phase, the chemical structure of C38 was used to search the ChemBridge online database for analogous compounds. During the search, the central benzo-furo-pyrimidine moiety of C38, that makes major protein contacts, was retained and substituents around this moiety were varied in the analogs. In total, 182 analogs were obtained which were then processed using Ligprep in Maestro (Bell et al., 2012) and the probable protonation states of each compound were determined. Then, macroModel was used to generate unique conformations of each compound (Bell et al., 2012). In total, 246 conformations were generated for the 182 analogs. These conformations were then docked to TXNIP and the resulting docked poses were optimized through combined side chain reassignment and minimization of the binding pockets using Prime/MMGBSA, followed by binding free energy calculation. For selecting the final hits, compounds with similar or improved binding energy over C38 were retained and the final compounds were selected through manual visualization and improved protein-ligand contacts over C38. Ten compounds from this phase were tested experimentally resulting in one positive hit E2 (Table 1).

Western blotting. Cell extraction buffer (Thermo Fisher Scientific) and protease inhibitor cocktail (Roche) were used to lyse cells after various treatments. SDS-PAGE-resolved proteins were transferred to nitrocellulose membrane. Antibodies used were rabbit anti-TXNIP (Cell Signaling) and mouse anti-TRX (Abcam ab16965).

RNA extraction and quantitative RT-PCR. RNA was extracted using the Direct-zol™ RNA MiniPrep Plus (Zymo Research). Reverse transcription of RNA samples into cDNA was performed using the GeneAmp RNA PCR Kit (Applied Biosystems), dNTP (from Roche Applied Science), Rnase inhibitor, MULV Reverse Transcriptase and Random hexamers reagent (all from Invitrogen). Diluted cDNA was quantified using real-time PCR performed with Power SYBR Green qPCR MasterMix (Applied Biosystem) and 7500 real-time PCR system (Applied Biosystems). The HPRT1 gene was used as an internal control.

Co-immunoprecipitation. THP1 cells were treated with compounds (up to 5 uM) overnight and glucose was added to 25 mM and cells cultured at 37° C. for 3-5 days. Co-IP with mouse anti-TRX antibody was performed using standard co-IP protocols. Rabbit anti-TXNIP antibody (Cell Signaling) was used for Western blotting.

Drug affinity responsive target stability (DARTS) assay. DARTS assay was conducted according to a published protocol (Lomenick et al., 2009; Pai et al., 2015). THP1 cells were lysed with extract buffer. Lysates were incubated on ice for 10 minutes and then centrifuged at 18,000 g for 10 minutes at 4° C. and the pellet discarded. After mixing with various amounts of pronase (Roche), lysate-pronase mixtures were incubated at room temperature for 5-30 minutes, and SDS loading buffer added and the mixture heated at 95° C. for 2 minutes. 10 μg of protein lysate was applied to SDS-polyacrylamide gels for electrophoresis and Western blotting.

RNA-seq: Sequence alignment and gene counts. RNA-Seq reads were trimmed to remove sequencing adapters using Trimmomatic (Bolger et al., 2014), and polyA tails using FASTP (Chen et al., 2018). The processed reads were mapped to the human genome (hg19) using STAR software (v. 020201) (Dobin et al., 2013). The HTSeq software (v.0.6.0) (Anders and Huber, 2010) was applied to generate the count matrix, with default parameters.

Differential gene expression analyses by RNA-seq. Differential expression analysis was conducted by adjusting read counts to normalized expression values using the TMM normalization method in edgeR package (Robinson et al., 2010). Genes with a fold change (FC) greater than 2 or less than 0.5 and an FDR-adjusted p-value less than 0.05 were considered significant up- and down-regulated genes, respectively. The finalized 60 genes were the overlapped up- and down-regulated genes amongst THP1 HG vs. THP1 NG and THP1 HG C30 or C38 treated vs. untreated. Prior to the alignment against the human genome (hg19) using STAR (Dobin et al., 2013), Trimmomatic (Bolger et al., 2014) was used to remove Illumina Sequencing adapters, while FASTP (Chen et al., 2018) was used to remove poly-A tails. Next, Raw counts for each gene in the GENCODE coding gene annotation (hg19) were measured using HTseq (Anders and Huber, 2010) with an argument of "-r pos-s reserve". Differential expression was calculated using these counts with edgeR (5,6) version 3.0. After correcting for differences in library sizes, a fold change of >1.5 and a p-value of <0.05 were applied to select expressed genes. The corrected measures of the latter were further processed using Cluster3.0 to generate a heatmap using Java TreeView.

Example 4: Additional Data

Animal Studies

Figure 14:
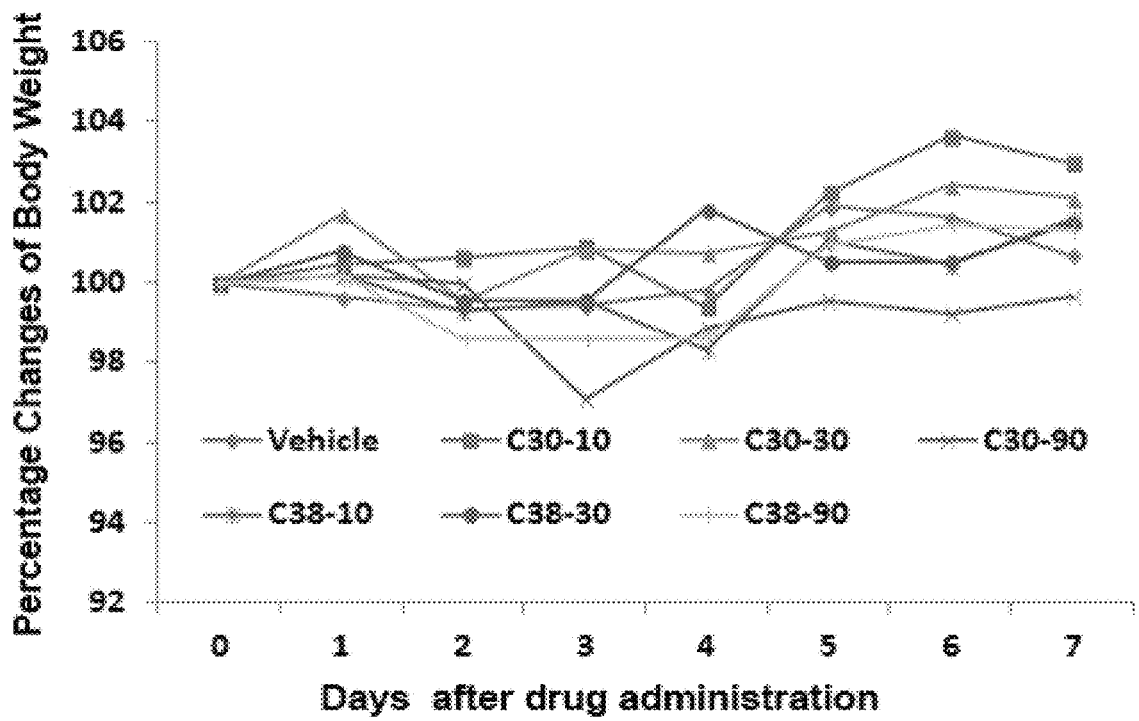
FIG. 14. Murine body weight during short-term treatment with increasing doses (10, 30, and 90 mg/kg) of lead compounds C30 and C38.

Testing toxicity in mice with three different doses of compounds given for five consecutive days. We tested toxicity of compounds C30 and C38 in an initial dose escalation study in 8-week-old male C57BL/6 mice. Briefly, 36 male C57BL/6 mice were divided into three groups (vehicle, C30 and C38). Each group was then subdivided into three sub-groups (three mice/subgroup). Animals received 10, 30 and 90 mg/kg dose daily by oral gavage for five consecutive days. Mice were humanely euthanized 24 hours following administration of the last drug dose (FIG. 14).

The results show that there was no significant change (decrease) in animal body weight regardless of the dose of the agent when administered short-term. Up to 90 mg/kg for five consecutive days was relatively safe.

Figure 15:
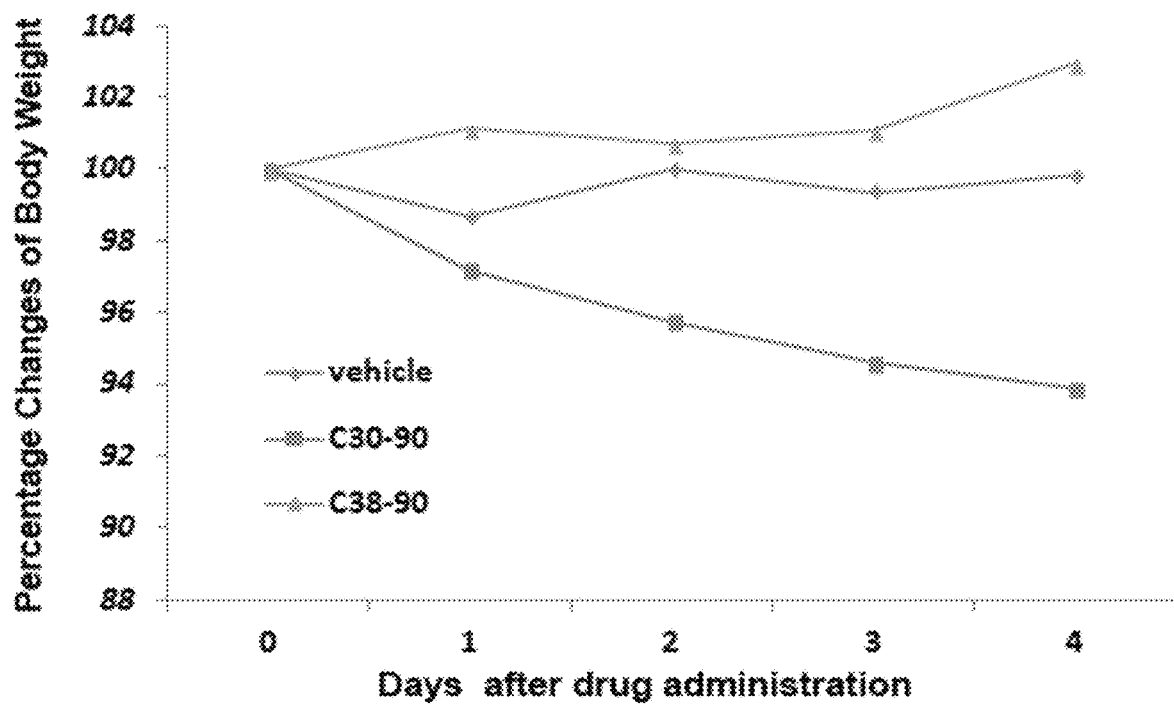
FIG. 15. Murine weight change after maximum dose regime (90 mg/kg).

The effects of compounds C30 and C38 at single high dose of 90 mg/kg. Twelve male mice were divided into three groups: 1) Control group (4 mice), 2) compound C30 (4 mice) and 3) compound C38 (4 mice). By oral gavage, animals were given 90 mg/kg of agent daily for 5 consecutive days (vehicle: 30% Solutol in saline). Mice were weighed every day during the treatment period. They were humanely euthanized 96 hours after the last dose. Tissues including the pancreas, liver and kidneys were collected (snap frozen in liquid nitrogen) for RNA extraction. Mice given the high dose (90 mg/kg) of C38 (C38-90) and euthanasia 96 hr after the last dose showed no significant weight loss. Those given compound C30 lost ~5% of body weight (FIG. 15).

Figure 16:
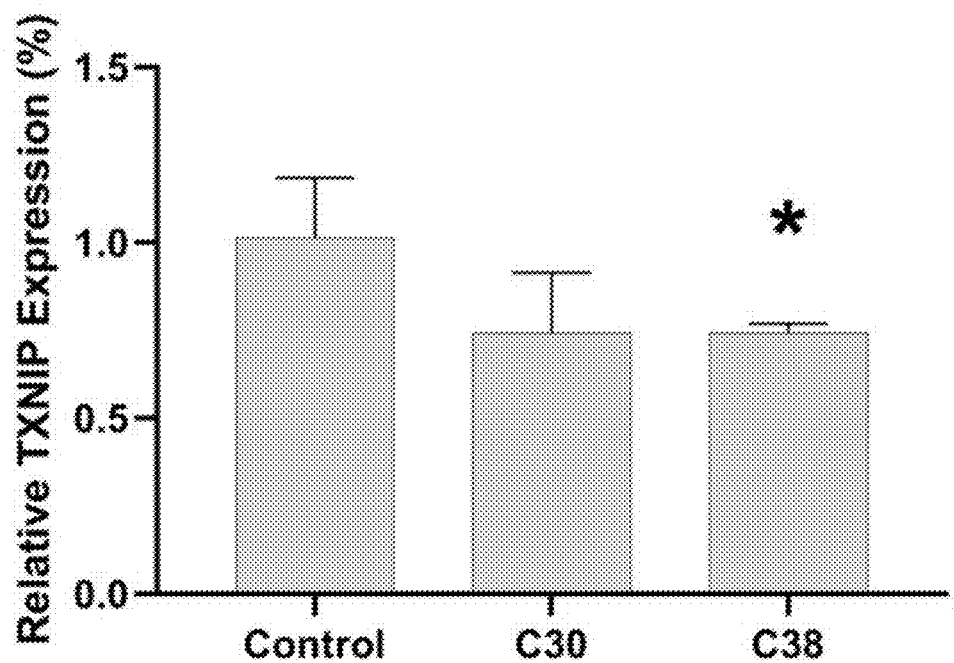
FIG. 16. Compounds C30 and C38 reduce TXNIP expression in murine blood. Twelve male C57BL/6 mice were divided into three groups (vehicle, C30 and C38). They received 90 mg/kg of the indicated compounds via oral gavage daily for five days. Animals were humanely euthanized 96 hours after administration of the last drug dose. Blood samples were collected for total RNA extraction. RT-PCR was performed in triplicate and data shown are the mean±SEM. Statistical analysis was performed using one-way ANOVA: *p<0.001.
Figure 17:
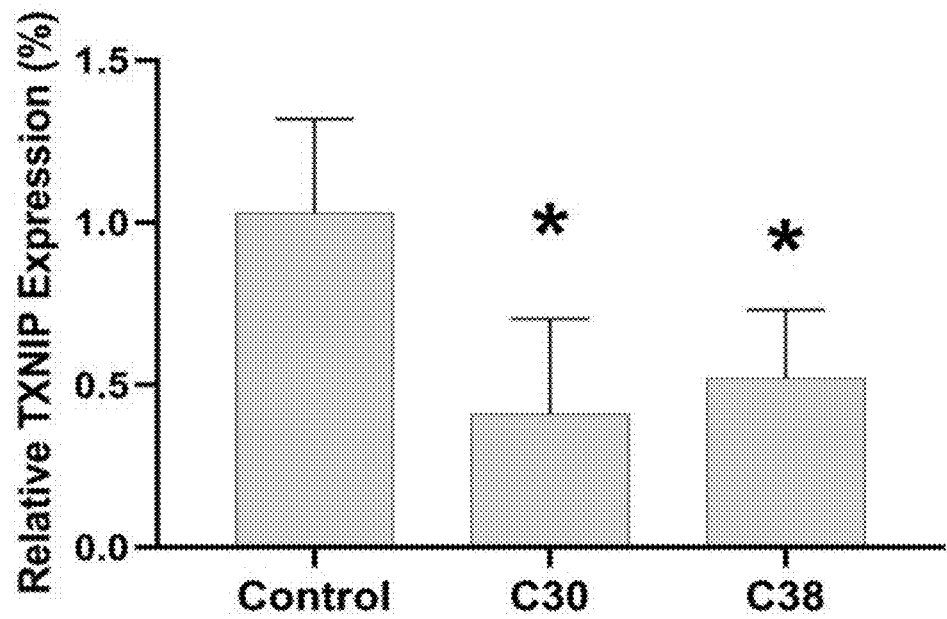
FIG. 17. Compounds C30 and C38 reduce TXNIP expression in murine kidneys. Twelve male C57BL/6 mice were divided into three groups (vehicle, C30 and C38, 4/group). They received 90 mg/kg dose of compounds daily for five consecutive days. Compounds were given through oral gavage and mice were humanely euthanized 96 hr after the last drug administration. Kidneys were collected for total RNA preparation. RT-PCR was performed in triplicate and data shown are the mean±SEM. Statistical analysis was performed using one-way ANOVA: *p<0.05.

Expression of TXNIP in vivo in treated mice. RNA expression level of TXNIP was found to be reduced in blood (FIG. 16) as well as in some key organs like kidneys (FIG. 17) after treatment with C30 and C38 compounds, suggesting in vivo suppression of TXNIP mRNA expression levels in rodents following administration of the indicated agents (FIGS. 16-17).

Lead compounds targeting TXNIP protect human islet cells from apoptosis.

In T1D, β-cell death involves necrosis and apoptosis. BCL2 limits BAX/BAK oligomerization, to impede the release of several apoptogenic molecules from mitochondria. Also, BCL2 binds to and inactivates BAX and other pro-apoptotic proteins, thereby inhibiting apoptosis. BAX and BAK disrupt the integrity of the mitochondrial outer membrane to promote apoptotic cell death. As such, the BCL2/BAX ratio is used as a marker of cell susceptibility to apoptosis. High levels of this ratio can serve as an indicator of the resistance of human cells to apoptosis.

Figure 18A:
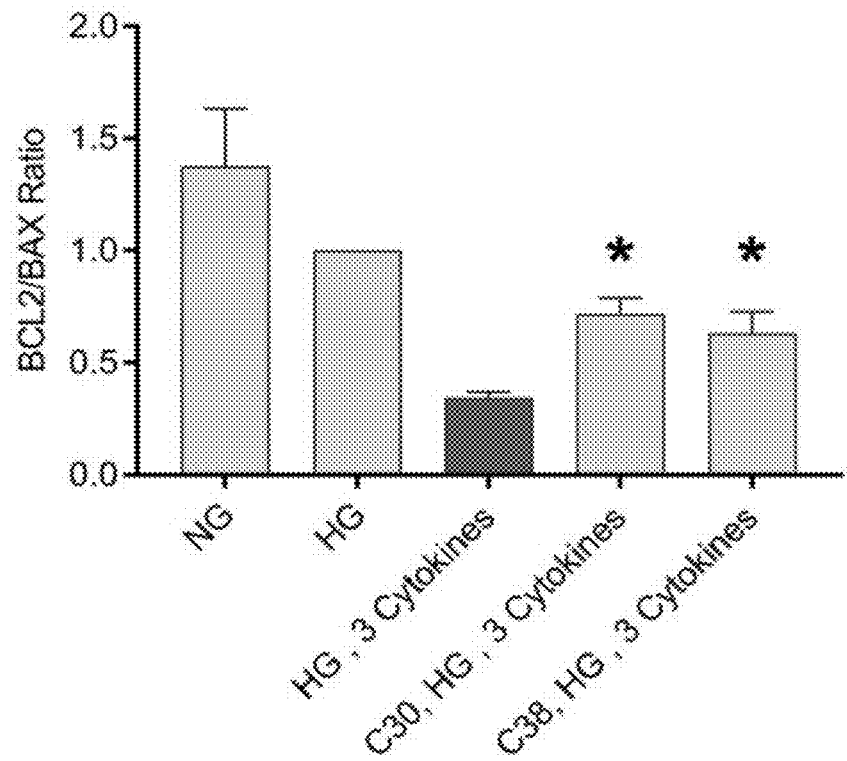
FIGS. 18A-18B. C30 and C38 compounds protect cells from apoptosis in human islets. 100 IEQ human islets (Hu 1178) were cultured in PIM(R)© containing NG (5.8 mM glucose) or HG (25 mM glucose), and TNFα (20 ng/ml), IL1β (20 ng/ml), IFNγ (200 ng/ml) for 40 hours with or without lead compounds. Total RNA was prepared and RT PCR performed.
Figure 18B:
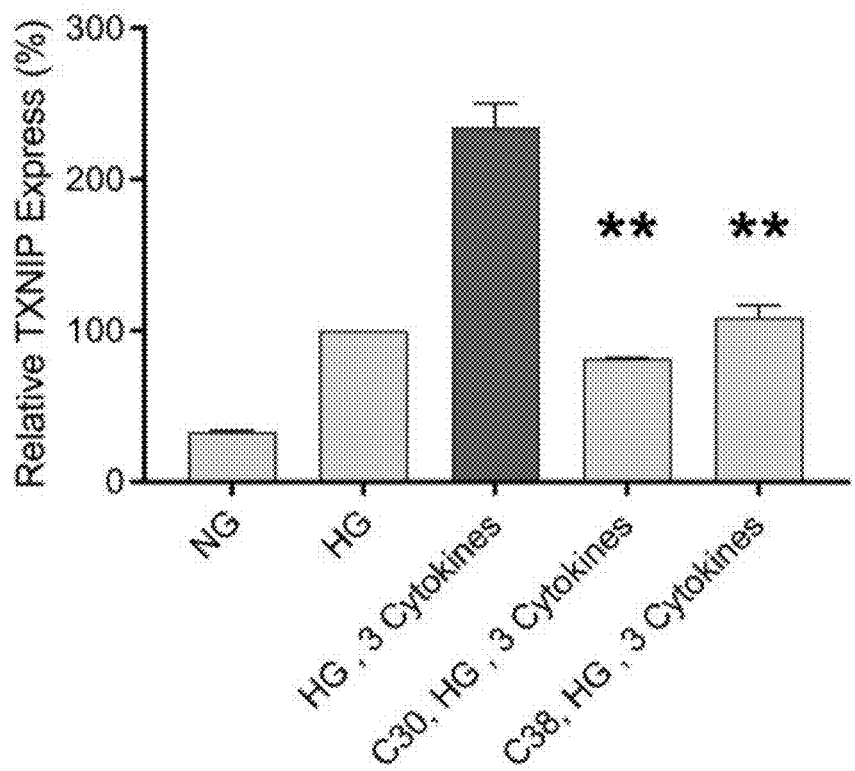

We mimicked T1D conditions in vitro (25 mM glucose, 20 mM TNF-α, 20 mM IL1β and 200 uM IFNγ) to induced apoptosis in human islets (obtained from the Southern California Islet Cell Resources Center at City of Hope). This high glucose/cytokine cocktail was able to induce apoptosis in cultured human islets as indicated by a decrease in the BCL2/BAX ratio (FIG. 18A). Islets that were also exposed to compounds C30 and C38 under these conditions showed a reversal of the proapoptotic effect of the HG/cytokine cocktail with significantly increased BCL2/BAX ratios. This suggests that these compounds can confer protection from apoptosis induced by diabetic conditions in primary human islets. Interestingly, in parallel, we found that TXNP expression is significantly increased during apoptosis and this was significantly ameliorated by treatment with both compounds C30 and C38 (FIG. 18B).

Figure 19:
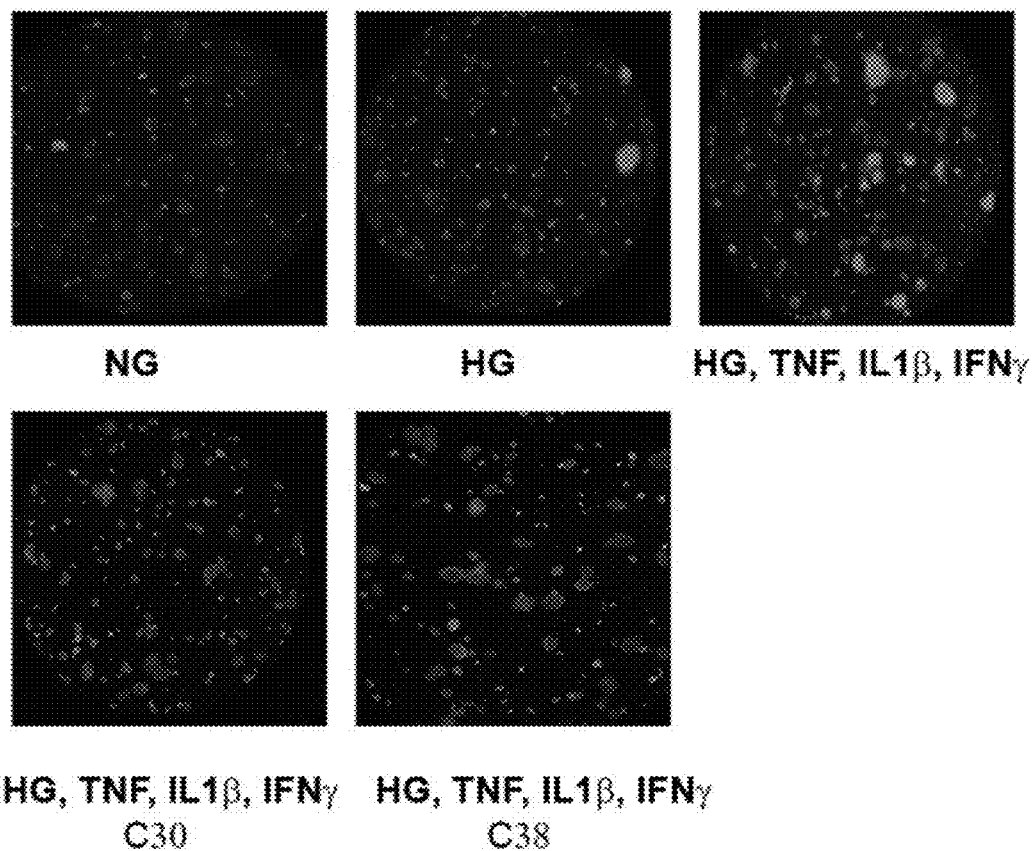
FIG. 19. Lead compounds enhance viability in human islets and protect them from apoptosis. 200 IEQ human islets (Hu 1183) were cultured in PIM(R)® medium containing NG (5.8 mM glucose) or HG (25 mM glucose), and mixture of TNFα (20 ng/ml), IL1β (20 ng/ml), and IFNγ (200 ng/ml) for 24 hours with or without C30 or C38. Islets were collected, washed with PBS once and stained with FDA and PI for 5 minutes and visualized with a Keyence All-in-One Fluorescence Microscope (BZ-X800E).

Lead compounds increase viability of human islets. The antiapoptotic effects of the lead compounds were also supported in separate experiments by an assay to determine viability of human islets which showed that C30 and C38 also help improve the viability of cultured human islets and reduce apoptosis (FIG. 19). Fluorescein diacetate/propidium iodide (FDA/PI) staining was employed to assess human islet viability. The results show that exposure to HG/cytokine cocktail (24 hr) results in greater cell death (reduced viability) than HG alone. Furthermore, treatment with 5 uM compound C30 or C38 protected human islets from death under these T1D-like conditions and improved their viability (FIG. 19).

Figure 20:
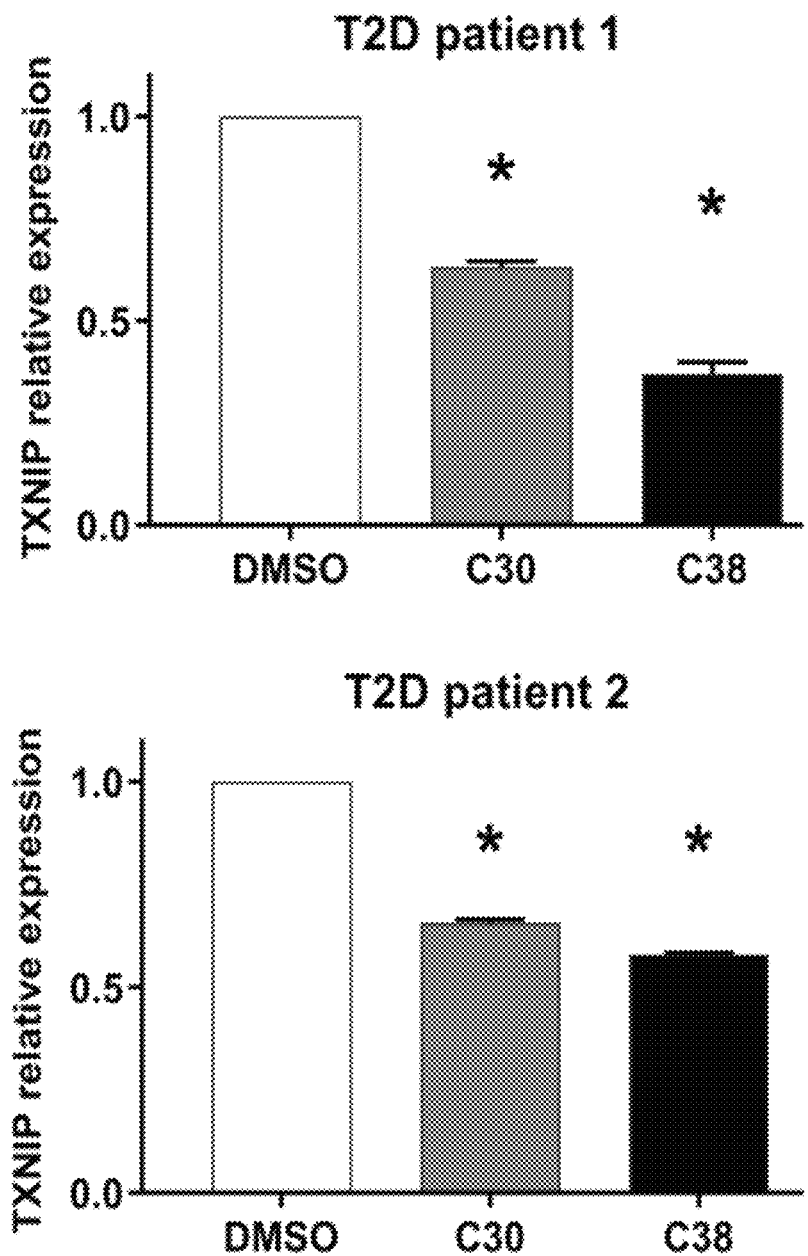
FIG. 20. Several lead compounds suppress TXNIP mRNA in T2D monocytes. CD14+ monocytes were isolated from T2D patient peripheral blood mononuclear cells (PBMCs) and cultured in RPMI 1640 medium with 5 uM of C30 or C38 for 45 hours. Total RNA was collected. RT-PCR was performed in triplicates and data shown are the mean±SEM. Statistical analysis was performed using one-way ANOVA: *p<0.0001.

Anti-inflammatory (protective) effects of lead compounds in monocytes isolated from peripheral blood obtained from type 2 diabetic subjects. In accordance with an approved IRB protocol and our published methods, we isolated CD14+ monocytes from the peripheral blood of two donors with documented type 2 diabetes (T2D). These monocytes were cultured in vitro with vehicle, 5 uM C30 or C38, and levels of human TXNIP transcript assessed by RT-qPCR. Results shown in FIG. 20 demonstrate that compounds C30 and C38 can inhibit the expression of TXNIP in these cells ex vivo. These data suggest the lead compounds can have anti-inflammatory protective effects in T2D (which in turn can help reduce severity of both T2D and its complications).

Example 5: Additional Data Related to C30 and C38

Figure 21:
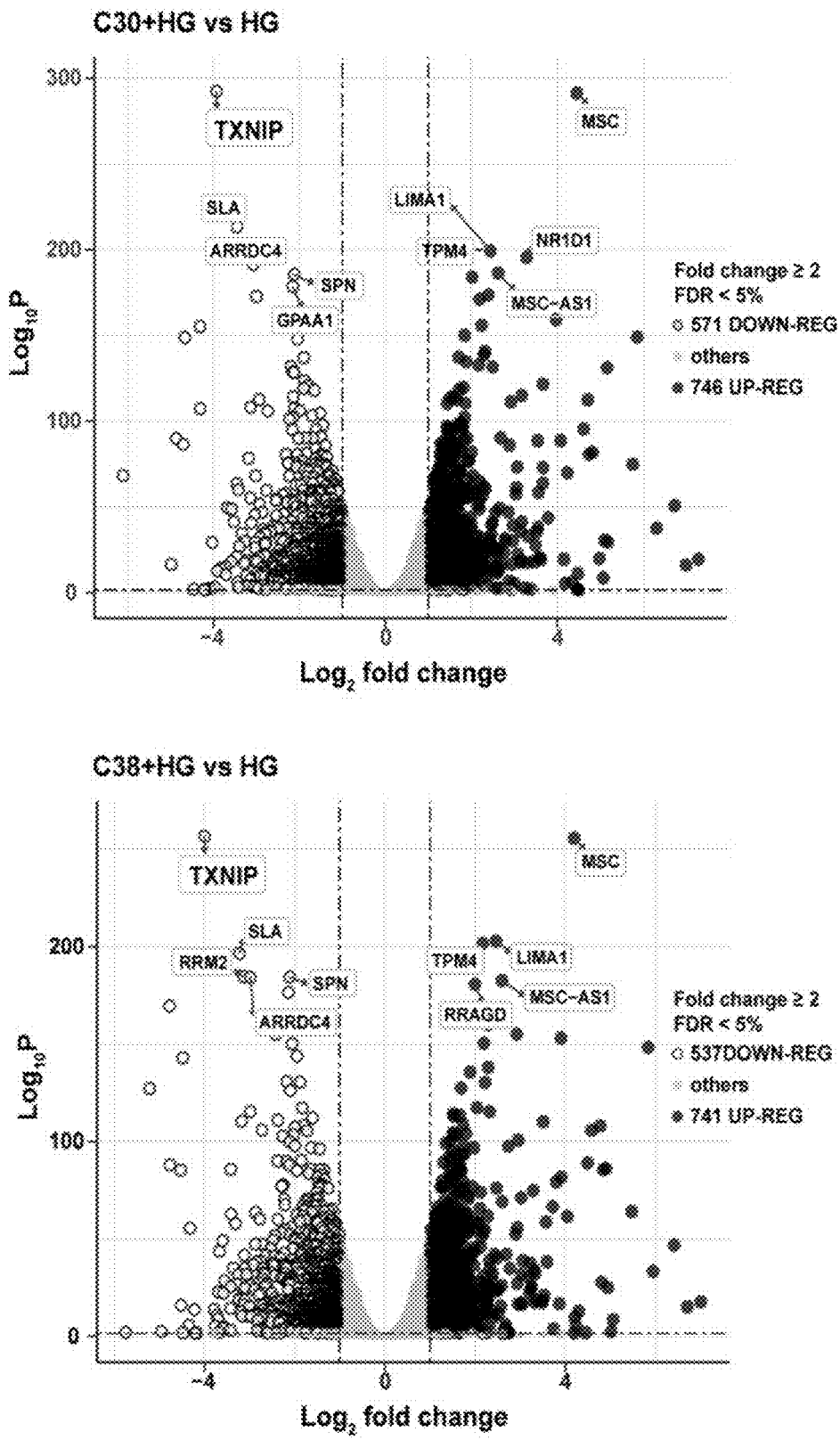
FIG. 21. Volcano plots on gene expression changes induced by TXNIP inhibitors (C30 or C38) under high glucose (HG) conditions in THP1 cells. Gene expression in THP cells grown in HG were treated with and without C30 or C38 and profiled by RNAseq. Expression of RefSeq genes with rpkm≥5 in at least one sample were TMM-normalized and compared in cells treated with HG plus C30 or C38 (C30+HG or C38+HG) versus the cells treated with HG alone using edgeR (v 3.28.1). Top panel shows data for C30 and bottom panel for C38. Each dot represents one gene with fold change (in log 2 format) in C30/C38+HG sample vs. HG as x-axis and significance level (in −log 10 format) as y-axis. Open black circles represent C30/C38-downregulated genes and solid black circles represent upregulated genes at fold change ≥2 and FDR<5%. TXNIP gene, which C30/C38 target, is the most significantly downregulated gene by both C30 and C38.
Figure 22:
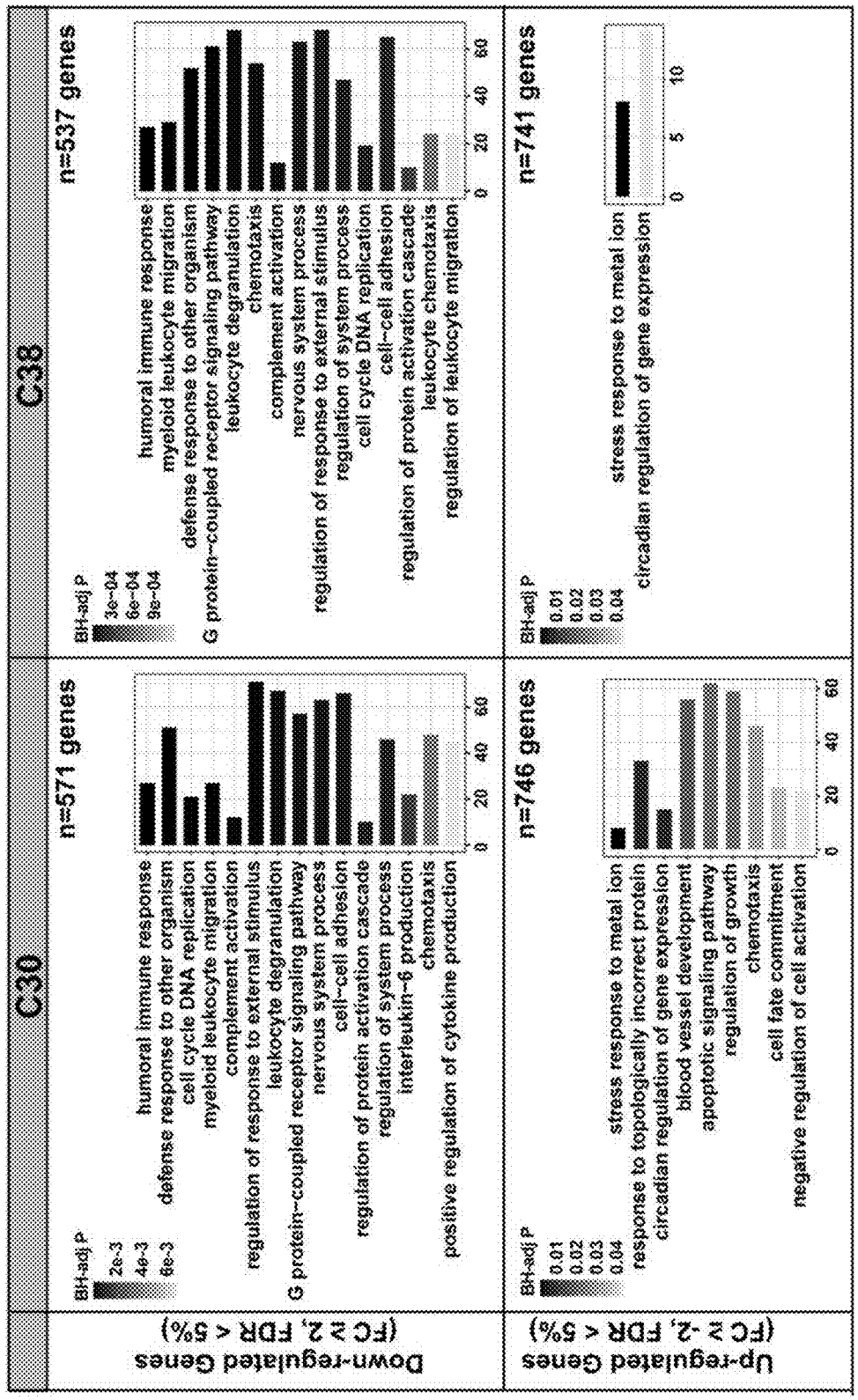
FIG. 22. Enriched BPs on DEGs induced by TXNIP inhibitors. Differentially downregulated or upregulated genes induced by C30 or C38 in THP1 cells were identified at fold change ≥2 and FDR<5%. For each treatment (C30 and C38 shown on the top), enriched BPs (level=4) were identified for downregulated genes (upper panel) and upregulated genes (lower panel) respectively as labeled on the left. The enriched BPs were identified at FDR<5% using enrichGO R package and up to 15 BPs with the most significant enrichment are shown as horizontal bar plots. In each bar, number of DEGs in the BP is presented by y-axis and the enrichment significance is represented by different grey-scale colors indicated in the color bar.

RNA-sequencing of human monocytes (THP-1 cells) treated with C30 or C38. We showed C30 and C38 reduce the expression of inflammatory genes in monocytes and other cells. To investigate the putative targets and mechanism(s) by which C30 and C38 reduce inflammation and other adverse effects of High glucose (HG), we performed unbiased transcriptome profiling by RNA-sequencing in duplicate to compare the changes in gene expression in culture THP1 human monocyte cells grown in HG (25 mM condition mimicking diabetes) with and without treatment with C30 or C38 (5 uM). Analyses of the RNA-seq data using our published methods reveal that C30 or C38 affect many genes in these human THP1 monocytes grown in HG (FIG. 21). Comparing THP1 cells treated with C30+HG versus HG only, we identified 571 downregulated and 746 upregulated genes with fold change ≥2 and FDR<5% (top panel). Similarly, 537 genes were downregulated and 741 upregulated by C38+HG versus HG (bottom panel). The gene names/symbols of the top 5 downregulated genes (upper left side) and upregulated genes (upper right side) by each compound are labeled. Among these, the gene encoding TXNIP protein which C30/C38 are designed to target, is the most-significantly downregulated gene by both C30 and C38 treatment with p-value close to 0. Due to the restriction on volcano plot (infinite log P value), the p-value of TXNIP on the plot was manually set to 1/10 of the p-value of the gene depicting the lowest non-zero p-value (i.e., the p-value of MSC gene). Notably, common top differentially-expressed genes (DEGs) other than TXNIP are also changed by both inhibitors. For example, Musculin encoded by MSC, the most significant upregulated gene by C30 and 38, is reported to have strong anti-inflammatory effects. (https://pubmed.ncbi.nlm.nih.gov/33448336/). Next, we performed Gene ontology (GO) analysis on the upregulated and downregulated genes induced by C30 or C38. Results (FIG. 22) revealed the downregulated genes are highly enriched in several biological processes (BPs) related to immune response and leukocyte activation/migration, suggesting C30 and C38 can substantially inhibit functions related to immune/inflammation response in these monocytes.

Figure 23:
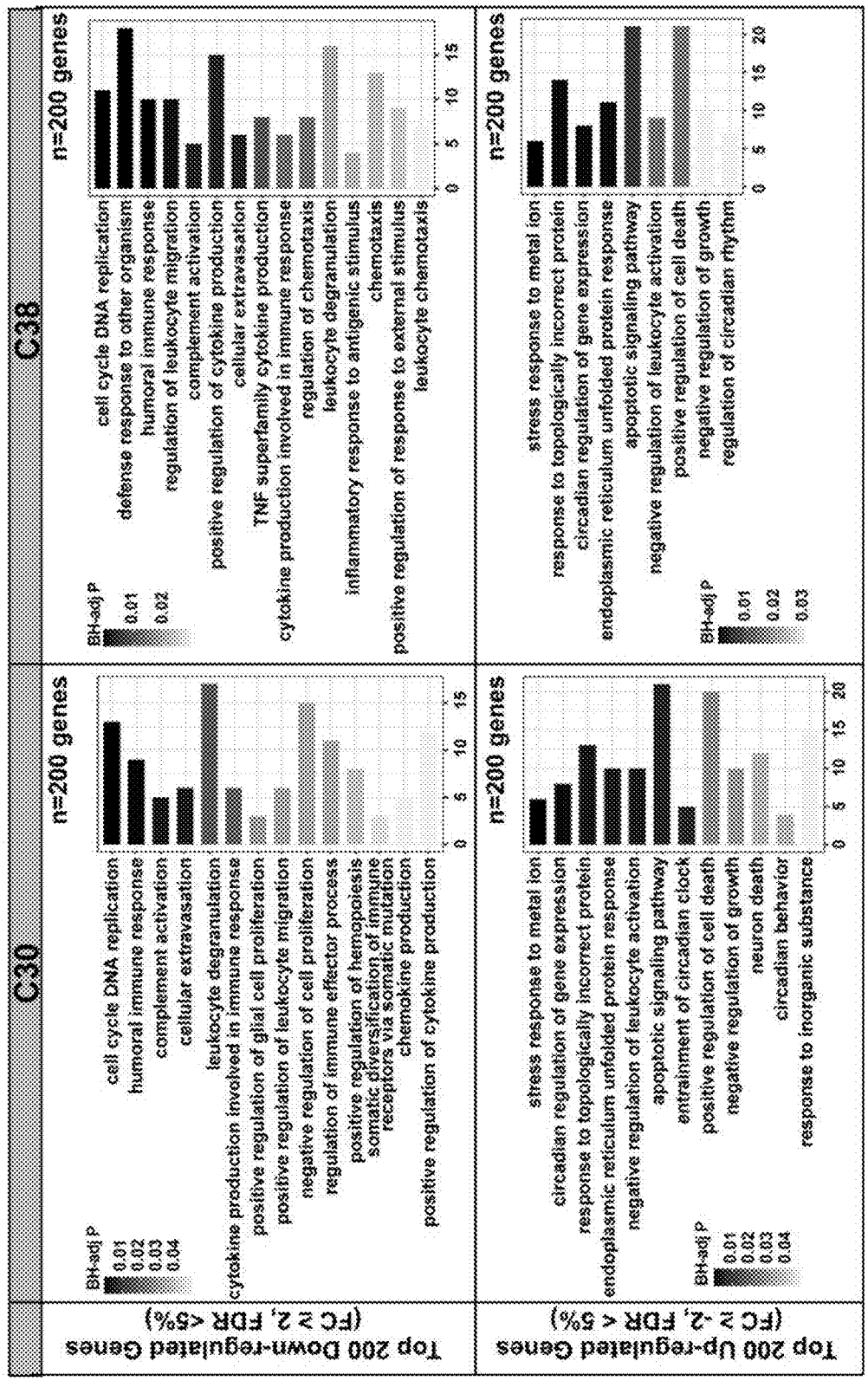
FIG. 23. Enriched BPs on the most-significant DEGs induced by TXNIP inhibitors. Top 200 differentially downor upregulated genes induced by C30 or C38 in HG treated THP1 cells were identified at fold change ≥2 and FDR<5%. For each treatment (C30 and C38 shown on the top), enriched BPs were identified for downregulated genes (upper panel) and upregulated genes (lower panel) respectively as labeled on the left side. The enriched BPs were identified at FDR<5% using enrichGO R package. The top 15 BPs with the most significant enrichment are shown as bar plots. In each bar, number of the top 200 up/downregulated genes in the corresponding BP is presented by y-axis and the enrichment significance shown as grey-scale colors indicated in the color bar.

We also performed Gene ontology analysis on the top 200 most significantly upregulated and downregulated genes induced by C30 or C38 in HG treated cells. Results shown in FIG. 23 again reveal that genes related to immune/inflammation/response, leukocyte activation and cytokine production are greatly downregulated by C30/C38, suggesting the TXNIP inhibitors appear to substantially inhibit these adverse effects of HG.

We next studied the impact of C30 or C38 on genes regulated by HG versus NG. By comparing duplicate THP-1 cells treated with HG vs. NG, we first identified a total of 83 HG-upregulated genes and 147 HG-downregulated genes at FC≥1.2 and FDR<0.05 with min RPKM≥5 in at least one sample. We then examined the expression of DEGs induced by HG (HG vs. NG, FC≥1.2 & FDR<5%) across all the 6 samples (from duplicate experiments with cells treated with HG, C30+HG and C38+HG). We found that majority of the genes upregulated by HG are downregulated by both C30 and C38, while majority of genes downregulated by HG are upregulated by both C30 and C38. Thus, these compounds seem to reverse the effects of HG in these cells with C38 having relatively more impact than C30. Interestingly, many of the HG-downregulated genes by C30 and C38 are common to both C30 and C38. At FC≥1.5 & FDR<5%, we found 23 of the HG upregulated genes (symbols listed in Table 3 below) were downregulated by both C30 and C38, suggesting they may have similar modes of action, at least in part.

TABLE 3

Gene Symbols of the 23 HG-upregulated genes which are downregulated by both C30 and C38 at FC >= 1.5 & FDR < 5%.

| ACP2 | ARRDC4 | CITED4 | CKB | DNPH1 |
| FAM20C | FLNA | G0S2 | H2AFX | HOXA11-AS |
| IMPA2 | KLF10 | LIMD2 | LY6E | MBOAT7 |
| MEGF8 | PAQR4 | PKMYT1 | SLC2A5 | TK1 |
| TKTL1 | TUBA4A | TXNIP | | |

Figure 24:
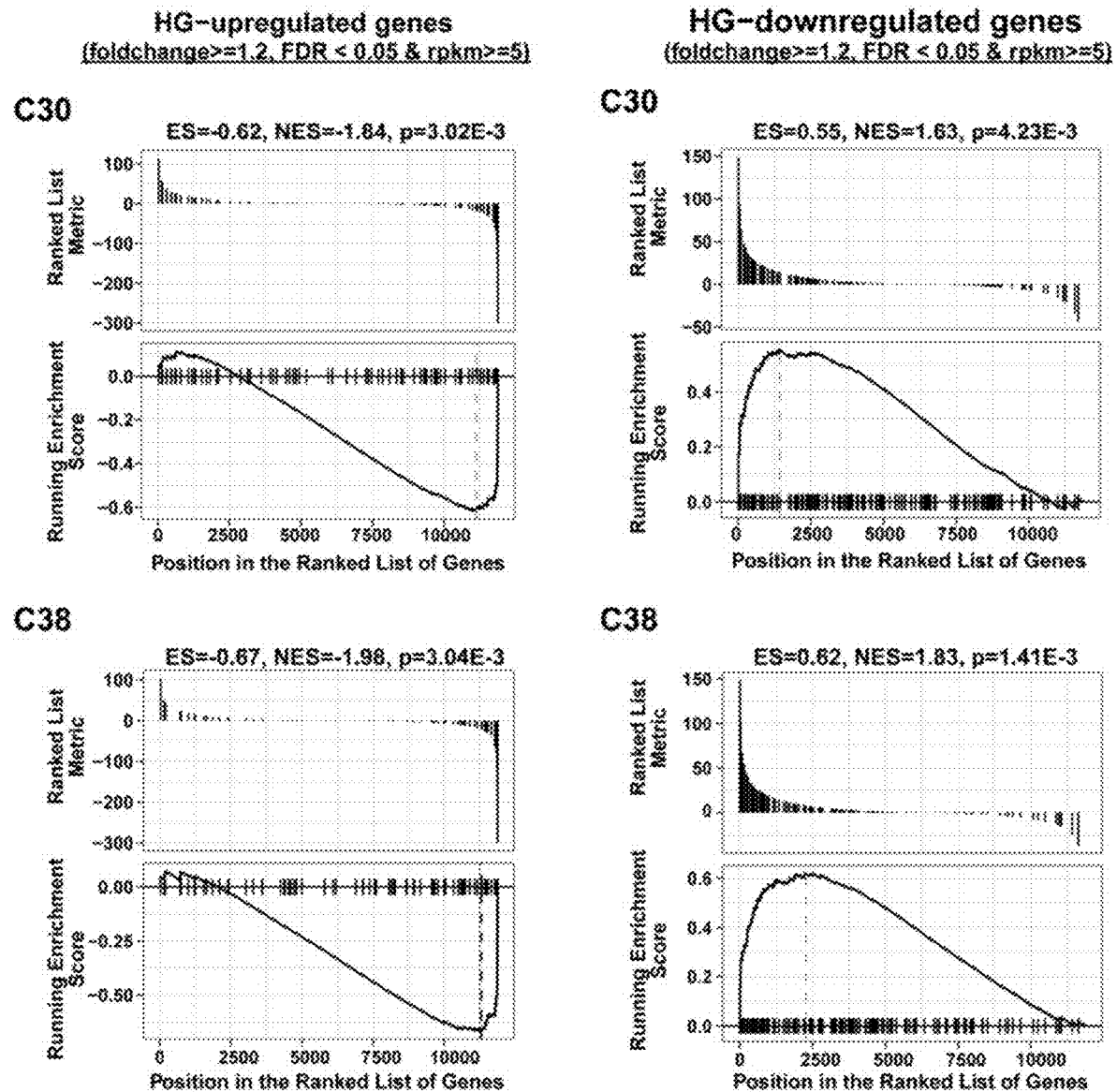
FIG. 24. Impact of C30/C38 treatment on HG-regulated genes by GSEA analysis. Two gene sets were generated with one containing 83 HG-upregulated genes and the other containing 147 HG-downregulated genes. In the analysis for each treatment (C30 or C38), all the expressed genes were ranked based on the signed significance levels, $-\log_{10}$ Pvalue with signs determined by FC (positive if FC>1 and negative if FC<1), on each gene's expression difference between samples with and without treatment. The overall gene expression difference in THP1 cells (in HG condition) treated with or without C30/C38 on these two genesets were analyzed using pre-ranked GSEA analysis.

The impact of C30/C38 on HG-regulated genes was further supported by Gene set enrichment analysis (GSEA) (FIG. 24) which confirmed both C30 and C38 can significantly reverse the expression changes induced by HG on HG up- and down-regulated genes. Specifically, both C30 and C38 can downregulate expression of HG-upregulated genes (two left panels) with normalized enrichment score (NES) at −1.84 (p=3.02E-3) and −1.98 (p=3.04E-3) respectively, and upregulate expression of HG-downregulated genes (two right panels) with NES at 1.63 (p=4.23E-3) and 1.83 (1.41E-3) respectively.

Figure 25:
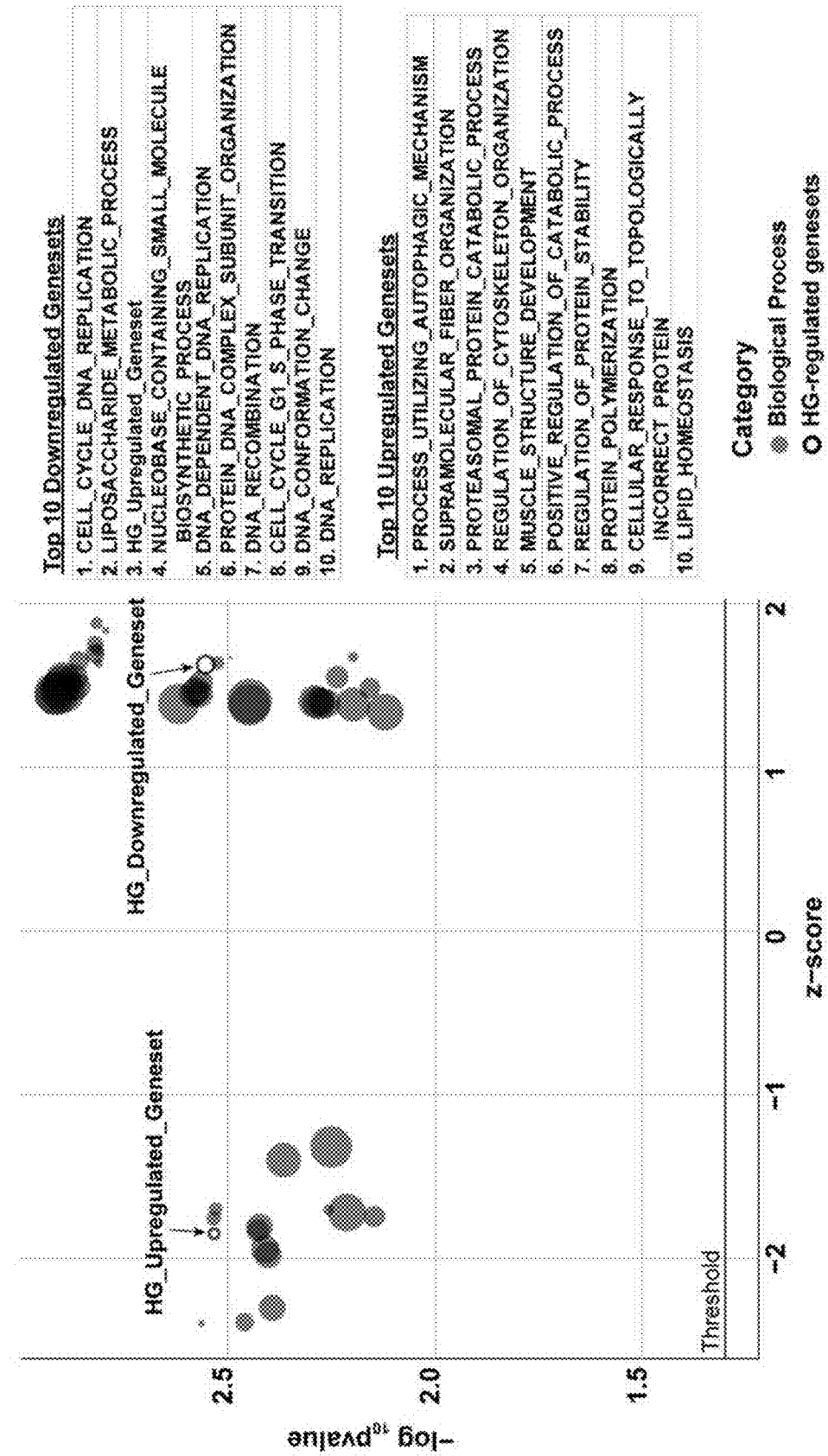
FIG. 25. Bubble plots on upregulated or downregulated genesets induced by C30 in HG treated cells using GSEA analysis. The overall gene expression difference in THP1 cells (in HG condition) treated with or without C30 on all the genesets related to BPs plus two genesets containing HG-upregulated genes (HG_Upregulated_Geneset) and HG-downregulated (HG_Downregulated_Geneset) at FC≥1.2, FDR<5% and RPKM≥5 (HG vs. NG) were analyzed using pre-ranked GSEA analysis. All the expressed genes were ranked based on the signed significance levels of each gene's expression difference (C30+HG vs. HG). The upregulated and downregulated genesets were thus identified at q-value <0.10. In the plot shown, each bubble represents one geneset. X-axis of the bubble center represents normalized enrichment score (negative values indicate downregulated and positive values indicate upregulated), and y-axis represents enrichment significance level in $-\log_{10}$ p format, and size represents number of genes in the genesets. Genesets related to BPs are represented by solid black bubbles and related to HG regulated genesets are shown as hollow black bubbles. The names of top 10 up- and down-regulated genesets identified are listed on the right side of the figure.

In addition, GSEA analyses were also applied to all the gene sets related to biological process (BPs) plus 2 HG-regulated genesets. As demonstrated in FIG. 25, C30 strongly suppresses BPs related to DNA replication, cell cycle, lipopolysaccharide metabolic process, etc, in HG treated THP1 cells, and activates BPs such as catabolic process, autophagic mechanisms, lipid homeostasis etc. The regulatory influence of C30 to reverse DEGs induced by HG (genesets for both HG-upregulated and HG-downregulated genes) are also observed.

Figure 26:
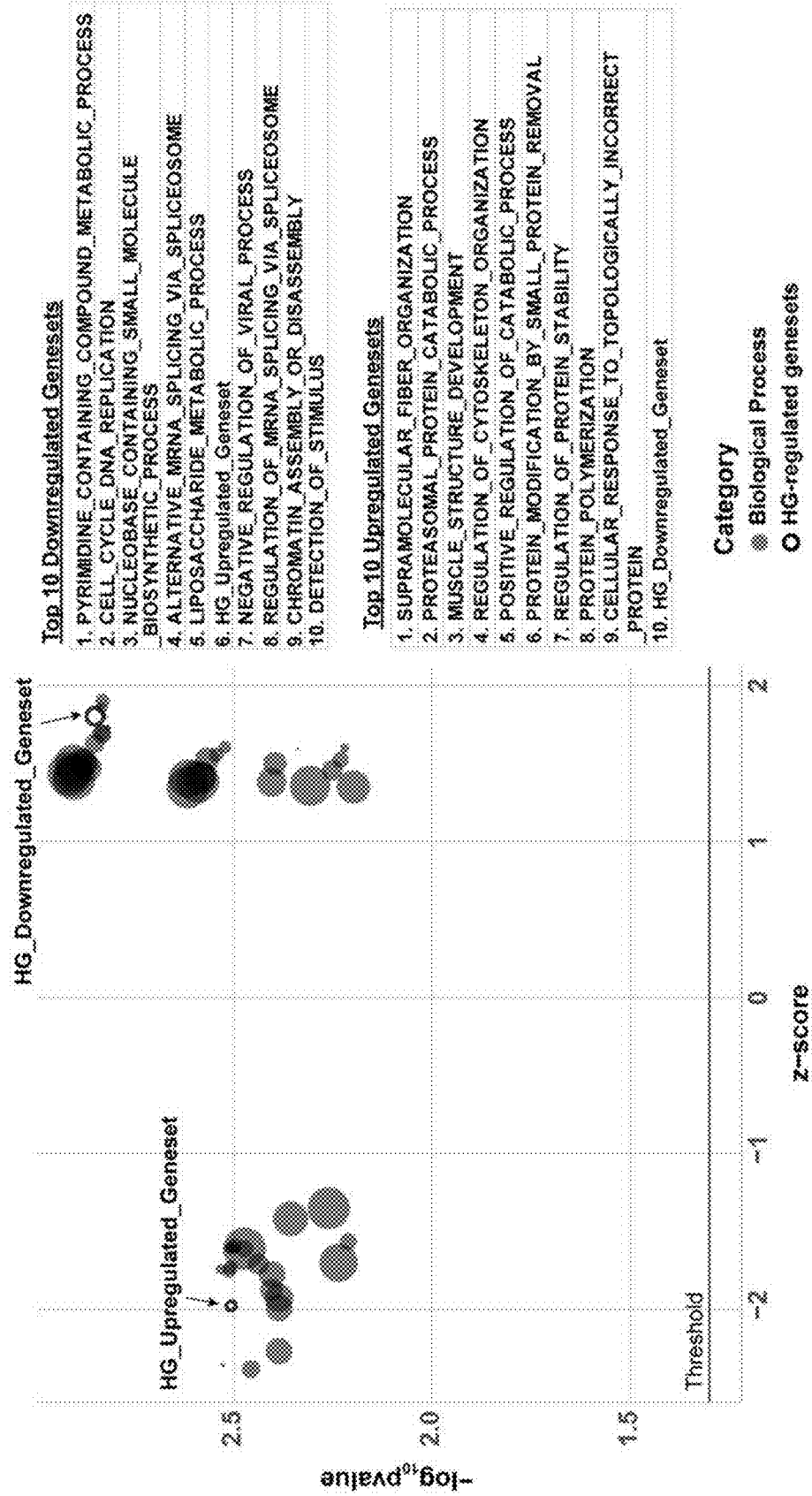
FIG. 26. Bubble plots on top 10 upregulated or downregulated genesets induced by C38 using GSEA analysis. The overall gene expression difference in THP1 cells (in HG condition) treated with or without C38 on all the genesets related to BP plus two genesets containing HG-upregulated genes (HG_Upregulated_Geneset) and HG-downregulated (HG_Downregulated_Geneset) at FC≥1.2, FDR<5% and RPKM≥5 (HG vs. NG) were analyzed using pre-ranked GSEA analysis. All the expressed genes were ranked based on the signed significance levels of each gene's expression difference (C38+HG vs. HG). The enriched upregulated and downregulated genesets were identified at q<0.10. In the plot, each bubble represents one geneset. X-axis of the bubble center represents normalized enrichment score (negative values indicate downregulated and positive values indicate upregulated), and y-axis represents enrichment significance level in $-\log_{10}$ p format, and size represents number of genes in the corresponding geneset. Genesets related to BPs are represented by solid black bubbles and genesets related to HG regulated genes are shown as hollow black bubbles. The names of top 10 up- and down-regulated genesets identified are listed on the right side of the figure.

GSEA analysis also identified a strong impact of C38 in HG treated THP1 cells (FIG. 26) including suppressing BPs involved in metabolic process, DNA replication, immune response, splicing etc., and activating BPs involved in catabolic process, cytoskeleton organization changes, and protein stability, etc. Interestingly, the influence of C38 to reverse regulate HG differentially-expressed genes (both HG-up- and HG-downregulated genesets) were among the top 10 genesets identified, further supporting C38 to be a good lead candidate.

REFERENCES

1. Chen Z*, Miao F*, Paterson A D, Lachin J M, Zhang L, Riggs A D, Schones D E, Wu X, Wang J, Tompkins J D, Genuth S M, Braffett B, DCCT/EDIC Research group, Natarajan R. *Proc Natl Acad Sci USA.* 2016 May 24; 113(21):E3002-11. 2. Bhattacharya S., and Vaidehi N., 2014, *BioPhys. J.,* 107, 422-34. 3. Bhattacharya S, Salomon-Ferrer R, Lee S, Vaidehi N. *J. Chemical Theory and Computation.* 2016 Oct. 17; 12(11):5575-84. 4. Vaidehi N, Bhattacharya S. *Current Opinion in Pharmacology.* 2016 Oct. 1; 30:76-83. 5. Anders, S., and Huber, W. (2010). Genome biology 11, R106. 6. Bell, J. A., Cao, Y., Gunn, J. R., Day, T., Gallicchio, E., Zhou, Z., Levy, R., and Farid, R. (2012). PrimeX and the Schrödinger computational chemistry suite of programs. In International Tables for Crystallography. 7. Bhattacharya, S., Salomon-Ferrer, R., Lee, S., and Vaidehi, N. (2016). J Chem Theory Comput 12, 5575-5584. 8. Bhattacharya, S., and Vaidehi, N. (2014). Biophys J 107, 422-434. 9. Bolger, A. M., Lohse, M., and Usadel, B. (2014). Bioinformatics 30, 2114-2120. 10. Chen, S., Zhou, Y., Chen, Y., and Gu, J. (2018). Bioinformatics 34, i884-i890. 11. Dobin, A., Davis, C. A., Schlesinger, F., Drenkow, J., Zaleski, C., Jha, S., Batut, P., Chaisson, M., and Gingeras, T. R. (2013). Bioinformatics 29, 15-21. 12. Duan, J. X., Dixon, S. L., Lowrie, J. F., and Sherman, W. (2010). J Mol Graph Model 29, 157-170. 13. Friesner, R. A., Banks, J. L., Murphy, R. B., Halgren, T. A., Klicic, J. J., Mainz, D. T., Repasky, M. P., Knoll, E. H., Shelley, M., Perry, J. K., et al. (2004). J Med Chem 47, 1739-1749. 14. Halgren, T. A., Murphy, R. B., Friesner, R. A., Beard, H. S., Frye, L. L., Pollard, W. T., and Banks, J. L. (2004). J Med Chem 47, 1750-1759. 15. Hwang, J., Suh, H. W., Jeon, Y. H., Hwang, E., Nguyen, L. T., Yeom, J., Lee, S. G., Lee, C., Kim, K. J., Kang, B. S., et al. (2014). Nat Commun 5, 10-23. 16. Li, H., Kasam, V., Tautermann, C. S., Seeliger, D., and Vaidehi, N. (2014). J Chem Inf Model 54, 1391-1400. 17. Lomenick, B., Hao, R., Jonai, N., Chin, R. M., Aghajan, M., Warburton, S., Wang, J., Wu, R. P., Gomez, F., Loo, J. A., et al. (2009). Proceedings of the National Academy of Sciences of the United States of America 106, 21984-21989. 18. Nivedha, A. K., Tautermann, C. S., Bhattacharya, S., Lee, S., Casarosa, P., Kollak, I., Kiechle, T., and Vaidehi, N. (2018). Mol Pharmacol 93, 288-296. 19. Pai, M. Y., Lomenick, B., Hwang, H., Schiestl, R., McBride, W., Loo, J. A., and Huang, J. (2015). Methods in molecular biology 1263, 287-298. 20. Robinson, M. D., McCarthy, D. J., and Smyth, G. K. (2010). Bioinformatics 26, 139-140. 21. Sastry, M., Lowrie, J. F., Dixon, S. L., and Sherman, W. (2010). J Chem Inf Model 50, 771-784. 22. Tautermann, C. S., Binder, F., Buttner, F. H., Eickmeier, C., Fiegen, D., Gross, U., Grundl, M. A., Heilker, R., Hobson, S., Hoerer, S., et al. (2019). J Med Chem 62, 306-316. 23. Vaidehi, N., and Bhattacharya, S. (2016). Curr Opin Pharmacol 30, 76-83. 24. Waldhart, A N, Dykstra, H., Peck, A. S., Boguslawski, E. A., Madaj, Z. B., Wen, J., Veldkamp, K., Hollowell, M., Zheng, B., Cantley, L. C., et al. (2017). Cell reports 19, 2005-2013. 25. Wu, N., Zheng, B., Shaywitz, A., Dagon, Y., Tower, C., Bellinger, G., Shen, C. H., Wen, J., Asara, J., McGraw, T. E., et al. (2013). Molecular cell 49, 1167-1175.

What is claimed is:

1. A pharmaceutical composition comprising a pharmaceutically acceptable excipient and a compound, or a pharmaceutically acceptable salt thereof, having the formula:

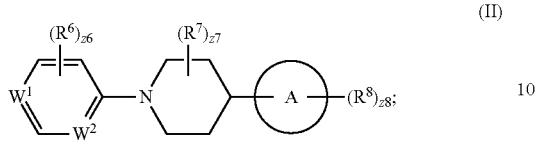

(II)

wherein

Ring A is $C_3$-$C_8$ cycloalkyl, 3 to 8 membered heterocycloalkyl, $C_6$-$C_{10}$ aryl, or 5 to 10 membered heteroaryl;

$W^1$ is N or $C(R^4)$;

$W^2$ is N or $C(R^5)$;

$R^4$ is halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-OCCl_3$, $-OCF_3$, $-OCBr_3$, $-OCI_3$, $-OCHCl_2$, $-OCHBr_2$, $-OCHF_2$, $-OCH_2Cl$, $-OCH_2Br$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted $C_1$-$C_8$ alkyl, unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

$R^5$ is hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2F$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

$R^6$ is independently halogen, $-CX^6_3$, $-CHX^6_2$, $-CH_2X^6$, $-OCX^6_3$, $-OCHX^6_2$, $-OCH_2X^6$, $-CN$, $-SO_{n6}R^{6D}$, $-SO_{v6}NR^{6A}R^{6B}$, $-NR^{6C}NR^{6A}R^{6B}$, $-ONR^{6A}R^{6B}$, $-NHC(O)NR^{6C}NR^{6A}R^{6B}$, $-NHC(O)NR^{6A}R^{6B}$, $-N(O)_{m6}$, $-NR^{6A}R^{6B}$, $-C(O)R^{6C}$, $-C(O)OR^{6C}$, $-C(O)NR^{6A}R^{6B}$, $-OR^{6D}$, $-SR^{6D}$, $-SeR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, $-SF_5$, $-N_3$, substituted or $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; two adjacent $R^6$ substituents may optionally be joined to form a substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

$R^7$ is independently halogen, oxo, $-CX^7_3$, $-CHX^7_2$, $-CH_2X^7$, $-OCX^7_3$, $-OCHX^7_2$, $-OCH_2X^7$, $-CN$, $-SO_{n7}R^{7D}$, $-SO_{v7}NR^{7A}R^{7B}$, $-NR^{7C}NR^{7A}R^{7B}$, $-ONR^{7A}R^{7B}$, $-NHC(O)NR^{7C}NR^{7A}R^{7B}$, $-NHC(O)NR^{7A}R^{7B}$, $-N(O)_{m7}$, $-NR^{7A}R^{7B}$, $-C(O)R^{7C}$, $-C(O)OR^{7C}$, $-C(O)NR^{7A}R^{7B}$, $-OR^{7D}$, $-SR^{7D}$, $-SeR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, $-SF_5$, $-N_3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; two adjacent $R^7$ substituents may optionally be joined to form a substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; two $R^7$ substituents bonded to the same carbon atom may optionally be joined to form a substituted or unsubstituted $C_3$-$C_8$ cycloalkyl, or substituted or unsubstituted 3 to 8 membered heterocycloalkyl;

$R^8$ is independently halogen, oxo, $-CX^8_3$, $-CHX^8_2$, $-CH_2X^8$, $-OCX^8_3$, $-OCHX^8_2$, $-OCH_2X^8$, $-CN$, $-SO_{n8}R^{8D}$, $-SO_{v8}NR^{8A}R^{8B}$, $-NR^{8C}NR^{8A}R^{8B}$, $-ONR^{8A}R^{8B}$, $-NHC(O)NR^{8C}NR^{8A}R^{8B}$, $-NHC(O)NR^{8A}R^{8B}$, $-N(O)_{m8}$, $-NR^{8A}R^{8B}$, $-C(O)R^{8C}$, $-C(O)OR^{8C}$, $-C(O)NR^{8A}R^{8B}$, $-OR^{8D}$, $-SR^{8D}$, $-SeR^{8D}$, $-NR^{8A}SO_2R^{8D}$, $-NR^{8A}C(O)R^{8C}$, $-NR^{8A}C(O)OR^{8C}$, $-NR^{8A}OR^{8C}$, $-SF_5$, $-N_3$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; two adjacent $R^8$ substituents may optionally be joined to form a substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

$R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, and $R^{8D}$ are independently hydrogen, oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SeH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $-SF_5$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, substituted or unsubstituted 5 to 10 membered heteroaryl; $R^{6A}$ and $R^{6B}$ substituents bonded to the same nitrogen atom may optionally be joined to form a substituted or unsubstituted 3 to 8 membered heterocycloalkyl or substituted or unsubstituted 5 to 10 membered heteroaryl; $R^{7A}$ and $R^{7B}$ substituents bonded to the same nitrogen atom may optionally be joined to form a substituted or unsubstituted 3 to 8 membered heterocycloalkyl or substituted or unsubstituted 5 to 10 membered heteroaryl; $R^{8A}$ and $R^{8B}$ substituents bonded to the same nitrogen atom may optionally be joined to form a substituted or unsubstituted 3 to 8 membered heterocycloalkyl or substituted or unsubstituted 5 to 10 membered heteroaryl;

$X^6$, $X^7$, and $X^8$ are independently —F, —Cl, —Br, or —I;

n6, n7, and n8 are independently an integer from 0 to 4;

m6, m7, m8, v6, v7, and v8 are independently 1 or 2;

z6 is an integer from 0 to 3;

z7 is an integer from 0 to 9; and z8 is an integer from 0 to 7;

wherein each substituted $C_1$-$C_8$ alkyl, substituted 2 to 8 membered heteroalkyl, substituted $C_3$-$C_8$ cycloalkyl, substituted 3 to 8 membered heterocycloalkyl, substituted $C_6$-$C_{10}$ aryl, and substituted 5 to 10 membered heteroaryl is independently substituted with at least one substituent group.

2. The pharmaceutical composition of claim 1, wherein the compound has the formula:

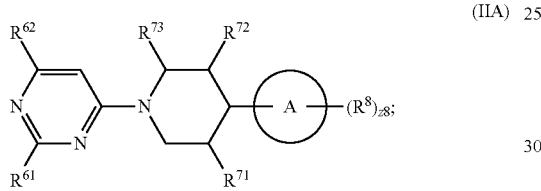

(IIA)

$R^{61}$ and $R^{62}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; and $R^{71}$, $R^{72}$, and $R^{73}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

3. The pharmaceutical composition of claim 1, wherein Ring A is naphthyl.

4. The pharmaceutical composition of claim 2, wherein $R^{61}$ and $R^{62}$ are independently hydrogen, halogen, —OH, —NH$_2$, or unsubstituted 2 to 6 membered heteroalkyl.

5. The pharmaceutical composition of claim 2, wherein $R^{71}$ is —OH, —NH$_2$, unsubstituted $C_1$-$C_4$ alkyl, unsubstituted 2 to 6 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

6. The pharmaceutical composition of claim 2, wherein $R^{72}$ and $R^{73}$ are independently hydrogen or unsubstituted $C_1$-$C_4$ alkyl.

7. The pharmaceutical composition of claim 1, wherein the compound has the formula

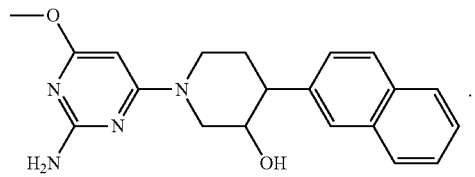 [SMILES: COc1cc(N2CCC(c3ccc4ccccc4c3)C(O)C2)nc(N)n1]

8. A method of treating diabetes or a cardiovascular disease, said method comprising administering to a subject in need thereof an effective amount of a compound, or a pharmaceutically acceptable salt thereof, having the formula:

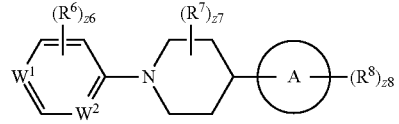

(II);

wherein

Ring A is $C_3$-$C_8$ cycloalkyl, 3 to 8 membered heterocycloalkyl, $C_6$-$C_{10}$ aryl, or 5 to 10 membered heteroaryl;

$W^1$ is N or $C(R^4)$;

$W^2$ is N or $C(R^5)$;

$R^4$ is halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted $C_1$-$C_8$ alkyl, unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

$R^5$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl;

R$^6$ is independently halogen, —CX$^6_3$, —CHX$^6_2$, —CH$_2$X$^6$, —OCX$^6_3$, —OCHX$^6_2$, —OCH$_2$X$^6$, —CN, —SO$_{n6}$R$^{6D}$, —SO$_{v6}$NR$^{6A}$R$^{6B}$, —NR$^{6C}$NR$^{6A}$R$^{6B}$, —ONR$^{6A}$R$^{6B}$, —NHC(O)NR$^{6C}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)OR$^{6C}$, —C(O)NR$^{6A}$R$^{6B}$, —OR$^{6D}$, —SR$^{6D}$, —SeR$^{6D}$, —NR$^{6A}$SO$_2$R$^{6D}$, —NR$^{6A}$C(O)R$^{6C}$, —NR$^{6A}$C(O)R$^{6C}$, —NR$^{6A}$OR$^{6C}$, —SF$_5$, —N$_3$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; two adjacent R$^6$ substituents may optionally be joined to form a substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl;

R$^7$ is independently halogen, oxo, —CX$^7_3$, —CHX$^7_2$, —CH$_2$X$^7$, —OCX$^7_3$, —OCHX$^7_2$, —OCH$_2$X$^7$, —CN, —SO$_{n7}$R$^{7D}$, —SO$_{v7}$NR$^{7A}$R$^{7B}$, —NR$^{7C}$NR$^{7A}$R$^{7B}$, —ONR$^{7A}$R$^{7B}$, —NHC(O)NR$^{7C}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)OR$^{7C}$, —C(O)NR$^{7A}$R$^{7B}$, —OR$^{7D}$, —SR$^{7D}$, —SeR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, —SF$_5$, —N$_3$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; two adjacent R$^7$ substituents may optionally be joined to form a substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; two R$^7$ substituents bonded to the same carbon atom may optionally be joined to form a substituted or unsubstituted C$_3$-C$_8$ cycloalkyl, or substituted or unsubstituted 3 to 8 membered heterocycloalkyl;

R$^8$ is independently halogen, oxo, —CX$^8_3$, —CHX$^8_2$, —CH$_2$X$^8$, —OCX$^8_3$, —OCHX$^8_2$, —OCH$_2$X$^8$, —CN, —SO$_{n8}$R$^{8D}$, —SO$_{v8}$NR$^{8A}$R$^{8B}$, —NR$^{8C}$NR$^{8A}$R$^{8B}$, —ONR$^{8A}$R$^{8B}$, —NHC(O)NR$^{8C}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)OR$^{8C}$, —C(O)NR$^{8A}$R$^{8B}$, —OR$^{8D}$, —SR$^{8D}$, —SeR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, —SF$_5$, —N$_3$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; two adjacent R$^8$ substituents may optionally be joined to form a substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl;

R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, and R$^{8D}$ are independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, substituted or unsubstituted 5 to 10 membered heteroaryl; R$^{6A}$ and R$^{6B}$ substituents bonded to the same nitrogen atom may optionally be joined to form a substituted or unsubstituted 3 to 8 membered heterocycloalkyl or substituted or unsubstituted 5 to 10 membered heteroaryl; R$^{7A}$ and R$^{7B}$ substituents bonded to the same nitrogen atom may optionally be joined to form a substituted or unsubstituted 3 to 8 membered heterocycloalkyl or substituted or unsubstituted 5 to 10 membered heteroaryl; R$^{8A}$ and R$^{8B}$ substituents bonded to the same nitrogen atom may optionally be joined to form a substituted or unsubstituted 3 to 8 membered heterocycloalkyl or substituted or unsubstituted 5 to 10 membered heteroaryl;

X$^6$, X$^7$, and X$^8$ are independently —F, —Cl, —Br, or —I;

n6, n7, and n8 are independently an integer from 0 to 4;

m6, m7, m8, v6, v7, and v8 are independently 1 or 2;

z6 is an integer from 0 to 3;

z7 is an integer from 0 to 9; and z8 is an integer from 0 to 7;

wherein each substituted C$_1$-C$_8$ alkyl, substituted 2 to 8 membered heteroalkyl, substituted C$_3$-C$_8$ cycloalkyl, substituted 3 to 8 membered heterocycloalkyl, substituted C$_6$-C$_{10}$ aryl, and substituted 5 to 10 membered heteroaryl is independently substituted with at least one substituent group.

9. The method of claim 8, wherein the diabetes is type 1 diabetes or type 2 diabetes.

10. The method of claim 8, wherein the compound is capable of inhibiting TXNIP protein activity or function.

11. The method of claim 8, wherein the compound is capable of inhibiting TXNIP protein binding to TRX.

12. The pharmaceutical composition of claim 1, wherein Ring A is C$_6$-C$_{10}$ aryl.

13. The pharmaceutical composition of claim 2, wherein R$^{61}$ is —NH$_2$.

14. The pharmaceutical composition of claim 2, wherein R$^{62}$ is —OCH$_3$.

15. The pharmaceutical composition of claim 2, wherein R$^{71}$ is —OH.

16. The pharmaceutical composition of claim 1, wherein the compound has the formula

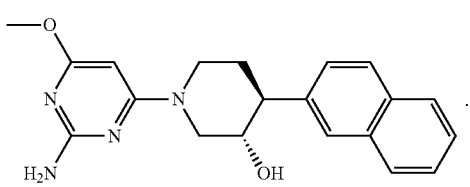 [SMILES: COc1cc(N2CC[C@@H](c3ccc4ccccc4c3)[C@H](O)C2)nc(N)n1]

17. The pharmaceutical composition of claim 1, wherein $W^1$ is N.

18. The method of claim 8, wherein the compound has the formula:

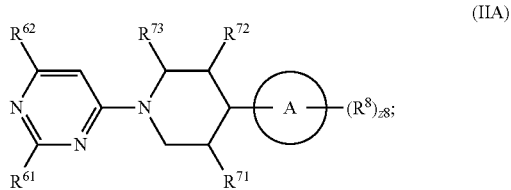

(IIA)

$R^{61}$ and $R^{62}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; and $R^{71}$, $R^{72}$, and $R^{73}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SeH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl.

19. The method of claim 8, wherein the compound has the formula

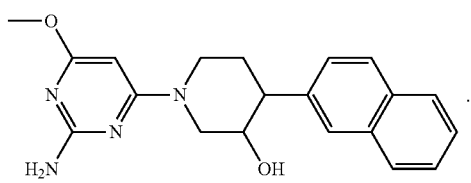 [SMILES: COc1cc(N2CCC(c3ccc4ccccc4c3)C(O)C2)nc(N)n1]

20. The method of claim 8, wherein the compound has the formula

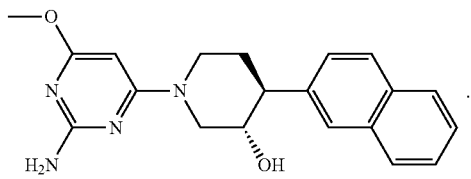

21. The pharmaceutical composition of claim 1, wherein the compound is capable of inhibiting TXNIP protein activity or function.

22. The pharmaceutical composition of claim 1, wherein the compound is capable of inhibiting TXNIP protein binding to TRX.

* * * * *

SEQUENCE LISTING

```
<160> NUMBER OF SEQ ID NOS: 2

<210> SEQ ID NO 1
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 1

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
                20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
        50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 2
<211> LENGTH: 391
<212> TYPE: PRT
<213> ORGANISM: Artificial Sequence
<220> FEATURE:
<223> OTHER INFORMATION: Synthetic polypeptide

<400> SEQUENCE: 2
```

```
Met Val Met Phe Lys Lys Ile Lys Ser Phe Glu Val Val Phe Asn Asp
1               5                   10                  15

Pro Glu Lys Val Tyr Gly Ser Gly Lys Val Ala Gly Arg Val Ile
            20                  25                  30

Val Glu Val Cys Glu Val Thr Arg Val Lys Ala Val Arg Ile Leu Ala
            35                  40                  45

Cys Gly Val Ala Lys Val Leu Trp Met Gln Gly Ser Gln Cys Lys
50                  55                  60

Gln Thr Ser Glu Tyr Leu Arg Tyr Glu Asp Thr Leu Leu Glu Asp
65                  70                  75                  80

Gln Pro Thr Gly Glu Asn Glu Met Val Ile Met Arg Pro Gly Asn Lys
                85                  90                  95

Tyr Glu Tyr Lys Phe Gly Phe Glu Leu Pro Gln Gly Pro Leu Gly Thr
            100                 105                 110

Ser Phe Lys Gly Lys Tyr Gly Cys Val Asp Tyr Trp Val Lys Ala Phe
            115                 120                 125

Leu Asp Arg Pro Ser Gln Pro Thr Gln Glu Thr Lys Lys Asn Phe Glu
130                 135                 140

Val Val Asp Leu Val Asp Val Asn Thr Pro Asp Leu Met Ala Pro Val
145                 150                 155                 160

Ser Ala Lys Lys Glu Lys Lys Val Ser Cys Met Phe Ile Pro Asp Gly
            165                 170                 175

Arg Val Ser Val Ser Ala Arg Ile Asp Arg Lys Gly Phe Cys Glu Gly
            180                 185                 190

Asp Glu Ile Ser Ile His Ala Asp Phe Glu Asn Thr Cys Ser Arg Ile
            195                 200                 205

Val Val Pro Lys Ala Ala Ile Val Ala Arg His Thr Tyr Leu Ala Asn
            210                 215                 220

Gly Gln Thr Lys Val Leu Thr Gln Lys Leu Ser Ser Val Arg Gly Asn
225                 230                 235                 240

His Ile Ile Ser Gly Thr Cys Ala Ser Trp Arg Gly Lys Ser Leu Arg
                245                 250                 255

Val Gln Lys Ile Arg Pro Ser Ile Leu Gly Cys Asn Ile Leu Arg Val
            260                 265                 270

Glu Tyr Ser Leu Leu Ile Tyr Val Ser Val Pro Gly Ser Lys Lys Val
            275                 280                 285

Ile Leu Asp Leu Pro Leu Val Ile Gly Ser Arg Ser Gly Leu Ser Ser
            290                 295                 300

Arg Thr Ser Ser Met Ala Ser Arg Thr Ser Ser Glu Met Ser Trp Val
305                 310                 315                 320

Asp Leu Asn Ile Pro Asp Thr Pro Glu Ala Pro Cys Tyr Met Asp
            325                 330                 335

Val Ile Pro Glu Asp His Arg Leu Glu Ser Pro Thr Thr Pro Leu Leu
            340                 345                 350

Asp Asp Met Asp Gly Ser Gln Asp Ser Pro Ile Phe Met Tyr Ala Pro
            355                 360                 365

Glu Phe Lys Phe Met Pro Pro Pro Thr Tyr Thr Glu Val Asp Pro Cys
            370                 375                 380

Ile Leu Asn Asn Asn Val Gln
385                 390
```